US012735424B2

(12) United States Patent
Wang et al.

(10) Patent No.: US 12,735,424 B2
(45) Date of Patent: Sep. 15, 2026

(54) FUSED PYRAZINE DERIVATIVES AS A2A / A2B INHIBITORS

(71) Applicant: Incyte Corporation, Wilmington, DE (US)

(72) Inventors: Xiaozhao Wang, Mount Laurel, NJ (US); Peter Niels Carlsen, Claymont, DE (US); Pei Gan, Claymont, DE (US); Gia Hoang, Wilmington, DE (US); Yong Li, Newark, DE (US); Chao Qi, Newark, DE (US); Liangxing Wu, Wilmington, DE (US); Wenqing Yao, Chadds Ford, PA (US); Zhiyong Yu, Wilmington, DE (US); Wenyu Zhu, Media, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/620,225

(22) Filed: Mar. 28, 2024

(65) Prior Publication Data

US 2024/0360140 A1 Oct. 31, 2024

Related U.S. Application Data

(60) Continuation of application No. 17/500,140, filed on Oct. 13, 2021, now Pat. No. 11,999,740, which is a division of application No. 16/502,826, filed on Jul. 3, 2019, now Pat. No. 11,161,850.

(60) Provisional application No. 62/755,845, filed on Nov. 5, 2018, provisional application No. 62/694,138, filed on Jul. 5, 2018.

(51) Int. Cl.

| | |
|---|---|
| ***C07D 487/04*** | (2006.01) |
| ***A61K 31/4985*** | (2006.01) |
| ***A61P 3/10*** | (2006.01) |
| ***A61P 9/00*** | (2006.01) |
| ***A61P 9/10*** | (2006.01) |
| ***A61P 25/00*** | (2006.01) |
| ***A61P 25/28*** | (2006.01) |
| ***A61P 29/00*** | (2006.01) |
| ***A61P 35/00*** | (2006.01) |
| ***C07D 519/00*** | (2006.01) |

(52) U.S. Cl.
CPC ......... *C07D 487/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,634,665 | A | 1/1987 | Axel et al. |
| 5,057,313 | A | 10/1991 | Shih et al. |
| 5,156,840 | A | 10/1992 | Goers et al. |
| 5,179,017 | A | 1/1993 | Axel et al. |
| 5,521,184 | A | 5/1996 | Zimmermann |
| 5,530,101 | A | 6/1996 | Queen et al. |
| 5,585,089 | A | 12/1996 | Queen et al. |
| 5,624,821 | A | 4/1997 | Winter et al. |
| 5,648,260 | A | 7/1997 | Winter et al. |
| 5,693,761 | A | 12/1997 | Queen et al. |
| 5,693,762 | A | 12/1997 | Queen et al. |
| 5,714,350 | A | 2/1998 | Co et al. |
| 5,731,168 | A | 3/1998 | Carter et al. |
| 5,849,992 | A | 12/1998 | Meade et al. |
| 5,859,205 | A | 1/1999 | Adair et al. |
| 5,869,046 | A | 2/1999 | Presta et al. |
| 6,222,035 | B1 | 4/2001 | Tsumuki et al. |
| 6,300,064 | B1 | 10/2001 | Knippik et al. |
| 6,350,861 | B1 | 2/2002 | Co et al. |
| 6,407,213 | B1 | 6/2002 | Carter et al. |
| 6,545,000 | B1 | 4/2003 | Shimada et al. |
| 6,803,192 | B1 | 10/2004 | Chen |
| 6,808,710 | B1 | 10/2004 | Wood et al. |
| 6,921,762 | B2 | 7/2005 | Cai et al. |

(Continued)

FOREIGN PATENT DOCUMENTS

| | | |
|---|---|---|
| AU | 2005260031 | 1/2006 |
| CL | 200202688 | 11/2003 |

(Continued)

OTHER PUBLICATIONS

Allard et al., "Targeting A2 adenosine receptors in cancer," Immunology and Cell Biology, Apr. 2017, 95(4):333-339.

(Continued)

*Primary Examiner* — Sun Jae Yoo

(74) *Attorney, Agent, or Firm* — Fish & Richardson P.C.

(57) ABSTRACT

This application relates to compounds of Formula (I):

(I)

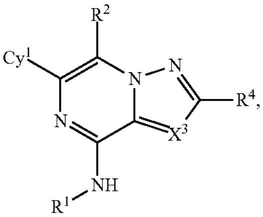

or pharmaceutically acceptable salts thereof, which modulate the activity of adenosine receptors, such as subtypes A2A and A2B receptors, and are useful in the treatment of diseases related to the activity of adenosine receptors including, for example, cancer, inflammatory diseases, cardiovascular diseases, and neurodegenerative diseases.

42 Claims, No Drawings

(56) References Cited

U.S. PATENT DOCUMENTS 7,041,666 B2 5/2006 Matasi et al.
7,101,550 B2 9/2006 Wood et al.
7,306,631 B2 12/2007 Glenn, Jr. et al.
7,452,892 B2 11/2008 Wu et al.
7,488,802 B2 2/2009 Collins et al.
7,501,411 B2 3/2009 Andrews et al.
7,511,050 B2 3/2009 Zheng et al.
7,563,788 B2 7/2009 Sciotti et al.
7,635,757 B2 12/2009 Freeman et al.
7,674,791 B2 3/2010 Dowling et al.
7,700,594 B2 4/2010 Chen et al.
7,709,468 B2 5/2010 Calderwood et al.
7,722,868 B2 5/2010 Freeman et al.
7,794,710 B2 9/2010 Chen et al.
7,834,014 B2 11/2010 Peng et al.
7,943,743 B2 5/2011 Korman et al.
8,008,449 B2 8/2011 Korman et al.
8,053,574 B2 11/2011 Bruce et al.
8,133,895 B2 3/2012 Andrews et al.
8,168,757 B2 5/2012 Finnefrock et al.
8,202,869 B2 6/2012 Kase et al.
8,217,149 B2 7/2012 Irving et al.
8,273,752 B2 9/2012 Siegel et al.
8,288,536 B2 10/2012 Dong et al.
8,349,850 B2 1/2013 Tworowski et al.
8,431,596 B2 4/2013 Pave et al.
8,569,300 B2 10/2013 Borchardt et al.
8,575,183 B2 11/2013 Cushing et al.
8,580,812 B2 11/2013 Ihle et al.
8,637,542 B2 1/2014 Liu et al.
8,865,731 B2 10/2014 Ouchi et al.
8,865,734 B2 10/2014 No et al.
9,029,389 B2 5/2015 No et al.
9,029,393 B2 5/2015 Schann et al.
9,034,872 B2 5/2015 Tworowski et al.
9,085,560 B2 7/2015 Ren et al.
9,090,697 B2 7/2015 Sim
9,127,000 B2 9/2015 Ren et al.
9,249,162 B2 2/2016 Campbell et al.
9,254,283 B2 2/2016 Ikeda et al.
9,328,121 B1 5/2016 Takahashi et al.
9,388,249 B2 7/2016 Sugioka et al.
9,394,301 B2 7/2016 Pave et al.
9,394,311 B2 7/2016 Flohr et al.
9,573,948 B2 2/2017 Cole et al.
9,605,080 B2 3/2017 Lonberg et al.
9,695,167 B2 7/2017 Wu et al.
9,938,356 B2 4/2018 Hay et al.
9,944,647 B2 4/2018 He et al.
10,100,129 B2 10/2018 Lonberg et al.
10,287,362 B2 5/2019 Hay et al.
10,577,422 B2 3/2020 Shah et al.
11,117,899 B2 9/2021 Chen et al.
11,161,850 B2 11/2021 Wang et al.
11,168,089 B2 11/2021 Wang et al.
11,312,705 B2 4/2022 Lu et al.
11,390,624 B2 7/2022 Huang et al.
11,673,894 B2 6/2023 Wang et al.
11,999,740 B2 6/2024 Wang et al.
2002/0193376 A1 12/2002 Gall
2003/0027820 A1 2/2003 Gall
2003/0143199 A1 7/2003 Carson et al.
2004/0110826 A1 6/2004 Uesaka et al.
2004/0142342 A1 7/2004 Barden et al.
2004/0186148 A1 9/2004 Shankar et al.
2005/0008625 A1 1/2005 Balint et al.
2005/0037000 A1 2/2005 Stavenhagen et al.
2005/0059051 A1 3/2005 Chen
2005/0079574 A1 4/2005 Bond
2005/0272765 A1 12/2005 Feng et al.
2005/0288502 A1 12/2005 Anderson et al.
2006/0040944 A1 2/2006 Gosselin et al.
2006/0058320 A1 3/2006 Iida et al.
2006/0154930 A1 7/2006 Brown et al.
2006/0178399 A1 8/2006 Nishizawa et al.
2006/0211739 A1 9/2006 Perez-Medrano et al.
2007/0009518 A1 1/2007 Novabrantseva et al.
2007/0010522 A1 1/2007 Vu et al.
2007/0117804 A1 5/2007 Zhao et al.
2007/0149548 A1 6/2007 Hellberg et al.
2007/0202100 A1 8/2007 Wood et al.
2007/0213332 A1 9/2007 Burkamp et al.
2007/0225286 A1 9/2007 Ren et al.
2007/0281942 A1 12/2007 Cao et al.
2008/0021026 A1 1/2008 Kahraman
2008/0021217 A1 1/2008 Borchardt et al.
2008/0096892 A1 4/2008 Cheng et al.
2008/0132501 A1 6/2008 Sun et al.
2008/0293739 A1 11/2008 Trede
2008/0311117 A1 12/2008 Collins et al.
2009/0055944 A1 2/2009 Korman et al.
2009/0105277 A1 4/2009 Kadowaki et al.
2009/0110667 A1 4/2009 Mozaffarian et al.
2009/0118301 A1 5/2009 Lu et al.
2009/0118499 A1 5/2009 Arnold et al.
2009/0163489 A1 6/2009 Booker et al.
2009/0176778 A1 7/2009 Schmitz et al.
2009/0258877 A1 10/2009 Siegel et al.
2009/0274666 A1 11/2009 Chen
2009/0313687 A1 12/2009 Popp et al.
2010/0105733 A1 4/2010 Lyttle et al.
2010/0160355 A1 6/2010 DeGoey et al.
2010/0168138 A1 7/2010 DeGoey et al.
2010/0261679 A1 10/2010 Sutton et al.
2010/0292232 A1 11/2010 Elleder et al.
2011/0105457 A1 5/2011 Taniyama et al.
2011/0190269 A1 8/2011 Baumann et al.
2011/0201649 A1 8/2011 Matsuzaki et al.
2011/0206607 A1 8/2011 Olsson et al.
2011/0288074 A1 11/2011 Schann et al.
2011/0300136 A1 12/2011 Benyunes
2012/0021519 A1 1/2012 Ichida et al.
2012/0083498 A1 4/2012 Kashanchi
2012/0121540 A1 5/2012 Schmitz et al.
2012/0232089 A1 9/2012 Kase et al.
2013/0225568 A1 8/2013 Burgdorf et al.
2015/0197503 A1 7/2015 Russo et al.
2016/0009711 A1 1/2016 Wu et al.
2016/0046648 A1 2/2016 Petrukhin et al.
2016/0096835 A1 4/2016 Cole et al.
2016/0129108 A1 5/2016 Sachsenmeier et al.
2016/0168154 A1 6/2016 Marineau et al.
2016/0354375 A1 12/2016 Sheridan et al.
2017/0107216 A1 4/2017 Wu et al.
2017/0114077 A1 4/2017 Frideman et al.
2017/0145025 A1 5/2017 Li et al.
2017/0174671 A1 6/2017 Wu et al.
2017/0174679 A1 6/2017 Lajkiewicz et al.
2017/0320875 A1 11/2017 Li et al.
2017/0342060 A1 11/2017 Lu et al.
2017/0362253 A1 12/2017 Xiao et al.
2018/0009816 A1 1/2018 Buesking et al.
2018/0009899 A1 1/2018 Griffin et al.
2018/0016260 A1 1/2018 Yu et al.
2018/0030144 A1 2/2018 Chanteux et al.
2018/0057486 A1 3/2018 Wu et al.
2018/0170908 A1 6/2018 Aspnes et al.
2018/0177784 A1 6/2018 Wu et al.
2018/0177870 A1 6/2018 Lu et al.
2018/0179179 A1 6/2018 Wu et al.
2018/0179197 A1 6/2018 Wu et al.
2018/0179201 A1 6/2018 Wu et al.
2018/0179202 A1 6/2018 Wu et al.
2018/0237536 A1 8/2018 Perrot et al.
2018/0258043 A1 9/2018 Gunzner-Toste et al.
2018/0264107 A1 9/2018 Curd et al.
2018/0273519 A1 9/2018 Wu et al.
2019/0031766 A1 1/2019 Prinz et al.
2019/0055250 A1 2/2019 He et al.
2019/0062345 A1 2/2019 Xiao et al.
2019/0076433 A1 3/2019 Willingham et al.
2019/0077873 A1 3/2019 Griffin et al.
2019/0092784 A1 3/2019 Wu et al.
2019/0144439 A1 5/2019 Wu et al.

(56) References Cited

U.S. PATENT DOCUMENTS

| | | | |
|---|---|---|---|
| 2019/0202824 | A1 | 7/2019 | Wu et al. |
| 2019/0225601 | A1 | 7/2019 | Wu et al. |
| 2019/0225703 | A1 | 7/2019 | Caux et al. |
| 2019/0256598 | A1 | 8/2019 | Wang et al. |
| 2019/0292188 | A1 | 9/2019 | Wang et al. |
| 2019/0300524 | A1 | 10/2019 | Wu et al. |
| 2019/0337957 | A1 | 11/2019 | Wang et al. |
| 2019/0345170 | A1 | 11/2019 | Wu et al. |
| 2019/0375752 | A1 | 12/2019 | Wang et al. |
| 2020/0031835 | A1 | 1/2020 | Wang et al. |
| 2020/0095322 | A1 | 3/2020 | Cornfeld et al. |
| 2020/0102315 | A1 | 4/2020 | Buesking et al. |
| 2020/0131184 | A1 | 4/2020 | Chen et al. |
| 2020/0172533 | A1 | 6/2020 | Wu et al. |
| 2020/0172541 | A1 | 6/2020 | Li et al. |
| 2020/0181126 | A1 | 6/2020 | Lu et al. |
| 2020/0255424 | A1 | 8/2020 | Wu et al. |
| 2020/0270244 | A1 | 8/2020 | Huang et al. |
| 2020/0277309 | A1 | 9/2020 | Wu et al. |
| 2020/0283423 | A1 | 9/2020 | Yu et al. |
| 2020/0325115 | A1 | 10/2020 | Wu et al. |
| 2020/0397893 | A1 | 12/2020 | Liu et al. |
| 2020/0407357 | A1 | 12/2020 | Lajkiewicz et al. |
| 2021/0002276 | A1 | 1/2021 | Wu et al. |
| 2021/0017164 | A1 | 1/2021 | Lu et al. |
| 2021/0017175 | A1 | 1/2021 | Li et al. |
| 2021/0040090 | A1 | 2/2021 | Jia et al. |
| 2021/0061809 | A1 | 3/2021 | Han et al. |
| 2021/0094976 | A1 | 4/2021 | Li et al. |
| 2021/0107900 | A1 | 4/2021 | Wu et al. |
| 2021/0115025 | A1 | 4/2021 | Yu et al. |
| 2021/0115068 | A1 | 4/2021 | Wu et al. |
| 2021/0139485 | A1 | 5/2021 | Wang et al. |
| 2021/0139511 | A1 | 5/2021 | Jia et al. |
| 2021/0205311 | A1 | 7/2021 | Wang et al. |
| 2021/0221819 | A1 | 7/2021 | Li et al. |
| 2021/0230294 | A1 | 7/2021 | Nastri et al. |
| 2021/0261555 | A1 | 8/2021 | Wang et al. |
| 2022/0135570 | A1 | 5/2022 | Wang et al. |
| 2022/0144830 | A1 | 5/2022 | Zhou et al. |
| 2022/0144831 | A1 | 5/2022 | Wang et al. |
| 2022/0144832 | A1 | 5/2022 | Jia et al. |
| 2022/0233529 | A1 | 7/2022 | Wang et al. |

FOREIGN PATENT DOCUMENTS

| | | |
|---|---|---|
| CL | 200500898 | 6/2006 |
| CL | 201802358 | 11/2018 |
| CL | 201900486 | 6/2019 |
| CL | 202002198 | 1/2021 |
| CL | 202101116 | 11/2021 |
| CN | 1328560 | 12/2001 |
| CN | 109535161 | 3/2019 |
| CO | 5540324 | 7/2005 |
| CO | 2017004785 | 8/2017 |
| DE | 102006041292 | 3/2008 |
| EP | 404097 | 12/1990 |
| EP | 0976753 | 2/2000 |
| EP | 1448564 | 8/2004 |
| EP | 1453835 | 9/2004 |
| EP | 1544200 | 6/2005 |
| EP | 1902716 | 3/2008 |
| EP | 1905418 | 4/2008 |
| EP | 2155747 | 2/2010 |
| JP | 2003/528811 | 9/2003 |
| JP | 2005/511698 | 4/2005 |
| JP | 2007/039633 | 2/2007 |
| JP | 2010/521506 | 6/2010 |
| JP | 2011/513417 | 4/2011 |
| WO | WO 1990/007861 | 7/1990 |
| WO | WO 1993/011161 | 6/1993 |
| WO | WO 1998/003511 | 1/1998 |
| WO | WO 1998/042711 | 10/1998 |
| WO | WO 2000/009495 | 2/2000 |
| WO | WO 2000/053595 | 9/2000 |
| WO | WO 2001/014402 | 3/2001 |
| WO | WO 2001/014557 | 3/2001 |
| WO | WO 2001/017999 | 3/2001 |
| WO | WO 2001/039722 | 6/2001 |
| WO | WO 2001/064655 | 9/2001 |
| WO | WO 2001/080884 | 11/2001 |
| WO | WO 2001/092264 | 12/2001 |
| WO | WO 2002/000196 | 1/2002 |
| WO | WO 2002/086083 | 10/2002 |
| WO | WO 2003/024967 | 3/2003 |
| WO | WO 2003/037347 | 5/2003 |
| WO | WO 2003/042402 | 5/2003 |
| WO | WO 2003/044021 | 5/2003 |
| WO | WO 2003/048164 | 6/2003 |
| WO | WO 2003/062236 | 7/2003 |
| WO | WO 2003/099771 | 12/2003 |
| WO | WO 2004/005281 | 1/2004 |
| WO | WO 2004/046120 | 6/2004 |
| WO | WO 2004/056786 | 7/2004 |
| WO | WO 2004/079013 | 9/2004 |
| WO | WO 2004/080980 | 9/2004 |
| WO | WO 2004/092173 | 10/2004 |
| WO | WO 2004/092177 | 10/2004 |
| WO | WO 2005/003175 | 1/2005 |
| WO | WO 2005/016892 | 2/2005 |
| WO | WO 2005/018572 | 3/2005 |
| WO | WO 2005/028444 | 3/2005 |
| WO | WO 2003/068776 | 6/2005 |
| WO | WO 2006/129626 | 12/2006 |
| WO | WO 2006/132275 | 12/2006 |
| WO | WO 2007/011759 | 1/2007 |
| WO | WO 2007/028051 | 3/2007 |
| WO | WO 2007/058942 | 5/2007 |
| WO | WO 2007/150025 | 12/2007 |
| WO | WO 2008/011560 | 1/2008 |
| WO | WO 2008/037607 | 4/2008 |
| WO | WO 2008/056176 | 5/2008 |
| WO | WO 2008/113469 | 9/2008 |
| WO | WO 2008/149168 | 12/2008 |
| WO | WO 2008/156712 | 12/2008 |
| WO | WO 2008/006563 | 1/2009 |
| WO | WO 2009/019505 | 2/2009 |
| WO | WO 2009/023179 | 2/2009 |
| WO | WO 2009/047514 | 4/2009 |
| WO | WO 2009/085185 | 7/2009 |
| WO | WO 2009/111449 | 9/2009 |
| WO | WO 2009/114870 | 9/2009 |
| WO | WO 2009/117421 | 9/2009 |
| WO | WO 2009/117734 | 9/2009 |
| WO | WO 2010/036959 | 4/2010 |
| WO | WO 2010/075074 | 7/2010 |
| WO | WO 2010/089411 | 8/2010 |
| WO | WO 2010/104306 | 9/2010 |
| WO | WO 2011/019780 | 2/2011 |
| WO | WO 2011/022439 | 2/2011 |
| WO | WO 2011/053508 | 5/2011 |
| WO | WO 2011/060207 | 5/2011 |
| WO | WO 2011/066342 | 6/2011 |
| WO | WO 2011/078143 | 6/2011 |
| WO | WO 2011/082400 | 7/2011 |
| WO | WO 2011/089004 | 7/2011 |
| WO | WO 2011/101409 | 8/2011 |
| WO | WO 2011/112766 | 9/2011 |
| WO | WO 2011/135303 | 11/2011 |
| WO | WO 2011/153588 | 12/2011 |
| WO | WO 2011/159877 | 12/2011 |
| WO | WO 2011/161699 | 12/2011 |
| WO | WO 2012/061156 | 5/2012 |
| WO | WO 2012/116237 | 8/2012 |
| WO | WO 2012/129344 | 9/2012 |
| WO | WO 2012/147890 | 11/2012 |
| WO | WO 2013/026516 | 2/2013 |
| WO | WO 2013/087943 | 6/2013 |
| WO | WO 2013/106254 | 7/2013 |
| WO | WO 2014/078479 | 5/2014 |
| WO | WO 2014/126580 | 8/2014 |
| WO | WO 2014/153424 | 9/2014 |
| WO | WO 2015/158283 | 10/2015 |
| WO | WO 2016/007235 | 1/2016 |

(56) References Cited

FOREIGN PATENT DOCUMENTS

| | | |
|---|---|---|
| WO | WO 2016/007722 | 1/2016 |
| WO | WO 2016/057522 | 4/2016 |
| WO | WO 2016/075099 | 5/2016 |
| WO | WO 2016/144703 | 9/2016 |
| WO | WO 2016/161282 | 10/2016 |
| WO | WO 2017/019846 | 2/2017 |
| WO | WO 2017/070089 | 4/2017 |
| WO | WO 2017/087777 | 5/2017 |
| WO | WO 2017/100670 | 6/2017 |
| WO | WO 2017/106634 | 6/2017 |
| WO | WO 2017/112730 | 6/2017 |
| WO | WO 2017/152085 | 9/2017 |
| WO | WO 2016/129684 | 11/2017 |
| WO | WO 2017/192961 | 11/2017 |
| WO | WO 2017/205464 | 11/2017 |
| WO | WO 2017/222976 | 12/2017 |
| WO | WO 2018/004478 | 1/2018 |
| WO | WO 2018/013789 | 1/2018 |
| WO | WO 2018/110555 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/136265 | 7/2018 |
| WO | WO 2018/137598 | 8/2018 |
| WO | WO 2018/166493 | 9/2018 |
| WO | WO 2018/184590 | 10/2018 |
| WO | WO 2018/187512 | 10/2018 |
| WO | WO 2018/215535 | 11/2018 |
| WO | WO 2018/226976 | 12/2018 |
| WO | WO 2018/237173 | 12/2018 |
| WO | WO 2019/002606 | 1/2019 |
| WO | WO 2019/081353 | 5/2019 |
| WO | WO 2019/099838 | 5/2019 |
| WO | WO 2019/152678 | 8/2019 |
| WO | WO 2019/152687 | 8/2019 |
| WO | WO 2019/159120 | 8/2019 |
| WO | WO 2019/168847 | 9/2019 |
| WO | WO 2019/170131 | 9/2019 |
| WO | WO 2019/173291 | 9/2019 |
| WO | WO 2019/173692 | 9/2019 |
| WO | WO 2019/191707 | 10/2019 |
| WO | WO 2019/200256 | 10/2019 |
| WO | WO 2019/217821 | 11/2019 |
| WO | WO 2019/222677 | 11/2019 |
| WO | WO 2019/246110 | 12/2019 |
| WO | WO 2020/010197 | 1/2020 |
| WO | WO 2020/035424 | 2/2020 |
| WO | WO 2020/035425 | 2/2020 |
| WO | WO 2020/038983 | 2/2020 |
| WO | WO 2020/039051 | 2/2020 |
| WO | WO 2020/052631 | 3/2020 |
| WO | WO 2020/069027 | 4/2020 |
| WO | WO 2020/073945 | 4/2020 |
| WO | WO 2020/106560 | 5/2020 |
| WO | WO 2020/108613 | 6/2020 |
| WO | WO 2020/159905 | 8/2020 |
| WO | WO 2021/041360 | 3/2021 |
| WO | WO 2021/138467 | 7/2022 |

OTHER PUBLICATIONS

Costa Rican Office Action in Costa Rican Application No. 2021-0071, dated Mar. 7, 2025, 22 pages (with English Translation).

European Office Action in European Application No. 19745853.2, dated Dec. 23, 2024, 10 pages.

Colombian Office Action in Colombian Application No. NC2023/0010247, dated Oct. 3, 2024, 27 pages (with English Translation).

Korean Office Action in Korean Application No. 10-2021-7003641, dated Sep. 9, 2024, 12 pages (with English Translation).

Egyptian Office Action in Egyptian Application No. 15/2021, dated May 19, 2024, 12 pages (with English Translation).

Malaysian Office Action in Malaysian Application No. PI2021000020, dated Jul. 17, 2024, 2 pages.

Mexican Office Action in Mexican Application No. MX/a/2021/000116, dated May 27, 2024, 14 pages (with Machine Translation).

Philippines Office Action in Philippines Application No. 1-2021-550019, dated Jul. 11, 2024, 5 pages.

Agata et al., "Expression of the PD-1 antigen on the surface of stimulated mouse T and B lymphocytes," (1996) Int. Immunol. 8(5):765-772.

Allard et al., "Immunosuppressive activities of adenosine in cancer," Curr Opin in Pharma., 2016, 29:7-16.

Allard et al., "Targeting CD73 Enhances the Antitumor Activity of Anti-PD-1 and Anti-CTLA-4 mAbs," Clin Canc Res., 2013, 19(20):5626-5635.

Angal et al., "A single amino acid substitution abolishes the heterogeneity of chimeric mouse/human (IgG4) antibody," Mol. Immunol., 1993, 30:105-108.

Antonioli et al., "Immunity, Inflammation and Cancer: a leading role for adenosine," Nature Reviews Cancer, Nov. 14, 2013, 13:842-857.

Baraldi et al., "Adenosine receptor antagonists: translating medicinal chemistry and pharmacology into clinical utility," Chem. Rev., Jan. 2008, 108(1):238-263.

Barber et al., "Restoring function in exhausted CD8 T cells during chronic viral infection," Nature, 2006, 439:682-687.

Beavis et al., "Blockade of A2A receptors potently suppresses the metastasis of CD73+ tumors," Proc Natl Acad Sci. USA, Sep. 3, 2013, 110(36):14711-14716.

Beavis et al., "Targeting the adenosine 2A receptor enhances chimeric antigen receptor T cell efficacy," Journ. of Clin Invest., Mar. 2017, 127(3):929-941.

Berge et al., "Pharmaceutical Salts," Journal of Pharmaceutical Science, 1977, vol. 66, 21 pages.

Better et al., "*Escherichia coli* secretion of an active chimeric antibody fragment," Science, 1988, 240:1041-1043.

Better et al., "Expression of engineered antibodies and antibody fragments in microorganisms," Methods in Enzymology, 1989, 178:476-496.

Bird et al., "Single chain antibody variable regions," TIBTECH, 1991, 9:132-137.

Blank et al., "PD-L1/B7H-1 inhibits the effector phase of tumor rejection by T cell receptor (TCR) transgenic CD8+ T cells," Cancer Res., 2004, 64(3):1140-1145.

Blank et al., "Contribution of the PD-L1/PD-1 pathway to T-cell exhaustion: an update on implications for chronic infections and tumor evasion," Immunol Immunother., 2006, 56(5):739-745.

Boknik et al., "Role of Cardiac A2A Receptors Under Normal and Pathophysiological Conditions," Frontiers in Pharmacology, Jan. 2021, 11:1-18.

Borrmann et al., "1-alkyl-8-(piperazine-1-sulfonyl)phenylxanthines: development and characterization of adenosine A2B receptor antagonists and a new radioligand with subnanomolar affinity and subtype specificity," J. Med. Chem., 2009, 52(13):3994-4006.

Boyd et al., "Some Practical Considerations and Applications of the National Cancer Institute In Vitro Anticancer Drug Discovery Screen," Drug Development Research, 1995, 34(2):91-109.

Braganhol et al., "Ecto-5'-nucleotidase/CD73 inhibition by quercetin in the human U138MG glioma cell line," Biochim. Biophys. Acta., 2007, 1770(9):1352-1359.

Brazilian Office Action in Brazilian Application No. BR112021000075-5, dated Mar. 25, 2024, 5 pages (with English Translation).

Carlsson et al., "Structure-based discovery of A2A adenosine receptor ligands," J. Med. Chem., 2010, 53(9):3748-3755.

Carter et al., "High level *Escherichia coli* expression and production of a bivalent humanized antibody fragment," Bio/Technology, 1992, 10:163-167.

Carter et al., "Humanization of an anti-p185HER2 antibody for human cancer therapy," PNAS, 1992, 89(10):4285-4289.

Carter et al., "PD-1:PD-L inhibitory pathway affects both CD4(+) and CD8(+) T cells and is overcome by IL-2," Eur J Immunol., 2002, 32(3):634-643.

(56) References Cited

OTHER PUBLICATIONS

CAS Reg. No. 1374853-91-4, "Pembrolizumab," retrieved on Aug. 12, 2021, retrieved from URL <https://chem.nlm.nih.gov/chemidplus/rn/1374853-91-4>, 1 page.
CAS Reg. No. 1380723-44-3, "Atezolizumab," retrieved on Aug. 12, 2021, retrieved from URL <https://chem.nlm.nih.gov/chemidplus/rn/1380723-44-3>, 1 page.
Cekic et al., "Adenosine A2B receptor blockade slows growth of bladder and breast tumors," J Immunol, Jan. 1, 2012, 188(1):198-205.
Chilean Office Action in Chilean Application No. 202100004, dated May 31, 2022, 14 pages.
Chilean Office Action in Chilean Application No. 2198-2020, dated Oct. 13, 2021, 24 pages.
Chothia et al., "Structural repertoire of the human VH segments," J Mol Bio., 1992, 227:799-817.
Co et al., "A humanized antibody specific for the platelet integrin gpIIb/IIIa," J Immunol., 1994, 152:2968-2976.
Collins et al., "The novel adenosine A2A antagonist Lu AA47070 reverses the motor and motivational effects produced by dopamine D2 receptor blockade," Pharmacol. Biochem. Behav., Jan. 2012, 100(3):498-505.
Columbian Office Action in Columbian Application No. NC2021/0001251, dated Oct. 11, 2023, 23 pages (with English Translation).
Columbian Office Action in Columbian Application No. NC2023/0010247, dated Oct. 23, 2023, 23 pages (with English Translation).
Cook et al., "The human immunoglobulin VH repertoire," Immunol Today., 1995, 16(5):237-242.
Davies et al., "Single antibody domains as small recognition units: design and in vitro antigen selection of camelized, human VH domains with improved protein stability," Protein Eng., 1996, 9(6):531-537.
Direnzo et al., "AB928 a Dual Antagonist of the A2aR and A2bR Adenosine Receptors, Relieves Adenosine-Mediated Immuno Suppression," Arcus Biosciences Poster, 2018, 1 page.
Dorai et al., "Aglycosylated Chimeric Mouse/Human IgG1 Antibody Retains Some Effector Function," Hybridoma, 1991, 10(2):211-217.
Dowling et al., "Synthesis of [1,2,4]triazolo[1,5-a]pyrazines as adenosine A2A receptor antagonists," Bioorganic & Medicinal Chemistry Letters., Nov. 1, 2005, 15(21):4809-4813.
Dunkin, "Treatments for Rheumatoid Arthritis," Jun. 12, 2022, retrieved from<https://www.arthritis.org/health-wellness/treatment/treatment-plan/disease-management/treatments-for-rheumatoid-arthritis>, 7 pages.
Ecuador Opposition in Ecuador Application No. SENADI-2020-60827, dated Apr. 27, 2021, 20 pages.
Ecuador Opposition in Ecuador Application No. SENADI-2020-60827, dated Jun. 2022, 19 pages.
Eisenhauer et al., "New response evaluation criteria in solid tumours: revised Recist guideline (version 1.1), " Eur J Cancer., 2009, 45(2):228-247.
Eisenstein et al., "The Many Faces of the A2b Adenosine Receptor in Cardiovascular and Metabolic Diseases," J Cell Physiol., Dec. 2015, 230(12):2891-2897.
Eurasian Office Action in Eurasian Application No. 202092016, dated Oct. 18, 2021, 7 pages.
Eurasian Office Action in Eurasian Application No. 202190204, dated Mar. 11, 2022, 9 pages (with English translation).
European Office Action in European Application No. 19733216.6, dated Feb. 23, 2023, 6 pages.
Figler et al. "Links Between Insulin Resistance, Adenosine A2B Receptors, and Inflammatory Markers in Mice and Humans," Diabetes, Feb. 2011, 60(2):669-679.
Flies et al., "The new B7s: playing a pivotal role in tumor immunity," J Immunother., 2007, 30(3):251-260.
Freeman et al., "Engagement of the PD-1 immunoinhibitory receptor by a novel B7 family member leads to negative regulation of lymphocyte activation," J Exp Med., 2000, 192(7):1027-1034.
Friend et al., "Phase I study of an engineered aglycosylated humanized CD3 antibody in renal transplant rejection," Transplantation, 1999, 68:1632-1637.
GenBank Accession No. NP_000667, "adenosine receptor A2b [*Homo sapiens*]," dated Apr. 22, 2022, 4 pages.
GenBank Accession No. NP_001265428, "adenosine receptor A2a [*Homo sapiens*], " dated May 3, 2022, 4 pages.
GenBank Accession No. NP_002517, "5'-nucleotidase isoform 1 preproprotein [*Homo sapiens*], " dated Apr. 17, 2022, 3 pages.
Genbank Accession No. NP_005009, "programmed cell death protein 1 precursor [*Homo sapiens*], " dated Aug. 2, 2021, 4 pages.
GenBank Accession No. NP_035981, "5'-nucleotidase preproprotein [Mus musculus]" dated May 3, 2022, 4 pages.
Georgian Office Action in Georgian Application No. AP 2019 15551, dated Dec. 2, 2021, 4 pages.
Georgian Office Action in Georgian Application No. AP 2019 15761, dated Jan. 11, 2022, 4 pages.
Gessi et al., "Inhibition of A2A Adenosine Receptor Signaling in Cancer Cells Proliferation by the Novel Antagonist TP455," Frontiers in Pharmacology, Dec. 2017, 8:1-13.
Globenewswire.com [website], "Corvus Pharmaceuticals Announces Interim Results from Ongoing Phase 1/1b Study Demonstrating Safety and Clinical Activity of Lead Checkpoint Inhibitor CPI-444 in Patients with Advanced Cancers," Apr. 4, 2017, [retrieved on Apr. 4, 2019] retrieved from URL <https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html>, 7 pages.
Graddis et al., "Designing proteins that work using recombinant technologies," Curr Pharm Biotechnol., 2002, 3:285-297.
Hackam, et al., "Translation of Research Evidence From Animals to Humans," JAMA, Oct. 2006, 296(14):1731-1732.
Hand et al., "Comparative biological properties of a recombinant chimeric anti-carcinoma mAb and a recombinant aglycosylated variant," Cancer Immunol Immunother., 1992, 35:165-174.
Harmsen et al., "Properties, production, and applications of camelid single-domain antibody fragments," Appl Microbiol Biotechnol., 2007, 77(1):13-22.
Hasko et al., "Shaping of monocyte and macrophage function by adenosine receptors," Pharmacol. Ther., Feb. 2007, 113(2):264-275.
Hobbs et al., "Interaction of aglycosyl immunoglobulins with the IgG Fc transport receptor from neonatal rat gut: comparison of deglycosylation by tunicamycin treatment and genetic engineering," Mol Immunol., 1992, 29(7-8):949-956.
Holliger et al., ""Diabodies": small bivalent and bispecific antibody fragments," Proc Natl Acad Sci USA., 1993, 90:6444-6448.
Huang et al., "The prognostic significance of PD-L1 in bladder cancer," Oncol Rep., 2015, 33(6):3075-84.
Hudson et al., "High avidity scFv multimers; diabodies and triabodies," J Immunol Methods., 1999, 231:177-189.
Huston et al., "Protein engineering of antibody binding sites: recovery of specific activity in an anti-digoxin single-chain Fv analogue produced in *Escherichia coli*," Proc Natl Acad Sci USA., 1988, 85:5879-5883.
Iannone et al., "Adenosine limits the therapeutic effectiveness of anti-CTLA4 mAb in a mouse melanoma model," Am. J. Cancer Res. 2014, 4(2):172-181.
Iannone et al., "Blockade of A2b Adenosine Receptor Reduces Tumor Growth and Immune Suppression Mediated by Myeloid-Derived Suppressor Cells in a Mouse Model of Melanoma," Neoplasia, 2013, 15:1400-1410.
Indian Office Action in Indian Patent Application No. 202017041726, dated Feb. 25, 2022, 7 pages.
International Preliminary Report on Patentability in International Application No. PCT/US2019/019582, dated Sep. 3, 2020, 11 pages.
International Preliminary Report on Patentability in International Application No. PCT/US2019/032948, dated Nov. 24, 2020, 9 pages.
International Preliminary Report on Patentability in International Application No. PCT/US2019/040496, dated Jan. 5, 2021, 9 pages.

(56) References Cited

OTHER PUBLICATIONS

International Preliminary Report on Patentability in International Application No. PCT/US2020/015294, dated Jul. 27, 2021, 7 pages.
International Preliminary Report on Patentability in International Application No. PCT/US2020/047714, dated Mar. 10, 2022, 8 pages.
International Preliminary Report on Patentability in International Application No. PCT/US2020/067593, dated Jul. 5, 2022, 12 pages.
International Preliminary Report on Patentability in International Application No. PCT/US2021/065472, mailed on Jul. 13, 2023, 9 pages.
International Search Report and Written Opinion in International Application No. PCT/US2019/019582, dated Jul. 18, 2019, 19 pages.
International Search Report and Written Opinion in International Application No. PCT/US2019/032948, dated Aug. 8, 2019, 15 pages.
International Search Report and Written Opinion in International Application No. PCT/US2019/040496, dated Sep. 17, 2019, 17 pages.
International Search Report and Written Opinion in International Application No. PCT/US2020/015294, dated May 6, 2020, 12 pages.
International Search Report and Written Opinion in International Application No. PCT/US2020/047714, dated Oct. 29, 2020, 15 pages.
International Search Report and Written Opinion in International Application No. PCT/US2020/067593, dated May 6, 2021, 20 pages.
International Search Report and Written Opinion in International Application No. PCT/US2021/065472, dated Jun. 15, 2022, 18 pages.
Invitation to Pay Additional Fees in International Application No. PCT/US2019/019582, dated May 20, 2019, 9 pages.
Isaacs et al., "Therapy with monoclonal antibodies. An in vivo model for the assessment of therapeutic potential," J Immunol., 1992, 148:3062-3071.
Ishida et al., "Induced expression of PD-1, a novel member of the immunoglobulin gene superfamily, upon programmed cell death," EMBO J., 1992, 11(11):3887-3895.
Iwai et al., "Involvement of PD-L1 on tumor cells in the escape from host immune system and tumor immunotherapy by PD-L1 blockade," PNAS., 2002, 99(19):12293-12297.
Japanese Office Action in Japanese Application No. 2020-564640, dated Jun. 6, 2023, 4 pages (with English translation).
Ji et al., "Modified toxicity probability interval design: a safer and more reliable method than the 3+3 design for practical phase I trials," J Clin Oncol., 2013, 31:1785-1791.
Ji et al., "A modified toxicity probability interval method for dose-finding trials," Clin Trials., 2010, 7:653-663.
Jordan, "Tamoxifen: a most unlikely pioneering medicine," Nature Reviews: Drug Discovery, 2003, 2:205-213.
Kaufman and Sharp "Amplification and expression of sequences cotransfected with a modular dihydrofolate reductase complementary dna gene," Mol Biol., 1982, 159:601-621.
Kerekes et al., "Aurora kinase inhibitors based on the imidazo[1,2-a]pyrazine core: fluorine and deuterium incorporation improve oral absorption and exposure," J. Med. Chem., Jan. 13, 2011, 54(1):201-210.
Knapp et al., "Crystal structure of the human ecto-5'-nucleotidase (CD73): insights into the regulation of purinergic signaling," Structure, 2012, 20(12):2161-2173.
Komiyama et al., "IL-17 plays an important role in the development of experimental autoimmune encephalomyelitis," J Immunol., 2006, 177:566-73.
Lamoyi, "Preparation of F(ab')2 fragments from mouse IgG of various subclasses," Methods in Enzymology, 1989, 121:652-663.
Latchman et al., "PD-L2 is a second ligand for PD-1 and inhibits T cell activation," Nat Immunol., 2001, 2(3):261-268.
Lawrence et al., "Safety and clinical activity of adenosine A2a receptor (A2aR) antagonist, CPI-444, in anti-PDI/PDLI treatment-refractory renal cell (RCC) and non-small cell lung cancer (NSCLC) patients," ASCO Annual meetings, 2017, retrieved from URL <https://www.corvuspharma.com/file.cfm/23/docs/FongASC017_3004.FINAL)6.05.2017.pdf>, 17 pages.
Leatherbarrow et al., "Effector functions of a monoclonal aglycosylated mouse IgG2a: Binding and activation of complement component C1 and interaction with human monocyte Fc receptor," Mol Immunol., 1985, 22(4):407-415.
Leatherbarrow et al., "The effect of aglycosylation on the binding of mouse IgG to staphylococcal protein A," FEBS Lett., Dec. 12, 1983, 164(2):227-230.
Lei et al., "Characterization of the Erwinia carotovora pelB gene and its product pectate lyase," J Bacteriol., 1987, 169:4379-4383.
Leone et al., "A2aR antagonists: Next generation checkpoint blockade for cancer immunotherapy," Computational and Structural Biotechnology Journal, 2015, 13:365-272.
Leone et al., "Inhibition of the adenosine A2a receptor modulates expression of T cell coinhibitory receptors and improves effector function for enhanced checkpoint blockade and ACT in murine cancer models," Cancer Immunol Immuother., Aug. 2018, 67(8):1271-1284.
Livingston et al., "Adenosine, inflammation and asthma—a review," Inflamm. Res., May 2004, 53(5):171-178.
Marshak et al., "Strategies for Protein Purification and Characterization: A Laboratory Course Manual," Ed Daniel R. Cold Spring Harbor Laboratory Press, 1996, 3(2/3):4 pages (Abstract and Table of Contents Only).
Martin-Orozco et al., "Inhibitory costimulation and anti-tumor immunity," Semin Cancer Biol., 2007, 17(4):288-298.
Matasi et al., "2-(2-Furanyl)-7-phenyl[1,2,4]triazolo[1,5-c]pyrimidin-5-amine analogs: Highly potent, orally active, adenosine A2A antagonists. Part 1," Bioorganic & Medicinal Chemistry Letters, Aug. 15, 2005, 15(16):3670-3674.
Matsumoto et al., "Alterations in vasoconstrictor responses to the endothelium-derived contracting factor uridine adenosine tetraphosphate are region specific in DOCA-salt hypertensive rats," Pharmacol. Res., Jan. 2012, 65(1):81-90.
Millstein et al., "Hybrid hybridomas and their use in immunohistochemistry," Nature, 1983, 305(5934):537-539.
Mizushima et al., "pEF-BOS, a powerful mammalian expression vector," Nucleic Acids Res., 1990, 18:5322.
Moller et al., "Intracellular activation of interferon regulatory factor-1 by nanobodies to the multifunctional (Mf1) domain," J Biol Chem., 2010, 285(49):38348-38361.
Morrison, "Transfectomas provide novel chimeric antibodies," Science, 1985, 229:1202-1207.
Mosely et al., "Rational Selection of Syngeneic Preclinical Tumor Models for Immunotherapeutic Drug Discovery," Cancer Immunol Res., Jan. 2017, 5(1):29-41.
Mulligan et al., "Synthesis of rabbit beta-globin in cultured monkey kidney cells following infection with a SV40 beta-globin recombinant genome," Nature, 1979, 277:108-114.
NHS inform [online], "Heart medicines—Heart treatments," 1st updated on Mar. 1, 2023, retrieved on Jun. 27, 2023, retrieved from URL<https://www.nhsinform.scot/tests-and-treatments/medicines-and-medical-aids/types-of-medicine/heart-medicines>, 4 pages.
Niemelä et al., "IFN-alpha induced adenosine production on the endothelium: a mechanism mediated by CD73 (ecto-5'-nucleotidase) up-regulation," J Immunol., 2004, 172:1646-1653.
Nishimura et al., "Development of lupus-like autoimmune diseases by disruption of the PD-1 gene encoding an ITIM motif-carrying immunoreceptor," Immunity, 1999, 11:141-151.
Nishimura et al., "Autoimmune dilated cardiomyopathy in PD-1 receptor-deficient mice," Science, 2001, 291(5502):319-322.
Nishimura et al., "Facilitation of beta selection and modification of positive selection in the thymus of PD-1-deficient mice," J Exp Med., 2000, 191:891-898.
Nomoto et al., "Clinical Nonmotor Aspect of A(2A) Antagonist in PD Treatment," International Review of Neurobiology, 2014, 119c:191-194 (Abstract Only).

(56) References Cited

OTHER PUBLICATIONS

Nose and Wigzell, "Biological significance of carbohydrate chains on monoclonal antibodies," Proc Natl Acad Sci USA., Nov. 1983, 80(21):6632-6636.
Parry et al., "CTLA-4 and PD-1 Receptors Inhibit T-Cell Activation by Distinct Mechanisms," Mol Cell Biol., 2005, 9543-9553.
Pluckthun and Skerra, "Expression of Functional Antibody Fv and Fab Fragments in *Escherichia coli*," Methods in Enzymology, 1989, 178:496-515.
Pluckthun, "Antibodies from *Escherichia coli*," The Pharmacology of Monoclonal Antibodies, 1994, 113:269-315 (Abstract Only).
Postow et al., "Immune Checkpoint Blockade in Cancer Therapy," J Clinical Oncology., Jun. 10, 2015, 33(17):1974-1982.
Powers et al., "Expression of single-chain Fv-Fc fusions in Pichia pastoris," J Immunol Methods., 2001, 251:123-135.
Raju "Glycosylation Variations with Expression Systems and Their Impact on Biological Activity of Therapeutic Immunoglobulins," BioProcess International, Apr. 2003, pp. 44-53.
Remington's Pharmaceutical Sciences, 17th ed., Mack Publishing Company, Easton, PA., 1985, pp. 1418.
Rousseaux et al., "Optimal conditions for the preparation of proteolytic fragments from monoclonal IgG of different rat IgG subclasses," Methods in Enzymology, 1989, 121:663-669.
Ryzhov et al., "Host A(2B) adenosine receptors promote carcinoma growth," Neoplasia, 2008, 10(9):987-995.
Sabatier et al., "Prognostic and predictive value of PDL1 expression in breast cancer," Oncotarget, 2015, 6(7):5449-5464.
Sachdeva et al., "Adenosine and its receptors as therapeutic targets: An overview," Saudi Pharma Journ., Jun. 23, 2012, 21(3):245-253.
Sadej et al., "Ecto-5'-nucleotidase (eN, CD73) is coexpressed with metastasis promoting antigens in human melanoma cells," Nucleosides Nucleotides Nucleic Acids, 2006, 25(9-11):1119-1123.
Salmi and Jalkanen, "Host CD73 impairs anti-tumor immunity," Oncoimmunology, Mar. 1, 2012, 1(2):247-248.
Sattin and Rall, "The effect of adenosine and adenine nucleotides on the cyclic adenosine 3', 5'-phosphate content of guinea pig cerebral cortex slices, " Mol Pharmacol., 1970, 6(1):13-23.
Sharpe et al., "The function of programmed cell death 1 and its ligands in regulating autoimmunity and infection," Nat Immunol., 2007, 8:239-245.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., Mar. 2, 2001, 276(9):6591-6604.
Shields et al., "Lack of fucose on human IgG1 N-linked oligosaccharide improves binding to human Fcgamma RIII and antibody-dependent cellular toxicity," J Biol Chem., 2002; 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., 2003, 278(5):3466-3473.
Stagg and Smyth, "Extracellular adenosine triphosphate and adenosine in cancer," Oncogene, 2010, 29(39):5346-5358.
Stagg, "The double-edge sword effect of anti-CD73 cancer therapy," OncoImmunology, 2012, 1:217-218.
STN Search Report, 2017-078, Jul. 19, 2017, 73 pages.
STN Search Report, 2017-133, Nov. 22, 2017, 140 pages.
Tamura et al., "A general synthesis of s-triazolo[1,5-x] diazines," J Hetero Chem., Feb. 1975, 12(1):107-110.
Tao, "Studies of aglycosylated chimeric mouse-human IgG. Role of carbohydrate in the structure and effector functions mediated by the human IgG constant region," J Immunol., Oct. 15, 1989., 143(8):2595-2601 (Abstract Only).
Tautenhahn et al. "Purinergic modulation of the excitatory synaptic input onto rat striatal neurons," Neuropharmacology, Mar. 2012, 62(4):1756-1766.
Tempest et al., "Reshaping a human monoclonal antibody to inhibit human respiratory syncytial virus infection in vivo," Biotechnology, 1991, 9:266-271.
Tomlinson et al., "The repertoire of human germline VH sequences reveals about fifty groups of VH segments with different hypervariable loops," J Mol Biol., 1992, 227:776-798.
Tomlinson et al., "The structural repertoire of the human V kappa domain," EMBO J., 1995, 14:4628-4638.
Umana et al., "Engineered glycoforms of an antineuroblastoma IgG1 with optimized antibody-dependent cellular cytotoxic activity," Nat Biotechnol., Feb. 1999, 17(2):176-180.
Urlaub and Chasin "Isolation of Chinese hamster cell mutants deficient in dihydrofolate reductase activity," Proc Natl Acad Sci USA., 1980, 77:4216-4220.
Vietnamese Office Action in Vietnamese Application No. 1-2020-05531, dated Jan. 11, 2021, 2 pages.
Vigano et al., "Targeting Adenosine in Cancer Immunotherapy to Enhance T-Cell Function," Front Immunol., Jun. 6, 2019, 2019, 10:925.
Walker et al., "Aglycosylation of human IgG1 and IgG3 monoclonal antibodies can eliminate recognition by human cells expressing FcγRI and/or FcγRII receptors," Biochem J., 1989, 259:347-353.
Wang et al., "The prognostic value of PD-L1 expression for non-small cell lung cancer patients: a meta-analysis," Eur J Surg Oncol., 2015, 41(4):450-456.
Ward and Ghetie, "The effector functions of immunoglobulins: implications for therapy," Therapeutic Immunology, 1995, 2:77-94.
Ward et al., "Binding activities of a repertoire of single immunoglobulin variable domains secreted from *Escherichia coli*," Nature, 1989, 341:544-546.
Willingham et al., "A2AR Antagonism with CPI-444 Induces Antitumor Responses and Augments Efficacy to Anti-PD-(L)1 and Anti-CTLA-4 in Preclinical Models," Cancer Immunol Res., Oct. 2018, 6(10):1136-1149.
Wright & Morrison, "Effect of glycosylation on antibody function: implications for genetic engineering," Trends in Biotechnology, Jan. 1997, 15(1):26-32.
Yamazaki et al., "Expression of programmed death 1 ligands by murine T cells and APC," J Immunol., 2002, 169:5538-5545.
Yao et al., "Synthesis of alkyne derivatives of a novel triazolopyrazine as A2A adenosine receptor antagonists," Bioorganic & Medicinal Chemistry Letters, 2005, 15:511-515.
Zhang, "CD73 promotes tumor growth and metastasis," OncoImmunology, 2012, 1(1):67-70.
Zhang, "CD73: a novel target for cancer immunotherapy," Cancer Res., 2010, 70:6407-6411.
Canadian Office Action in Canadian Application No. 3,105,721, dated Jun. 5, 2025, 7 pages.
Chinese Office Action in Chinese Application No. 2023108522850, dated Jul. 26, 2025, 16 pages (with English Translation).
Japanese Office Action in Japanese Application No. 2023-186994, dated on Sep. 3, 2024, 4 pages (with English Translation).
Korean Office Action in Korean Application No. 10-2021-7003641, dated May 19, 2025, 16 pages (with English Translation).
Saudi Arabian Office Action in Saudi Arabian Application No. 524462217, dated Jun. 22, 2025, 7 pages (with English Translation).
Vietnamese Office Action in Vietnamese Application No. 1-2021-00647, dated May 9, 2025, 3 pages (with English Translation).

FUSED PYRAZINE DERIVATIVES AS A2A / A2B INHIBITORS

TECHNICAL FIELD

The present invention provides fused pyrazine derivatives that modulate the activity of adenosine receptors, such as subtypes A2A and A2B, and are useful in the treatment of diseases related to the activity of adenosine receptors including, for example, cancer, inflammatory diseases, cardiovascular diseases, and neurodegenerative diseases.

BACKGROUND

Adenosine is an extracellular signaling molecule that can modulate immune responses through many immune cell types. Adenosine was first recognized as a physiologic regulator of coronary vascular tone by Drury and Szent-Györgyu (Sachdeva, S. and Gupta, M. *Saudi Pharmaceutical Journal,* 2013, 21, 245-253), however it was not until 1970 that Sattin and Rall showed that adenosine regulates cell function via occupancy of specific receptors on the cell surface (Sattin, A., and Rall, T. W., 1970. Mol. Pharmacol. 6, 13-23; Hasko', G., at al., 2007*, Pharmacol. Ther.* 113, 264-275).

Adenosine plays a vital role in various other physiological functions. It is involved in the synthesis of nucleic acids, when linked to three phosphate groups; it forms ATP, the integral component of the cellular energy system. Adenosine can be generated by the enzymatic breakdown of extracellular ATP, or can be also released from injured neurons and glial cells by passing the damaged plasma membrane (Tautenhahn, M. et al. *Neuropharmacology,* 2012, 62, 1756-1766). Adenosine produces various pharmacological effects, both in periphery and in the central nervous system, through an action on specific receptors localized on cell membranes (Matsumoto, T. et al. *Pharmacol. Res.,* 2012, 65, 81-90). Alternative pathways for extracellular adenosine generation have been described. These pathways include the production of adenosine from nicotinamide dinucleotide (NAD) instead of ATP by the concerted action of CD38, CD203a and CD73. CD73-independent production of adenosine can also occur by other phosphates such as alkaline phosphatase or prostate-specific phosphatase.

There are four known subtypes of adenosine receptor in humans including A1, A2A, A2B and A3 receptors. A1 and A2A are high affinity receptors, whereas A2B and A3 are low affinity receptors. Adenosine and its agonists can act via one or more of these receptors and can modulate the activity of adenylate cyclase, the enzyme responsible for increasing cyclic AMP (cAMP). The different receptors have differential stimulatory and inhibitory effects on this enzyme. Increased intracellular concentrations of cAMP can suppress the activity of immune and inflammatory cells (Livingston, M. et al., *Inflamm. Res.,* 2004, 53, 171-178).

The A2A adenosine receptor can signal in the periphery and the CNS, with agonists explored as anti-inflammatory drugs and antagonists explored for neurodegenerative diseases (Carlsson, J. et al., *J. Med. Chem.,* 2010, 53, 3748-3755). In most cell types the A2A subtype inhibits intracellular calcium levels whereas the A2B potentiates them. The A2A receptor generally appears to inhibit inflammatory response from immune cells (Borrmann, T. et al., *J. Med. Chem.,* 2009, 52(13), 3994-4006).

A2B receptors are highly expressed in the gastrointestinal tract, bladder, lung and on mast cells (Antonioli, L. et al., *Nature Reviews Cancer,* 2013, 13, 842-857). The A2B receptor, although structurally closely related to the A2A receptor and able to activate adenylate cyclase, is functionally different. It has been postulated that this subtype may utilize signal transduction systems other than adenylate cyclase (Livingston, M. et al., *Inflamm. Res.,* 2004, 53, 171-178). Among all the adenosine receptors, the A2B adenosine receptor is a low affinity receptor that is thought to remain silent under physiological conditions and to be activated in consequence of increased extracellular adenosine levels (Ryzhov, S. et al. *Neoplasia,* 2008, 10, 987-995). Activation of A2B adenosine receptor can stimulate adenylate cyclase and phospholipase C through activation of Gs and Gq proteins, respectively. Coupling to mitogen activated protein kinases has also been described (Borrmann, T. et al., *J. Med. Chem.,* 2009, 52(13), 3994-4006).

In the immune system, engagement of adenosine signaling can be a critical regulatory mechanism that protects tissues against excessive immune reactions. Adenosine can negatively modulate immune responses through many immune cell types, including T-cells, natural-killer cells, macrophages, dendritic cells, mast cells and myeloid-derived suppressor cells (Allard, B. et al. *Current Opinion in Pharmacology,* 2016, 29, 7-16).

In tumors, this pathway is hijacked by tumor micro-environments and sabotages the antitumor capacity of immune system, promoting cancer progression. In the tumor micro-environment, adenosine was mainly generated from extracellular ATP by CD39 and CD73. Multiple cell types can generate adenosine by expressing CD39 and CD73. This is the case for tumor cells, T-effector cells, T-regulatory cells, tumor associated macrophages, myeloid derived suppressive cells (MDSCs), endothelial cells, cancer-associated fibroblast (CAFs) and mesenchymal stromal/stem cells (MSCs). Hypoxia, inflammation and other immune-suppressive signaling in tumor micro-environment can induce expression of CD39, CD73 and subsequent adenosine production. As a result, adenosine level in solid tumors is unusually high compared to normal physiological conditions.

A2A are mostly expressed on lymphoid-derived cells, including T-effector cells, T regulatory cells and nature killing cells. Blocking A2A receptor can prevent downstream immunosuppressive signals that temporarily inactivate T cells. A2B receptors are mainly expressed on monocyte-derived cells including dendritic cells, tumor-associated macrophages, myeloid derived suppressive cells (MDSCs), and mesenchymal stromal/stem cells (MSCs). Blocking A2B receptor in preclinical models can suppress tumor growth, block metastasis, and increase the presentation of tumor antigens.

In terms of safety profile of ADORA2A/ADORA2B (A2A/A2B) blockage, the A2A and A2B receptor knockout mice are all viable, showing no growth abnormalities and are fertile (Allard, B. et al. *Current Opinion in Pharmacology,* 2016, 29, 7-16). A2A KO mice displayed increased levels of pro-inflammatory cytokines only upon challenge with LPS and no evidence of inflammation at baseline (Antonioli, L. et al., *Nature Reviews Cancer,* 2013, 13, 842-857). A2B KO mice exhibited normal platelet, red blood, and white cell counts but increased inflammation at baseline (TNF-alpha, IL-6) in naive A2B KO mice (Antonioli, L. et al., *Nature Reviews Cancer,* 2013, 13, 842-857). Exaggerated production of TNF-alpha and IL-6 was detected following LPS treatment. A2B KO mice also exhibited increased vascular adhesion molecules that mediate inflammation as well leukocyte adhesion/rolling; enhanced mast-cell activation; increased sensitivity to IgE-mediated anaphylaxis and increased vascular leakage and neutrophil influx under hypoxia (Antonioli, L. et al., *Nature Reviews Cancer,* 2013, 13, 842-857).

In summary, there is a need to develop new adenosine receptor selective ligands, such as for subtypes A2A and A2B, for the treatment of diseases such as cancer, inflammatory diseases, cardiovascular diseases and neurodegenerative diseases. This application is directed to this need and others.

SUMMARY

The present invention relates to, inter alia, compounds of Formula (I):

(I)

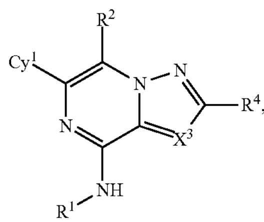

or a pharmaceutically acceptable salt thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of an adenosine receptor, comprising contacting the receptor with a compound of Formula (I), or a pharmaceutically acceptable salt thereof.

The present invention further provides methods of treating a disease or a disorder associated with abnormal expression of adenosine receptors, comprising administering to said patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, compounds of Formula (I):

(I)

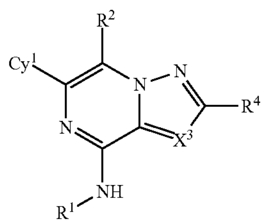

or a pharmaceutically acceptable salt thereof, wherein:

$R^1$ is selected from H, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, and $C_{1-6}$ haloalkyl of $R^1$ are each optionally substituted with 1, 2, 3, or 4 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl of $R^{a1}$, $R^{b1}$, $R^{c1}$, and $R^{d1}$ are each optionally substituted with 1, 2, 3, or 4 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{1A}$ is independently selected from OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

$X^3$ is N or $CR^3$;

$R^3$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$Cy^1$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^1$ are each optionally substituted with 1, 2, 3, 4, 5, or 6 independently selected $R^7$ substituents;

each $R^7$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{c7}NR^{c7}C(O)OR^{a7}$, $NR^{c7}C(O)NR^{c7}R^{d7}$, $C(=NR^{e7})R^{b7}$, $C(=NOH)R^{b7}$, $C(=NCN)R^{b7}$, $C(=NR^{e7})NR^{c7}R^{d7}$, $NR^{c7}C(=NR^{e7})NR^{c7}R^{d7}$, $NR^{c7}C(=NOH)NR^{c7}R^{d7}$, $NR^{c7}C(=NCN)NR^{c7}R^{d7}$, $NR^{c7}C(=NR^{e7})R^{b7}$, $NR^{c7}S(O)NR^{c7}R^{d7}$, $NR^{c7}S(O)R^{b7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^7$ are each optionally substituted with 1, 2, 3, or 4 independently selected $R^{7A}$ substituents;

each $R^{a7}$, $R^{b7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a7}$, $R^{b7}$, $R^{c7}$ and $R^{d7}$ are each optionally substituted with 1, 2, 3, or 4 independently selected $R^{7A}$ substituents;

or, any $R^{c7}$ and $R^{d7}$, attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-5}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOH)R^{b2}$, $C(=NCN)R^{b2}$, $C(=NR^{e2})NR^{c2}R^{d2}$, $NR^{c2}C(=NR^{e2})NR^{e2}R^{d2}$, $NR^{c2}C(=NOH)NR^{c2}R^{d2}$, $NR^{c2}C(=NCN)NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{e2}S(O)_2R^{b2}$, $NR^{c2}S(O)(=NR^{e2})R^{b2}$, $NR^{e2}S(O)_2NR^{e2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, or 6 independently selected $R^{2A}$ substituents;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $R^{c4}C(O)OR^{a4}$, $NR^{c4}C(O)NR^{c4}R^{d4}$, $C(=NR^{e4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^{c4}C(=NOH)NR^{c4}R^{d4}$, $NR^{c4}C(=NCN)NR^{c4}R^{d4}$, $NR^{c4}C(=NR^{e4})R^{b4}$, $NR^{c4}S(O)NR^{c4}R^{d4}$, $NR^{c4}S(O)R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents;

provided that:

(a) when $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, 4, 5, or 6 independently selected $R^{2A}$ substituents;

then $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{c4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^{c4}C(=NOH)NR^{c4}R^{d4}$, $NR^{c4}C(=NCN)NR^{c4}R^{d4}$, $NR^{c4}C(=NR^{e4})R^{b4}$, $NR^{c4}S(O)NR^{c4}R^{d4}$, $NR^{c4}S(O)R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents;

or, alternatively, (b) when $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$ $NR^{c2}C(O)OR^{a2}$, $NR^{c2}C(O)NR^{c2}R^{d2}$, $C(=NR^{e2})R^{b2}$, $C(=NOH)R^{b2}$, $C(=NCN)R^{b2}$, $C(=NR^{e2})NR^{c2}R^{d2}$, $NR^{c2}C(=NR^{e2})NR^{c2}R^{d2}$, $NR^{c2}C(=NOH)NR^{c2}R^{d2}$, $NR^{c2}C(=NCN)NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$ $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, or 6 independently selected $R^{2A}$ substituents;

then $R^4$ is selected from D, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{c4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^{c4}C(=NOH)NR^{c4}R^{d4}$, $NR^{c4}C(=NCN)NR^{c4}R^{d4}$, $NR^{c4}C(=NR^{e4})R^{b4}$, $NR^{c4}S(O)NR^{c4}R^{d4}$, $NR^{c4}S(O)R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents;

each $R^{a2}$, $R^{b2}$, $R^{e2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{e2}$ and $R^{d2}$ are each optionally substituted with 1, 2, 3, 4, 5, or 6 independently selected $R^{2A}$ substituents;

or, any $R^{c2}$ and $R^{d2}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{e21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NOH)R^{b21}$, $C(=NCN)R^{b21}$, $C(=NR^{e21})R^{c21}R^{d21}$, $NR^{c21}C(=NR^{e21})NR^{c21}R^{d21}$, $NR^{c21}C(=NOH)NR^{c21}R^{d21}$, $NR^{c21}C(=NCN)NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, $OS(O)_2R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{b21}$, $R^{c21}$ and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{e21}$ and $R^{d21}$ are each optionally substituted with 1, 2, 3, or 4 independently selected $R^{2B}$ substituents;

or, any $R^{c21}$ and $R^{d21}$, attached to the same N atom, together with the N atom to which they are attached, form a 4-10 membered heterocycloalkyl group, wherein 4-10 membered heterocycloalkyl group is optionally substituted with 1, 2, 3, or 4 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f21}$ and $R^{g21}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h21}$ and $R^{i21}$ is independently selected from H, $C_{1-6}$ alkyl, $C_{1-6}$ haloalkyl, $C_2$-6 alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NOH)R^{b22}$, $C(=NCN)R^{b22}$, $C(=NR^{e22})NR^{c22}R^{d22}$, $NR^{c22}C(=NR^{e22})NR^{c22}R^{d22}$, $NR^{c22}C(=NOH)NR^{c22}R^{d22}$, $NR^{c22}C(=NCN)NR^{c22}R^{d22}$, $NR^{c22}C(=R^{e22})R^{b22}$, $NR^{e22}S(O)_2NR^{c22}R^{d22}$, $NR^{c22}S(O)R^{b22}$, $NR^{c22}S(O)_2R^{b22}$, $NR^{c22}S(O)(=NR^{e22})R^{b22}$, $NR^{c22}S(O)_2NR^{c22}R^{d22}$ $S(O)R^{b22}$, $S(O)NR^{c22}R^{d22}$, $S(O)_2R^{b22}$, $S(O)_2NR^{c22}R^{d22}$, $OS(O)(=NR^{e22})R^{b22}$, $OS(O)_2R^{b22}$, $SF_5$, $P(O)R^{f22}R^{g22}$, $OP(O)(OR^{h22})(OR^{i22})$, $P(O)(OR^{h22})(OR^{i22})$, and $BR^{j22}R^{k22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{b22}$, $R^{c22}$ and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{b22}$, $R^{e22}$ and $R^{d22}$ are each optionally substituted with 1, 2, 3, or 4 independently selected $R^{2C}$ substituents;

or, any $R^{e22}$ and $R^{d22}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f22}$ and $R^{g22}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h22}$ and $R^{i22}$ is independently selected from H, $C_{1-6}$ alkyl, $C_{1-6}$ haloalkyl, $C_2$-6 alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j22}$ and $R^{k22}$ is independently selected from OH, $C_{1-6}$ alkoxy, and $C_{1-6}$ haloalkoxy;

or any $R^{j22}$ and $R^{k22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2C}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$ and $R^{d4}$ are each optionally substituted with 1, 2, 3, or 4 independently selected $R^{4A}$ substituents;

or, any $R^{c4}$ and $R^{d4}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}$, $C(O)OR^{a41}$, $NR^{c41}C(O)NR^{c41}R^{d41}$, $C({=}NR^{e41})R^{b41}$, $C({=}NOH)R^{b41}$, $C({=}NCN)R^{b41}$, $C({=}NR^{e41})NR^{c41}R^{d41}$, $NR^{c41}C({=}NR^{e41})NR^{c41}R^{d41}$, $NR^{c41}C({=}NOH)NR^{c41}R^{d41}$, $NR^{c41}C({=}NCN)NR^{c41}R^{d41}$, $NR^{c41}C({=}NR^{e41})R^{b41}$, $NR^{c41}S(O)NR^{c41}R^{d41}$, $NR^{c41}S(O)R^{b41}$, $NR^{c41}S(O)_2R^{b41}$, $NR^{c41}S(O)({=}NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)({=}NR^{e41})R^{b41}$, $OS(O)_2R^{b41}$, $SF_5$, $P(O)R^{f41}R^{g41}$, $OP(O)(OR^{h41})(OR^{i41})$, $P(O)(OR^{h41})(OR^{i41})$, and $BR^{j41}R^{k41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, or 4 independently selected $R^{4B}$ substituents;

each $R^{a41}$, $R^{b41}$, $R^{c41}$ and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{b41}$, $R^{c41}$ and $R^{d41}$ are each optionally substituted with 1, 2, 3, or 4 independently selected $R^{4B}$ substituents;

or, any $R^{c41}$ and $R^{d41}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f41}$ and $R^{g41}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h41}$ and $R^{i41}$ is independently selected from H, $C_{1-6}$ alkyl, $C_{1-6}$ haloalkyl, $C_2$-6 alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j41}$ and $R^{k41}$ is independently selected from OH, $C_{1-6}$ alkoxy, and $C_{1-6}$ haloalkoxy;

or any $R^{j41}$ and $R^{k41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C({=}NR^{e42})R^{b42}$, $C({=}NOH)R^{b42}$, $C({=}NCN)R^{b42}$, $C({=}NR^{e42})NR^{c42}R^{d42}$, $NR^{c42}C({=}NR^{e42})NR^{c42}R^{d42}$, $NR^{c42}C({=}NOH)NR^{c42}R^{d42}$, $NR^{c42}C(=NCN)NR^{c42}R^{d42}$, $NR^{c42}C(=NR^{e42})R^{b42}$, $NR^{c42}S(O)NR^{c42}R^{d42}$, $NR^{c42}S(O)R^{b42}$, $NR^{c42}S(O)_2R^{b42}$, $NR^{c42}S(O)(=NR^{e42})R^{b42}$, $NR^{c42}S(O)_2NR^{c42}R^{d42}$ $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, $OS(O)_2R^{b42}$, $SF_5$, $P(O)R^{f42}R^{g42}$, $OP(O)(OR^{h42})(OR^{i42})$, $P(O)(OR^{h42})(OR^{i42})$, and $BR^{j42}R^{k42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, or 4 independently selected $R^{4C}$ substituents;

each $R^{a42}$, $R^{b42}$, $R^{c42}$ and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{b42}$, $R^{c42}$ and $R^{d42}$ are each optionally substituted with 1, 2, 3, or 4 independently selected $R^{4C}$ substituents;

or, any $R^{c42}$ and $R^{d42}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{e42}$ and $R^{g42}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h42}$ and $R^{i42}$ is independently selected from H, $C_{1-6}$ alkyl, $C_{1-6}$ haloalkyl, $C_2$-6 alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j42}$ and $R^{k42}$ is independently selected from OH, $C_{1-6}$ alkoxy, and $C_{1-6}$ haloalkoxy;

or any $R^{j42}$ and $R^{k42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})R^{b43}$, $C(=NOH)R^{b43}$, $C(=NCN)R^{b43}$, $C(=NR^{e43})NR^{c43}R^{d43}$, $NR^{c43}C(=NR^{e43})NR^{c43}R^{d43}$, $NR^{c43}C(=NOH)NR^{c43}R^{d43}$, $NR^{c43}C(=NCN)NR^{c43}R^{d43}$, $NR^{c43}C(=NR^{e43})R^{b43}$, $NR^{c43}S(O)NR^{c43}R^{d43}$, $NR^{c43}S(O)R^{b43}$, $NR^{c43}S(O)_2R^{b43}$, $NR^{c43}S(O)(=NR^{e43})R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, $OS(O)(=NR^{e43})R^{b43}$, $OS(O)_2R^{b43}$, $SF_5$, $P(O)R^{c43}R^{g43}$, $OP(O)(OR^{h43})(OR^{i43})$, $P(O)(OR^{h43})(OR^{i43})$, and $BR^{j43}R^{k43}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4C}$ are each optionally substituted with 1, 2, 3, or 4 independently selected $R^{4D}$ substituents;

each $R^{a43}$, $R^{b43}$, $R^{c43}$ and $R^{d43}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a43}$, $R^{b43}$, $R^{c43}$ and $R^{d43}$ are each optionally substituted with 1, 2, 3, or 4 independently selected $R^{4D}$ substituents;

or, any $R^{c43}$ and $R^{d43}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{4D}$ substituents;

each $R^{c43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f43}$ and $R^{g43}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h43}$ and $R^{i43}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j43}$ and $R^{k43}$ is independently selected from OH, $C_{1-6}$ alkoxy, and $C_{1-6}$ haloalkoxy;

or any $R^{j43}$ and $R^{k43}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4D}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, (4-7 membered heterocycloalkyl)-$C_{1-6}$ alkyl-, CN, $NO_2$, $OR^{a44}SR^{a44}$, $NHOR^{a44}$, $C(O)R^{b44}$, $C(O)NR^{c44}R^{d44}$, $C(O)NR^{c44}(OR^{a44})$, $C(O)OR^{a44}$, $OC(O)R^{b44}$, $OC(O)NR^{c44}R^{d44}$, $NR^{c44}R^{d44}$, $NR^{c44}NR^{c44}R^{d44}$, $NR^{c44}C(O)R^{b44}$, $NR^{c44}C(O)OR^{a44}$, $NR^{c44}C(O)NR^{c44}R^{d44}$, $C(=NR^{e44})R^{b44}$, $C(=NOH)R^{b44}$, $C(=NCN)R^{b44}$, $C(=NR^{e44})NR^{c44}R^{d44}$, $NR^{c44}C(=NR^{c44})NR^{c44}R^{d44}$, $NR^{c44}C(=NOH)NR^{c44}R^{d44}$, $NR^{c44}C(=NCN)NR^{c44}R^{d44}$, $NR^{c44}C(=NR^{e44})R^{b44}$, $NR^{c44}S(O)NR^{c44}R^{d44}$, $NR^{c44}S(O)R^{b44}$, $NR^{c44}S(O)_2R^{b44}$, $NR^{c44}S(O)(=NR^{e44})R^{b44}$, $NR^{c44}S(O)_2NR^{c44}R^{d44}$, $S(O)R^{b44}$, $S(O)NR^{c44}R^{d44}$, $S(O)_2R^{b44}$, $S(O)_2NR^{c44}R^{d44}$, $OS(O)(=NR^{e44})R^{b44}$, $OS(O)_2R^{b44}$, $SF_5$, $P(O)R^{f44}R^{g44}$, $OP(O)(OR^{h44})(OR^{i44})$, $P(O)(OR^{h44})(OR^{i44})$, and $BR^{j44}R^{k44}$, wherein the $C_{1-6}$ alkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl- of $R^{4D}$ are each optionally substituted with 1, 2, 3, or 4 independently selected $R^{4E}$ substituents;

each $R^{a44}$, $R^{b44}$, $R^{c44}$ and $R^{d44}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-7 membered heteroaryl, 4-10 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl- of $R^{a44}$, $R^{b44}$, $R^{c44}$ and $R^{d44}$ are each optionally substituted with 1, 2, 3, or 4 independently selected $R^{4E}$ substituents;

or, any $R^{c44}$ and $R^{d44}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{4E}$ substituents;

each $R^{e44}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f44}$ and $R^{g44}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl-;

each $R^{h44}$ and $R^{i44}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl-;

each $R^{j44}$ and $R^{k44}$ is independently selected from OH, $C_{1-6}$ alkoxy, and $C_{1-6}$ haloalkoxy;

or any $R^{j44}$ and $R^{k44}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{4E}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, 1, 2, 3, 4, 5, 6, 7, or 8 hydrogen atoms, attached to carbon atoms of any "alkyl", "alkenyl", "alkynyl", "aryl", "cycloalkyl", "heterocycloalkyl", or "heteroaryl" substituents or "—$C_{1-6}$ alkyl-", "alkylene", "alkenylene", and "alkynylene" linking groups, are each optionally replaced by a deuterium atom.

In some embodiments, the compound of Formula (I) provided herein, or a pharmaceutically acceptable salt thereof, is a compound of Formula (II):

(II)

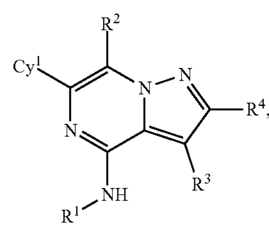

or a pharmaceutically acceptable salt thereof.

In some embodiments of Formulas (I) and (II), $R^1$ is selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl of $R^1$ are each optionally substituted with 1, 2, 3, or 4 independently selected RA substituents.

In some embodiments of Formulas (I) and (II), $R^1$ is selected from H, $C_{1-6}$ alkyl, $C_{2-6}$ alkenyl, $C_{2-6}$ alkynyl, and $C_{1-6}$ haloalkyl.

In some embodiments of Formulas (I) and (II), $R^1$ is H or $C_{1-3}$ alkyl.

In some embodiments of Formulas (I) and (II), $R^1$ is H.

In some embodiments of Formulas (I) and (II), $R^3$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of Formulas (I) and (II), $R^3$ is selected from H, D, halo, OH, CN, $NO_2$, $C_{1-6}$ alkyl, $C_{1-6}$ haloalkyl, $C_{2-6}$ alkenyl, and $C_{2-6}$ alkynyl.

In some embodiments of Formulas (I) and (II), $R^3$ is CN or H.

In some embodiments of Formulas (I) and (II), $R^3$ is H.

In some embodiments of Formulas (I) and (II), $R^2$ is selected from H, halo, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C_{6-10}$ aryl, $C_{3-10}$ cycloalkyl, 5-10 membered heteroaryl, 4-10 membered heterocycloalkyl, and $C_{6-10}$ aryl-$C_{1-6}$ alkyl-, wherein the $C_{6-10}$ aryl, $C_{3-10}$ cycloalkyl, 5-10 membered heteroaryl, 4-10 membered heterocycloalkyl, and $C_{6-10}$ aryl-$C_{1-6}$ alkyl-, of $R^2$ are each optionally substituted with 1, 2, 3, or 4 independently selected $R^{2A}$ substituents.

In some embodiments of Formulas (I) and (II), $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents.

In some embodiments of Formulas (I) and (II), each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}$, $R^{d21}$, $C(O)OR^{a21}$, $OC(O)R^{b21}$, $OC(O)NR^{e21}R^{d21}$, $NR^{c2}R^{d21}$, $NR^{c21}C(O)R^{b21}$, $NR^{c21}C(O)OR^{a21}$, $NR^{c21}C(O)NR^{e21}R^{d21}S(O)R^{b21}$, and $S(O)_2R^{b21}$.

In some embodiments of Formulas (I) and (II), each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{e21}R^{d21}$, $NR^{c21}R^{d21}$, $NR^{c21}C(O)R^{b21}$, $NR^{c21}C(O)OR^{a21}$, $NR^{c2}C(O)NR^{e21}R^{d21}S(O)R^{b21}$, and $S(O)_2R^{b21}$.

In some embodiments of Formulas (I) and (II), each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$ and $R^{d21}$ are each optionally substituted with 1 or 2 independently selected $R^{2B}$ substituents.

In some embodiments of Formulas (I) and (II), each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl.

In some embodiments of Formulas (I) and (II), $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents; and each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}S(O)R^{b21}$, and $S(O)_2R^{b21}$.

In some embodiments of Formulas (I) and (II), $R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents.

In some embodiments of Formulas (I) and (II), each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{e21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}$, and $S(O)R^{b21}$ In some embodiments of Formulas (I) and (II), each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl.

In some embodiments of Formulas (I) and (II), $R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}$, and $S(O)R^{b21}$; and each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl.

In some embodiments of Formulas (I) and (II), $R^2$ is selected from cyclopropyl, pyrazolyl, pyridyl, pyrimidinyl, dihydropyridin-(2H)-yl, and pyridinonyl, each of which is optionally substituted with 1 or 2 independently selected $R^{2A}$ substituents.

In some embodiments of Formulas (I) and (II), each $R^{2A}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{e21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}$, and $S(O)R^{b21}$.

In some embodiments of Formulas (I) and (II), each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^2$ is selected from cyclopropyl, pyrazolyl, pyridyl, pyrimidinyl, dihydropyridin-(2H)-yl, and pyridinonyl, each of which is optionally substituted with 1 or 2 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, and $S(O)R^{b21}$; and each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^2$ is selected from phenyl, $C_{3-7}$ cycloalkyl, 5-6 membered heteroaryl and 4-7 membered heterocycloalkyl, wherein the phenyl, $C_{3-7}$ cycloalkyl, 5-6 membered heteroaryl and 4-7 membered heterocycloalkyl of $R^2$ are each optionally substituted with 1, 2, or 3 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}$ $S(O)R^{b21}$, and $S(O)_2R^{b21}$, wherein said phenyl, $C_{3-7}$ cycloalkyl, 5-6 membered heteroaryl and 4-7 membered heterocycloalkyl of $R^{2A}$ are optionally substituted with 1, 2, or 3 independently selected $R^{2B}$ substitutents;

each $R^{a21}$, $R^{b21}$, $R^{c21}$, and $R^{d21}$ is independently selected from H, $C_{1-6}$ alkyl, and $C_{1-6}$ haloalkyl; and each $R^{2B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

In some embodiments of Formulas (I) and (II), $R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents; each $R^{2A}$ is independently selected from halo, $C_{1-4}$ alkyl, $C_{1-4}$ haloalkyl, and $C(O)NR^{c21}R^{d21}$, wherein said $C_{1-4}$ alkyl of $R^{2A}$ is optionally substituted with 1, 2, or 3 independently selected $R^{2B}$ substitutents;

each $R^{a21}$, $R^{b21}$, $R^{c21}$, and $R^{d21}$ is independently selected from H, $C_{1-6}$ alkyl, and $C_{1-6}$ haloalkyl; and each $R^{2B}$ is independently selected from halo and OH.

In some embodiments of Formulas (I) and (II), $R^2$ is selected from cyclopropyl, oxazolyl, triazolyl, pyrazolyl, pyridyl, pyrimidinyl, dihydropyridin-(2H)-yl, and pyridinonyl, each of which is optionally substituted with 1 or 2 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, and $S(O)R^{b21}$, wherein said $C_{1-6}$ alkyl of $R^{2A}$ is optionally substituted with 1, 2, or 3 independently selected $R^{21}$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl; and each $R^{2B}$ is independently selected from halo and OH.

In some embodiments of Formulas (I) and (II), $R^2$ is selected from 1-(trifluoromethyl)cycloprop-1-yl, 1-ethyl-1H-pyrazol-5-yl, 1-propyl-1H-pyrazol-5-yl, 1-methyl-6-oxo-1,6-dihydropyridin-3-yl, pyrimidin-4-yl, 3,6-dihydropyridin-4-yl-1(2H)-carboxamide, pyridin-4-yl, 4-(1-hydroxyethyl)-2-methyloxazol-5-yl, 2,2-difluoro-1-hydroxyethyl)-2-methyloxazol-5-yl, 1-ethyl-1H-1,2,3-triazol-5-yl, and 1-methyl-1H-1,2,3-triazol-5-yl.

In some embodiments of Formulas (I) and (II), $R^2$ is selected from 1-(trifluoromethyl)cycloprop-1-yl, 1-ethyl-1H-pyrazol-5-yl, 1-propyl-1H-pyrazol-5-yl, 1-methyl-6-oxo-1,6-dihydropyridin-3-yl, pyrimidin-4-yl, 3,6-dihydropyridin-4-yl-1(2H)-carboxamide, pyridin-4-yl, 4-(1-hydroxyethyl)-2-methyloxazol-5-yl, 2,2-difluoro-1-hydroxyethyl)-2-methyloxazol-5-yl, 1-ethyl-1H-1,2,3-triazol-5-yl, and 1-methyl-1H-1,2,3-triazol-5-yl.

In some embodiments of Formulas (I) and (II), $R^2$ is selected from 1-(trifluoromethyl)cycloprop-1-yl, 1-ethyl-1H-pyrazol-5-yl, 1-propyl-1H-pyrazol-5-yl, 1-methyl-6-oxo-1,6-dihydropyridin-3-yl, pyrimidin-4-yl, 3,6-dihydropyridin-4-yl-1(2H)-carboxamide, and pyridin-4-yl.

In some embodiments of Formulas (I) and (II), $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents.

In some embodiments of Formulas (I) and (II), each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, of $R^{4A}$ are each optionally substituted with 1, 2, 3, or 4 independently selected $R^{4B}$ substituents.

In some embodiments of Formulas (I) and (II), each $R^{4B}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments of Formulas (I) and (II), each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$.

In some embodiments of Formulas (I) and (II), $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents; and each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$.

In some embodiments of Formulas (I) and (II), $R^4$ is selected from H, D, halo, $C_{1-6}$ alkyl, $C_{1-6}$ haloalkyl, $C_{2-6}$ alkenyl, $C_{2-6}$ alkynyl, phenyl, 5-6 membered heteroaryl, phenyl-$C_{1-6}$ alkyl-, (5-6 membered heteroaryl)-$C_{1-6}$ alkyl-, $C(O)R^{b4}$, $C(O)NR^{c4}R^{d4}$, $C(O)OR^{a4}$, $NR^{c4}C(O)R^{b4}$, $NR^{c4}C(O)OR^{a4}$, and $NR^{c4}C(O)NR^{c4}R^{d4}$, wherein the $C_{1-6}$ alkyl, $C_{2-6}$ alkenyl, $C_{2-6}$ alkynyl, phenyl, 5-6 membered heteroaryl, phenyl-$C_{1-6}$ alkyl-, and (5-6 membered heteroaryl)-$C_{1-6}$ alkyl- of $R^4$ are each optionally substituted with 1 or 2 independently selected $R^{4A}$ substituents.

In some embodiments of Formulas (I) and (II), each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, and $OR^{a41}$.

In some embodiments of Formulas (I) and (II), each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), each $R^{a41}$ is independently selected from H, $C_{1-6}$ alkyl, $C_{1-6}$ haloalkyl, $C_{2-6}$ alkenyl, and $C_{2-6}$ alkynyl.

In some embodiments, any $R^{c4}$ and $R^{d4}$, attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{4A}$ substituents.

In some embodiments, any $R^{c4}$ and $R^{d4}$, attached to the same N atom, together with the N atom to which they are attached, form a 4-10 membered heterocycloalkyl group, wherein the 4-10 membered heterocycloalkyl group is optionally substituted with 1 or 2 independently selected $R^{4A}$ substituents.

In some embodiments of Formulas (I) and (II), $R^4$ is selected from H, D, halo, $C_{1-6}$ alkyl, $C_{1-6}$ haloalkyl, $C_{2-6}$ alkenyl, $C_{2-6}$ alkynyl, phenyl, 5-6 membered heteroaryl, phenyl-$C_{1-6}$ alkyl-, (5-6 membered heteroaryl)-$C_{1-6}$ alkyl-, $C(O)R^{14}$, $C(O)NR^{c4}R^{d4}$, $C(O)OR^{a4}$, $NR^{c4}C(O)R^{b4}$, $NR^{c4}C(O)OR^{a4}$, and $NR^{c4}C(O)NR^{c4}R^{d4}$, wherein the $C_{1-6}$ alkyl, $C_{2-6}$ alkenyl, $C_{2-6}$ alkynyl, phenyl, 5-6 membered heteroaryl, phenyl-$C_{1-6}$ alkyl-, and (5-6 membered heteroaryl)-$C_{1-6}$ alkyl- of $R^4$ are each optionally substituted with 1 or 2 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, and $OR^{a4}1$;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl; and each $R^{a41}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^4$ is selected from $C_{1-6}$ alkyl, phenyl-$C_{1-6}$ alkyl-, (5-6 membered heteroaryl)-$C_{1-6}$ alkyl-, $C(O)NR^{c4}R^{d4}$, and $NR^{c4}C(O)OR^{a4}$, wherein the $C_{1-6}$ alkyl, phenyl-$C_{1-6}$ alkyl-, and (5-6 membered heteroaryl)-$C_{1-6}$ alkyl- of $R^4$ are each optionally substituted with 1 or 2 independently selected $R^{4A}$ substituents;

In some embodiments of Formulas (I) and (II), each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, and $OR^{a41}$.

In some embodiments of Formulas (I) and (II), each $R^{a4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl;

or, any $R^{c4}$ and $R^{d4}$, attached to the same N atom, together with the N atom to which they are attached, form a 4-6 membered heterocycloalkyl group.

In some embodiments of Formulas (I) and (II), each $R^{a41}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $S(O)R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, phenyl, $C_{3-7}$ cycloalkyl, 5-6 membered heteroaryl, and 4-7 membered heterocycloalkyl, wherein said $C_{1-6}$ alkyl, phenyl, $C_{3-7}$ cycloalkyl, 5-6 membered heteroaryl, and 4-7 membered heterocycloalkyl of $R^{a4}$, $R^{b4}$, $R^{c4}$, and $R^{d4}$ are each optionally substituted by 1, 2, or 3 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{4A}$ are each optionally substituted by 1 or 2 independently selected $R^{4B}$ substituents;

each $R^{a41}$, $R^{b41}$, $R^{c41}$, and $R^{d41}$ is independently selected from H, $C_{1-6}$ alkyl, and $C_{1-6}$ haloalkyl, wherein said $C_{1-6}$ alkyl of $R^{a41}$, $R^{b41}$, $R^{c41}$, and $R^{d41}$ is optionally substituted by 1, 2, or 3 independently selected $R^{4B}$ substituents; and each $R^{4B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

In some embodiments of Formulas (I) and (II), $R^4$ is selected from phenyl, 5-6 membered heteroaryl, 4-7 membered heterocycloalkyl, phenyl-$C_{1-3}$ alkyl-, (5-10 membered heteroaryl)-$C_{1-3}$ alkyl-, (4-7 membered heterocycloalkyl)-$C_{1-3}$ alkyl-, $C(O)R^{b4}$, $C(O)NR^{c4}R^{d4}$, and $NR^{c4}R^{d4}$, wherein the phenyl, 5-6 membered heteroaryl, 4-7 membered heterocycloalkyl, phenyl-$C_{1-3}$ alkyl-, (5-10 membered heteroaryl)-$C_{1-3}$ alkyl-, and (4-7 membered heterocycloalkyl)-$C_{1-3}$ alkyl- of $R^4$ are each optionally substituted with 1 or 2 independently selected $R^{4A}$ substituents;

each $R^{a4}$, $R^{b4}$, $R^{c4}$, and $R^{d4}$ is independently selected from H, $C_{1-6}$ alkyl, phenyl, and 4-7 membered heterocycloalkyl, wherein said $C_{1-6}$ alkyl, phenyl, and 4-7 membered heterocycloalkyl of $R^{a4}$, $R^{b4}$, $R^{c4}$, and $R^{d4}$ are optionally substituted with 1, 2, or 3 independently selected $R^{4A}$ substituents;

each $R^{4A}$ is independently selected from halo, 4-7 membered heterocycloalkyl, and OH, wherein said 4-7 membered heterocycloalkyl of $R^{4A}$ is optionally substituted with 1 or 2 independently selected $R^{4B}$ substituents; and each $R^{4B}$ is independently selected from halo, OH, and $C_{1-4}$ alkyl In some embodiments of Formulas (I) and (II), $R^4$ is selected from phenyl-$C_{1-6}$ alkyl-, (5-6 membered heteroaryl)-$C_{1-6}$ alkyl-, $C(O)NR^{c4}R^{d4}$, and $NR^{c4}C(O)OR^{a4}$, wherein the $C_{1-6}$ alkyl, phenyl-$C_{1-6}$ alkyl-, and (5-6 membered heteroaryl)-$C_{1-6}$ alkyl- of $R^4$ are each optionally substituted with 1 or 2 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, and $OR^{a41}$;

each $R^{a4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl;

or, any $R^{c4}$ and $R^{d4}$, attached to the same N atom, together with the N atom to which they are attached, form a 4-6 membered heterocycloalkyl group; and each $R^{a41}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^4$ is selected from $C(O)NHC_{1-6}$alkyl, C(O)-azetidinyl, C(O)-pyrrolidinyl, C(O)-piperidinyl, $C(O)N(C_{1-6}\ alkyl)_2$, $NHC(O)OC_{1-6}$ alkyl, (azetidinyl)-$C_{1-6}$ alkyl, (pyridyl)-$C_{1-6}$ alkyl, (phenyl)-$C_{1-6}$ alkyl, (fluorophenyl)-$C_{1-6}$ alkyl, 3,6-dihydro-2H-pyranyl, NH-(phenyl), and pyridyl.

In some embodiments of Formulas (I) and (II), $R^4$ is selected from $C(O)NHC_{1-6}$alkyl, C(O)-azetidinyl, C(O)-pyrrolidinyl, C(O)-piperidinyl, $C(O)N(C_{1-6}\ alkyl)_2$, $NHC(O)OC_{1-6}$ alkyl, (azetidinyl)-$C_{1-6}$ alkyl, (pyridyl)-$C_{1-6}$ alkyl, (phenyl)-$C_{1-6}$ alkyl, (fluorophenyl)-$C_{1-6}$ alkyl, 3,6-dihydro-2H-pyranyl, NH-(phenyl), pyridyl, and (pyrrolo[3,2-b]pyridinyl)-$C_{1-6}$ alkyl, wherein each $C_{1-6}$ alkyl and azetidinyl group is optionally substituted by 1 or 2 OH groups; and each pyridyl is optionally substituted by a methylpiperazinyl group.

In some embodiments of Formulas (I) and (II), $R^4$ is selected from $C(O)NHC_{1-6}$alkyl, C(O)-azetidinyl, C(O)-pyrrolidinyl, C(O)-piperidinyl, $C(O)N(C_{1-6}\ alkyl)_2$, $NHC(O)OC_{1-6}$ alkyl, (azetidinyl)-$C_{1-6}$ alkyl, (pyridyl)-$C_{1-6}$ alkyl, (phenyl)-$C_{1-6}$ alkyl, (fluorophenyl)-$C_{1-6}$ alkyl, 3,6-dihydro-2H-pyranyl, NH-(phenyl), and pyridyl, wherein each $C_{1-6}$ alkyl and azetidinyl group is optionally substituted by 1 or 2 OH groups; and each pyridyl is optionally substituted by a methylpiperazinyl group.

In some embodiments of Formulas (I) and (II), $R^4$ is selected from $C(O)NHCH_2CH_3$, $C(O)N(CH_3)(CH_2CH_3)$, $C(O)N(CH_2CH_3)_2$, $NHC(O)OCH_2CH_3$, C(O)-azetidinyl, C(O)-hydroxyazetidinyl, C(O)-pyrrolidinyl, C(O)-piperidinyl, $CH_2$-azetidinyl, $CH_2$-pyridyl, $CH_2$-fluorophenyl, CH(OH)-fluorphenyl, NH-phenyl, 3,6-dihydro-2H-pyranyl, (methylpiperazinyl)pyridinyl, and (1H-pyrrolo[3,2-b]pyridin-3-yl)methyl In some embodiments of Formulas (I) and (II), $R^4$ is selected from $C(O)NHCH_2CH_3$, $C(O)N(CH_3)(CH_2CH_3)$, $C(O)N(CH_2CH_3)_2$, $NHC(O)OCH_2CH_3$, C(O)-azetidinyl, C(O)-hydroxyazetidinyl, C(O)-pyrrolidinyl, C(O)-piperidinyl, $CH_2$-azetidinyl, $CH_2$-pyridyl, $CH_2$-fluorophenyl, CH(OH)-fluorphenyl, NH-phenyl, 3,6-dihydro-2H-pyranyl, and (methylpiperazinyl)pyridinyl.

In some embodiments of Formulas (I) and (II), $R^2$ is selected from H, D, halo, $C_{1-6}$ alkyl, $C_{1-6}$ haloalkyl, $C_{2-6}$ alkenyl, $C_{2-6}$ alkynyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{e2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$ $S(O)R^{b2}$, and $S(O)_2R^{b2}$.

In some embodiments of Formulas (I) and (II), each $R^{a2}$, $R^{b2}$, $R^{e2}$, and $R^{d2}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^2$ is selected from H, D, halo, $C_{1-6}$ alkyl, $C_{1-6}$ haloalkyl, $C_{2-6}$ alkenyl, $C_{2-6}$ alkynyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $S(O)R^{b2}$, and $S(O)_2R^{b2}$; and each $R^{a2}$, $R^{b2}$, $R^{e2}$, and $R^{d2}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (II), $R^2$ is selected from H, D, halo, $C_{1-6}$ alkyl, $C_{1-6}$ haloalkyl, and CN.

In some embodiments of Formulas (I) and (II), $R^2$ is selected from H, difluoroethyl, bromo, and CN.

In some embodiments of Formulas (I) and (II), $R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents.

In some embodiments of Formulas (I) and (II), each $R^{a4}$, $R^{c4}$, and $R^{d4}$ is independently selected from H and $C_{1-6}$ alkyl.

In some embodiments of Formulas (I) and (II), each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$.

In some embodiments of Formulas (I) and (II), $R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{14}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{b4}$, $R^{c4}$, and $R^{d4}$ is independently selected from H and $C_{1-6}$ alkyl; and each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$ $NR^{c41}C(O)OR^{a41}$, $NR^{c41}C(O)NR^{c41}R^{d41}$, $S(O)R^{b41}$, and $S(O)_2R^{b41}$.

In some embodiments of Formulas (I) and (II), $R^4$ is selected from phenyl-$C_{1-6}$ alkyl-, (5-6 membered heteroaryl)-$C_{1-6}$ alkyl-, $C(O)NR^{c4}R^{d4}$, and $NR^{c4}C(O)OR^{a4}$, wherein each $C_{1-6}$ alkyl is optionally substituted by 1 or 2 OH groups; and the phenyl-$C_{1-6}$ alkyl- is optionally substituted with 1 or 2 independently selected halo groups.

In some embodiments of Formulas (I) and (II), each $R^{a4}$, $R^{b4}$, $R^{c4}$, and $R^{d4}$ is independently selected from H and $C_{1-6}$ alkyl.

In some embodiments of Formulas (I) and (II), each $R^4$ is selected from phenyl-$C_{1-6}$ alkyl-, (5-6 membered heteroaryl)-$C_{1-6}$ alkyl-, and $C(O)NR^{c4}R^{d4}$, wherein the phenyl-$C_{1-6}$ alkyl- and (5-6 membered heteroaryl)-$C_{1-6}$ alkyl- of $R^4$ are each optionally substituted with 1 or 2 substituents independently selected from OH and halo; and each $R^{a4}$, $R^{c4}$, and $R^{d4}$ is independently selected from H and $C_{1-6}$ alkyl.

In some embodiments of Formulas (I) and (II), $R^4$ is selected from phenyl-$C_{1-6}$ alkyl-, (5-6 membered heteroaryl)-$C_{1-6}$ alkyl-, $C(O)NR^{c4}R^{d4}$, $NR^{c4}C(O)OR^{a4}$, wherein each $C_{1-6}$ alkyl is optionally substituted by 1 or 2 OH groups; and the phenyl-$C_{1-6}$ alkyl- is optionally substituted with 1 or 2 independently selected halo groups; and each $R^{a4}$, $R^{c4}$, and $R^{d4}$ is independently selected from H and $C_{1-6}$ alkyl.

In some embodiments of Formulas (I) and (II), $R^4$ is selected from $C(O)NHCH_2CH_3$, —$CH_2$-pyridyl, $CH_2$-fluorophenyl, and CH(OH)-fluorophenyl.

In some embodiments of Formula (II), $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOH)R^{b2}$, $C(=NCN)R^{b2}$, $C(=NR^{e2})NR^{c2}R^{d2}$, $NR^{c2}C(=NR^{e2})NR^{c2}R^{d2}$, $NR^{c2}C(=NOH)NR^{c2}R^{d2}$, $NR^{c2}C(=NCN)NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, or 6 independently selected $R^{2A}$ substituents; and $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOH)R^{b4}$, $C(=NCN)R^{b4}$, $C(=NR^{e4})NR^{c4}R^{d4}$, $NR^{c4}C(=NR^{e4})NR^{c4}R^{d4}$, $NR^{c4}C(=NOH)NR^{c4}R^{d4}$, $NR^{c4}C(=NCN)NR^{c4}R^{d4}$, $NR^{c4}C(=NR^{e4})R^{b4}$, $NR^{c4}S(O)NR^{c4}R^{d4}$, $NR^{c4}S(O)R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents.

In some embodiments of Formulas (I) and (II), $Cy^1$ is $C_{6-10}$ aryl which is optionally substituted by 1, 2, 3, or 4 independently selected $R^7$ substituents.

In some embodiments of Formulas (I) and (II), $Cy^1$ is phenyl which is optionally substituted by 1 or 2 independently selected $R^7$ substituents.

In some embodiments of Formulas (I) and (II), each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (II), $Cy^1$ is phenyl which is optionally substituted by 1 or 2 independently selected $R^7$ substituents; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (II), $Cy^1$ is phenyl which is substituted by 1 or 2 independently selected $R^7$ substituents; and each $R^7$ is independently selected from halo and CN.

In some embodiments of Formulas (I) and (II), $Cy^1$ is unsubstituted phenyl.

In some embodiments of Formulas (I) and (II), $Cy^1$ is cyanophenyl.

In some embodiments of Formulas (I) and (II), $Cy^1$ is 3-cyanophenyl.

In some embodiments of Formulas (I) and (II), $Cy^1$ is 3-cyanophenyl or 3-cyano-2-fluorophenyl.

In some embodiments of Formulas (I) and (II), $Cy^1$ is phenyl substituted by $C(O)NR^{c7}R^{d7}$, wherein $R^{c7}$ and $R^{d7}$ are each independently selected from H and $C_{1-6}$ alkyl.

In some embodiments of Formulas (I) and (II), $Cy^1$ is phenyl substituted by $C(O)NH_2$.

In some embodiments of Formulas (I) and (II), $Cy^1$ is 3-formylphenyl.

In some embodiments of Formulas (I) and (II):

$R^1$ is H;

$Cy^1$ is $C_{6-10}$ aryl which is optionally substituted by 1, 2, 3, or 4 independently selected $R^7$ substituents; and $R^2$ is selected from $C_{6-10}$ aryl, $C_{3-10}$ cycloalkyl, 5-10 membered heteroaryl, 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments of Formulas (I) and (II):

$R^1$ is H;

$Cy^1$ is phenyl which is optionally substituted by 1 or 2 independently selected $R^7$ substituents; and $R^2$ is selected from $C_{6-10}$ aryl, $C_{3-10}$ cycloalkyl, 5-10 membered heteroaryl, 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments of the compounds of Formulas (I) and (II):

$R^1$ is selected from H, $C_{1-6}$ alkyl, $C_{2-6}$ alkenyl, $C_{2-6}$ alkynyl, and $C_{1-6}$ haloalkyl;

$R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}$, $R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $S(O)R^{b21}$, and $S(O)_2R^{b2}$;

each $R^{c21}$ and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b4}$;

$Cy^1$ is $C_{6-10}$ aryl which is optionally substituted by 1, 2, 3, or 4 independently selected $R^7$ substituents;

each $R^{a4}$, $R^{b4}$, $R^{c4}$, and $R^4$ is independently selected from H, $C_{1-6}$ alkyl, $C_{1-6}$ haloalkyl, $C_{2-6}$ alkenyl, and $C_{2-6}$ alkynyl;

or, any $R^{c4}$ and $R^{d4}$, attached to the same N atom, together with the N atom to which they are attached, form a 4-6 membered heterocycloalkyl group;

each $R^{a41}$, $R^{b41}$, $R^{c41}$, and $R^{d41}$ is independently selected from H, $C_{1-6}$ alkyl, $C_{1-6}$ haloalkyl, $C_{2-6}$ alkenyl, and $C_{2-6}$ alkynyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of the compounds of Formulas (I) and (II):

$R^1$ is selected from H, $C_{1-6}$ alkyl, $C_{2-6}$ alkenyl, $C_{2-6}$ alkynyl, and $C_{1-6}$ haloalkyl;

$R^2$ is selected from H, D, halo, $C_{1-6}$ alkyl, $C_{1-6}$ haloalkyl, $C_{2-6}$ alkenyl, $C_{2-6}$ alkynyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$ $S(O)R^{b2}$, and $S(O)_2R^{b2}$;

$R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $S(O)R^{b4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b4}$;

$Cy^1$ is $C_{6-10}$ aryl which is optionally substituted by 1, 2, 3, or 4 independently selected $R^7$ substituents;

each $R^{a4}$, $R^{b4}$, $R^{c4}$, and $R^4$ is independently selected from H, $C_{1-6}$ alkyl, $C_{1-6}$ haloalkyl, $C_{2-6}$ alkenyl, and $C_{2-6}$ alkynyl;

or, any $R^{c4}$ and $R^{d4}$, attached to the same N atom, together with the N atom to which they are attached, form a 4-6 membered heterocycloalkyl group;

each $R^{a41}$, $R^{b41}$, $R^{c41}$, and $R^{d41}$ is independently selected from H, $C_{1-6}$ alkyl, $C_{1-6}$ haloalkyl, $C_{2-6}$ alkenyl, and $C_{2-6}$ alkynyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of the compounds of Formulas (I) and (II):

$R^1$ is H;

$R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents;

$R^4$ is selected from $C_{1-6}$ alkyl, phenyl-$C_{1-6}$ alkyl-, (5-6 membered heteroaryl)-$C_{1-6}$ alkyl-, $C(O)NR^{c4}R^{d4}$, and $NR^{c4}C(O)OR^{a4}$, wherein the $C_{1-6}$ alkyl, phenyl-$C_{1-6}$ alkyl-, and (5-6 membered heteroaryl)-$C_{1-6}$ alkyl- of $R^4$ are each optionally substituted with 1 or 2 independently selected $R^{4A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}$, $R^{d21}$, $NR^{c21}C(O)R^{b21}$, $NR^{c21}C(O)OR^{a21}$, $NR^{c21}C(O)NR^{c21}R^{d21}$, and $S(O)R^{b21}$;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, and $OR^{a41}$;

$Cy^1$ is phenyl which is optionally substituted by 1 or 2 independently selected $R^7$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl;

or, any $R^{c4}$ and $R^{d4}$, attached to the same N atom, together with the N atom to which they are attached, form a 4-6 membered heterocycloalkyl group;

each $R^{a41}$ is independently selected from H, $C_{1-6}$ alkyl, $C_{1-6}$ haloalkyl, $C_{2-6}$ alkenyl, and $C_{2-6}$ alkynyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of the compounds of Formulas (I) and (II):

$R^1$ is H;

$R^2$ is selected from H, D, halo, $C_{1-6}$ alkyl, $C_{1-6}$ haloalkyl, and CN;

$R^4$ is selected from phenyl-$C_{1-6}$ alkyl-, (5-6 membered heteroaryl)-$C_{1-6}$ alkyl-, $C(O)NR^{c4}R^{d4}$, $NR^{c4}C(O)OR^{a4}$, wherein each $C_{1-6}$ alkyl is optionally substituted by 1 or 2 OH groups; and the phenyl-$C_{1-6}$ alkyl- is optionally substituted with 1 or 2 independently selected halo groups;

$Cy^1$ is phenyl which is optionally substituted by 1 or 2 independently selected $R^7$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl;

or, any $R^{c4}$ and $R^{d4}$, attached to the same N atom, together with the N atom to which they are attached, form a 4-6 membered heterocycloalkyl group; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of the compounds of Formulas (I) and (II):

$R^1$ is H;

$R^2$ is selected from cyclopropyl, pyrazolyl, pyridyl, pyrimidinyl, dihydropyridin-(2H)-yl, and pyridinonyl, each of which is optionally substituted with 1 or 2 independently selected $R^{2A}$ substituents;

$R^4$ is selected from $C(O)NHC_{1-6}$alkyl, C(O)-azetidinyl, C(O)-pyrrolidinyl, C(O)-piperidinyl, $C(O)N(C_{1-6}\ alkyl)_2$, $NHC(O)OC_{1-6}$ alkyl, (azetidinyl)-$C_{1-6}$ alkyl, (pyridyl)-$C_{1-6}$ alkyl, (phenyl)-$C_{1-6}$ alkyl, (fluorophenyl)-$C_{1-6}$ alkyl, 3,6-dihydro-2H-pyranyl, NH-(phenyl), and pyridiyl, wherein each $C_{1-6}$ alkyl and azetidinyl group is optionally substituted by 1 or 2 OH groups; and each pyridyl is optionally substituted by a methylpiperazinyl group;

each $R^{2A}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{e21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, and $S(O)R^{b21}$;

$Cy^1$ is cyanophenyl; and each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl.

In some embodiments of the compounds of Formulas (I) and (II):

$R^1$ is H;

$R^2$ is selected from H, difluoroethyl, bromo, and CN;

$R^4$ is selected from phenyl-$C_{1-6}$ alkyl-, (5-6 membered heteroaryl)-$C_{1-6}$ alkyl-, $C(O)NR^{c4}R^{d4}$, $NR^{c4}C(O)OR^{a4}$, wherein each $C_{1-6}$ alkyl is optionally substituted by 1 or 2 OH groups; and the phenyl-$C_{1-6}$ alkyl- is optionally substituted with 1 or 2 independently selected halo groups;

$Cy^1$ is cyanophenyl; and each $R^{a4}$, $R^{c4}$, and $R^{d4}$ is independently selected from H and $C_{1-6}$ alkyl.

In some embodiments of Formulas (I) and (II), the compound is a compound of Formula (IIa):

(IIa)

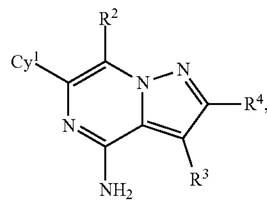

or a pharmaceutically acceptable salt thereof, wherein variables $R^2$, $R^3$, $R^4$, and $Cy^1$ are defined according to the definitions provided herein for compounds of Formulas (I) and (II).

In some embodiments of Formula (IIa), $R^3$ is H or CN;

$Cy^1$ is phenyl which is substituted by 1 or 2 independently selected $R^7$ substituents;

each $R^7$ is independently selected from halo and CN;

$R^2$ is selected from phenyl, $C_{3-7}$ cycloalkyl, 5-6 membered heteroaryl and 4-7 membered heterocycloalkyl, wherein the phenyl, $C_{3-7}$ cycloalkyl, 5-6 membered heteroaryl and 4-7 membered heterocycloalkyl of $R^2$ are each optionally substituted with 1, 2, or 3 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}$, $R^{d21}$, $NR^{c21}C(O)R^{b21}$, $NR^{c21}C(O)OR^{a21}$, $NR^{c21}C(O)NR^{c21}R^{d21}S(O)R^{b21}$, and $S(O)_2R^{b21}$, wherein said phenyl, $C_{3-7}$ cycloalkyl, 5-6 membered heteroaryl and 4-7 membered heterocycloalkyl of $R^{2A}$ are optionally substituted with 1, 2, or 3 independently selected $R^{2B}$ substitutents;

each $R^{a21}$, $R^{b21}$, $R^{c21}$, and $R^{d21}$ is independently selected from H, $C_{1-6}$ alkyl, and $C_{1-6}$ haloalkyl;

each $R^{2B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, phenyl, $C_{3-7}$ cycloalkyl, 5-6 membered heteroaryl, and 4-7 membered heterocycloalkyl, wherein said $C_{1-6}$ alkyl, phenyl, $C_{3-7}$ cycloalkyl, 5-6 membered heteroaryl, and 4-7 membered heterocycloalkyl of $R^{a4}$, $R^{b4}$, $R^{c4}$, and $R^{d4}$ are each optionally substituted by 1, 2, or 3 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a41}$, $SR^{a41}$, $NHOR^{a41}$, $C(O)R^{b41}$, $C(O)NR^{c4}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d4}1$ $S(O)R^{b41}$, and $S(O)_2R^{b41}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{4A}$ are each optionally substituted by 1 or 2 independently selected $R^{4B}$ substituents;

each $R^{a41}$, $R^{b41}$, $R^{c41}$, and $R^{d4}1$ is independently selected from H, $C_{1-6}$ alkyl, and $C_{1-6}$ haloalkyl, wherein said $C_{1-6}$ alkyl of $R^{a41}$, $R^{b41}$, $R^{c41}$, and $R^{d4}1$ is optionally substituted by 1, 2, or 3 independently selected $R^{4B}$ substituents; and each $R^{4B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

In some embodiments of Formula (IIa), $R^3$ is H or CN;

$Cy^1$ is 3-cyanophenyl or 3-cyano-2-fluorophenyl;

$R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents;

each $R^{2A}$ is independently selected from halo, $C_{1-4}$ alkyl, $C_{1-4}$ haloalkyl, and $C(O)NR^{c21}R^{d21}$, wherein said $C_{1-4}$ alkyl of $R^{2A}$ is optionally substituted with 1, 2, or 3 independently selected $R^{2B}$ substitutents;

each $R^{a21}$, $R^{b21}$, $R^{c21}$, and $R^{d21}$ is independently selected from H, $C_{1-6}$ alkyl, and $C_{1-6}$ haloalkyl; and each $R^{2B}$ is independently selected from halo and OH.

$R^4$ is selected from phenyl, 5-6 membered heteroaryl, 4-7 membered heterocycloalkyl, phenyl-$C_{1-3}$ alkyl-, (5-10 membered heteroaryl)-$C_{1-3}$ alkyl-, (4-7 membered heterocycloalkyl)-$C_{1-3}$ alkyl-, $C(O)R^{b4}$, $C(O)NR^{c4}R^{d4}$, and $NR^{c4}R^{d4}$, wherein the phenyl, 5-6 membered heteroaryl, 4-7 membered heterocycloalkyl, phenyl-$C_{1-3}$ alkyl-, (5-10 membered heteroaryl)-$C_{1-3}$ alkyl-, and (4-7 membered heterocycloalkyl)-$C_{1-3}$ alkyl- of $R^4$ are each optionally substituted with 1 or 2 independently selected $R^{4A}$ substituents;

each $R^{a4}$, $R^{b4}$, $R^{c4}$, and $R^{d4}$ is independently selected from H, $C_{1-6}$ alkyl, phenyl, and 4-7 membered heterocycloalkyl, wherein said $C_{1-6}$ alkyl, phenyl, and 4-7 membered heterocycloalkyl of $R^{a4}$, $R^{b4}$, $R^{c4}$, and $R^{d4}$ are optionally substituted with 1, 2, or 3 independently selected $R^{4A}$ substituents;

each $R^{4A}$ is independently selected from halo, 4-7 membered heterocycloalkyl, and OH, wherein said 4-7 membered heterocycloalkyl of $R^{4A}$ is optionally substituted with 1 or 2 independently selected $R^{4B}$ substituents; and each $R^{4B}$ is independently selected from halo, OH, and $C_{1-4}$ alkyl.

In some embodiments of Formula (IIa), $R^3$ is H or CN;

$Cy^1$ is phenyl which is substituted by 1 or 2 independently selected $R^7$ substituents;

each $R^7$ is independently selected from halo and CN;

$R^2$ is selected from H, halo, $C_{1-6}$ alkyl, $C_{1-6}$ haloalkyl, and CN;

$R^4$ is selected from phenyl-$C_{1-6}$ alkyl-, (5-6 membered heteroaryl)-$C_{1-6}$ alkyl-, and $C(O)NR^{c4}R^{d4}$, wherein the phenyl-$C_{1-6}$ alkyl- and (5-6 membered heteroaryl)-$C_{1-6}$ alkyl of $R^4$ are each optionally substituted with 1 or 2 substituents independently selected from OH and halo; and each $R^{a4}$, $R^{c4}$, and $R^{d4}$ is independently selected from H and $C_{1-6}$ alkyl.

In some embodiments of Formulas (I) and (II), the compound is a compound of Formula (IIb):

(IIb)

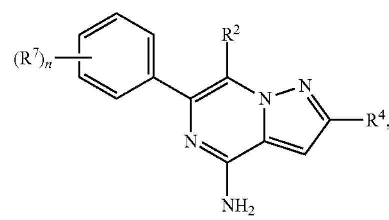

or a pharmaceutically acceptable salt thereof, wherein n is an integer from 0 to 4, and wherein variables $R^2$, $R^4$, and $R^7$ are defined according to the definitions provided herein for compounds of Formulas (I) and (II).

In some embodiments of Formulas (I) and (II), the compound is a compound of Formula (IIc):

(IIc)

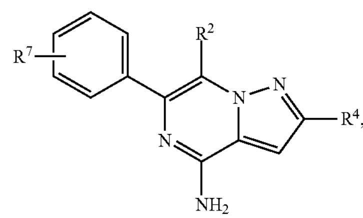

or a pharmaceutically acceptable salt thereof, wherein variables $R^2$, $R^4$, and $R^7$ are defined according to the definitions provided herein for compounds of Formulas (I) and (II).

In some embodiments, the compound of Formula (I) provided herein, or a pharmaceutically acceptable salt thereof, is a compound of Formula (III):

(III)

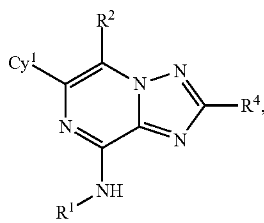

or a pharmaceutically acceptable salt thereof.

In some embodiments of Formulas (I) and (III), $R^1$ is selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl of $R^1$ are each optionally substituted with 1, 2, 3, or 4 independently selected RA substituents.

In some embodiments of Formulas (I) and (III), $R^1$ is selected from H, $C_{1-6}$ alkyl, $C_{2-6}$ alkenyl, $C_{2-6}$ alkynyl, and $C_{1-6}$ haloalkyl.

In some embodiments of Formulas (I) and (III), $R^1$ is H or $C_{1-6}$ alkyl.

In some embodiments of Formulas (I) and (III), $R^1$ is H.

In some embodiments of Formulas (I) and (III), $R^2$ is selected from H, $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments of Formulas (I) and (III), $R^2$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments of Formulas (I) and (III), each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{e21}R^{d21}$, $NR^{c2}R^{d21}$, $NR^{c21}C(O)R^{b21}$, $NR^{c21}C(O)OR^{a21}$, $NR^{c2}C(O)NR^{e21}R^{d21}S(O)R^{b21}$, and $S(O)_2R^{b21}$.

In some embodiments of Formulas (I) and (III), $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}$, $R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}$, $S(O)R^{b21}$, and $S(O)_2R^{b21}$, wherein said $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{2A}$ are each optionally substituted by 1, 2, or 3 independently selected $R^{2B}$ substitutents;

each $R^{a21}$, $R^{241}$, $R^{c21}$, and $R^{d21}$ is independently selected from H, $C_{1-6}$ alkyl, and $C_{1-6}$ haloalkyl, wherein said $C_{1-6}$ alkyl of $R^{a21}$, $R^{241}$, $R^{c21}$, and $R^{d21}$ is optionally substituted by 1, 2, or 3 independently selected $R^{2A}$ substituents; and each $R^{2B}$ is independently selected from D, halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

In some embodiments of Formulas (I) and (III), $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents; and each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $S(O)R^{b21}$, and $S(O)_2R^{b21}$.

In some embodiments of Formulas (I) and (III), $R^2$ is selected from 5-10 membered heteroaryl and 4-7 membered heterocycloalkyl, wherein the 5-10 membered heteroaryl and 4-7 membered heterocycloalkyl of $R^2$ are each optionally substituted with 1, 2, or 3 independently selected $R^{2A}$ substituents;

each $R^{2A}$ is independently selected from halo, $C_{1-6}$ alkyl, $C_{1-6}$ haloalkyl, and OH, wherein said $C_{1-6}$ alkyl of $R^{2A}$ is optionally substituted by 1, 2, or 3 independently selected $R^{2B}$ substitutents; and each $R^{2B}$ is independently selected from D, halo, and OH.

In some embodiments of Formulas (I) and (III), $R^2$ is selected from 5-6 membered heteroaryl and 4-6 membered heterocycloalkyl, wherein the 5-6 membered heteroaryl and 4-6 membered heterocycloalkyl of $R^2$ are each optionally substituted with 1 or 2 independently selected $R^{2A}$ substituents.

In some embodiments of Formulas (I) and (III), each $R^{2A}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{e21}R^{d21}$, $NR^{c21}R^{d21}$, $NR^{c21}C(O)R^{b21}$, $NR^{c21}C(O)OR^{a21}$, $NR^{c2}C(O)NR^{c21}R^{d21}$, and $S(O)R^{b21}$.

In some embodiments of Formulas (I) and (III), each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (III), $R^2$ is selected from 5-6 membered heteroaryl and 4-6 membered heterocycloalkyl, wherein the 5-6 membered heteroaryl and 4-6 membered heterocycloalkyl of $R^2$ are each optionally substituted with 1 or 2 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, OC(O)

$NR^{e21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, and $S(O)R^{b21}$; and each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (III), $R^2$ is a 5-6 membered heteroaryl, optionally substituted with 1, 2, or 3 independently selected $R^{2A}$ substituents.

In some embodiments of Formulas (I) and (III), $R^2$ is a 5-6 membered heteroaryl.

In some embodiments of Formulas (I) and (III), $R^2$ is a 5-6 membered heterocycloalkyl.

In some embodiments of Formulas (I) and (III), $R^2$ is selected from 6-oxo-1,6-dihydropyridin-3-yl, pyrimidin-4-yl, 1-methyl-6-oxo-1,6-dihydropyridin-3-yl, 1-methyl-6-oxo-1,6-dihydropyridazin-3-yl, 4-methyloxazol-5-yl, 4-ethyloxazol-5-yl, 3-methylpyridin-4-yl, 4-(2,2-difluoro-1-hydroxyethyl)-2-methyloxazol-5-yl, 2-methyl-4-(2,2,2-trifluoro-1-hydroxyethyl)oxazol-5-yl, 1-ethyl-1H-pyrazol-5-yl, 6-hydroxypyridin-3-yl, 2,6-dimethylpyridin-4-yl, 3-methyl-1H-pyrazol-4-yl, [1,2,4]triazolo[4,3-a]pyridin-6-yl, oxazol-5-yl, imidazo[1,2-a]pyridine-6-yl, 3-fluoropyridin-4-yl, and 1-(methyl-d3)-6-oxo-1,6-dihydropyridazin-3-yl.

In some embodiments of Formulas (I) and (III), $R^2$ is selected from 6-oxo-1,6-dihydropyridin-3-yl, pyrimidin-4-yl, 1-methyl-6-oxo-1,6-dihydropyridin-3-yl, 1-methyl-6-oxo-1,6-dihydropyridazin-3-yl, 4-methyloxazol-5-yl, 4-ethyloxazol-5-yl, and 3-methylpyridin-4-yl.

In some embodiments of Formulas (I) and (III), $R^2$ is pyridinonyl.

In some embodiments of Formulas (I) and (III), $R^2$ is 6-oxo-1,6-dihydropyridin-3-yl.

In some embodiments of Formulas (I) and (III), $R^2$ is pyrimidin-4-yl.

In some embodiments of Formulas (I) and (III), $R^2$ is selected from the group consisting of 1-methyl-6-oxo-1,6-dihydropyridazin-3-yl, pyrimidin-4-yl, and 2,6-dimethylpyridin-4-yl.

In some embodiments of Formulas (I) and (III), $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1 or 2 independently selected $R^{4A}$ substituents.

In some embodiments of Formulas (I) and (III), each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c4}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, or 4 independently selected $R^{4B}$ substituents.

In some embodiments of Formulas (I) and (III), $R^4$ is selected from H, D, halo, $C_{1-6}$ alkyl, $C_{1-6}$ haloalkyl, $C_{2-6}$ alkenyl, and $C_{2-6}$ alkynyl.

In some embodiments of Formulas (I) and (III), $R^4$ is H.

In some embodiments of Formulas (I) and (III), $R^2$ is selected from H, D, halo, $C_{1-6}$ alkyl, $C_{1-6}$ haloalkyl, $C_{2-6}$ alkenyl, and $C_{2-6}$ alkynyl.

In some embodiments of Formulas (I) and (III), $R^2$ is H.

In some embodiments of Formulas (I) and (III), $R^2$ is 6-oxo-1,6-dihydropyridin-3-yl or imidazo[1,2-a]pyridin-6-yl; and $R^4$ is H.

In some embodiments of Formulas (I) and (III), $R^2$ is H; and $R^4$ is —NHC(O)O$C_{1-6}$ alkyl.

In some embodiments of Formulas (I) and (III), $R^4$ is selected from $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{14}$, and $S(O)_2R^{b4}$.

In some embodiments of Formulas (I) and (III), each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (III), $R^4$ is selected from $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{14}$, and $S(O)_2R^{b4}$; and each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl.

In some embodiments of Formulas (I) and (III), $R^4$ is selected from $C(O)NR^{c4}R^{d4}$ and $NR^{c4}C(O)OR^{a4}$.

In some embodiments of Formulas (I) and (III), $R^4$ is $NR^{c4}C(O)OR^{a4}$.

In some embodiments of Formulas (I) and (III), each $R^{a4}$, $R^{c4}$, and $R^{d4}$ is independently selected from H and $C_{1-6}$ alkyl.

In some embodiments of Formulas (I) and (III), $R^4$ is selected from $C(O)NR^{c4}R^{d4}$ and $NR^{c4}C(O)OR^{a4}$; and each $R^{a4}$, $R^{c4}$, and $R^{d4}$ is independently selected from H and $C_{1-6}$ alkyl.

In some embodiments of Formulas (I) and (III), $R^4$ is —NHC(O)O$C_{1-6}$ alkyl.

In some embodiments of Formulas (I) and (III), $R^4$ is —$NHC(O)OCH_2CH_3$.

In some embodiments of Formulas (I) and (III), $R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a4}$, $C(O)R^{b4}$, $C(O)NR^{c4}R^{d4}$, $C(O)OR^{a4}$, $NR^{c4}R^{d4}$, $S(O)_2NR^{c4}R^{d4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a41}$, C(O)$R^{b41}$, C(O)$NR^{c41}R^{d41}$, C(O)$OR^{a41}$, $NR^{c41}R^{d4}1$ $S(O)_2NR^{c41}R^{d41}$, and $S(O)_2R^{b41}$, wherein the $C_{1-6}$ alkyl, 5 $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, or 3 independently selected $R^{4B}$ substituents;

each $R^{a41}$, $R^{b41}$, $R^{c41}$ and $R^{d4}1$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a41}$, $R^{b41}$, $R^{c41}$ and $R^{d4}1$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl-, CN, $OR^{a42}$, C(O)$R^{42}$, C(O)$NR^{c42}R^{d42}$, C(O)$OR^{a42}$, $NR^{c42}R^{d42}$ $S(O)_2NR^{c42}R^{d42}$, and $S(O)_2R^{b42}$, wherein the $C_{1-6}$ alkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, $C_{1-6}$ haloalkyl, CN, $OR^{a43}$, C(O)$R^{b43}$, C(O)$NR^{c43}R^{d43}$, C(O)$OR^{a43}$, $NR^{c43}R^{d43}$ $S(O)_2NR^{c43}R^{d43}$, and $S(O)_2R^{b43}$, wherein the $C_{1-6}$ alkyl of $R^{4C}$ is optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents; and each $R^{4D}$ is independently selected from $C_{1-3}$ alkyl and OH.

In some embodiments of Formulas (I) and (III), $R^4$ is selected from phenyl-$C_{1-3}$ alkyl-, (4-7 membered heterocycloalkyl)-$C_{1-3}$ alkyl-, (5-10 membered heteroaryl)-$C_{1-3}$ alkyl-, $OR^{a4}$, C(O)$R^{b4}$, and $S(O)_2R^{b4}$, wherein the phenyl-$C_{1-3}$ alkyl-, (4-7 membered heterocycloalkyl)-$C_{1-3}$ alkyl- and (5-10 membered heteroaryl)-$C_{1-3}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from phenyl, 4-7 membered heterocycloalkyl, and (5-6 membered heteroaryl)-$C_{1-3}$ alkyl-, wherein the phenyl, 4-7 membered heterocycloalkyl, and (5-6 membered heteroaryl)-$C_{1-3}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, 5-6 membered heteroaryl, (4-10 membered heterocycloalkyl)-$C_{1-3}$ alkyl-, $OR^{a41}$, $S(O)_2R^{b41}$, and $NR^{c41}R^{d41}$, wherein the $C_{1-6}$ alkyl, 5-6 membered heteroaryl, and (4-10 membered heterocycloalkyl)-$C_{1-3}$ alkyl- of $R^{4A}$ are each optionally substituted with 1, 2, or 3 independently selected $R^{4B}$ substituents;

each $R^{a41}$, $R^{b41}$, $R^{c41}$ and $R^{d4}1$ is independently selected from H, $C_{1-6}$ alkyl, $C_{1-6}$ haloalkyl, and 5-6 membered heteroaryl, wherein the $C_{1-6}$ alkyl and 5-6 membered heteroaryl of $R^{a41}$, $R^{b41}$, $R^{c41}$ and $R^{d4}1$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, $C_{3-6}$ cycloalkyl, 4-7 membered heterocycloalkyl, (5-6 membered heteroaryl)-$C_{1-3}$ alkyl-, CN, $OR^{a42}$, C(O)$R^{b42}$, C(O)$OR^{a42}$, and $NR^{c42}R^{d42}$, wherein the $C_{1-6}$ alkyl, $C_{3-6}$ cycloalkyl, 5-6 membered heteroaryl, 4-7 membered heterocycloalkyl, and (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{3-6}$ cycloalkyl, 5-6 membered heteroaryl, and 5-7 membered heterocycloalkyl, wherein the $C_{1-6}$ alkyl, $C_{3-6}$ cycloalkyl, 5-6 membered heteroaryl, and 5-7 membered heterocycloalkyl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, CN, C(O)$NR^{c43}R^{d43}$, C(O)$OR^{a43}$, $NR^{c43}R^{d43}$ and $S(O)_2R^{b43}$, wherein the $C_{1-6}$ alkyl of $R^{4C}$ is optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents;

each $R^{4D}$ is independently selected from $C_{1-3}$ alkyl and OH.

In some embodiments of Formulas (I) and (III), $R^4$ is selected from $C_{6-10}$ aryl-$C_{1-6}$ alkyl-, (5-10 membered heteroaryl)-$C_{1-6}$ alkyl-, $OR^{a4}$, C(O)$R^{b4}$, and $S(O)_2R^{b4}$, wherein the $C_{6-10}$ aryl-$C_{1-6}$ alkyl- and (5-10 membered heteroaryl)-$C_{1-6}$ alkyl- of $R^4$ are each optionally substituted with 1, 2, 3, or 4 independently selected $R^{4A}$ substituents; and each $R^{4A}$ is independently selected from D, halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a41}$, $SR^{a41}$, and $NR^{c41}R^{d41}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, or 4 independently selected $R^{41}$ substituents.

In some embodiments of Formulas (I) and (III), $R^4$ is selected from $C_{6-10}$ aryl-$C_{1-3}$ alkyl-, (5-10 membered heteroaryl)-$C_{1-3}$ alkyl-, $OR^{a4}$, $C(O)R^{b4}$, and $S(O)_2R^{b4}$, wherein the $C_{6-10}$ aryl-$C_{1-6}$ alkyl- and (5-10 membered heteroaryl)-$C_{1-3}$ alkyl- of $R^4$ are each optionally substituted with 1, 2, 3, or 4 independently selected $R^{4A}$ substituents;

each $R^{4A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-3}$ alkyl-, $C_{3-10}$ cycloalkyl-$C_{1-3}$ alkyl-, (5-10 membered heteroaryl)-$C_{1-3}$ alkyl-, (4-10 membered heterocycloalkyl)-$C_{1-3}$ alkyl-, CN, $OR^{a41}$, $SR^{a41}$, and $NR^{c41}R^{d41}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-3}$ alkyl-, $C_{3-10}$ cycloalkyl-$C_{1-3}$ alkyl-, (5-10 membered heteroaryl)-$C_{1-3}$ alkyl-, and (4-10 membered heterocycloalkyl)-$C_{1-3}$ alkyl- of $R^{4A}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, $OR^{a42}$, $COOR^{a42}$, and $NR^{c42}R^{d42}$;

each $R^{a4}$ and $R^{b4}$, is independently selected from H, $C_{1-6}$ alkyl, $C_{1-6}$ haloalkyl, phenyl, and azetidinyl wherein the phenyl is optionally substituted with 1 or 2 groups selected from halo, $C_{1-6}$ alkyl, and $C_{1-6}$ haloalkyl;

each $R^{a41}$, $R^{c41}$ and $R^{d4}1$ is independently selected from H and $C_{1-6}$ alkyl; and each $R^{a42}$, $R^{c42}$ and $R^{d42}$ is independently selected from H and $C_{1-6}$ alkyl.

In some embodiments of Formulas (I) and (III), $R^4$ is selected from $C_{6-10}$ aryl-$C_{1-3}$ alkyl- and (5-10 membered heteroaryl)-$C_{1-3}$ alkyl- wherein the $C_{6-10}$ aryl-$C_{1-3}$ alkyl- and (5-10 membered heteroaryl)-$C_{1-3}$ alkyl- of $R^4$ are each optionally substituted with 1, 2, 3, or 4 independently selected $R^{4A}$ substituents;

each $R^{4A}$ is independently selected from halo, $C_{1-6}$ alkyl, $C_{1-6}$ haloalkyl, and $OR^{a41}$; and each $R^{a41}$ is independently selected from H and $C_{1-3}$ alkyl.

In some embodiments of Formulas (I) and (III), $R^4$ is $C_6$ aryl-$C_{1-3}$ alkyl-optionally substituted with 1, 2, or 3 substituents independently selected from OH and halo.

In some embodiments of Formulas (I) and (III), $R^4$ is selected from pyridin-2-ylmethyl, 1H-Pyrrolo[2,3-b]pyridin-1-yl, 7H-pyrrolo[2,3-b]pyridin-7-yl, 2-fluorophenoxy, hydroxy(pyridin-2-yl)methyl, 2-(1-methyl-1H-pyrazol-4-yl) benzyl, (imidazo[1,2-a]pyridin-8-yl)methyl, (pyrazolo[1,5-a]pyridin-7-yl)methyl, (2H-indazol-2-yl)methyl, (1H-indazol-1-yl)methyl, (2,6-difluorophenyl)(hydroxy)methyl, (2,5-difluorophenyl)(hydroxy)methyl, (2,3-difluorophenyl)(hydroxy)methyl, (2-fluorophenyl)(hydroxy)methyl, (2-chlorophenyl)(hydroxy)methyl, hydroxy(phenyl)methyl, phenylsulfonyl, azetidine-1-carbonyl, benzo[d]oxazol-4-ylmethyl, 2-fluoro-6-(1-methyl-1H-pyrazol-5-yl)benzyl, 2-fluoro-6-((6-methyl-5-oxo-2,6-diazaspiro[3.4]octan-2-yl) methyl)benzyl, 2-fluoro-6-((6-oxohexahydropyrrolo[1,2-a] pyrazin-2(1H)-yl)methyl)benzyl, 2-fluoro-6-(((2-oxopyrrolidin-3-yl)amino)methyl)benzyl, 2-fluoro-6-((3-oxopiperazin-1-yl)methyl)benzyl, 2-fluoro-6-(((1-methyl-2-oxopyrrolidin-3-yl)amino)methyl)benzyl, 2-fluoro-6-(((2-methyl-2H-1,2,3-triazol-4-yl)amino)methyl)benzyl, 2-(((2-oxopyrrolidin-3-yl)amino)methyl)benzyl, amino(2,6-difluorophenyl)methyl, (2,6-difluorophenyl)(methylamino) methyl, (2,6-difluorophenyl)((2-hydroxyethyl)amino) methyl, amino(2-fluorophenyl)methyl, amino(2,6-difluorophenyl)methyl, (3-(oxazol-5-yl)pyridin-2-yl) methyl, 2-fluoro-6-(1-methyl-1H-pyrazol-4-yl)benzyl, (1-((1-methyl-1H-imidazol-4-yl)sulfonyl)pyrrolidin-2-yl) methyl, 2-((1-acetylpiperidin-4-yl)methyl)-6-fluorobenzyl, (2-(difluoromethoxy)-6-fluorophenyl)(hydroxy)methyl, 2-fluoro-6-(1-((1-methyl-1H-pyrazol-4-yl)methyl)-1H-pyrazol-4-yl)benzyl, (2-((dimethylamino)methyl)-6-fluorophenyl)(hydroxy)methyl, 2-fluoro-6-(1-(pyridin-2-ylmethyl)-1H-pyrazol-4-yl)benzyl, (2-fluoro-6-(pyrrolidin-1-ylmethyl)phenyl)(hydroxy)methyl, 2-fluoro-6-(1-(2-(methylsulfonyl)ethyl)-1H-pyrazol-4-yl)benzyl, 2-fluoro-6-((6-oxohexahydropyrrolo[1,2-a]pyrazin-2(1H)-yl)methyl) phenyl)(hydroxy)methyl, 2-fluoro-6-(1-((trans)-3-(methylamino)cyclobutyl)-1H-pyrazol-4-yl)benzyl, 2-(1-(2-cyanoethyl)-1H-pyrazol-4-yl)-6-fluorobenzyl, 2-fluoro-6-(1-(2-(3-hydroxyazetidin-1-yl)-2-oxoethyl)-1H-pyrazol-4-yl)benzyl, (3-methylpyridin-2-yl)methoxy, (3-((1-(pyridin-4-ylmethyl)-1H-pyrazol-4-yl)amino)pyridin-2-yl)methyl, (3-((1-(tetrahydro-2H-pyran-4-yl)-1H-pyrazol-4-yl)amino) pyridin-2-yl)methyl, (3-(1-methyl-1H-pyrazol-4-yl)pyridin-2-yl)methyl, 2-((3-hydroxypyrrolidin-1-yl)methyl)benzyl, and (6-methoxypyridin-2-yl)methyl.

In some embodiments of Formulas (I) and (III), $R^4$ is selected from pyridin-2-ylmethyl, 1H-pyrrolo[2,3-b]pyridin-1-yl, 7H-pyrrolo[2,3-b]pyridin-7-yl, 2-fluorophenoxy, hydroxy(pyridin-2-yl)methyl, 2-(1-methyl-1H-pyrazol-4-yl) benzyl, imidazo[1,2-a]pyridin-8-ylmethyl, pyrazolo[1,5-a] pyridin-7-ylmethyl, (2H-Indazol-2-yl)methyl, 1H-indazol-1-yl)methyl, (2,6-difluorophenyl)(hydroxy)methyl, (2,5-difluorophenyl)(hydroxy)methyl, (2,3-difluorophenyl) (hydroxy)methyl, (2-fluorophenyl)(hydroxy)methyl, (2-chlorophenyl)(hydroxy)methyl, hydroxy(phenyl)methyl, phenylsulfonyl, and azetidine-1-carbonyl.

In some embodiments of Formulas (I) and (III), $Cy^1$ is $C_{6-10}$ aryl which is optionally substituted by 1, 2, 3, or 4 independently selected $R^7$ substituents.

In some embodiments of Formulas (I) and (III), $Cy^1$ is phenyl which is optionally substituted by 1 or 2 independently selected $R^7$ substituents.

In some embodiments of Formulas (I) and (III), each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (III), $Cy^1$ is phenyl which is optionally substituted by 1 or 2 independently selected $R^7$ substituents; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (III), $Cy^1$ is phenyl which is substituted by 1 or 2 independently selected $R^7$ substituents; and each $R^7$ is independently selected from halo and CN.

In some embodiments of Formulas (I) and (III), $Cy^1$ is phenyl which is optionally substituted by 1 or 2 substituents independently selected from $C_{1-6}$ alkyl, halo, and CN.

In some embodiments of Formulas (I) and (III), $Cy^1$ is phenyl which is optionally substituted by 1 or 2 substituents independently selected from $C_{1-6}$ alkyl and CN.

In some embodiments of Formulas (I) and (III), $Cy^1$ is unsubstituted phenyl.

In some embodiments of Formulas (I) and (III), $Cy^1$ is cyanophenyl or cyanofluorophenyl.

In some embodiments of Formulas (I) and (III), $Cy^1$ is cyanophenyl.

In some embodiments of Formulas (I) and (III), $Cy^1$ is 3-cyanophenyl or 3-cyano-2-fluorophenyl.

In some embodiments of Formulas (I) and (III):

$R^1$ is H;

$Cy^1$ is $C_{6-10}$ aryl which is optionally substituted by 1, 2, 3, or 4 independently selected $R^7$ substituents; and $R^2$ is selected from $C_{6-10}$ aryl, $C_{3-10}$ cycloalkyl, 5-10 membered heteroaryl, 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments of Formulas (I) and (III):

$R^1$ is H;

$Cy^1$ is phenyl which is optionally substituted by 1 or 2 independently selected $R^7$ substituents; and $R^2$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments of Formulas (I) and (III):

$R^1$ is H or $C_{1-6}$ alkyl;

$R^2$ is 5-6 membered heteroaryl, optionally substituted with 1, 2, or 3 independently selected $R^{2A}$ substituents;

$R^4$ is selected from $C_{6-10}$ aryl-$C_{1-3}$ alkyl-, (5-10 membered heteroaryl)-$C_{1-3}$ alkyl-, $OR^{a4}$, $C(O)R^{b4}$, and $S(O)_2R^{b4}$, wherein the $C_{6-10}$ aryl-$C_{1-3}$ alkyl- and (5-10 membered heteroaryl)-$C_{1-3}$ alkyl- of $R^4$ are each optionally substituted with 1, 2, 3, or 4 independently selected $R^{4A}$ substituents;

each $R^{4A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-3}$ alkyl-, $C_{3-10}$ cycloalkyl-$C_{1-3}$ alkyl-, (5-10 membered heteroaryl)-$C_{1-3}$ alkyl-, (4-10 membered heterocycloalkyl)-$C_{1-3}$ alkyl-, CN, $OR^{a41}$, $SR^{a41}$, and $NR^{c41}R^{d41}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-3}$ alkyl-, $C_{3-10}$ cycloalkyl-$C_{1-3}$ alkyl-, (5-10 membered heteroaryl)-$C_{1-3}$ alkyl-, and (4-10 membered heterocycloalkyl)-$C_{1-3}$ alkyl- of $R^{4A}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, $OR^{a42}$, $COOR^{a42}$, and $NR^{c42}R^{d42}$.

$Cy^1$ is phenyl which is optionally substituted by 1, 2, or 3 independently selected $R^7$ substituents;

each $R^{a4}$ and $R^{b4}$, is independently selected from H, $C_{1-6}$ alkyl, $C_{1-6}$ haloalkyl, phenyl, and azetidinyl wherein the phenyl is optionally substituted with 1 or 2 groups selected from halo, $C_{1-6}$ alkyl, and $C_{1-6}$ haloalkyl;

each $R^{a41}$, $R^{c41}$, and $R^{d4}1$ is independently selected from H and $C_{1-6}$ alkyl;

each $R^{a42}$, $R^{c42}$, and $R^{d42}$ is independently selected from H and $C_{1-6}$ alkyl; and each $R^7$ is independently selected from halo, $C_{1-6}$ alkyl, $C_{1-6}$ haloalkyl, and CN.

In some embodiments of Formulas (I) and (III):

$R^1$ is H or $C_{1-6}$ alkyl;

$R^2$ is 5-6 membered heteroaryl, optionally substituted with 1, 2, or 3 independently selected $R^{2A}$ substituents;

$R^4$ is selected from $C_{6-10}$ aryl-$C_{1-3}$ alkyl- and (5-10 membered heteroaryl)-$C_{1-3}$ alkyl-, wherein the $C_{6-10}$ aryl-$C_{1-3}$ alkyl- and (5-10 membered heteroaryl)-$C_{1-3}$ alkyl- of $R^4$ are each optionally substituted with 1, 2, 3, or 4 independently selected $R^{4A}$ substituents;

each $R^{4A}$ is independently selected from halo, $C_{1-6}$ alkyl, $C_{1-6}$ haloalkyl, and $OR^{a41}$, $Cy^1$ is phenyl which is optionally substituted by 1 or 2 substituents independently selected from $C_{1-6}$ alkyl and CN; and each $R^{a41}$ is independently selected from H and $C_{1-3}$ alkyl.

In some embodiments of Formulas (I) and (III):

$R^1$ is selected from H, $C_{1-6}$ alkyl, $C_{2-6}$ alkenyl, $C_{2-6}$ alkynyl, and $C_{1-6}$ haloalkyl;

$R^2$ is selected from H, D, halo, $C_{1-6}$ alkyl, $C_{1-6}$ haloalkyl, $C_{2-6}$ alkenyl, and $C_{2-6}$ alkynyl;

$R^4$ is selected from $C(O)R^{14}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$ $S(O)R^{b4}$, and $S(O)_2R^{b4}$;

$Cy^1$ is $C_{6-10}$ aryl which is optionally substituted by 1, 2, 3, or 4 independently selected $R^7$ substituents;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (III):

$R^1$ is selected from H, $C_{1-6}$ alkyl, $C_{2-6}$ alkenyl, $C_{2-6}$ alkynyl, and $C_{1-6}$ haloalkyl;

$R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents;

$R^4$ is selected from H, D, halo, $C_{1-6}$ alkyl, $C_{1-6}$ haloalkyl, $C_{2-6}$ alkenyl, and $C_{2-6}$ alkynyl;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $S(O)R^{b21}$, and $S(O)_2R^{b2}$;

$Cy^1$ is $C_{6-10}$ aryl which is optionally substituted by 1, 2, 3, or 4 independently selected $R^7$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (III):

$R^1$ is H;

$R^2$ is selected from H, D, halo, $C_{1-6}$ alkyl, $C_{1-6}$ haloalkyl, $C_{2-6}$ alkenyl, and $C_{2-6}$ alkynyl;

$R^4$ is selected from $C(O)NR^{c4}R^{d4}$ and $NR^{c4}C(O)OR^{a4}$;

$Cy^1$ is phenyl which is optionally substituted by 1 or 2 independently selected $R^7$ substituents;

each $R^{a4}$, $R^{c4}$ and $R^{d4}$ is independently selected from H and $C_{1-6}$ alkyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (III):

$R^1$ is H;

$R^2$ is selected from 5-6 membered heteroaryl and 4-6 membered heterocycloalkyl, wherein the 5-6 membered heteroaryl and 4-6 membered heterocycloalkyl of $R^2$ are each optionally substituted with 1 or 2 independently selected $R^{2A}$ substituents;

$R^4$ is selected from H, D, halo, $C_{1-6}$ alkyl, $C_{1-6}$ haloalkyl, $C_{2-6}$ alkenyl, and $C_{2-6}$ alkynyl;

each $R^{2A}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{e21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, and $S(O)R^{b21}$;

$Cy^1$ is phenyl which is optionally substituted by 1 or 2 independently selected $R^7$ substituents;

each $R^{a21}$, $R^{b21}$, $R^{c21}$, and $R^{d21}$ is independently selected from H and $C_{1-6}$ alkyl; and each $R^7$ is independently selected from halo, $C_{1-6}$ alkyl, $C_{1-6}$ haloalkyl, $C_{2-6}$ alkenyl, $C_{2-6}$ alkynyl, CN, and $NO_2$.

In some embodiments of Formulas (I) and (III):

$R^1$ is H;

$R^2$ is H;

$R^4$ is $NR^{c4}C(O)OR^{a4}$;

$Cy^1$ is cyanophenyl; and $R^{a4}$ and $R^{c4}$ are each independently selected from H and $C_{1-6}$ alkyl.

In some embodiments of Formulas (I) and (III):

$R^1$ is H;

$R^2$ is selected from 5-6 membered heteroaryl and 4-6 membered heterocycloalkyl;

$R^4$ is H; and $Cy^1$ is cyanophenyl.

In some embodiments of Formulas (I) and (III):

$R^1$ is H;

$R^2$ is selected from 5-6 membered heteroaryl and 4-6 membered heterocycloalkyl, wherein the 5-6 membered heteroaryl and 4-6 membered heterocycloalkyl are each optionally substituted with 1 or 2 $C_{1-3}$ alkyl groups;

$R^4$ is phenyl-$C_{1-3}$ alkyl- or pyridyl-$C_{1-3}$ alkyl-, wherein the phenyl-$C_{1-3}$ alkyl- and pyridyl-$C_{1-3}$ alkyl- are each optionally substituted with 1, 2, or 3 substituents independently selected from OH and halo; and $Cy^1$ is cyanophenyl.

In some embodiments of Formulas (I) and (III):

$R^1$ is H;

$R^2$ is selected from 5-6 membered heteroaryl and 4-6 membered heterocycloalkyl;

$R^4$ is phenyl-$C_{1-3}$ alkyl- optionally substituted with 1, 2, or 3 substituents independently selected from OH and halo; and $Cy^1$ is cyanophenyl.

In some embodiments of Formulas (I) and (III):

$R^1$ is H;

$R^2$ is pyrimidin-4-yl;

$R^4$ is phenyl-$C_{1-3}$ alkyl- optionally substituted with 1, 2, or 3 substituents independently selected from OH and halo; and $Cy^1$ is cyanophenyl.

In some embodiments of Formulas (I) and (III), the compound is a compound of Formula (IIIa):

(IIIa)

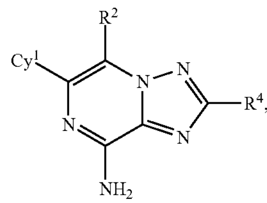

or a pharmaceutically acceptable salt thereof, wherein variables $R^2$, $R^4$, and $Cy^1$ are defined according to the definitions provided herein for compounds of Formulas (I) and (III).

In some embodiments of Formula (IIIa), $Cy^1$ is phenyl which is substituted by 1 or 2 independently selected $R^7$ substituents;

each $R^7$ is independently selected from halo and CN;

$R^2$ is selected from H, $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $S(O)R^{b21}$, and $S(O)_2R^{b21}$, wherein said $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{2A}$ are each optionally substituted by 1, 2, or 3 independently selected $R^{2B}$ substituents;

each $R^{a21}$, $R^{241}$, $R^{c21}$ and $R^{d21}$ is independently selected from H, $C_{1-6}$ alkyl, and $C_{1-6}$ haloalkyl, wherein said $C_{1-6}$ alkyl of $R^{a21}$, $R^{241}$, $R^{c21}$, and $R^{d21}$ is optionally substituted by 1, 2, or 3 independently selected $R^{2A}$ substituents; and each $R^{2B}$ is independently selected from D, halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

$R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a4}$, $C(O)R^{b4}$, $C(O)NR^{c4}R^{d4}$, $C(O)OR^{a4}$, $NR^{c4}R^{d4}$ $S(O)_2NR^{c4}R^{d4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a41}$, $C(O)R^{b41}$, $C(O)NR^{c41}R^{d41}$, $C(O)OR^{a41}$, $NR^{c41}R^{d4}1$ $S(O)_2NR^{c41}R^{d41}$, and $S(O)_2R^{b41}$, wherein the $C_{1-6}$ alkyl, 5 $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, or 3 independently selected $R^{4B}$ substituents;

each $R^{a41}$, $R^{b41}$, $R^{c41}$ and $R^{d4}1$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a41}$, $R^{b41}$, $R^{c41}$ and $R^{d41}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl-, CN, $OR^{a42}$, $C(O)R^{b42}$, $C(O)NR^{c42}R^{d42}$, $C(O)OR^{a42}NR^{c42}R^{d42}$ $S(O)_2NR^{c42}R^{d42}$, and $S(O)_2R^{b42}$, wherein the $C_{1-6}$ alkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, $C_{1-6}$ haloalkyl, CN, $OR^{a43}$, $C(O)R^{b43}$, $C(O)NR^{c43}R^{d43}$, $C(O)OR^{a43}$, $NR^{c43}R^{d43}$ $S(O)_2NR^{c43}R^{d43}$, and $S(O)_2R^{b43}$, wherein the $C_{1-6}$ alkyl, 4-7 membered heterocycloalkyl, and (5-6 membered heteroaryl)-$C_{1-3}$ alkyl- of $R^{4C}$ are each optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents; and each $R^{4D}$ is independently selected from $C_{1-3}$ alkyl and OH.

In some embodiments of Formula (IIIa), $Cy^1$ is 3-cyanophenyl or 3-cyano-2-fluorophenyl;

$R^2$ is selected from H, 5-10 membered heteroaryl and 4-7 membered heterocycloalkyl, wherein the 5-10 membered heteroaryl and 4-7 membered heterocycloalkyl of $R^2$ are each optionally substituted with 1, 2, or 3 independently selected $R^{2A}$ substituents;

each $R^{2A}$ is independently selected from halo, $C_{1-6}$ alkyl, $C_{1-6}$ haloalkyl, and OH, wherein said $C_{1-6}$ alkyl of $R^{2A}$ is optionally substituted by 1, 2, or 3 independently selected $R^{2B}$ substituents;

each $R^{2B}$ is independently selected from D, halo, and OH;

$R^4$ is selected from phenyl-$C_{1-3}$ alkyl-, (4-7 membered heterocycloalkyl)-$C_{1-3}$ alkyl-, (5-10 membered heteroaryl)-$C_{1-3}$ alkyl-, $OR^{a4}$, $C(O)R^{b4}$, and $S(O)_2R^{b4}$, wherein the phenyl-$C_{1-3}$ alkyl-, (4-7 membered heterocycloalkyl)-$C_{1-3}$ alkyl- and (5-10 membered heteroaryl)-$C_{1-3}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from phenyl, 4-7 membered heterocycloalkyl, and (5-6 membered heteroaryl)-$C_{1-3}$ alkyl-, wherein the phenyl, 4-7 membered heterocycloalkyl, and (5-6 membered heteroaryl)-$C_{1-3}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, 5-6 membered heteroaryl, (4-10 membered heterocycloalkyl)-$C_{1-3}$ alkyl-, $OR^{a41}$, $S(O)_2R^{b41}$, and $NR^{c41}R^{d41}$, wherein the $C_{1-6}$ alkyl, 5-6 membered heteroaryl, and (4-10 membered heterocycloalkyl)-$C_{1-3}$ alkyl- of $R^{4A}$ are each optionally substituted with 1, 2, or 3 independently selected $R^{4B}$ substituents;

each $R^{a41}$, $R^{b41}$, $R^{c41}$ and $R^{d4}1$ is independently selected from H, $C_{1-6}$ alkyl, $C_{1-6}$ haloalkyl, and 5-6 membered heteroaryl, wherein the $C_{1-6}$ alkyl and 5-6 membered heteroaryl of $R^{a41}$, $R^{b41}$, $R^{c41}$ and $R^{d4}1$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, $C_{3-6}$ cycloalkyl, 4-7 membered heterocycloalkyl, (5-6 membered heteroaryl)-$C_{1-3}$ alkyl-, CN, $OR^{a42}$, $C(O)R^{b42}$, $C(O)OR^{a42}$, and $NR^{c42}R^{d42}$, wherein the $C_{1-6}$ alkyl, $C_{3-6}$ cycloalkyl, 5-6 membered heteroaryl, 4-7 membered heterocycloalkyl, and (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{3-6}$ cycloalkyl, 5-6 membered heteroaryl, and 5-7 membered heterocycloalkyl, wherein the $C_{1-6}$ alkyl, $C_{3-6}$ cycloalkyl, 5-6 membered heteroaryl, and 5-7 membered heterocycloalkyl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, CN, $C(O)NR^{c43}R^{d43}$, $C(O)OR^{a43}$, $NR^{c43}R^{d43}$ and $S(O)_2R^{b43}$, wherein the $C_{1-6}$ alkyl, 4-7 membered heterocycloalkyl, and (5-6 membered heteroaryl)-$C_{1-3}$ alkyl- of $R^{4C}$ are each optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents; and each $R^{4D}$ is independently selected from $C_{1-3}$ alkyl and OH.

In some embodiments of Formula (IIIa), $R^2$ is selected from 5-6 membered heteroaryl and 4-6 membered heterocycloalkyl, wherein the 5-6 membered heteroaryl and 4-6 membered heterocycloalkyl are each optionally substituted with 1 or 2 $C_{1-3}$ alkyl groups;

$R^4$ is phenyl-$C_{1-3}$ alkyl- or pyridyl-$C_{1-3}$ alkyl-, wherein the phenyl-$C_{1-3}$ alkyl- and pyridyl-$C_{1-3}$ alkyl- are each optionally substituted with 1, 2, or 3 substituents independently selected from OH and halo; and $Cy^1$ is 3-cyanophenyl.

In some embodiments of Formulas (I) and (III), the compound is a compound of Formula (IIIb):

(IIIb)

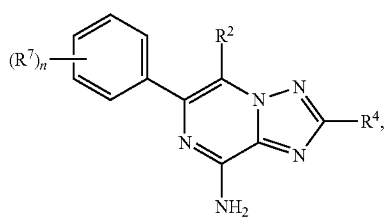

or a pharmaceutically acceptable salt thereof, wherein n is an integer from 0 to 4, and wherein variables $R^2$, $R^4$, and $R^7$ are defined according to the definitions provided herein for compounds of Formulas (I) and (III).

In some embodiments of Formulas (I) and (III), the compound is a compound of Formula (IIIc):

(IIIc)

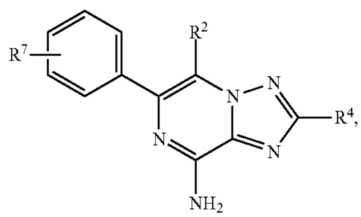

or a pharmaceutically acceptable salt thereof, wherein variables $R^2$, $R^4$, and $R^7$ are defined according to the definitions provided herein for compounds of Formulas (I) and (III).

In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, $—NR(CR'R'')_n—$ includes both $—NR(CR'R'')_n—$ and $—(CR'R'')_nNR—$. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula $—NH_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "thio" refers to a group of formula-SH.

As used herein, the term "carbamyl" to a group of formula —$C(O)NH_2$.

As used herein, the term "carbonyl", employed alone or in combination with other terms, refers to a —C(O)— group.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "cyano-$C_{1-n}$ alkyl" refers to a group of formula —($C_{1-n}$ alkylene)-CN, wherein the alkyl group has 1 to n carbon atoms. In some embodiments, the alkyl group has 1 to 6, 1 to 4, or 1 to 3 carbon atoms, e.g., —($C_{1-3}$ alkylene)-CN.

As used herein, the term "HO—$C_{1-n}$ alkyl" refers to a group of formula —($C_{1-n}$ alkylene)-OH, wherein the alkyl group has 1 to n carbon atoms. In some embodiments, the alkyl group has 1 to 6, 1 to 4, or 1 to 3 carbon atoms, e.g., —($C_{1-3}$ alkylene)-OH.

As used herein, the term "$C_{1-n}$ alkoxy-$C_{1-n}$ alkyl" refers to a group of formula —($C_{1-n}$ alkylene)-O($C_{1-n}$ alkyl), wherein the alkyl group has 1 to n carbon atoms. In some embodiments, the alkyl group has 1 to 6, 1 to 4, or 1 to 3 carbon atoms, e.g., —($C_{1-6}$ alkylene)-O($C_{1-6}$ alkyl).

As used herein, the term "carboxy" refers to a group of formula —C(O)OH.

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —$C(O)N(alkyl)_2$, wherein the two alkyl groups each has, independently, n to m carbon atoms.

In some embodiments, each alkyl group independently has 1 to 6, 1 to 4, or 1 to 3 carbon atoms.

As used herein, the term "$C_{n-m}$ alkylcarbonyloxy" is a group of formula —OC(O)— alkyl, wherein the alkyl group has n to m carbon atoms.

As used herein, "aminocarbonyloxy" is a group of formula —OC(O)—$NH_2$.

As used herein, "$C_{n-m}$ alkylaminocarbonyloxy" is a group of formula —OC(O)—NH— alkyl, wherein the alkyl group has n to m carbon atoms.

As used herein, "di($C_{n-m}$alkyl)aminocarbonyloxy" is a group of formula —OC(O)—N(alkyl)$_2$, wherein each alkyl group has, independently, n to m carbon atoms.

As used herein "$C_{n-m}$ alkoxycarbonylamino" refers to a group of formula —NHC(O)O($C_{n-m}$ alkyl), wherein the alkyl group has n to m carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S, and B. In some embodiments, the heteroaryl is a 5-6 monocyclic heteroaryl having 1 or 2 heteroatom ring members independently selected from N, O, and S. In some embodiments, the heteroaryl group contains 3 to 10, 4 to 10, 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or S(O)$_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2]octanyl, azaadamantanyl, diazaadamantanyl, oxo-adamantanyl, azaspiro[3.3]heptanyl, diazaspiro[3.3]heptanyl, oxo-azaspiro[3.3]heptanyl, azaspiro[3.4]octanyl, diazaspiro[3.4]octanyl, oxo-azaspiro[3.4]octanyl, azaspiro[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxohexahydropyrrolo[1,2-a]pyrazinyl, 3-oxopiperazinyl, oxo-pyrrolidinyl, oxo-pyridinyl and the like. For example, heterocycloalkyl groups include the following groups (with and without N-methyl substitution):

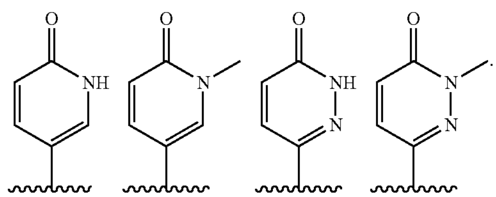

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent, e.g., $R^7$ or $R^{2A}$, are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamineimine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of formula 1-14 and 1-15 can be prepared via the synthetic route outlined in Scheme 1. Alkylation of commercially available starting material 1-1 with carbonyl adduct 1-2 (Hal is a halide, such as F, Cl, Br, or I), followed by a condensation reaction at elevated temperature, using an appropriate reagent, such as ammonium acetate, generates bicyclic compound 1-3. Compound 1-3 can then react with reagents, such as phosphoryl chloride ($POCl_3$), to give intermediate 1-4. A nucleophilic aromatic substitution ($S_NAr$) reaction of intermediate 1-4 with amine adduct 1-5 (PG is a suitable protecting group, such as 2,4-dimethoxybenzyl), followed by reduction of the ester functionality with a suitable reductant (e.g., DIBAL-H), affords alcohol 1-6. Halogenation of 1-6 with an appropriate reagent, such as phosphorous tribromide ($PBr_3$), generates intermediate 1-7. Compound 1-7 can then be cross-coupled with an adduct of formula 1-8, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to afford the cross-coupling product, which undergoes protecting group removal to generate intermediate 1-9. In some embodiments, $Cy^4$ can be a $R^4$ or a $R^4$-$R^{4a}$. Halogenation of 1-9 with an appropriate reagent, such as N-bromosuccinimide (NBS), affords two isomers 1-10 and 1-11. The final products 1-14 and 1-15 can then be prepared by reacting the two isomers 1-10 and 1-11 with either adduct 1-12 or 1-13 using reaction conditions similar to that described for the preparation of 1-9 from 1-7.

Scheme 1.

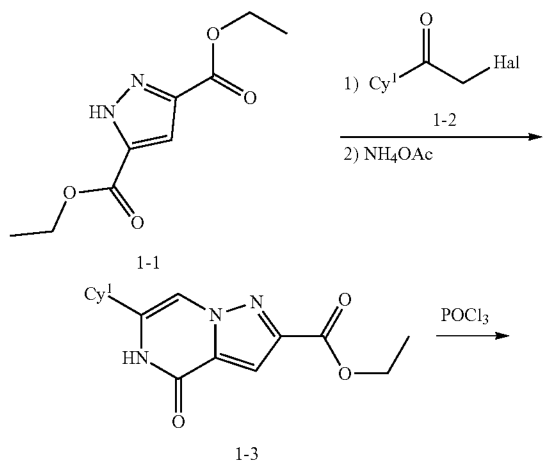

1-1

1-3

-continued

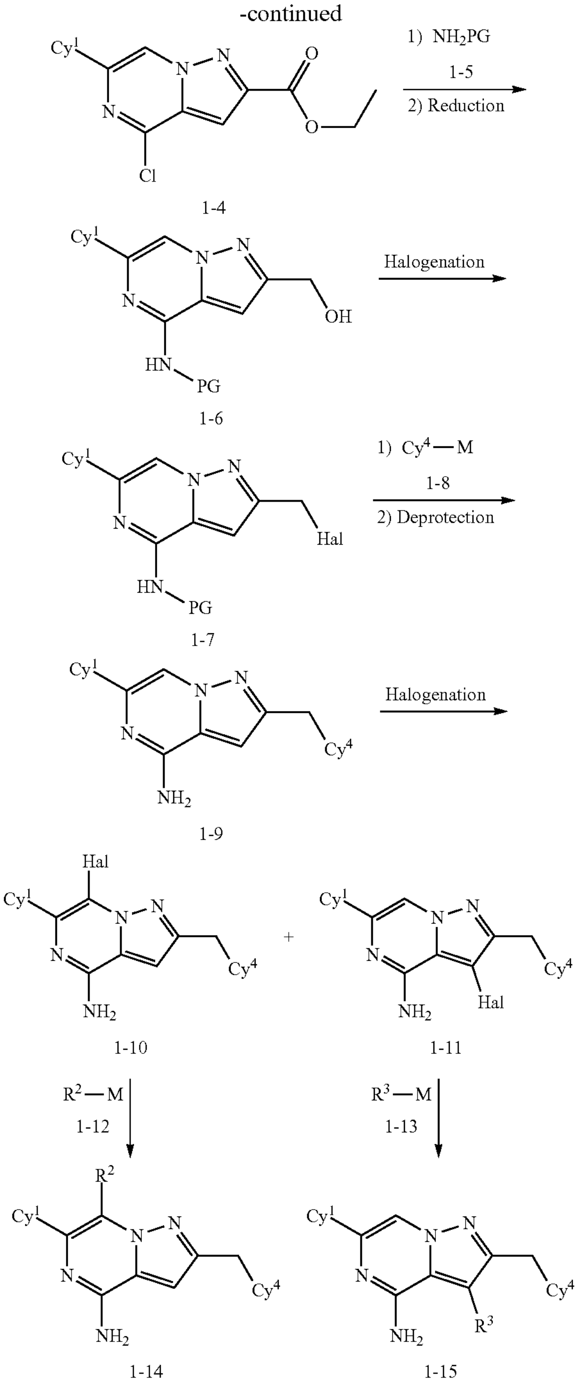

Compounds of formula 2-7 can be prepared via the synthetic route outlined in Scheme 2. Alkylation of commercially available starting material 2-1 (Hal is a halide, such as F, Cl, Br, or I) with carbonyl adduct 1-2, followed by condensation using an appropriate reagent, such as ammonium acetate, at elevated temperature generates bicyclic compound 2-2. Compound 2-2 can then react with a suitable reagent, such as phosphoryl chloride ($POCl_3$), to give intermediate 2-3. A nucleophilic aromatic substitution ($S_NAr$) reaction of intermediate 2-3 with amine adduct 1-5 (PG is a suitable protecting group, such as 2,4-dimethoxybenzyl), followed by removal of the protecting group, affords compound 2-4. Halogenation of 2-4 with a suitable reagent, such as N-bromosuccinimide (NBS), gives compound 2-5. Intermediate 2-5 can be cross-coupled with an adduct of formula 1-12, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to afford compound 2-6. Intermediate 2-6 then undergoes a second cross-coupling reaction with compound 1-8, using a similar procedure as described for the preparation of 2-6 from 2-5, to generate the product 2-7.

Scheme 2.

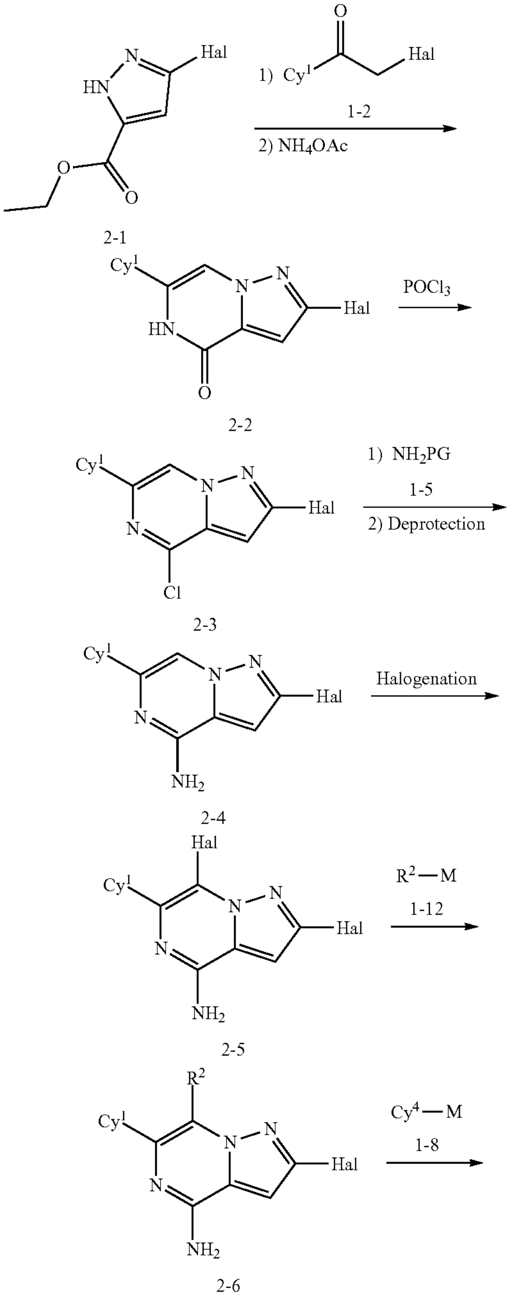

-continued

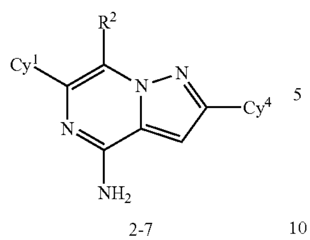

2-7

-continued

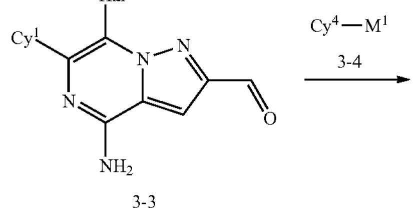

3-3

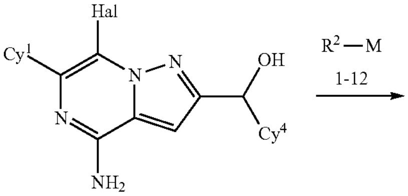

3-5

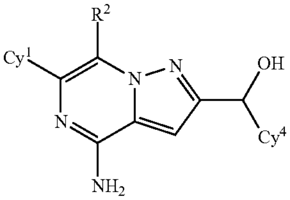

3-6

Compounds of formula 3-6 can be prepared via the synthetic route outlined in Scheme 3. A nucleophilic aromatic substitution ($S_NAr$) reaction of compound 1-4 (prepared using procedures described in Scheme 1) with amine adduct 1-5 (PG is a suitable protecting group, such as 2,4-dimethoxybenzyl), followed by removal of the protecting group, affords intermediate 3-1. Halogenation of 3-1 with an appropriate reagent, such as N-bromosuccinimide (NBS), followed by reduction of the ester functionality with a suitable reductant (e.g., DIBAL-H), generates alcohol 3-2. Intermediate 3-2 can then be oxidized with an appropriate oxidant (e.g., Dess-Martin periodinane) to afford aldehyde 3-3. An addition reaction between 3-3 and 3-4 ($M^1$ is a metal group, such as MgBr or Li) then affords secondary alcohol 3-5. The final product 3-6 can be prepared via a cross-coupling reaction between intermediate 3-5 and an adduct of formula 1-12, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst).

Scheme 3.

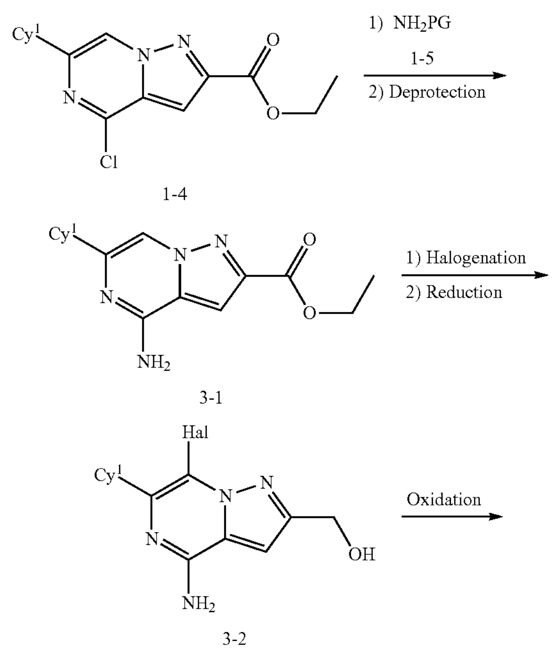

1-4

3-1

3-2

Compound of formula 4-5 can be prepared via the synthetic route outlined in Scheme 4. A halogenation reaction of compound 3-1 (prepared using procedures from Scheme 3) with an appropriate reagent, such as N-bromosuccinimide (NBS), affords compound 4-1 (Hal is a halide, such as F, Cl, Br, or I). Compound 4-1 can then be cross-coupled with an adduct of formula 1-12, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to generate intermediate 4-2. Hydrolysis of 4-2 with a suitable reagent, such as sodium hydroxide, gives carboxylic acid 4-3. Compound 4-3 can then react with amine 4-4 under standard amide coupling conditions, such as using HATU as coupling reagent and DIPEA as base, to generate product 4-5.

Scheme 4.

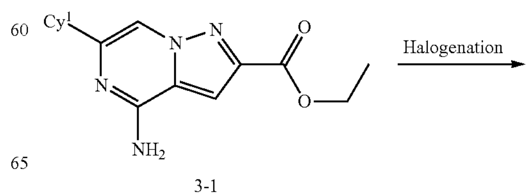

3-1

-continued

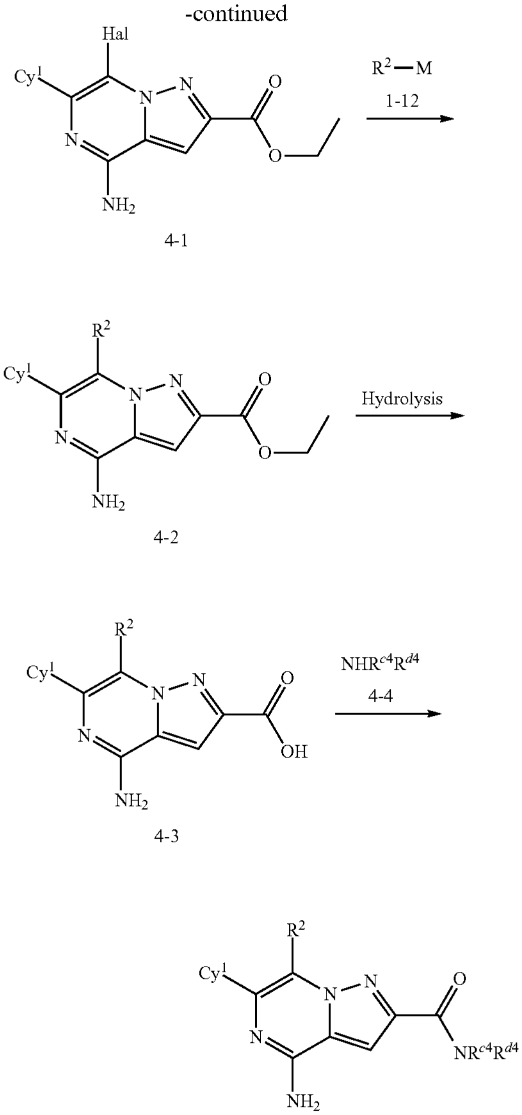

4-1

4-2

4-3

4-5

Scheme 5.

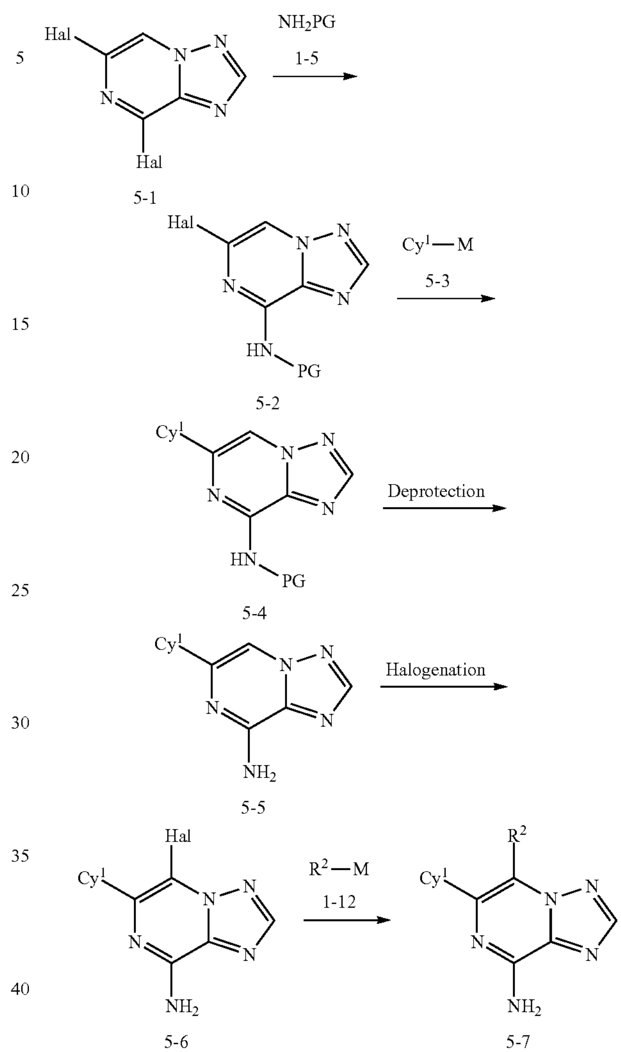

5-1

5-2

5-4

5-5

5-6

5-7

Compounds of formula 5-7 can be prepared via the synthetic route outlined in Scheme 5. A nucleophilic aromatic substitution ($S_NAr$) reaction of commercially available starting material 5-1 (Hal is a halide, such as F, Cl, Br, or I) with amine 1-5 (PG is a suitable protecting group, such as 2,4-dimethoxybenzyl) affords compound 5-2. Compound 5-2 can then be cross-coupled with an adduct of formula 5-3, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to generate intermediate 5-4. The protecting group in 5-4 can be removed to give compound 5-5. Halogenation of 5-5 with an appropriate reagent, such as N-bromosuccinimide (NBS), affords intermediate 5-6. Compound 5-6 can then be cross-coupled with an adduct of formula 1-12 to give the product 5-7, using a procedure similar to that described for the preparation of 5-4 from 5-2.

Compounds of formula 6-9 can be prepared via the synthetic route outlined in Scheme 6. Commercially available starting material 6-1 (Hal is a halide, such as F, Cl, Br, or I) can react with an appropriate reagent, such as t-butyl O-mesitylene carbamate (*Journal of Heterocyclic Chemistry,* 1975, 12, 107), to form pyrazinium salt 6-2. Intermediate 6-2 can then undergo a condensation reaction with an adduct of formula 6-3 to form compound 6-4. A nucleophilic aromatic substitution ($S_NAr$) reaction of 6-4 with amine 1-5 (PG is a suitable protecting group, such as 2,4-dimethoxybenzyl) affords compound 6-5. Compound 6-6 can then be prepared via a cross-coupling reaction between intermediate 6-5 and an adduct of formula 5-3, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). The protecting group in 6-6 can be removed to afford compound 6-7, which undergoes a halogenation reaction using an appropriate reagent, such as N-bromosuccinimide (NBS), to form compound 6-8. The final product 6-9 can be synthesized by coupling 6-8 with an adduct of formula 1-12, using similar procedures as described for the preparation of compound 6-6 from 6-5.

Scheme 6.

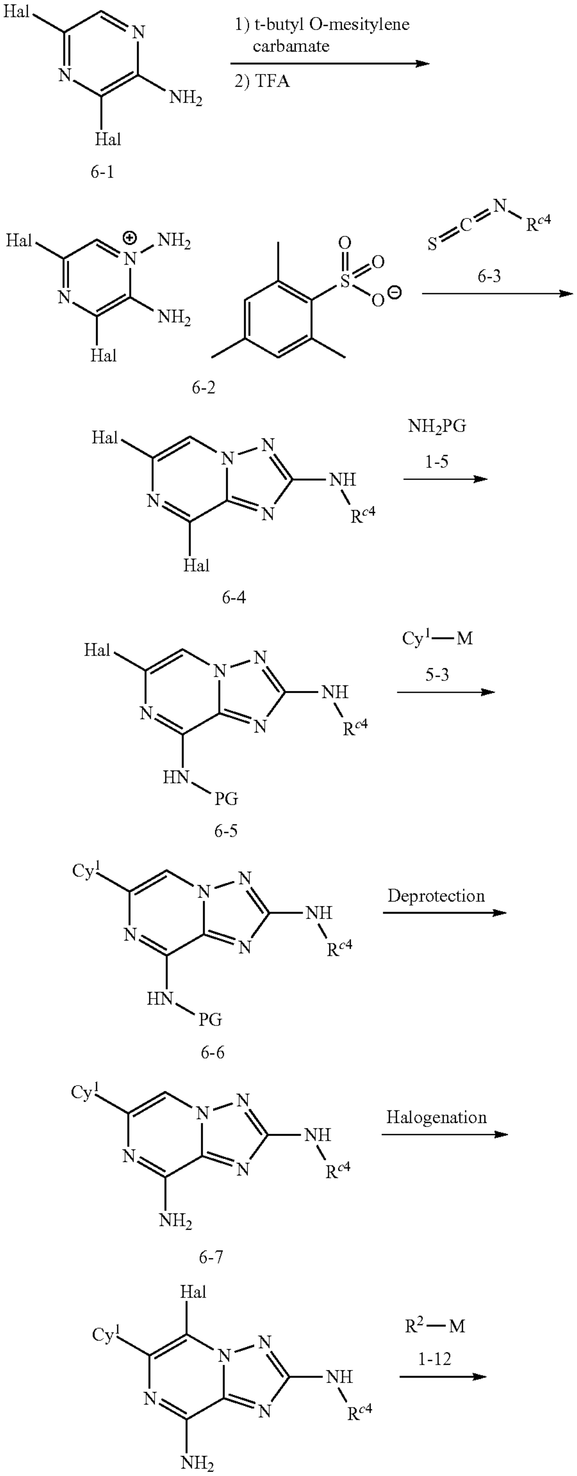

6-1, 6-2, 6-4, 6-5, 6-6, 6-7, 6-8

-continued

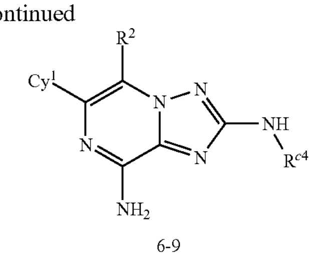

6-9

Compounds of formula 7-9 can be prepared via the synthetic route outlined in Scheme 7. Alkylation of commercially available starting material 7-1 (Hal is a halide, such as F, Cl, Br, or I) with carbonyl adduct 1-2, followed by a condensation reaction at elevated temperature, using an appropriate reagent, such as ammonium acetate, generates bicyclic compound 7-2. Compound 7-2 can then react with reagents, such as phosphoryl chloride ($POCl_3$), to give intermediate 7-3. A nucleophilic aromatic substitution ($S_NAr$) reaction of intermediate 7-3 with amine adduct 7-4 (PG is a suitable protecting group, such as 4-methoxybenzyl) affords intermediate 7-5. Compound 7-5 can then be cross-coupled with an adduct of formula 7-6, in which M is a boronic acid, boronic ester or an appropriately substituted metal [e.g., M is $B(OR)_2$, $Sn(Alkyl)_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to generate compound 7-7. The protecting groups in 7-7 are removed, and the resulting intermediate undergoes a halogenation reaction with an appropriate reagent, such as N-Bromosuccinimide (NBS), to afford adduct 7-8. The final product 7-9 can then be synthesized by coupling 7-8 with an adduct of formula 1-12, using similar procedures as described for the preparation of compound 7-7 from 7-5.

Scheme 7

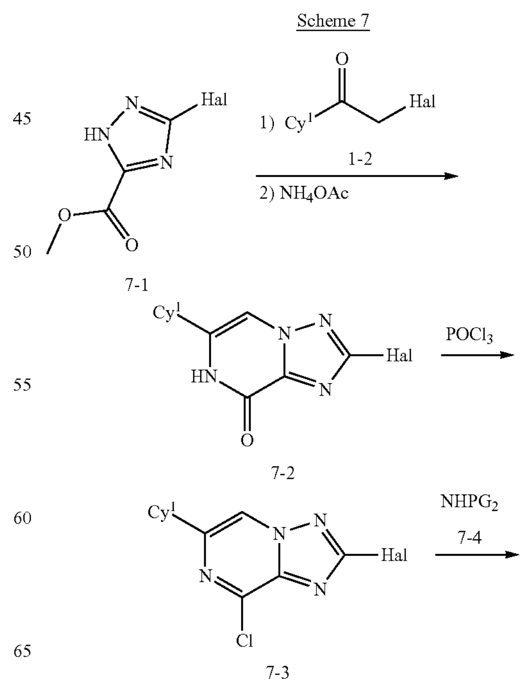

7-1, 7-2, 7-3

-continued

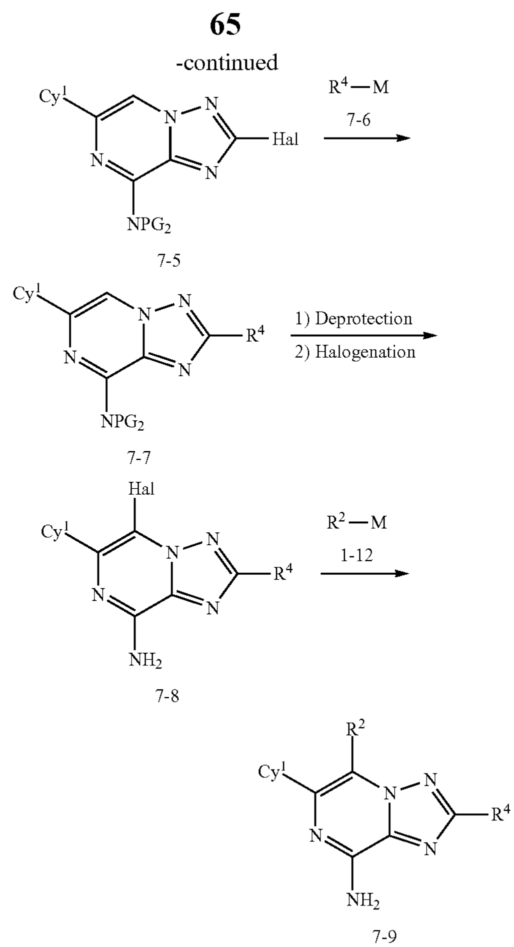

7-5

7-7

7-8

7-9

Compounds of formula 8-7, 8-10, and 8-11 can be prepared via the synthetic route outlined in Scheme 8. Compound 7-5 (can be prepared as described in Scheme 7) can first be cross-coupled with reagent of formula 8-1, in which M is a boronic acid, boronic ester or an appropriately substituted metal [e.g., M is $B(OR)_2$, $Sn(Alkyl)_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to generate compound 8-2. A halogenation reaction of 8-2 can then be carried out using an appropriate reagent, such as 1-bromopyrrolidine-2,5-dione, to afford intermediate 8-3. Another cross-coupling reaction between 8-3 and reagent 1-12 can then be performed using similar conditions as described for the transformation from 7-5 to 8-2 to deliver compound 8-4. The vinyl group in 8-4 is cleaved under suitable conditions, such as using osmium (VIII) oxide and sodium periodate, and the resulting aldehyde 8-5 is reacted with 3-4 in an 1,2-addition reaction ($M^1$ is a metal group, such as MgCl or Li) to generate alcohol 8-6. The protecting group (PG) in 8-6 can then be removed to generate the desired product 8-7.

On the other hand, aldehyde 8-5 can undergo a reduction reaction using appropriate reagents, such as $NaBH_4$, to afford alcohol 8-8. A halogenation reaction of 8-8 then affords intermediate 8-9 using reagents such as $PBr_3$. A cross-coupling reaction between 8-9 and 1-8 (using conditions described for the synthesis of 8-2 from 7-5), followed by the removal of protecting groups (PG), will generate product 8-10. Alternatively, 8-9 can react with amine 4-4 in a nucleophilic substitution ($S_N2$) reaction, followed by removal of protecting groups (PG), to afford product 8-11. The reaction sequence described in this scheme can be rearranged and adjusted accordingly to fit the need of each analogue synthesis.

Scheme 8

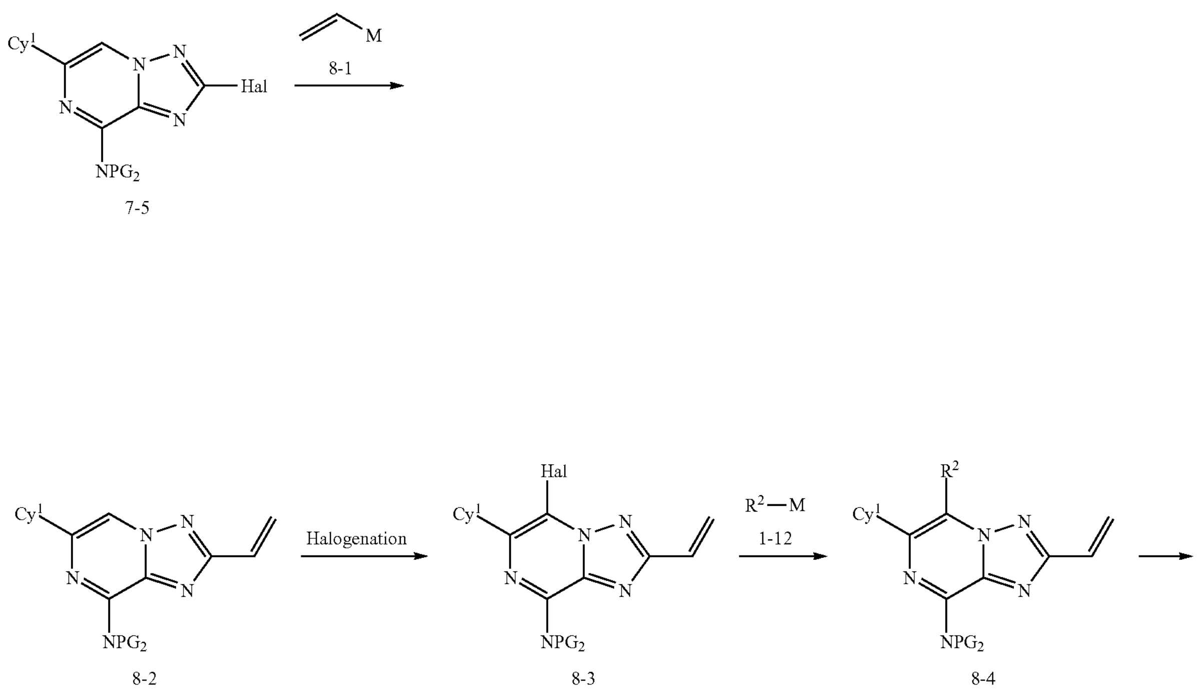

7-5

8-2

8-3

8-4

-continued

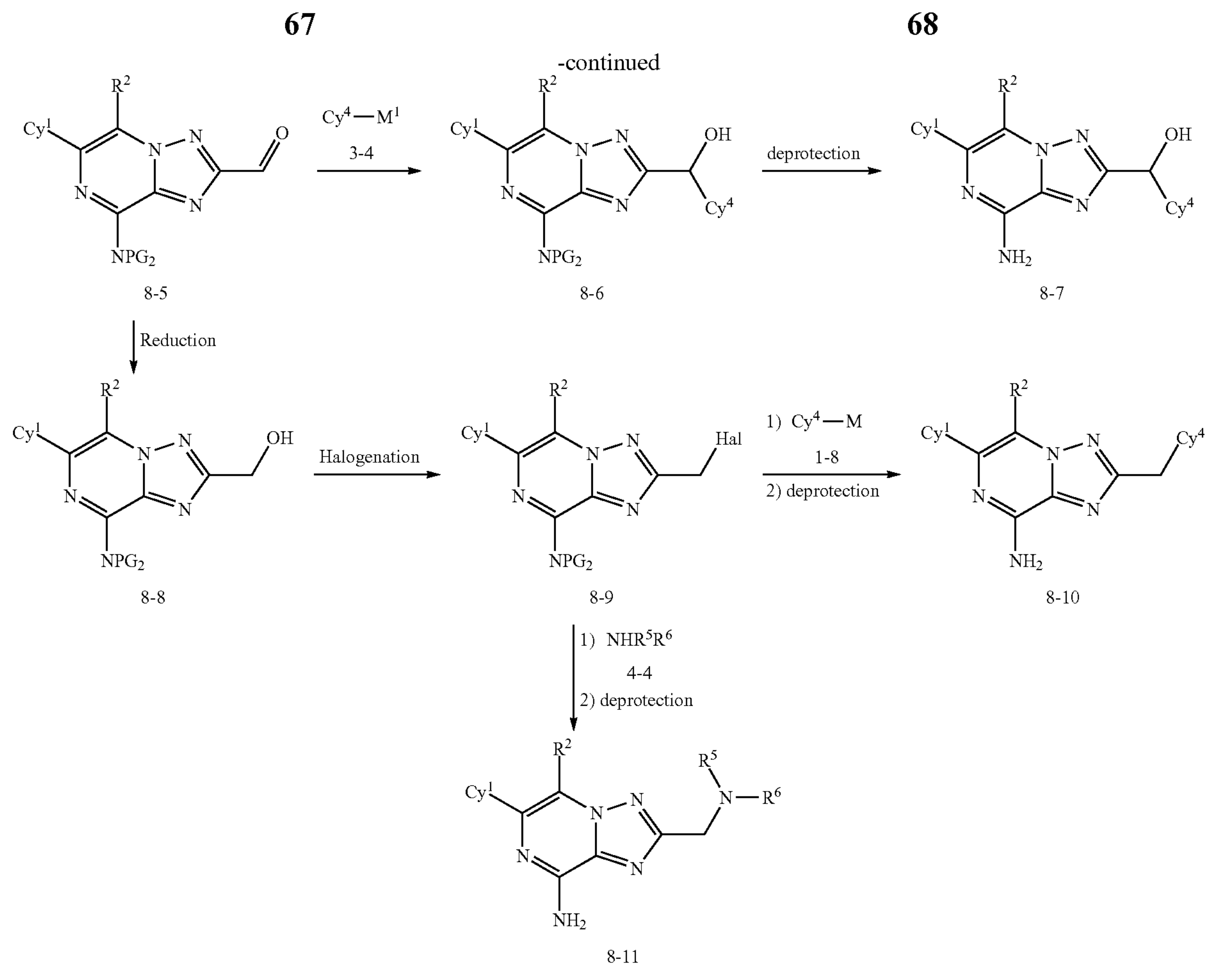

8-5 8-6 8-7 8-8 8-9 8-10 8-11

Compounds of formula 9-9 can be prepared using the synthetic route outlined in Scheme 9. Commercially available starting material 9-1 (Hal is a halide, such as F, Cl, Br, or I) can be subjected to nucleophilic aromatic substitution ($S_NAr$) with amine 7-4 (PG is a suitable protecting group, such as 4-methoxybenzyl) to afford compound 9-2. Intermediate 9-2 can react with an appropriate reagent, such as O-(mesitylsulfonyl)hydroxylamine (*Journal of Heterocyclic Chemistry,* 1975, 12, 107), to form pyrazinium salt 9-3. Intermediate 9-3 can then undergo a condensation reaction with an intermediate of formula 9-4 to form compound 9-5. Compound 9-6 can then be prepared using a cross-coupling reaction between intermediate 9-5 and an intermediate of formula 5-3, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). Compound 9-6 can undergo halogenation using an appropriate reagent, such as N-bromosuccinimide (NBS), to form compound 9-7. Compound 9-8 can be synthesized by coupling 9-7 with an intermediate of formula 1-12, using similar procedures as described for the preparation of compound 9-6 from 9-5. The final product 9-9 can be formed after removal of the protecting group in intermediate 9-8. Certain synthetic steps described herein can be rearranged, and/or omitted, to prepare different analogues.

Scheme 9.

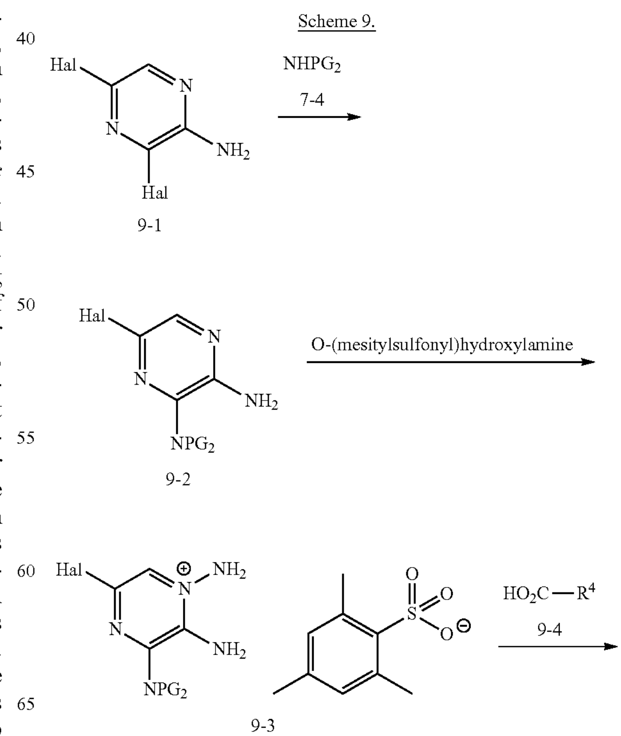

9-1 9-2 9-3

-continued

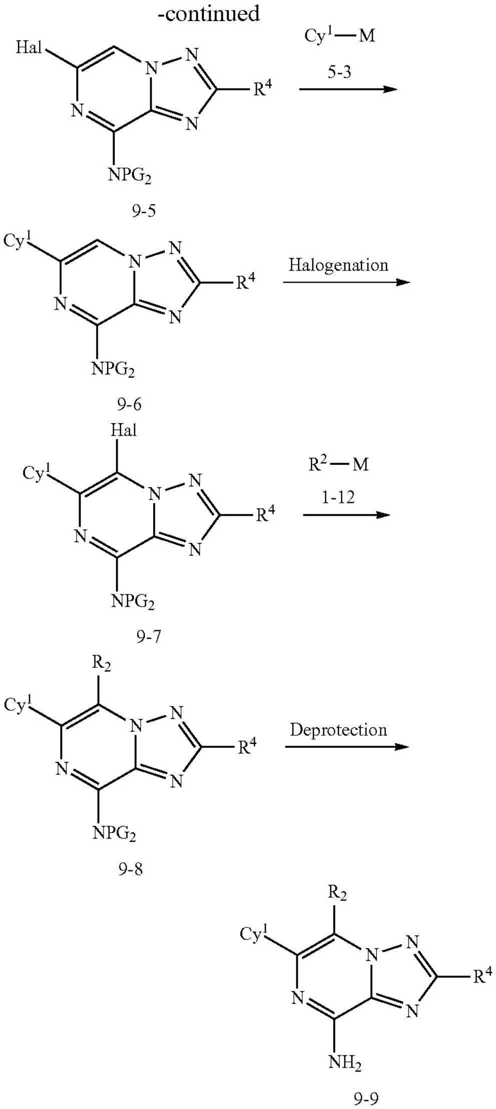

9-5

9-6

9-7

9-8

9-9

Methods of Use

The compounds of the present disclosure can modulate the activity of adenosine receptors, such as subtypes A2A and A2B receptors. Accordingly, the compounds, salts or stereoisomers described herein can be used in methods of inhibiting adenosine receptors (e.g., A2A and/or A2B receptors) by contacting the receptor with any one or more of the compounds, salts, or compositions described herein. In some embodiments, the compounds or salts can be used in methods of inhibiting activity of an adenosine receptor in an individual/patient in need of the inhibition by administering an effective amount of a compound or salt of described herein. In some embodiments, modulating is inhibiting. In some embodiments, the contacting is in vivo. In some embodiments, the contacting is ex vivo or in vitro.

The compounds or salts described herein can be selective. By "selective," it is meant that the compound binds to or inhibits an adenosine receptor with greater affinity or potency, respectively, compared to at least one other receptor, kinase, etc. The compounds of the present disclosure can also be dual antagonists (i.e., inhibitors) of adenosine receptors, e.g., A2A and A2B adenosine receptors.

Another aspect of the present disclosure pertains to methods of treating an adenosine receptor associated disease or disorder in an individual (e.g., patient) by administering to the individual in need of such treatment a therapeutically effective amount or dose of one or more compounds of the present disclosure or a pharmaceutical composition thereof. An adenosine receptor associated disease or disorder can include any disease, disorder or condition that is directly or indirectly linked to expression or activity of the adenosine receptor, including overexpression and/or abnormal activity levels.

The compounds of the present disclosure are useful in the treatment of diseases related to the activity of adenosine receptors including, for example, cancer, inflammatory diseases, cardiovascular diseases, neurodegenerative diseases, immunomodulatory disorders, central nerve system diseases, and diabetes.

Based on the compelling roles of adenosine, e.g., A2A, A2B, receptors in multiple immunosuppressive mechanisms, developing inhibitors can boost the immune system to suppress tumor progression. Adenosine receptor inhibitors can be used to treat, alone or in combination with other therapies, bladder cancer, lung cancer (e.g., non-small cell lung cancer (NSCLC), lung metastasis), melanoma (e.g., metastatic melanoma), breast cancer, cervical cancer, ovarian cancer, colorectal cancer, pancreatic cancer, esophageal cancer, prostate cancer, kidney cancer, skin cancer, thyroid cancer, liver cancer, uterine cancer, head and neck cancer, and renal cell carcinoma (Antonioli, L. et al., *Nature Reviews Cancer,* 2013, 13, 842-857). See also, https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html; Cekic C. et al., *J Immunol,* 2012, 188:198-205; Iannone, R. et al., *Am. J. Cancer Res.* 2014, 4:172-181 (study shows that both A2A and CD73 blockade enhance the antitumor activity of anti-CTLA-4 mAb therapy in a B16F10 murine melanoma model); Iannone, R. et al., *Neoplasia,* 2013, 15:1400-1410 and Beavis PA., et al., *Proc Natl Acad Sci. USA,* 2013, 110:14711-14716 (study shows that A2A and CD73 blockade decreased metastasis in 4T1 breast tumor model with has high CD73 expression). In some embodiments, the prostate cancer is metastatic castrate-resistant prostate carcinoma (mCRPC). In some embodiments, the colorectal cancer is colorectal carcinoma (CRC).

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the compounds of the disclosure can be used in treating pulmonary inflammation, including bleomycin-induced pulmonary fibrosis and injury related to adenosine deaminase deficiency (Baraldi, et al., *Chem. Rev.,* 2008, 108, 238-263).

In some embodiments, the compounds of the disclosure can be used as a treatment for inflammatory disease such as allergic reactions (e.g., A2B adenosine receptor dependent allergic reactions) and other adenosine receptor dependent immune reactions. Further inflammatory diseases that can be treated by compounds of the disclosure include respiratory disorders, sepsis, reperfusion injury, and thrombosis.

In some embodiments, the compounds of the disclosure can be used as a treatment for cardiovascular disease such as coronary artery disease (myocardial infarction, angina pectoris, heart failure), cerebrovascular disease (stroke, transient ischemic attack), peripheral artery disease, and aortic atherosclerosis and aneurysm. Atherosclerosis is an underlying etiologic factor in many types of cardiovascular disease. Atherosclerosis begins in adolescence with fatty streaks, which progress to plaques in adulthood and finally results in thrombotic events that cause occlusion of vessels leading to clinically significant morbidity and mortality. Antagonists to the A2B adenosine receptor and A2A adenosine receptor may be beneficial in preventing atherosclerotic plaque formation (Eisenstein, A. et al., *J. Cell Physiol.,* 2015, 230(12), 2891-2897).

In some embodiments, the compounds of the disclosure can be used as a treatment for disorders in motor activity; deficiency caused by degeneration of the striatonigral dopamine system; and Parkinson's disease; some of the motivational symptoms of depression (Collins, L. E. et al. *Pharmacol. Biochem. Behav.,* 2012, 100, 498-505).

In some embodiments, the compounds of the disclosure can be used as a treatment for diabetes and related disorders, such as insulin resistance. Diabetes affects the production of adenosine and the expression of A2B adenosine receptors (A2BRs) that stimulate IL-6 and CRP production, insulin resistance, and the association between $A_{2B}R$ gene single-nucleotide polymorphisms (ADORA2B SNPs) and inflammatory markers. The increased A2BR signaling in diabetes may increase insulin resistance in part by elevating pro-inflammatory mediators. Selective A2BR blockers may be useful to treat insulin resistance (Figler, R. A. et al. *Diabetes,* 2011, 60 (2), 669-679).

It is believed that compounds provided herein, e.g., compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient", used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, A2A and A2B dual inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the A2A and A2B dual inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab or utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is INCB086550.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3, tumor specific antigens (e.g., CD70) or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein.

The compounds of the present disclosure can be used in combination with one or more additional pharmaceutical agents such as, for example, chemotherapeutics, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-PR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti- EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), *Influenza, Herpes, Giardia, Malaria, Leishmania, Staphylococcus aureus, Pseudomonas aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*Mucor, absidia, rhizophus*), *Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating A2A and/or A2B receptors in tissue samples, including human, and for identifying A2A and/or A2B antagonists by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes adenosine receptor (e.g., A2A and/or A2B) assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as $—CD_3$ being substituted for $—CH_3$). In some embodiments, alkyl groups in any of the disclosed Formulas, e.g., Formula (I), can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as $—CD_3$ being substituted for $—CH_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any "alkyl", "alkenyl", "alkynyl", "aryl", "phenyl", "cycloalkyl", "heterocycloalkyl", or "heteroaryl" substituents or "—$C_{1-6}$ alkyl-", "alkylene", "alkenylene" and "alkynylene" linking groups, as described herein, are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind an adenosine receptor by monitoring its concentration variation when contacting with the adenosine receptor, through tracking of the labeling. For example, a test compound (labeled) can be evaluated for its ability to reduce binding of another compound which is known to bind to a an adenosine receptor (i.e., standard compound). Accordingly, the ability of a test compound to compete with the standard compound for binding to the adenosine receptor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of adenosine receptor-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of an adenosine receptor (e.g., A2A and/or A2B) according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.,* 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Example 1. 4-Amino-6-(3-cyanophenyl)-N-ethyl-7-(1-ethyl-1H-pyrazol-5-yl)pyrazolo[1,5-a]pyrazine-2-carboxamide

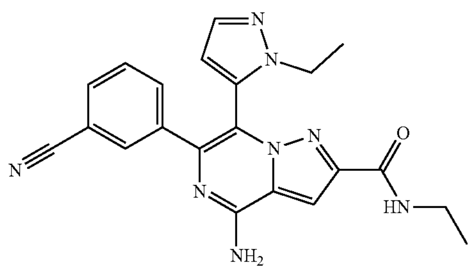 [SMILES: CCNC(=O)c1cc2c(N)nc(-c3cccc(C#N)c3)c(-c3ccnn3CC)n2n1]

Step 1: Diethyl 1-(2-(3-cyanophenyl)-2-oxoethyl)-1H-pyrazole-3,5-dicarboxylate

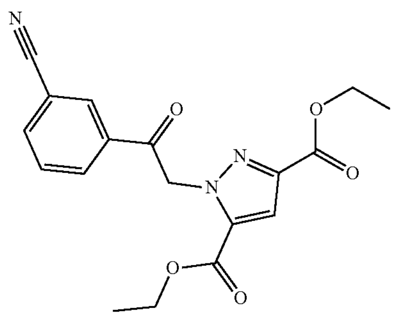 [SMILES: CCOC(=O)c1cc(C(=O)OCC)n(CC(=O)c2cccc(C#N)c2)n1]

To a solution of diethyl 1H-pyrazole-3,5-dicarboxylate (12.9 g, 60.8 mmol), 3-(2-bromoacetyl)benzonitrile (13.62 g, 60.8 mmol) in acetone (253 mL) was added potassium carbonate (9.24 g, 66.9 mmol). The mixture was stirred at room temperature (rt or RT) for 12 h. The reaction mixture was concentrated and the residue was taken up in water and dichloromethane (DCM). The organic phase was washed with brine, dried over $Na_2SO_4$, filtered, and concentrated. The residue was purified with flash chromatography to give the desired product as a white solid (21.6 g, 100%). LC-MS calculated for $C_{18}H_{18}N_3O_5$ $(M+H)^+$: m/z=356.1; found 356.1.

Step 2: Ethyl 6-(3-cyanophenyl)-4-oxo-4,5-dihydropyrazolo[1,5-a]pyrazine-2-carboxylate

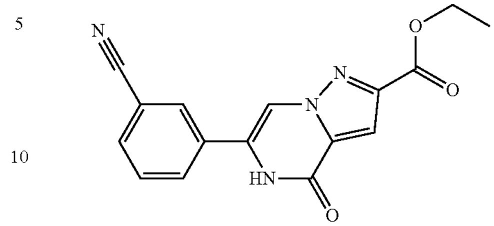

Diethyl 1-(2-(3-cyanophenyl)-2-oxoethyl)-1H-pyrazole-3,5-dicarboxylate (21.6 g, 60.8 mmol) was dissolved in acetic acid (260 mL), and ammonium acetate (46.9 g, 608 mmol) was added. The mixture was stirred at 110° C. for 36 h. After cooling to rt, the mixture was diluted with water, the precipitate was collected via filtration, washed with water, and dried to give the product. LC-MS calculated for $C_{16}H_{13}N_4O_3$ $(M+H)^+$: m/z=309.1; found 309.1.

Step 3: Ethyl 4-chloro-6-(3-cyanophenyl)pyrazolo[1,5-a]pyrazine-2-carboxylate

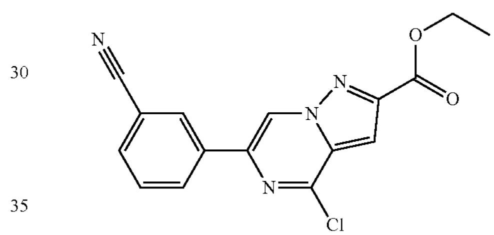

A mixture of ethyl 6-(3-cyanophenyl)-4-oxo-4,5-dihydropyrazolo[1,5-a]pyrazine-2-carboxylate (15.8 g, 51.2 mmol) and $POCl_3$ (96 mL, 1025 mmol) was heated at 110° C. for 4 h. After cooling to rt, the mixture was slowly added to a flask containing ice and sodium bicarbonate. The resulting precipitate was collected, washed with water, and dried to give the product (15.8 g, 94%). LC-MS calculated for $C_{16}H_{12}ClN_4O_2$ $(M+H)^+$: m/z=327.1; found 327.1.

Step 4. Ethyl 6-(3-cyanophenyl)-4-((2,4-dimethoxybenzyl)amino)pyrazolo[1,5-a]pyrazine-2-carboxylate

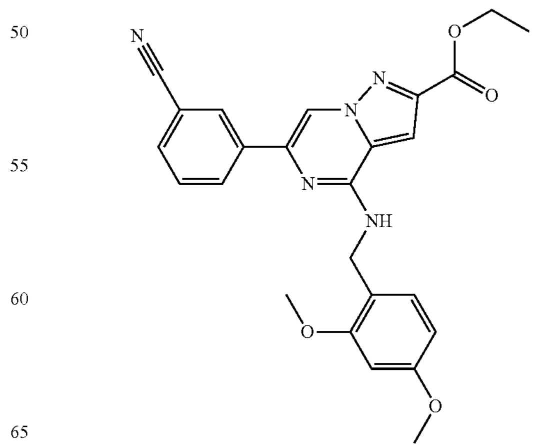

A microwave vial was charged with ethyl 4-chloro-6-(3-cyanophenyl)pyrazolo[1,5-a]pyrazine-2-carboxylate (1.22 g, 3.73 mmol), (2,4-dimethoxyphenyl)methanamine (0.749 g, 4.48 mmol), N,N-diisopropylethylamine (DIEA, 1.304 mL, 7.47 mmol) and butan-1-ol (13.0 mL). The mixture was heated at 180° C. for 30 min in microwave reactor. The mixture was diluted with water, and the resulting precipitate was collected via filtration, washed with water, and dried to give the product (1.5 g, 88%). LC-MS calculated for $C_{25}H_{24}N_5O_4$ $(M+H)^+$: m/z=458.2; found 458.2.

Step 5: 6-(3-Cyanophenyl)-4-((2,4-dimethoxybenzyl)amino)pyrazolo[1,5-a]pyrazine-2-carboxylic acid

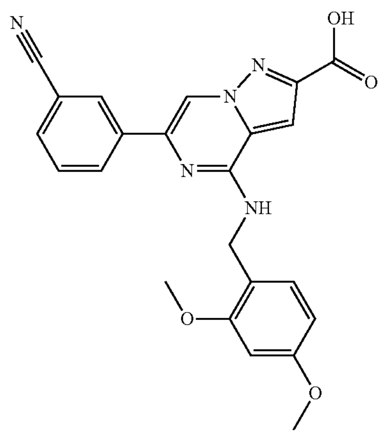 [SMILES: COc1ccc(CNc2nc(-c3cccc(C#N)c3)cn3nc(C(=O)O)cc23)c(OC)c1]

A mixture of ethyl 6-(3-cyanophenyl)-4-((2,4-dimethoxybenzyl)amino)pyrazolo[1,5-a]pyrazine-2-carboxylate (1.35 g, 2.95 mmol), sodium hydroxide (5.90 mL, 5.90 mmol), and acetonitrile (20 mL) was stirred at room temperature for 2 h, The reaction was diluted with 1 N HCl (6 mL). The precipitate was collected via filtration, washed with water, and dried to give the product (1.0 g, 79%). LC-MS calculated for $C_{23}H_{20}N_5O_4$ $(M+H)^+$: m/z=430.1; found 430.1.

Step 6. 4-Amino-6-(3-cyanophenyl)-N-ethylpyrazolo[1,5-a]pyrazine-2-carboxamide

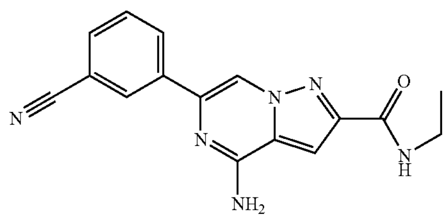 [SMILES: CCNC(=O)c1cc2c(N)nc(-c3cccc(C#N)c3)cn2n1]

To a vial was added 6-(3-cyanophenyl)-4-((2,4-dimethoxybenzyl)amino)pyrazolo[1,5-a]pyrazine-2-carboxylic acid (0.5 g, 1.164 mmol), PyBOP (0.727 g, 1.397 mmol), and dimethylformamide (DMF, 1.0 mL), followed by 2.0 M ethanamine in tetrahydrofuran (THF, 1.164 mL, 2.329 mmol) and N,N-diisopropylethylamine (1.017 mL, 5.82 mmol). After stirring at room temperature (rt) for 2 h, the reaction mixture was diluted with water and DCM. The organic layer was dried over $Na_2SO_4$, filtered, and concentrated. The crude was treated with trifluoroacetic acid (TFA, 0.5 mL) and heated at 90° C. for 30 min. After removing the solvent, the resulting precipitate was washed with water and ethyl acetate to give the desired product as white solid (0.32 g, 90%). LC-MS calculated for $C_{16}H_{15}N_6O$ $(M+H)^+$: m/z=307.1; found 307.1.

Step 7. 4-Amino-7-bromo-6-(3-cyanophenyl)-N-ethylpyrazolo[1,5-a]pyrazine-2-carboxamide

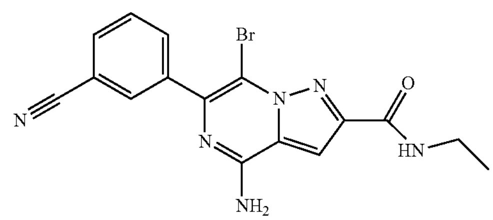 [SMILES: CCNC(=O)c1cc2c(N)nc(-c3cccc(C#N)c3)c(Br)n2n1]

To a solution of 4-amino-6-(3-cyanophenyl)-N-ethylpyrazolo[1,5-a]pyrazine-2-carboxamide (747 mg, 2.439 mmol) in DCM (5 mL) and DMF (1.250 mL) was added N-bromosuccinimide (NBS, 421 mg, 2.365 mmol). The resulting mixture was stirred at room temperature for 1 hour. The reaction mixture was diluted with DCM and water. The organic layer was dried over $Na_2SO_4$, filtered, and concentrated. The precipitate was collected and washed with ethyl acetate to give the desired product as white solid (0.75 g, 80%). LC-MS calculated for $C_{16}H_{14}BrN_6O$ $(M+H)^+$: m/z=385.0, 387.0; found 385.0, 387.0.

Step 8. 4-Amino-6-(3-cyanophenyl)-N-ethyl-7-(1-ethyl-1H-pyrazol-5-yl)pyrazolo[1,5-a]pyrazine-2-carboxamide A mixture of 4-amino-7-bromo-6-(3-cyanophenyl)-N-ethylpyrazolo[1,5-a]pyrazine-2-carboxamide (14 mg, 0.036 mmol), 1-ethyl-5-(4,4,5,5-tetramethyl-1,3,2-dioxaborolan-2-yl)-1H-pyrazole (9.69 mg, 0.044 mmol), dicyclohexyl(2',4',6'-triisopropylbiphenyl-2-yl)phosphine-(2'-aminobiphenyl-2-yl)(chloro)palladium (1:1) (2.86 mg, 3.63 μmol) and tripotassium phosphate hydrate (18.41 mg, 0.080 mmol) in 1,4-dioxane (0.6 mL)/water (0.200 mL) was stirred at 80° C. for 1 h. The residue was dissolved in methanol and 1 N HCl and purified with prep-LCMS (pH 2, acetonitrile/water+TFA) to give the desired product as TFA salt. LC-MS calculated for $C_{21}H_{21}N_8O$ $(M+H)^+$: m/z=401.2; found 401.2. $^1H$ NMR (600 MHz, DMSO) δ 8.07 (t, J=6.0 Hz, 1H), 7.80-7.73 (m, 3H), 7.73-7.70 (m, 1H), 7.56-7.46 (m, 4H), 6.32 (d, J=1.8 Hz, 1H), 3.87 (m, 1H), 3.75 (m, 1H), 3.27 (m, 2H), 1.16 (t, J=7.2 Hz, 3H), 1.08 (t, J=7.1 Hz, 3H).

Example 2. 4-Amino-6-(3-cyanophenyl)-N-ethyl-7-(1-propyl-1H-pyrazol-5-yl)pyrazolo[1,5-a]pyrazine-2-carboxamide

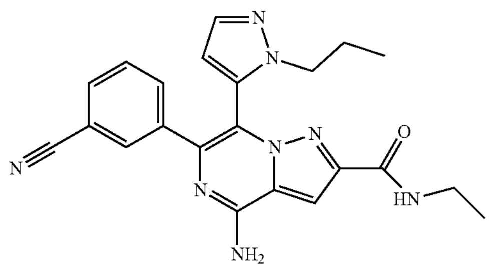 [SMILES: CCCn1nccc1-c1c(-c2cccc(C#N)c2)nc(N)c2cc(C(=O)NCC)nn12]

The title compound was prepared using similar procedures as described for Example 1, with 1-propyl-5-(4,4,5,5-tetramethyl-1,3,2-dioxaborolan-2-yl)-1H-pyrazole replacing 1-ethyl-5-(4,4,5,5-tetramethyl-1,3,2-dioxaborolan-2-yl)-1H-pyrazole in Step 8. The reaction mixture was purified by prep-HPLC (pH=2, acetonitrile/water+TFA) to give the desired product as TFA salt. LC-MS calculated for $C_{22}H_{23}N_8O$ $(M+H)^+$: m/z=415.2; found 415.2.

Example 3. 4-Amino-6-(3-cyanophenyl)-N-ethyl-7-(1-methyl-6-oxo-1,6-dihydropyridin-3-yl)pyrazolo[1,5-a]pyrazine-2-carboxamide

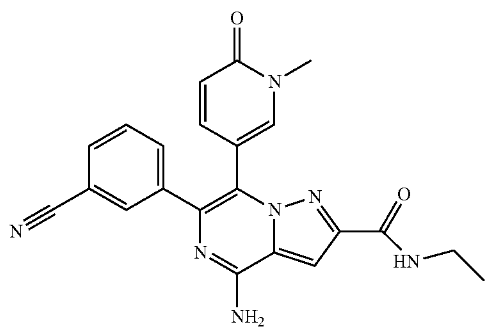 [SMILES: CCNC(=O)c1cc2c(N)nc(-c3cccc(C#N)c3)c(-c3ccc(=O)n(C)c3)n2n1]

The title compound was prepared using similar procedures as described for Example 1 with 1-methyl-5-(4,4,5,5-tetramethyl-1,3,2-dioxaborolan-2-yl)pyridin-2(1H)-one replacing 1-ethyl-5-(4,4,5,5-tetramethyl-1,3,2-dioxaborolan-2-yl)-1H-pyrazole in Step 8. The reaction mixture was purified by prep-HPLC (pH=2, acetonitrile/water+TFA) to give the desired product as TFA salt. LC-MS calculated for $C_{22}H_{20}N_7O_2$ $(M+H)^+$: m/z=414.2; found 414.2.

Example 4. 4-Amino-6-(3-cyanophenyl)-N-ethyl-7-(pyrimidin-4-yl)pyrazolo[1,5-a]pyrazine-2-carboxamide

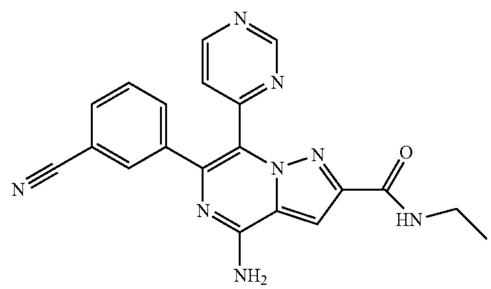 [SMILES: CCNC(=O)c1cc2c(N)nc(-c3cccc(C#N)c3)c(-c3ccncn3)n2n1]

A mixture of 4-amino-7-bromo-6-(3-cyanophenyl)-N-ethylpyrazolo[1,5-a]pyrazine-2-carboxamide (Example 1, Step 7; 10 mg, 0.026 mmol), 4-(tributylstannyl)pyrimidine (14.4 mg, 0.039 mmol), and copper(I) chloride (3.1 mg, 0.031 mmol), lithium chloride (1.3 mg, 0.031 mmol) and tetrakis(triphenylphosphine)palladium(0) (3.0 mg, 2.60 μmol) in THE (1.0 mL) was first purged with $N_2$, and then heated and stirred at 90° C. for 2 h. The reaction mixture was purified by prep-HPLC (pH=2, acetonitrile/water+TFA) to give the desired product as TFA salt (4.2 mg, 42%). LC-MS calculated for $C_{20}H_{17}N_8O$ $(M+H)^+$: m/z=385.1; found 385.1.

Example 5. 4-Amino-6-(3-cyanophenyl)-7-(1,1-difluoroethyl)-N-ethylpyrazolo[1,5-a]pyrazine-2-carboxamide

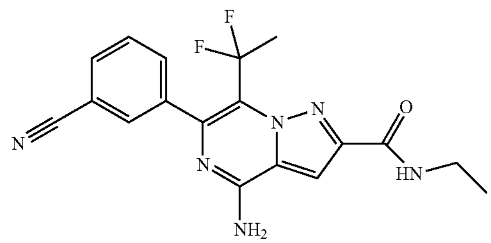 [SMILES: CCNC(=O)c1cc2c(N)nc(-c3cccc(C#N)c3)c(C(C)(F)F)n2n1]

To a vial was added 4-amino-6-(3-cyanophenyl)-N-ethylpyrazolo[1,5-a]pyrazine-2-carboxamide (Example 1, Step 6; 20.0 mg, 0.065 mmol), sodium 1,1-difluoroethane-1-sulfinate (59.6 mg, 0.392 mmol), diethyl carbonate (2.0 mL), water (1.3 mL) and tert-butyl hydroperoxide (0.090 mL, 0.653 mmol). The resulting mixture was heated at 90° C. for 3 h. The reaction mixture was purified by prep-LCMS (pH=2, acetonitrile/water+TFA) to give the desired product as TFA salt (5.6 mg, 23%). LC-MS calculated for $C_{18}H_{17}F_2N_6O$ $(M+H)^+$: m/z=371.1; found 371.1.

Example 6. 4-Amino-6-(3-cyanophenyl)-N-ethyl-7-(1-(trifluoromethyl)cyclopropyl)pyrazolo[1,5-a]pyrazine-2-carboxamide

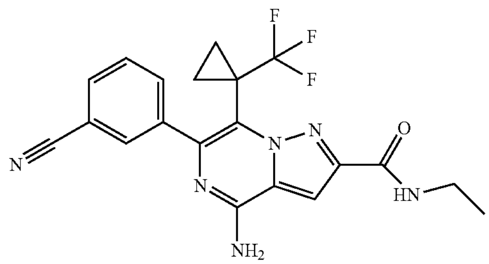 [SMILES: CCNC(=O)c1cc2c(N)nc(-c3cccc(C#N)c3)c(C3(C(F)(F)F)CC3)n2n1]

The title compound was prepared using similar procedures as described for Example 5 with sodium 1-(trifluoromethyl)cyclopropane-1-sulfinate replacing sodium 1,1-difluoroethane-1-sulfinate. The reaction mixture was purified by prep-LCMS (pH=2, acetonitrile/water+TFA) to give the desired product as TFA salt. LC-MS calculated for $C_{20}H_{18}F_3N_6O$ $(M+H)^+$: m/z=415.1; found 415.1.

Example 7. 3-(4-Amino-2-(azetidine-1-carbonyl)-7-(pyrimidin-4-yl)pyrazolo[1,5-a]pyrazin-6-yl)benzonitrile

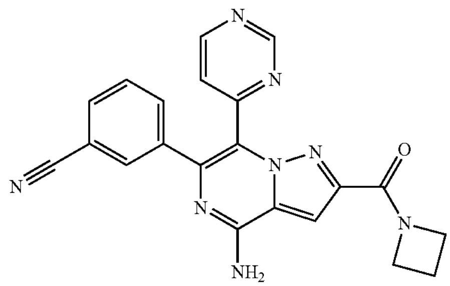 [SMILES: N#Cc1cccc(-c2nc(N)c3cc(C(=O)N4CCC4)nn3c2-c2ccncn2)c1]

Step 1. Ethyl 4-amino-7-bromo-6-(3-cyanophenyl)pyrazolo[1,5-a]pyrazine-2-carboxylate

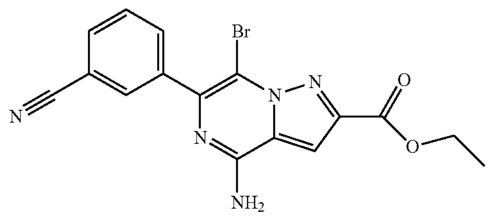 [SMILES: CCOC(=O)c1cc2c(N)nc(-c3cccc(C#N)c3)c(Br)n2n1]

To a solution of ethyl 6-(3-cyanophenyl)-4-((2,4-dimethoxybenzyl)amino)pyrazolo[1,5-a]pyrazine-2-carboxylate (Example 1, Step 4; 8.35 g, 18.26 mmol) was treated with TFA (20 mL) and heated at 90° C. for 30 min. After removing the solvent, the resulting precipitate was washed with water and ethyl acetate. The crude product was dissolved in DCM (73.0 mL) and DMF (18.26 mL), to this solution NBS (3.15 g, 17.71 mmol) was added. The resulting mixture was stirred at room temperature for 1 h. The reaction mixture was diluted with DCM and water. The precipitate was collected vial filtration and washed with water to give the desired product as a white solid (5.6 g, 79%). LC-MS calculated for $C_{16}H_{13}BrN_5O_2$ $(M+H)^+$: m/z=386.0; found 386.0.

Step 2. Ethyl 4-amino-6-(3-cyanophenyl)-7-(pyrimidin-4-yl)pyrazolo[1,5-a]pyrazine-2-carboxylate

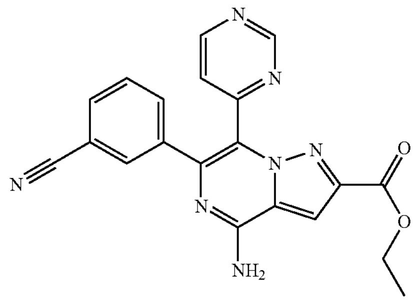 [SMILES: CCOC(=O)c1cc2c(N)nc(-c3cccc(C#N)c3)c(-c3ccncn3)n2n1]

A mixture of ethyl 4-amino-7-bromo-6-(3-cyanophenyl)pyrazolo[1,5-a]pyrazine-2-carboxylate (904 mg, 2.341 mmol), 4-(tributylstannyl)pyrimidine (1.3 g, 3.51 mmol), copper(I) chloride (278 mg, 2.81 mmol), lithium chloride (119 mg, 2.81 mmol), and tetrakis(triphenylphosphine)palladium(0) (270 mg, 0.234 mmol) in THE (15 mL) was first purged with $N_2$, and then heated and stirred at 90° C. for 2 h. The reaction was diluted with ethyl acetate and water, and the aqueous layer was extracted with ethyl acetate. The combined organic layers were washed with brine, dried over $Na_2SO_4$, filtered, and concentrated. The residue was purified with flash chromatography to give the desired product (0.34 g, 38%). LC-MS calculated for $C_{20}H_{16}N_7O_2$ $(M+H)^+$: m/z=386.1; found 386.2.

Step 3. 4-Amino-6-(3-cyanophenyl)-7-(pyrimidin-4-yl)pyrazolo[1,5-a]pyrazine-2-carboxylic acid

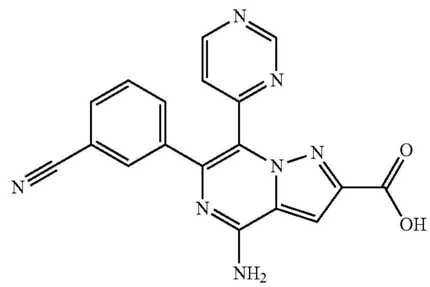 [SMILES: N#Cc1cccc(-c2nc(N)c3cc(C(=O)O)nn3c2-c2ccncn2)c1]

A mixture of ethyl 4-amino-6-(3-cyanophenyl)-7-(pyrimidin-4-yl)pyrazolo[1,5-a]pyrazine-2-carboxylate (340 mg, 0.882 mmol), 1.0 M sodium hydroxide (4.41 mL, 4.41 mmol), acetonitrile (10 mL), and THF (5.00 mL) was stirred at room temperature for 2 h. The reaction was quenched with 1 N HCl to pH 4. After removing most of the organic solvent, the precipitate was collected via filtration, washed with water, and dried under vacuum to give the desired product as a white solid (295 mg, 94%). LC-MS calculated for $C_{18}H_{12}N_7O_2$ $(M+H)^+$: m/z=358.1; found 358.1.

Step 4. 3-(4-Amino-2-(azetidine-1-carbonyl)-7-(pyrimidin-4-yl)pyrazolo[1,5-a]pyrazin-6-yl)benzonitrile To a solution of 4-amino-6-(3-cyanophenyl)-7-(pyrimidin-4-yl)pyrazolo[1,5-a]pyrazine-2-carboxylic acid (8.0 mg, 0.022 mmol) and HATU (8.51 mg, 0.022 mmol) in N,N-dimethylformamide (1.0 mL), was added azetidine (3.02 μl, 0.045 mmol) and DIEA (7.82 μl, 0.045 mmol). After stirring at rt for 2 h, The reaction mixture was purified by prep-HPLC (pH=2, acetonitrile/water+TFA) to give the desired product as TFA salt (2.5 mg, 28%). LC-MS calculated for $C_{21}H_{17}N_8O$ $(M+H)^+$: m/z=397.1; found 397.1. $^1H$ NMR (500 MHz, DMSO) δ 9.11 (m, 1H), 8.94 (d, J=5.2 Hz, 1H), 7.96-7.90 (m, 2H), 7.79-7.73 (m, 3H), 7.55 (m, 2H), 7.47 (t, J=7.7 Hz, 1H), 4.29 (t, J=7.7 Hz, 2H), 4.03 (t, J=7.7 Hz, 2H), 2.24 (m, 2H).

Example 8. 3-(4-Amino-7-(pyrimidin-4-yl)-2-(pyrrolidine-1-carbonyl)pyrazolo[1,5-a]pyrazin-6-yl)benzonitrile

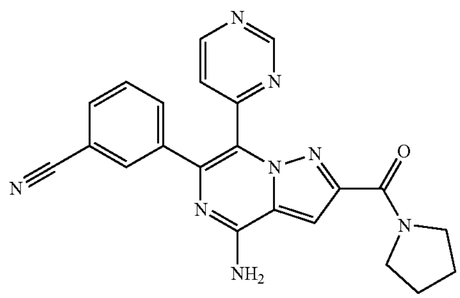 [SMILES: N#Cc1cccc(-c2nc(N)c3cc(C(=O)N4CCCC4)nn3c2-c2ccncn2)c1]

The title compound was prepared using similar procedures as described for Example 7 with pyrrolidine replacing azetidine in Step 4. The reaction mixture was purified by prep-HPLC (pH=2, acetonitrile/water+TFA) to give the desired product as TFA salt. LC-MS calculated for $C_{22}H_{19}N_8O$ $(M+H)^+$: m/z=411.2; found 411.2.

Example 9. 3-(4-Amino-2-(piperidine-1-carbonyl)-7-(pyrimidin-4-yl)pyrazolo[1,5-a]pyrazin-6-yl)benzonitrile

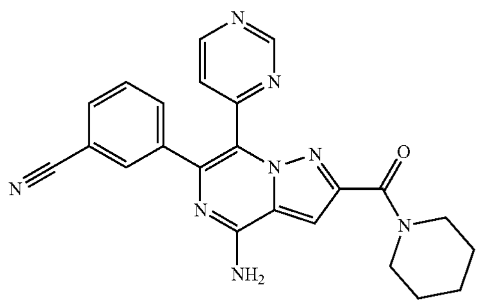 [SMILES: N#Cc1cccc(-c2nc(N)c3cc(C(=O)N4CCCCC4)nn3c2-c2ccncn2)c1]

The title compound was prepared using similar procedures as described for Example 7 with piperidine replacing azetidine in Step 4. The reaction mixture was purified by prep-HPLC (pH=2, acetonitrile/water+TFA) to give the desired product as TFA salt. LC-MS calculated for $C_{23}H_{21}N_8O$ $(M+H)^+$: m/z=425.2; found 425.3.

Example 10. 4-Amino-6-(3-cyanophenyl)-N,N-diethyl-7-(pyrimidin-4-yl)pyrazolo[1,5-a]pyrazine-2-carboxamide

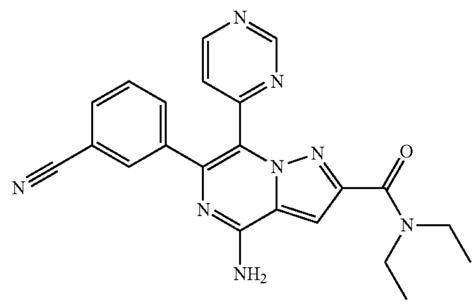 [SMILES: CCN(CC)C(=O)c1cc2c(N)nc(-c3cccc(C#N)c3)c(-c3ccncn3)n2n1]

The title compound was prepared using similar procedures as described for Example 7 with diethylamine replacing azetidine in Step 4. The reaction mixture was purified by prep-HPLC (pH=2, acetonitrile/water+TFA) to give the desired product as TFA salt. LC-MS calculated for $C_{22}H_{21}N_8O$ $(M+H)^+$: m/z=413.2; found 413.2. $^1H$ NMR (500 MHz, DMSO) δ 9.16 (d, J=1.3 Hz, 1H), 8.93 (d, J=5.2 Hz, 1H), 8.02-7.95 (m, 2H), 7.87 (m, 1H), 7.83-7.75 (m, 2H), 7.58-7.38 (m, 3H), 3.50 (q, J=6.8 Hz, 2H), 3.41 (q, J=7.0 Hz, 2H), 1.12 (t, J=7.0 Hz, 3H), 1.00 (t, J=6.9 Hz, 3H).

Example 11. 4-Amino-6-(3-cyanophenyl)-N-ethyl-N-methyl-7-(pyrimidin-4-yl)pyrazolo[1,5-a]pyrazine-2-carboxamide

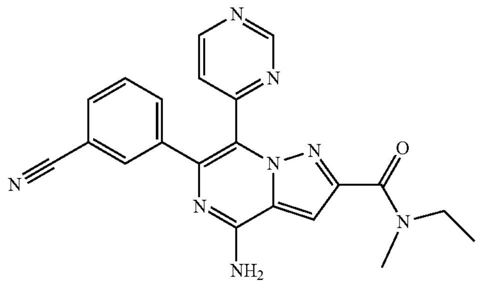 [SMILES: CCN(C)C(=O)c1cc2c(N)nc(-c3cccc(C#N)c3)c(-c3ccncn3)n2n1]

The title compound was prepared using similar procedures as described for Example 7 with N-methylethanamine replacing azetidine in Step 4. The reaction mixture was purified by prep-HPLC (pH=2, acetonitrile/water+TFA) to give the desired product as TFA salt. LC-MS calculated for $C_{21}H_{19}N_8O$ $(M+H)^+$: m/z=399.2; found 399.2.

Example 12. 3-(4-Amino-2-(3-hydroxyazetidine-1-carbonyl)-7-(pyrimidin-4-yl)pyrazolo[1,5-a]pyrazin-6-yl)benzonitrile

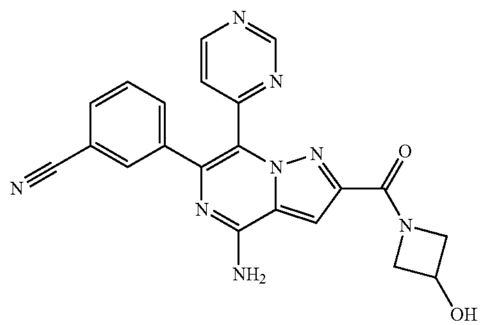 [SMILES: N#Cc1cccc(-c2nc(N)c3cc(C(=O)N4CC(O)C4)nn3c2-c2ccncn2)c1]

The title compound was prepared using similar procedures as described for Example 7 with azetidin-3-ol replacing azetidine in Step 4. The reaction mixture was purified by prep-HPLC (pH=2, acetonitrile/water+TFA) to give the desired product as TFA salt. LC-MS calculated for $C_{21}H_{17}N_8O_2$ $(M+H)^+$: m/z=413.1; found 413.1.

Example 13. 3-(4-Amino-2-(azetidin-1-ylmethyl)-7-(pyrimidin-4-yl)pyrazolo[1,5-a]pyrazin-6-yl)benzonitrile

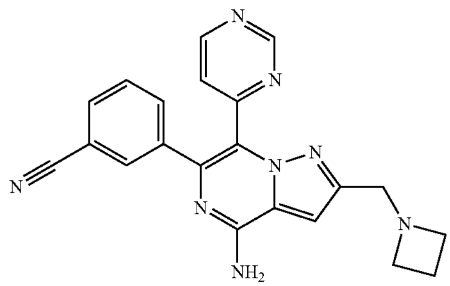 [SMILES: N#Cc1cccc(-c2nc(N)c3cc(CN4CCC4)nn3c2-c2ccncn2)c1]

Step 1. 3-(4-Amino-7-bromo-2-(hydroxymethyl)pyrazolo[1,5-a]pyrazin-6-yl)benzonitrile

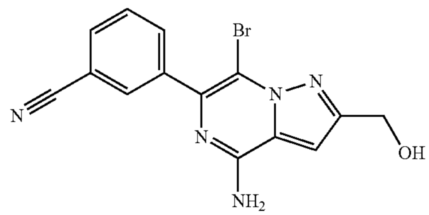 [SMILES: N#Cc1cccc(-c2nc(N)c3cc(CO)nn3c2Br)c1]

To a solution of ethyl 4-amino-7-bromo-6-(3-cyanophenyl)pyrazolo[1,5-a]pyrazine-2-carboxylate (Example 7, Step 1; 0.547 g, 1.416 mmol) in $CH_2Cl_2$ (7.08 mL) and THE (7.08 mL) was added 1.0 M DIBAL-H in THE (4.25 mL, 4.25 mmol) at 0° C. The resulting mixture was warmed to room temperature and stirred overnight. The reaction was diluted with DCM and 1 N NaOH solution. The organic layer was separated and dried over $Na_2SO_4$, filtered, and concentrated. The crude was used in the next step without purification. LC-MS calculated for $C_{14}H_{11}BrN_5O$ $(M+H)^+$: m/z=344.0; found 344.0.

Step 2. 3-(4-Amino-2-(hydroxymethyl)-7-(pyrimidin-4-yl)pyrazolo[1,5-a]pyrazin-6-yl)benzonitrile

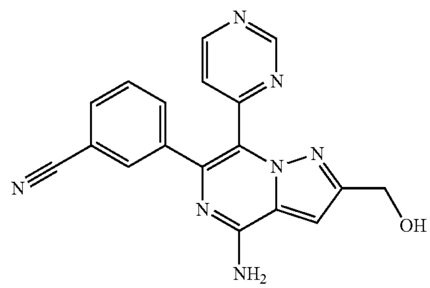 [SMILES: N#Cc1cccc(-c2nc(N)c3cc(CO)nn3c2-c2ccncn2)c1]

A mixture of 3-(4-amino-7-bromo-2-(hydroxymethyl)pyrazolo[1,5-a]pyrazin-6-yl)benzonitrile (487 mg, 1.415 mmol), 4-(tributylstannyl)pyrimidine (575 mg, 1.556 mmol), copper(I) chloride (168 mg, 1.698 mmol), lithium chloride (72.0 mg, 1.698 mmol) and tetrakis(triphenylphosphine)palladium(0) (164 mg, 0.141 mmol) in THE (12 mL) was first purged with $N_2$, and then heated and stirred at 90° C. for 2 h. The reaction was diluted with ethyl acetate and water, the aqueous layer was extracted with ethyl acetate once. The combined organic layers were washed with brine, dried over $Na_2SO_4$, filtered and concentrated. The residue was purified with flash chromatography to give the desired product (0.16 g, 34% for 2 steps). LC-MS calculated for $C_{18}H_{14}N_7O$ $(M+H)^+$: m/z=344.1; found 344.1.

Step 3. 3-(4-Amino-2-formyl-7-(pyrimidin-4-yl)pyrazolo[1,5-a]pyrazin-6-yl)benzonitrile

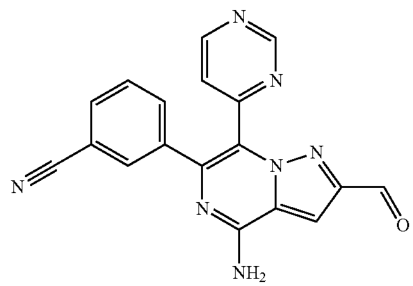 [SMILES: N#Cc1cccc(-c2nc(N)c3cc(C=O)nn3c2-c2ccncn2)c1]

A mixture of 3-(4-amino-2-(hydroxymethyl)-7-(pyrimidin-4-yl)pyrazolo[1,5-a]pyrazin-6-yl)benzonitrile (160 mg, 0.466 mmol), Dess-Martin periodinane (237 mg, 0.559 mmol), and $CH_2Cl_2$ (4660 μL) was stirred at room temperature for 2 h. The reaction was diluted with DCM and saturated $NaHCO_3$ solution. After stirring for 30 min, the organic layer was separated and dried over $Na_2SO_4$, filtered, and concentrated. The crude was used in the next step without purification. LC-MS calculated for $C_{18}H_{12}N_7O$ $(M+H)^+$: m/z=342.1; found 342.1.

Step 4. 3-(4-Amino-2-(azetidin-1-ylmethyl)-7-(pyrimidin-4-yl)pyrazolo[1,5-a]pyrazin-6-yl)benzonitrile To a mixture of 3-(4-amino-2-formyl-7-(pyrimidin-4-yl)pyrazolo[1,5-a]pyrazin-6-yl)benzonitrile (10 mg, 0.029 mmol) and azetidine (3.35 mg, 0.059 mmol) in DCM (1 mL) was added sodium triacetoxyborohydride (12.4 mg, 0.059 mmol). After stirring at room temperature for 2.5 h, solvent was removed in vacuo. The resulting residue was dissolved in methanol and 1 N HCl (1 N) and purified with prep-LCMS (pH=2, acetonitrile/water+TFA) to give the desired product as TFA salt. LC-MS calculated for $C_{21}H_{19}N_8$ $(M+H)^+$: m/z=383.2; found 383.2.

Example 14. Ethyl (8-amino-6-(3-cyanophenyl)-[1,2,4]triazolo[1,5-a]pyrazin-2-yl)carbamate

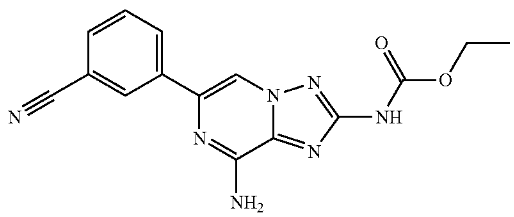 [SMILES: CCOC(=O)Nc1nc2c(N)nc(-c3cccc(C#N)c3)cn2n1]

Step 1. tert-Butyl ((mesitylsulfonyl)oxy)carbamate

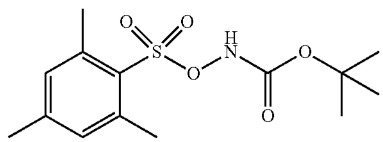 [SMILES: Cc1cc(C)c(S(=O)(=O)ONC(=O)OC(C)(C)C)c(C)c1]

To a solution of 2,4,6-trimethylbenzenesulfonyl chloride (9.10 g, 41.6 mmol) and tert-butyl N-hydroxycarbamate (5.54 g, 41.6 mmol) in methyl tert-butyl ether (MTBE, 90 mL) was added triethylamine (TEA, 6.09 mL, 43.7 mmol) dropwise while stirring at 0° C. The resulting suspension was stirred at 0° C. for an additional 30 min and then warmed to ambient temperature. The reaction was then diluted with water (90 mL) and adjusted to pH 4 with 1 N HCl. The organic layer was washed with brine, dried over $Na_2SO_4$, filtered, and concentrated to give the desired product. LC-MS calculated for $C_{14}H_{22}NO_5S$ $(M+H)^+$: m/z=316.1; found 316.1.

Step 2. O-(Mesitylsulfonyl)hydroxylamine

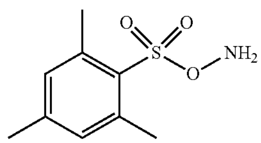

To TFA (37.7 mL, 490 mmol) at 0° C. was slowly added tert-butyl ((mesitylsulfonyl)oxy)carbamate (12.56 g, 39.8 mmol). The reaction mixture was stirred at 0° C. for 1.5 h and then quenched with the sequential addition of crushed ice and water. The resulting white suspension was vigorously stirred at ambient temperature for 5 min. Without allowing the filter cake to run dry, the solids were collected by careful vacuum filtration followed by subsequent rinsing with water until the filtrate reached pH 6. The wet filtrate was taken up in DCM and the resulting biphasic solution was separated. The DCM layer was dried over $MgSO_4$ for 30 min and then filtered and rinsed with DCM to provide the compound as a solution. LC-MS calculated for $C_9H_{14}NO_3S$ $(M+H)^+$: m/z=216.1; found 216.1.

Step 3. 1,2-Diamino-3,5-dibromopyrazin-1-ium 2,4,6-trimethylbenzenesulfonate

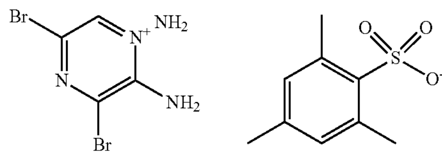

To a solution of O-(mesitylsulfonyl)hydroxylamine (2.468 g, 11.47 mmol) in $CH_2Cl_2$ (50 mL) was added 3,5-dibromopyrazin-2-amine (2.90 g, 11.47 mmol), and the resulting solution was stirred at ambient temperature overnight. The precipitate was collected vial filtration and dried under vacuum. LC-MS calculated for $C_4H_5Br_2N_4(M)^+$: m/z=266.9; found 266.9.

Step 4. Ethyl (6,8-dibromo-[1,2,4]triazolo[1,5-a]pyrazin-2-yl)carbamate

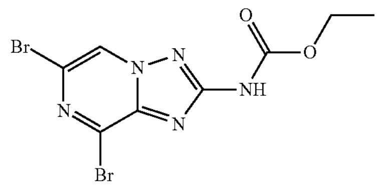 [SMILES: CCOC(=O)Nc1nc2c(Br)nc(Br)cn2n1]

To a suspension of 1,2-diamino-3,5-dibromopyrazin-1-ium 2,4,6-trimethylbenzenesulfonate (190 mg, 0.406 mmol) in DCM (1.0 mL) and N,N-dimethylformamide (1 mL) was added O-ethyl carbonisothiocyanatidate (52.7 μl, 0.446 mmol). The resulting mixture as stirred at room temperature for 3 h. The reaction mixture was diluted with DCM and water. The organic layer was separated and dried over $Na_2SO_4$, filtered, and concentrated in vacuo. The residue was purified with flash chromatography to give the desired product (10 mg, 8%) LC-MS calculated for $C_8H_8Br_2N_5O_2$ $(M+H)^+$: m/z=365.9; found 365.8.

Step 5. Ethyl (6-bromo-8-((2,4-dimethoxybenzyl) amino)-[1,2,4]triazolo[1,5-a]pyrazin-2-yl)carbamate

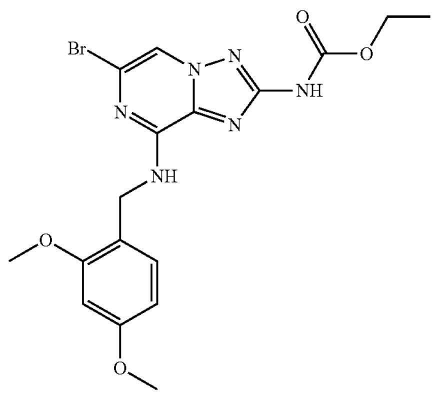 [SMILES: CCOC(=O)Nc1nc2c(NCc3ccc(OC)cc3OC)nc(Br)cn2n1]

To a mixture of ethyl (6,8-dibromo-[1,2,4]triazolo[1,5-a] pyrazin-2-yl)carbamate (10 mg, 0.027 mmol) and (2,4-dimethoxyphenyl)methanamine (4.58 mg, 0.027 mmol) in DCM (1 mL) was added DIEA (9.57 μl, 0.055 mmol). After stirring at 40° C. for 2.5 h, the solvent was removed in vacuo. The residue was purified with flash chromatography to give the desired product (6.0 mg, 49%). LC-MS calculated for $C_{17}H_{20}BrN_6O_4$ $(M+H)^+$: m/z=451.1, 453.1; found 451.1, 453.1.

Step 6. Ethyl (6-(3-cyanophenyl)-8-((2,4-dimethoxybenzyl)amino)-[1,2,4]triazolo[1,5-a]pyrazin-2-yl)carbamate

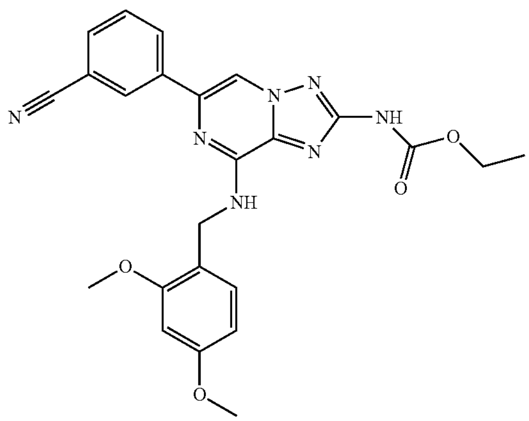 [SMILES: CCOC(=O)Nc1nc2c(NCc3ccc(OC)cc3OC)nc(-c3cccc(C#N)c3)cn2n1]

A mixture of ethyl (6-bromo-8-((2,4-dimethoxybenzyl) amino)-[1,2,4]triazolo[1,5-a]pyrazin-2-yl)carbamate (6.0 mg, 0.013 mmol), (3-cyanophenyl)boronic acid (1.954 mg, 0.013 mmol), dicyclohexyl(2',4',6'-triisopropylbiphenyl-2-yl)phosphine-(2'-aminobiphenyl-2-yl)(chloro)palladium (1:1) (1.046 mg, 1.330 μmol) and tripotassium phosphate hydrate (6.74 mg, 0.029 mmol) in 1,4-dioxane (0.6 mL)/ water (0.200 mL) was stirred at 70° C. for 1 h. The resulting residue was dissolved in methanol and 1 N HCl and purified with prep-LCMS (pH 2) to give the desired product as white solid (4.2 mg, 66%). LC-MS calculated for $C_{24}H_{24}N_7O_4$ $(M+H)^+$: m/z=474.2; found 474.2.

Step 7. Ethyl (8-amino-6-(3-cyanophenyl)-[1,2,4] triazolo[1,5-a]pyrazin-2-yl)carbamate A mixture of ethyl (6-(3-cyanophenyl)-8-((2,4-dimethoxybenzyl)amino)-[1,2,4]triazolo[1,5-a]pyrazin-2-yl)carbamate (6.3 mg, 0.013 mmol) and trifluoroacetic acid (0.3 mL) was stirred at 90° C. for 30 min. The volatiles were removed and the resulting residue was diluted with methanol and purified with prep-LCMS (pH=2, acetonitrile/water+ TFA) to give the desired product as TFA salt (0.3 mg, 7%). LC-MS calculated for $C_{15}H_{14}N_7O_2$ $(M+H)^+$: m/z=324.1; found 324.1.

Example 15. 3-(8-Amino-5-(6-oxo-1,6-dihydropyridin-3-yl)-[1,2,4]triazolo[1,5-a]pyrazin-6-yl)benzonitrile

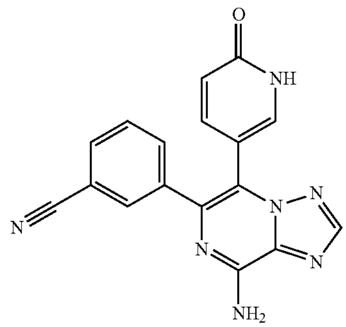 [SMILES: N#Cc1cccc(-c2nc(N)c3ncnn3c2-c2ccc(=O)[nH]c2)c1]

Step 1. 6-Bromo-N-(2,4-dimethoxybenzyl)-[1,2,4] triazolo[1,5-a]pyrazin-8-amine

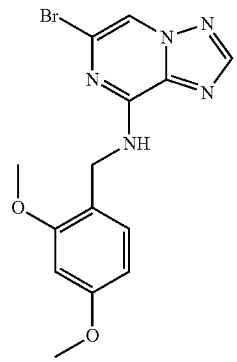 [SMILES: COc1ccc(CNc2nc(Br)cn3ncnc23)c(OC)c1]

A vial was charged with 6,8-dibromo-[1,2,4]triazolo[1,5-a]pyrazine (720 mg, 2.59 mmol), (2,4-dimethoxyphenyl) methanamine (433 mg, 2.59 mmol), DIEA (679 μl, 3.89 mmol), 2-propanol (6 mL), and N,N-dimethylformamide (6 mL). The mixture was heated at 90° C. for 2 h and then diluted with water. The resulting precipitate was collected vial filtration (0.94 g, 100%). LC-MS calculated for $C_{14}H_{15}BrN_5O_2$ $(M+H)^+$: m/z=364.0, 366.0; found 364.0, 366.0.

Step 2. 3-(8-((2,4-Dimethoxybenzyl)amino)-[1,2,4]triazolo[1,5-a]pyrazin-6-yl)benzonitrile

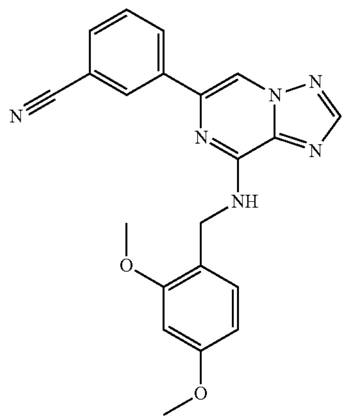 [SMILES: COc1ccc(CNc2nc(-c3cccc(C#N)c3)cn3ncnc23)c(OC)c1]

A mixture of 6-bromo-N-(2,4-dimethoxybenzyl)-[1,2,4]triazolo[1,5-a]pyrazin-8-amine (0.94 g, 2.58 mmol), (3-cyanophenyl)boronic acid (0.417 g, 2.84 mmol), dicyclohexyl(2',4',6'-triisopropylbiphenyl-2-yl)phosphine-(2'-aminobiphenyl-2-yl)(chloro)palladium (1:1) (0.203 g, 0.258 mmol) and tripotassium phosphate hydrate (1.486 g, 6.45 mmol) in 1,4-dioxane (9.68 mL)/water (3.23 mL) was stirred at 70° C. for 1 h. After cooling to rt, the mixture was diluted with water. The resulting precipitate was collected via filtration (0.7 g, 70%). LC-MS calculated for $C_{21}H_{19}N_6O_2$ $(M+H)^+$: m/z=387.1; found 387.1.

Step 3. 3-(8-Amino-[1,2,4]triazolo[1,5-a]pyrazin-6-yl)benzonitrile

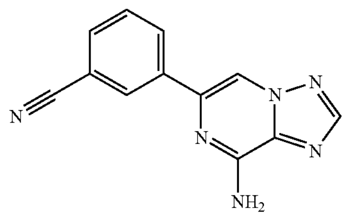 [SMILES: N#Cc1cccc(-c2cn3ncnc3c(N)n2)c1]

A mixture of 3-(8-((2,4-dimethoxybenzyl)amino)-[1,2,4]triazolo[1,5-a]pyrazin-6-yl)benzonitrile (0.70 g, 1.812 mmol) and trifluoroacetic acid (4.19 mL, 54.3 mmol) was heated at 90° C. for 30 min. The volatiles were removed in vacuo. The resulting solid was washed with water and ethyl acetate and dried under vacuum (0.35 g, 82%). LC-MS calculated for $C_{12}H_9N_6$ $(M+H)^+$: m/z=237.1; found 237.1.

Step 4. 3-(8-Amino-5-bromo-[1,2,4]triazolo[1,5-a]pyrazin-6-yl)benzonitrile

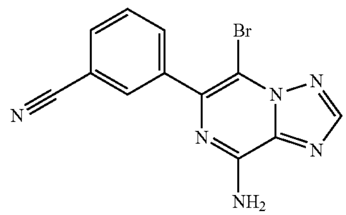

To a solution of 3-(8-amino-[1,2,4]triazolo[1,5-a]pyrazin-6-yl)benzonitrile (129 mg, 0.546 mmol) in DCM (5 mL) and DMF (1.250 mL) was added NBS (94 mg, 0.530 mmol). The resulting mixture was stirred at room temperature for 1 h. The reaction mixture was diluted with DCM and water. The precipitate was collected via filtration and washed with water and ethyl acetate (135 mg, 78%) LC-MS calculated for $C_{12}H_8BrN_6$ $(M+H)^+$: m/z=315.0, 317.0; found 315.0, 317.0.

Step 5. 3-(8-Amino-5-(6-methoxypyridin-3-yl)-[1,2,4]triazolo[1,5-a]pyrazin-6-yl)benzonitrile

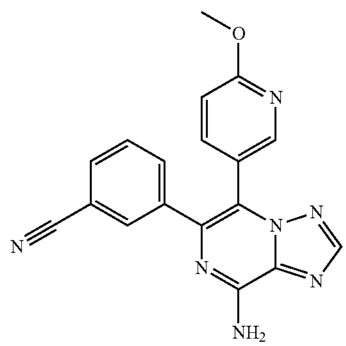 [SMILES: COc1ccc(-c2c(-c3cccc(C#N)c3)nc(N)c3ncnn23)cn1]

A mixture of 3-(8-amino-5-bromo-[1,2,4]triazolo[1,5-a]pyrazin-6-yl)benzonitrile (20 mg, 0.063 mmol), (6-methoxypyridin-3-yl)boronic acid (9.71 mg, 0.063 mmol), dicyclohexyl(2',4',6'-triisopropylbiphenyl-2-yl)phosphine-(2'-aminobiphenyl-2-yl)(chloro)palladium (1:1) (5.0 mg, 6.35 μmol), and tripotassium phosphate hydrate (32.2 mg, 0.140 mmol) in 1,4-dioxane (0.6 mL)/water (0.200 mL) was stirred at 70° C. for 1 h. The residue was dissolved in methanol and 1 N HCl and purified with prep-LCMS (pH=2, acetonitrile/water+TFA) to give the desired product as white solid (12 mg, 55%). LC-MS calculated for $C_{18}H_{14}N_7O$ $(M+H)^+$: m/z=344.1; found 344.1.

Step 6. 3-(8-Amino-5-(6-oxo-1,6-dihydropyridin-3-yl)-[1,2,4]triazolo[1,5-a]pyrazin-6-yl)benzonitrile A mixture of 3-(8-amino-5-(6-methoxypyridin-3-yl)-[1,2,4]triazolo[1,5-a]pyrazin-6-yl)benzonitrile (10 mg, 0.029 mmol), potassium iodide (14.50 mg, 0.087 mmol), and acetic acid (1.0 mL) was heated at 90° C. for 1 h. The mixture was diluted with methanol and purified with prep-LCMS (pH=2, acetonitrile/water+TFA) to give the desired product as TFA salt (3.5 mg, 37%). LC-MS calculated for $C_{17}H_{12}N_7O$ $(M+H)^+$: m/z=330.1; found 330.1.

Example 16. 3-(4-Amino-2-(pyridin-2-ylmethyl)pyrazolo[1,5-a]pyrazin-6-yl)benzonitrile

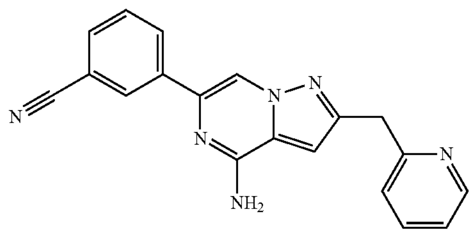 [SMILES: N#Cc1cccc(-c2cn3nc(Cc4ccccn4)cc3c(N)n2)c1]

Step 1: 3-(4-(2,4-Dimethoxybenzylamino)-2-(hydroxymethyl)pyrazolo[1,5-a]pyrazin-6-yl)benzonitrile

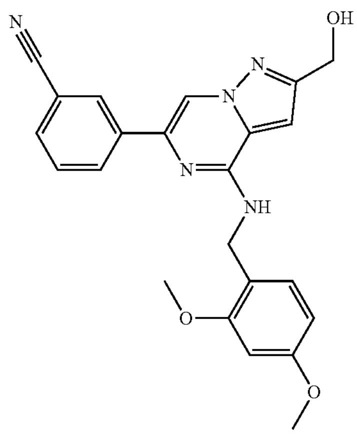 [SMILES: COc1ccc(CNc2nc(-c3cccc(C#N)c3)cn3nc(CO)cc23)c(OC)c1]

To a solution of ethyl 6-(3-cyanophenyl)-4-((2,4-dimethoxybenzyl)amino)pyrazolo[1,5-a]pyrazine-2-carboxylate (Example 1, Step 4; 4.00 g, 8.74 mmol) in THE (200 mL) was added diisobutylaluminum hydride (1.0 M toluene solution, 35.0 mL, 35.0 mmol) at −78° C. The reaction mixture was warmed to rt and stirred at rt for 30 min. The reaction mixture was quenched by adding 300 mL of saturated Rochelle's salt water solution. The resulting mixture was stirred at rt for 1 h, which was then concentrated and the residue was extracted with DCM. The organic phase was washed with brine, dried over $Na_2SO_4$, filtered and concentrated. The residue was purified with flash chromatography to give the desired product as white solid (2.1 g, 58%). LC-MS calculated for $C_{23}H_{22}N_5O_3$ $(M+H)^+$: m/z=416.1; found 416.2.

Step 2: 3-(2-(Bromomethyl)-4-(2,4-dimethoxybenzylamino)pyrazolo[1,5-a]pyrazin-6-yl)benzonitrile

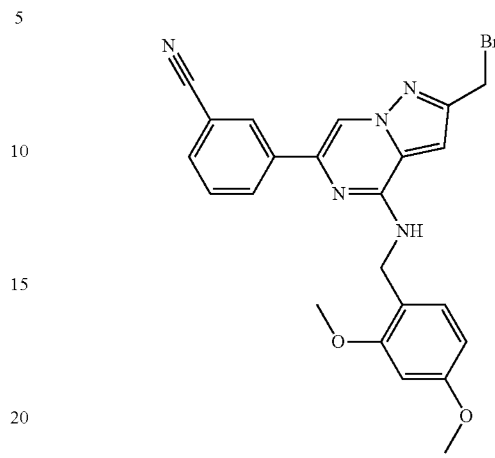

3-(4-(2,4-Dimethoxybenzylamino)-2-(hydroxymethyl)pyrazolo[1,5-a]pyrazin-6-yl)benzonitrile (3.0 g, 7.22 mmol) was dissolved in DCM (200 mL), and $PBr_3$ (1.4 mL, 14.44 mmol) was added. The mixture was stirred at rt for 5 h. After completion, the reaction was quenched by adding sat. $NaHCO_3$, the mixture was then extracted with DCM. The organic phase was washed with brine, dried over $Na_2SO_4$, filtered, and concentrated. The residue was purified with flash chromatography to give the desired product as white solid (2.4 g, 69%). LC-MS calculated for $C_{23}H_{21}BrN_5O_2$ $(M+H)^+$: m/z=478.1; found 478.1.

Step 3: 3-(4-(2,4-Dimethoxybenzylamino)-2-(pyridin-2-ylmethyl)pyrazolo[1,5-a]pyrazin-6-yl)benzonitrile

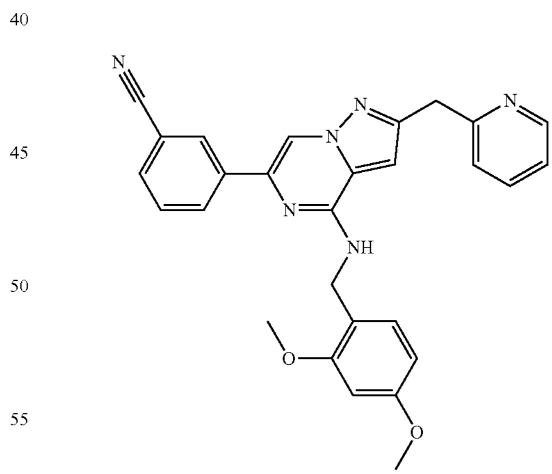

A mixture of 3-(2-(bromomethyl)-4-(2,4-dimethoxybenzylamino)pyrazolo[1,5-a]pyrazin-6-yl)benzonitrile (700 mg, 1.46 mmol), CuI (55.7 mg, 0.293 mmol), CsF (445 mg, 2.93 mmol), tetrakis(triphenylphosphine)palladium(0) (169 mg, 0.146 mmol), and 2-(tributylstannyl)pyridine (646 mg, 1.756 mmol) in 1,4-dioxane (2 mL) was heated at 140° C. for 1 h in a microwave reactor. The reaction was diluted with water and extracted with DCM. The organic phase was washed with brine, dried over $Na_2SO_4$, filtered, and concentrated. The residue was purified with flash chromatography to give the desired product as white solid (428 mg, 62%). LC-MS calculated for $C_{28}H_{25}N_6O_2$ (M+H)$^+$: m/z=477.2; found 477.2.

Step 4. 3-(4-Amino-2-(pyridin-2-ylmethyl)pyrazolo[1,5-a]pyrazin-6-yl)benzonitrile A reaction vial was charged with 3-(4-(2,4-dimethoxybenzylamino)-2-(pyridin-2-ylmethyl)pyrazolo[1,5-a]pyrazin-6-yl)benzonitrile (428 mg, 0.9 mmol) and TFA (1 mL). The mixture was heated at 70° C. for 20 min. The mixture was diluted with water and quenched with sat. $NaHCO_3$. The mixture was extracted with DCM. The organic phase was washed with brine, dried over $Na_2SO_4$, filtered, and concentrated. The residue was purified with flash chromatography to give the desired product as a light yellow solid (260 mg, 89%). LC-MS calculated for $C_{19}H_{15}N_6$ (M+H)$^+$: m/z=327.1; found 327.2.

Example 17. 3-(4-Amino-2-(pyridin-2-ylmethyl)-7-(pyrimidin-4-yl)pyrazolo[1,5-a]pyrazin-6-yl)benzonitrile

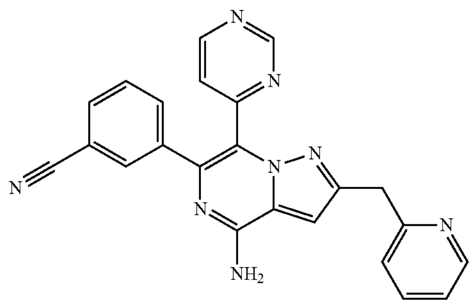 [SMILES: N#Cc1cccc(-c2nc(N)c3cc(Cc4ccccn4)nn3c2-c2ccncn2)c1]

Step 1: 3-(4-Amino-7-bromo-2-(pyridin-2-ylmethyl)pyrazolo[1,5-a]pyrazin-6-yl)benzonitrile

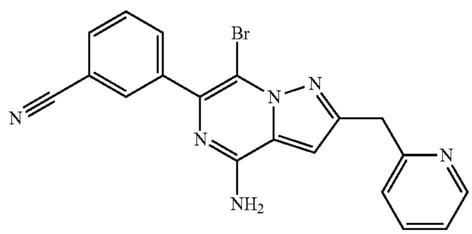 [SMILES: N#Cc1cccc(-c2nc(N)c3cc(Cc4ccccn4)nn3c2Br)c1]

To a solution of 3-(4-amino-2-(pyridin-2-ylmethyl)pyrazolo[1,5-a]pyrazin-6-yl)benzonitrile (Example 16, Step 4; 260 mg, 0.8 mmol) in DMF (2 mL) was added a DMF (0.5 mL) solution of N-bromosuccinimide (122 mg, 0.68 mmol) dropwise at 0° C. The resulting mixture was stirred at 0° C. for 10 min. The reaction mixture was diluted with water. The mixture was extracted with DCM. The organic phase was washed with brine, dried over $Na_2SO_4$, filtered, and concentrated. The residue was purified with flash chromatography to give the desired product as a light yellow oil (202 mg, 62%). LC-MS calculated for $C_{19}H_{14}BrN_6$ (M+H)$^+$: m/z=405.0; found 405.1.

Step 2. 3-(4-Amino-2-(pyridin-2-ylmethyl)-7-(pyrimidin-4-yl)pyrazolo[1,5-a]pyrazin-6-yl)benzonitrile A mixture of 3-(4-amino-7-bromo-2-(pyridin-2-ylmethyl)pyrazolo[1,5-a]pyrazin-6-yl)benzonitrile (15 mg, 0.037 mmol), CuI (1.4 mg, 0.007 mmol), CsF (11 mg, 0.074 mmol), tetrakis(triphenylphosphine)palladium(0) (4.2 mg, 0.004 mmol), and 4-(tributylstannyl)pyrimidine (16.4 mg, 0.044 mmol) in 1,4-dioxane was heated at 140° C. for 1 h in a microwave reactor. The reaction mixture was concentrated under vacuum and the resulting residue was dissolved in methanol, added a few drops of TFA, and purified with prep-LCMS (pH 2, acetonitrile/water+TFA) to give the desired product as TFA salt. LC-MS calculated for $C_{23}H_{17}N_8$ (M+H)$^+$: m/z=405.2 found 405.2.

Example 18. 3-(4-Amino-7-(1-ethyl-1H-pyrazol-5-yl)-2-(pyridin-2-ylmethyl)pyrazolo[1,5-a]pyrazin-6-yl)benzonitrile

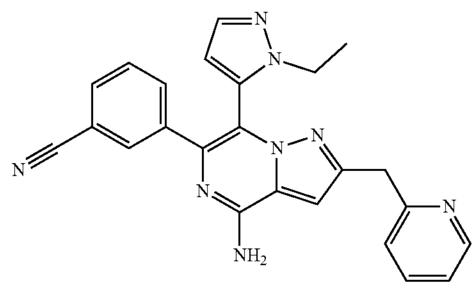 [SMILES: CCn1nccc1-c1c(-c2cccc(C#N)c2)nc(N)c2cc(Cc3ccccn3)nn12]

A mixture of 3-(4-amino-7-bromo-2-(pyridin-2-ylmethyl)pyrazolo[1,5-a]pyrazin-6-yl)benzonitrile (Example 17, Step 1; 15 mg, 0.037 mmol), 1-ethyl-5-(4,4,5,5-tetramethyl-1,3,2-dioxaborolan-2-yl)-1H-pyrazole (9.69 mg, 0.044 mmol), dicyclohexyl(2',4',6'-triisopropylbiphenyl-2-yl)phosphine-(2'-aminobiphenyl-2-yl)(chloro)palladium (1:1) (2.86 mg, 3.63 μmol) and $Cs_2CO_3$ (23.2 mg, 0.071 mmol) in 1,4-dioxane (1 mL)/water (0.200 mL) was stirred at 90° C. for 1 h. The reaction mixture was concentrated under vacuum and the resulting residue was dissolved in methanol and purified with prep-LCMS (pH 2, acetonitrile/water+TFA) to give the desired product as TFA salt. LC-MS calculated for $C_{24}H_{21}N_8$ (M+H)$^+$: m/z=421.2; found 421.2.

Example 19. 4-(4-Amino-6-(3-cyanophenyl)-2-(2-fluorobenzyl)pyrazolo[1,5-a]pyrazin-7-yl)-5,6-dihydropyridine-1(2H)-carboxamide

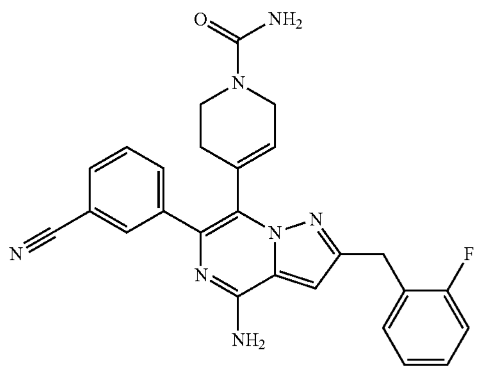 [SMILES: N#Cc1cccc(-c2nc(N)c3cc(Cc4ccccc4F)nn3c2C2=CCN(C(N)=O)CC2)c1]

Step 1. 3-(4-(2,4-Dimethoxybenzylamino)-2-(2-fluorobenzyl)pyrazolo[1,5-a]pyrazin-6-yl)benzonitrile

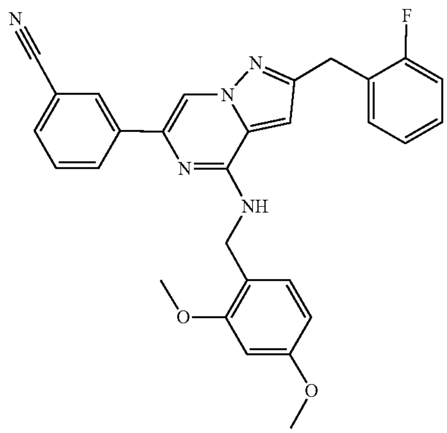 [SMILES: COc1ccc(CNc2nc(-c3cccc(C#N)c3)cn3nc(Cc4ccccc4F)cc23)c(OC)c1]

A mixture of 3-(2-(bromomethyl)-4-(2,4-dimethoxybenzylamino)pyrazolo[1,5-a]pyrazin-6-yl)benzonitrile (Example 16, Step 2; 200 mg, 0.42 mmol), (2-fluorophenyl) boronic acid (70.2 mg, 0.502 mmol), dicyclohexyl(2',4',6'-triisopropylbiphenyl-2-yl)phosphine-(2'-aminobiphenyl-2-yl)(chloro)palladium (1:1) (32.9 mg, 0.042 mmol) and $Cs_2CO_3$ (272 mg, 0.836 mmol) in 1,4-dioxane (2 mL)/water (0.2 mL) was stirred at 90° C. for 3 h. The reaction was diluted by water and extracted with DCM. The organic phase was washed with brine, dried over $Na_2SO_4$, filtered, and concentrated. The residue was purified with flash chromatography to give the desired product as white solid (157 mg, 76%). LC-MS calculated for $C_{29}H_{25}FN_5O_2$ $(M+H)^+$: m/z=494.2; found 494.1.

Step 2. 3-(4-Amino-2-(2-fluorobenzyl)pyrazolo[1,5-a]pyrazin-6-yl)benzonitrile

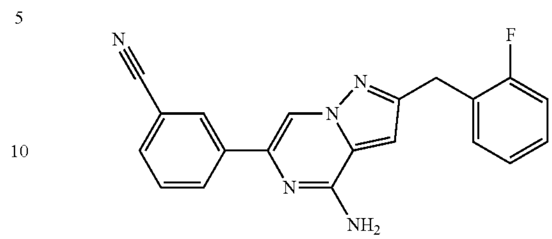

To a reaction vial was charged with 3-(4-(2,4-dimethoxybenzylamino)-2-(2-fluorobenzyl)pyrazolo[1,5-a]pyrazin-6-yl)benzonitrile (157 mg, 0.32 mmol), TFA (1 mL). The mixture was heated at 70° C. for 20 min. The mixture was diluted with water, and quenched with sat. $NaHCO_3$. The mixture was extracted with DCM. The organic phase was washed with brine, dried over $Na_2SO_4$, filtered, and concentrated. The residue was purified with flash chromatography to give the desired product as white solid (96 mg, 87%). LC-MS calculated for $C_{20}H_{15}FN_5$ $(M+H)^+$: m/z=344.1; found 344.2.

Step 3. 3-(4-Amino-7-bromo-2-(2-fluorobenzyl)pyrazolo[1,5-a]pyrazin-6-yl)benzonitrile and 3-(4-amino-3-bromo-2-(2-fluorobenzyl)pyrazolo[1,5-a]pyrazin-6-yl)benzonitrile

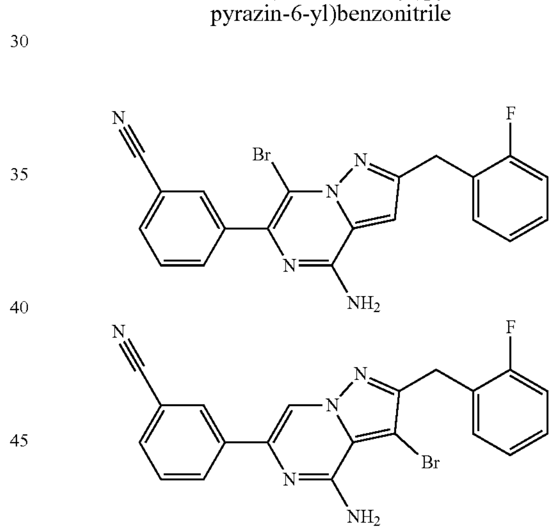

To a solution of 3-(4-amino-2-(2-fluorobenzyl)pyrazolo[1,5-a]pyrazin-6-yl)benzonitrile (96 mg, 0.28 mmol) in DMF (1 mL) was added a DMF (0.5 mL) solution of N-bromosuccinimide (39.8 mg, 0.22 mmol) dropwise at 0° C. The resulting mixture was stirred at 0° C. for 10 min. The reaction mixture was diluted with water and extracted with DCM. The organic phase was washed with brine, dried over $Na_2SO_4$, filtered, and concentrated. The residue was purified with flash chromatography to give two regioisomers (101 mg, 0.24 mmol 86%), which are used directly in the next step. LC-MS calculated for $C_{20}H_{14}FBrN_5$ $(M+H)^+$: m/z=422.0; found 422.1.

Step 4. 4-(4-Amino-6-(3-cyanophenyl)-2-(2-fluorobenzyl)pyrazolo[1,5-a]pyrazin-7-yl)-5,6-dihydropyridine-1(2H)-carboxamide A mixture of 3-(4-amino-7-bromo-2-(2-fluorobenzyl)pyrazolo[1,5-a]pyrazin-6-yl)benzonitrile, 3-(4-amino-3- bromo-2-(2-fluorobenzyl)pyrazolo[1,5-a]pyrazin-6-yl)benzonitrile (15 mg, 0.037 mmol), 4-(4,4,5,5-tetramethyl-1,3,2-dioxaborolan-2-yl)-3,6-dihydropyridine-1(2H)-carboxamide (13.4 mg, 0.053 mmol), dicyclohexyl(2',4',6'-triisopropylbiphenyl-2-yl)phosphine-(2'-aminobiphenyl-2-yl)(chloro)palladium (1:1) (2.86 mg, 3.63 μmol) and $Cs_2CO_3$ (23.2 mg, 0.071 mmol) in 1,4-dioxane (0.6 mL)/water (0.200 mL) was stirred at 90° C. for 1 h. The reaction was concentrated under vacuum and the residue was dissolved in methanol and purified with prep-LCMS (pH 2, acetonitrile/water+TFA) to give two compounds. Compound with shorter retention time was assigned as title compound as a TFA salt. LC-MS calculated for $C_{26}H_{23}FN_7O$ $(M+H)^+$: m/z=468.2; found 468.2.

Example 20. 4-Amino-6-(3-cyanophenyl)-2-(2-fluorobenzyl)pyrazolo[1,5-a]pyrazine-7-carbonitrile

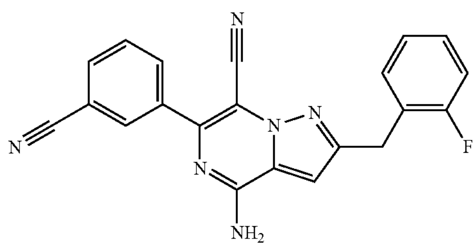 [SMILES: N#Cc1cccc(-c2nc(N)c3cc(Cc4ccccc4F)nn3c2C#N)c1]

A mixture of 3-(4-amino-7-bromo-2-(2-fluorobenzyl)pyrazolo[1,5-a]pyrazin-6-yl)benzonitrile, 3-(4-amino-3-bromo-2-(2-fluorobenzyl)pyrazolo[1,5-a]pyrazin-6-yl)benzonitrile (15 mg, 0.037 mmol) (Example 19, Step 3), zinc cyanide (8.3 mg, 0.071 mmol), and tBuXPhos-Pd-G3 (2.8 mg, 3.6 μmol) in 1,4-dioxane (1 mL)/water (1 mL) was stirred at 100° C. for 4 h. The reaction mixture was concentrated under vacuum and the resulting residue was dissolved in methanol and purified with prep-LCMS (pH 2, acetonitrile/water+TFA) to give two compounds. Compound with shorter retention time was assigned as title compound as a TFA salt. LC-MS calculated for $C_{21}H_{14}FN_6$ $(M+H)^+$: m/z=369.1; found 369.2.

Example 21. 4-Amino-6-(3-cyanophenyl)-2-(2-fluorobenzyl)pyrazolo[1,5-a]pyrazine-3-carbonitrile

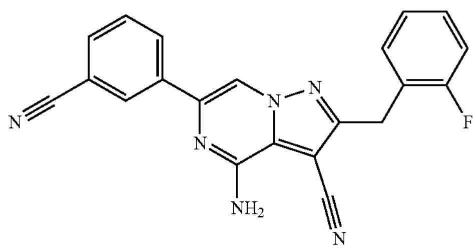 [SMILES: N#Cc1cccc(-c2cn3nc(Cc4ccccc4F)c(C#N)c3c(N)n2)c1]

The title compound was prepared using same procedures as described for Example 20. The reaction mixture was purified by prep-HPLC (pH=2, acetonitrile/water+TFA) to give two compounds. Compound with longer retention time was assigned as title compound as a TFA salt. LC-MS calculated for $C_{21}H_{14}FN_6$ $(M+H)^+$: m/z=369.1; found 369.2.

Example 22. 3-(4-Amino-7-bromo-2-((2-fluorophenyl)(hydroxy)methyl)pyrazolo[1,5-a]pyrazin-6-yl)benzonitrile

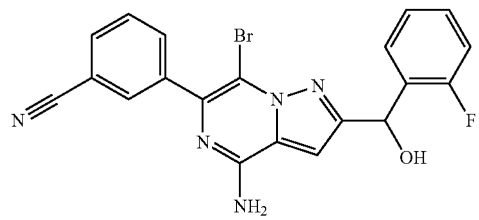 [SMILES: N#Cc1cccc(-c2nc(N)c3cc(C(O)c4ccccc4F)nn3c2Br)c1]

Step 1. 3-(4-Amino-7-bromo-2-formylpyrazolo[1,5-a]pyrazin-6-yl)benzonitrile

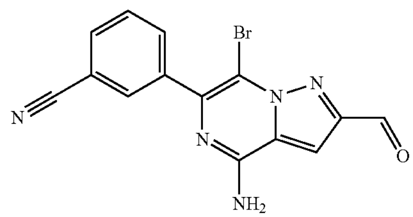 [SMILES: N#Cc1cccc(-c2nc(N)c3cc(C=O)nn3c2Br)c1]

To a solution of 3-(4-amino-7-bromo-2-(hydroxymethyl)pyrazolo[1,5-a]pyrazin-6-yl)benzonitrile (Example 13, Step 1; 1.06 g, 3.1 mmol) in DCM (30 mL) was added Dess-Martin periodinane (1.44 g, 3.39 mmol). The resulting mixture was stirred at room temperature for 30 min. The reaction mixture was diluted with sat. $NaHCO_3$. The organic phase was washed with brine, dried over $Na_2SO_4$, filtered, and concentrated. The residue was purified with flash chromatography to give the desired product as white solid (0.64 g, 61%). LC-MS calculated for $C_{14}H_9BrN_5O$ $(M+H)^+$: m/z=342.0; found 342.0.

Step 2. 3-(4-Amino-7-bromo-2-((2-fluorophenyl)(hydroxy)methyl)pyrazolo[1,5-a]pyrazin-6-yl)benzonitrile To a THE (20 mL) solution of 1-fluoro-2-iodobenzene (0.31 mL, 2.7 mmol) was added isopropylmagnesium bromide (0.8 mL, 2.3 mmol) in THE dropwise at −20° C., and the solution was stirred for 1 h. Then to the solution was added a THF (2 mL) solution of 3-(4-amino-7-bromo-2-formylpyrazolo[1,5-a]pyrazin-6-yl)benzonitrile (228 mg, 0.67 mmol). The mixture was stirred for 12 h while warming to room temperature. After completion, the reaction was quenched by adding sat. $NH_4Cl$. The aqueous phase was extracted with DCM, and the organic phase was washed with brine, dried over $Na_2SO_4$, filtered, and concentrated. The residue was purified with flash chromatography to give the desired product as white solid (0.18 g, 63%). LC-MS calculated for $C_{20}H_{14}BrFN_5O$ $(M+H)^+$: m/z=438.0; found 438.1.

Example 23. 3-(4-Amino-2-((2-fluorophenyl)(hydroxy)methyl)-7-(pyrimidin-4-yl)pyrazolo[1,5-a]pyrazin-6-yl)benzonitrile

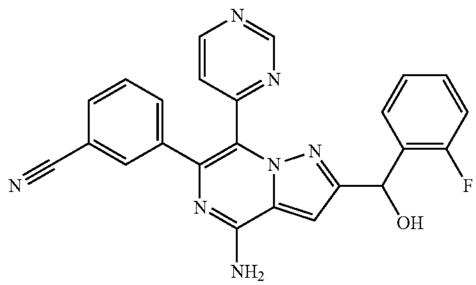 [SMILES: N#Cc1cccc(-c2nc(N)c3cc(C(O)c4ccccc4F)nn3c2-c2ccncn2)c1]

A mixture of 3-(4-amino-7-bromo-2-((2-fluorophenyl)(hydroxy)methyl)pyrazolo[1,5-a]pyrazin-6-yl)benzonitrile (Example 22; 16.0 mg, 0.037 mmol), CuI (1.4 mg, 0.007 mmol), CsF (11.0 mg, 0.074 mmol), tetrakis(triphenylphosphine)palladium(0) (4.2 mg, 0.004 mmol), and 4-(tributylstannyl)pyrimidine (16.4 mg, 0.044 mmol) in 1,4-dioxane was heated at 140° C. for 1 h in a microwave reactor. The reaction mixture was concentrated under vacuum and the resulting residue was dissolved in methanol, mixed with a few drops of TFA, and purified with prep-LCMS (pH 2, acetonitrile/water+TFA) to give the desired product as TFA salt. LC-MS calculated for $C_{24}H_{17}FN_7O$ $(M+H)^+$: m/z=438.1 found 438.2.

Example 24. 3-(4-Amino-2-(3,6-dihydro-2H-pyran-4-yl)-7-(pyrimidin-4-yl)pyrazolo[1,5-a]pyrazin-6-yl)benzonitrile

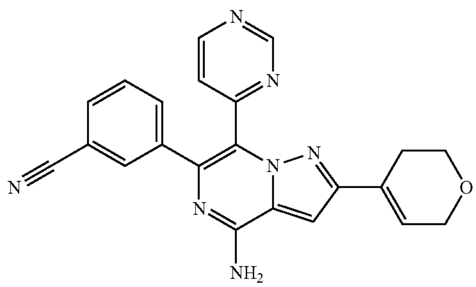 [SMILES: N#Cc1cccc(-c2nc(N)c3cc(C4=CCOCC4)nn3c2-c2ccncn2)c1]

Step 1. 3-(2-Chloro-4-oxo-4,5-dihydropyrazolo[1,5-a]pyrazin-6-yl)benzonitrile

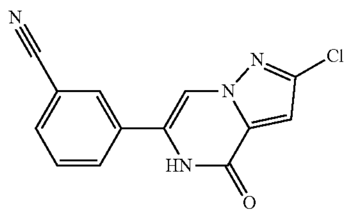 [SMILES: N#Cc1cccc(-c2cn3nc(Cl)cc3c(=O)[nH]2)c1]

To a solution of methyl 3-chloro-1H-pyrazole-5-carboxylate (901 mg, 5.61 mmol) and 3-(2-bromoacetyl)benzonitrile (1257 mg, 5.61 mmol) in acetone (253 mL) was added potassium carbonate (853 mg, 6.17 mmol). The mixture was stirred at rt for 12 h. The reaction mixture was then concentrated and the resulting residue was taken up in water and DCM. The organic phase was washed with brine, dried over $Na_2SO_4$, filtered, and concentrated. The residue was dissolved in acetic acid (30 mL), and ammonium acetate (4.7 g, 60.8 mmol) was added. The mixture was stirred at 110° C. for 36 h. After cooling to rt, the mixture was diluted with water and the precipitate was collected via filtration and washed with water to give the desired product as white solid. LC-MS calculated for $C_{13}H_8ClN_4O$ $(M+H)^+$: m/z=271.0; found 271.1.

Step 2. 3-(2,4-Dichloropyrazolo[1,5-a]pyrazin-6-yl)benzonitrile

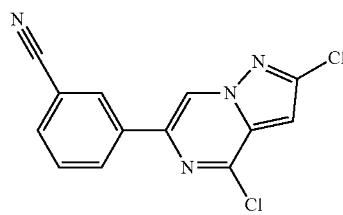 [SMILES: N#Cc1cccc(-c2cn3nc(Cl)cc3c(Cl)n2)c1]

A mixture of 3-(2-chloro-4-oxo-4,5-dihydropyrazolo[1,5-a]pyrazin-6-yl)benzonitrile (1.6 g, 5.9 mmol) and $POCl_3$ (2 mL, 20.1 mmol) was heated at 110° C. overnight. After cooling to rt, the mixture was added to a flask containing ice. The resulting precipitate was collected and washed with water to give the desired product as white solid. (1.18 g, 69%). LC-MS calculated for $C_{13}H_7C_{12}N_4$ $(M+H)^+$: m/z=289.0; found 289.1.

Step 3. 3-(4-Amino-2-chloropyrazolo[1,5-a]pyrazin-6-yl)benzonitrile

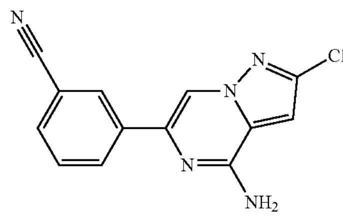 [SMILES: N#Cc1cccc(-c2cn3nc(Cl)cc3c(N)n2)c1]

A microwave vial was charged with 3-(2,4-dichloropyrazolo[1,5-a]pyrazin-6-yl)benzonitrile (1.4 g, 4.84 mmol), (2,4-dimethoxyphenyl)methanamine (0.90 g, 5.4 mmol), DIEA (1.304 mL, 7.47 mmol) and butan-1-ol (10 mL). The mixture was heated at 150° C. for 30 min in a microwave reactor. The mixture was diluted with water, and the resulting precipitate was collected via filtration. The solid was then treated with TFA (10 mL) and heated at 70° C. for 30 min. The reaction was then quenched with sat. $NaHCO_3$, and the resulting solid was collected via filtration and washed with water to give the desired product as a white solid (860 mg, 3.2 mmol, 67%). LC-MS calculated for $C_{13}H_9ClN_5$ $(M+H)^+$: m/z=270.0; found 270.0.

Step 4. 3-(4-Amino-7-bromo-2-chloropyrazolo[1,5-a]pyrazin-6-yl)benzonitrile

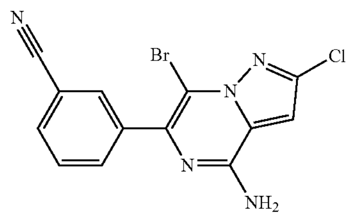 [SMILES: N#Cc1cccc(-c2nc(N)c3cc(Cl)nn3c2Br)c1]

To a solution of 3-(4-amino-2-chloropyrazolo[1,5-a]pyrazin-6-yl)benzonitrile (860 mg, 3.2 mmol) in DMF (5 mL) was added NBS (570 mg, 3.2 mmol). The resulting mixture was stirred at room temperature for 30 min. The reaction mixture was diluted with water. The resulting precipitate was collected and washed with water to give the desired product as white solid (972 mg, 88%). LC-MS calculated for $C_{13}H_8ClBrN_5$ $(M+H)^+$: m/z=348.0; found 348.0.

Step 5. 3-(4-Amino-2-chloro-7-(pyrimidin-4-yl)pyrazolo[1,5-a]pyrazin-6-yl)benzonitrile

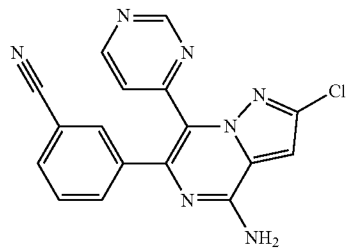 [SMILES: N#Cc1cccc(-c2nc(N)c3cc(Cl)nn3c2-c2ccncn2)c1]

A mixture of 3-(4-amino-7-bromo-2-chloropyrazolo[1,5-a]pyrazin-6-yl)benzonitrile (100 mg, 0.288 mmol), CuI (14 mg, 0.07 mmol), CsF (110 mg, 0.74 mmol), tetrakis(triphenylphosphine)palladium(0) (42 mg, 0.04 mmol), and 4-(tributylstannyl)pyrimidine (118 mg, 0.34 mmol) in 1,4-dioxane (3 mL) was heated at 140° C. for 1 h in a microwave reactor. The reaction mixture was concentrated under vacuum and the resulting residue was purified using flash chromatography to give the desired product as white solid (52 mg, 52%). LC-MS calculated for $C_{17}H_{11}ClN_7$ $(M+H)^+$: m/z=348.1; found 348.1.

Step 6. 3-(4-Amino-2-(3,6-dihydro-2H-pyran-4-yl)-7-(pyrimidin-4-yl)pyrazolo[1,5-a]pyrazin-6-yl)benzonitrile A mixture of 3-(4-amino-2-chloro-7-(pyrimidin-4-yl)pyrazolo[1,5-a]pyrazin-6-yl)benzonitrile (13 mg, 0.037 mmol), 2-(3,6-dihydro-2H-pyran-4-yl)-4,4,5,5-tetramethyl-1,3,2-dioxaborolane (8.4 mg, 0.04 mmol), dicyclohexyl(2',4',6'-triisopropylbiphenyl-2-yl)phosphine-(2'-aminobiphenyl-2-yl)(chloro)palladium (1:1) (2.86 mg, 3.63 μmol), and $Cs_2CO_3$ (23.2 mg, 0.071 mmol) in 1,4-dioxane (1 mL)/water (0.200 mL) was stirred at 90° C. for 1 h. The reaction mixture was concentrated under vacuum and the resulting residue was dissolved in methanol and purified with prep-LCMS (pH 2, acetonitrile/water+TFA) to give the desired product as TFA salt. LC-MS calculated for $C_{22}H_{18}N_7O$ $(M+H)^+$: m/z=396.2; found 396.1.

Example 25. 3-(4-Amino-2-(phenylamino)-7-(pyridin-4-yl)pyrazolo[1,5-a]pyrazin-6-yl)benzonitrile

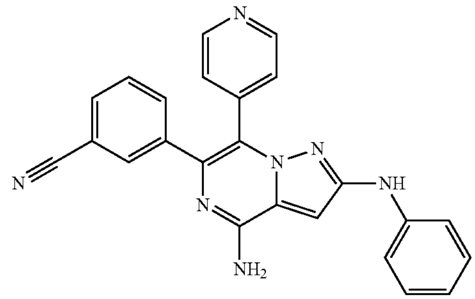 [SMILES: N#Cc1cccc(-c2nc(N)c3cc(Nc4ccccc4)nn3c2-c2ccncc2)c1]

Step 1: 3-(4-Amino-2-chloro-7-(pyridin-4-yl)pyrazolo[1,5-a]pyrazin-6-yl)benzonitrile

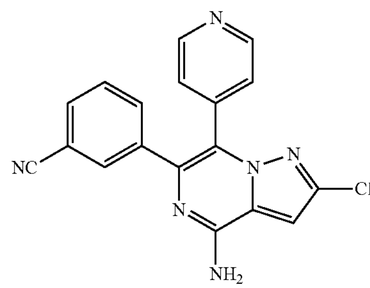 [SMILES: N#Cc1cccc(-c2nc(N)c3cc(Cl)nn3c2-c2ccncc2)c1]

A mixture of 3-(4-amino-7-bromo-2-chloropyrazolo[1,5-a]pyrazin-6-yl)benzonitrile (Example 24 Step 4; 129 mg, 0.370 mmol), pyridin-4-ylboronic acid (45.5 mg, 0.370 mmol), $PdCl_2(dppf)$-$CH_2C_{12}$ adduct (30.2 mg, 0.037 mmol), sodium carbonate (78 mg, 0.740 mmol) in 1,4-dioxane (1682 μL), and water (168 μL) was purged with $N_2$ and heated at 95° C. for 5 h. The mixture was then concentrated and purified by silica gel chromatograph eluting with 0 to 13% MeOH in DCM to afford the desired product. LCMS calculated for $C_{18}H_{12}ClN_6$ (M+H)+. 347.1; found 347.1.

Step 2: 3-(4-Amino-2-(phenylamino)-7-(pyridin-4-yl)pyrazolo[1,5-a]pyrazin-6-yl)benzonitrile A mixture of 3-(4-amino-2-chloro-7-(pyridin-4-yl)pyrazolo[1,5-a]pyrazin-6-yl)benzonitrile (10 mg, 0.029 mmol), aniline (8.06 mg, 0.087 mmol), cesium carbonate (18.79 mg, 0.058 mmol), chloro[(4,5-bis(diphenylphosphino)-9,9-dimethylxanthene)-2-(2'-amino-1,1'-biphenyl)]palladium(II) (2.56 mg, 2.88 μmol) (XantPhos Pd G2) in 1,4-dioxane (144 μl) was purged with $N_2$ and heated at 95° C. for 1 h. The mixture was concentrated and purified by preparative LCMS (pH 2, acetonitrile/water with TFA) to afford the desired product as TFA salt. LCMS calculated for $C_{24}H_{18}N_7$ $(M+H)^+$: 404.2; found 404.1.

Example 26. 3-(4-Amino-2-(2-(4-methylpiperazin-1-yl)pyridin-4-yl)-7-(pyridin-4-yl)pyrazolo[1,5-a]pyrazin-6-yl)benzonitrile

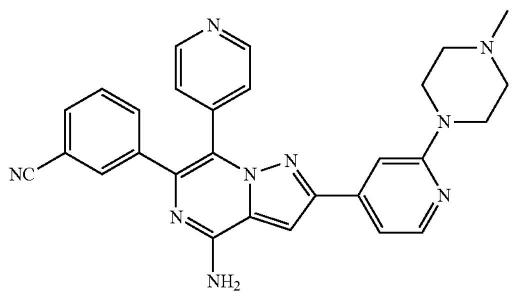 [SMILES: CN1CCN(c2cc(-c3cc4c(N)nc(-c5cccc(C#N)c5)c(-c5ccncc5)n4n3)ccn2)CC1]

Chloro(2-dicyclohexylphosphino-2',4',6'-triisopropyl-1,1'-biphenyl)[2-(2'-amino-1,1'-biphenyl)]palladium(II) (11.34 mg, 0.014 mmol) was added to a mixture of 3-(4-amino-2-chloro-7-(pyridin-4-yl)pyrazolo[1,5-a]pyrazin-6-yl)benzonitrile (Example 25, Step 1; 50 mg, 0.144 mmol), 1-methyl-4-(4-(4,4,5,5-tetramethyl-1,3,2-dioxaborolan-2-yl)pyridin-2-yl)piperazine (52.5 mg, 0.173 mmol), sodium carbonate (15.28 mg, 0.144 mmol) in 1,4-dioxane (655 µl) and water (65.5 µl). The mixture was purged with $N_2$ and heated at 90° C. for 2 h. The resulting mixture was concentrated and purified by preparative LCMS (pH 2, acetonitrile/water with TFA) to afford the product as TFA salt. LCMS calculated for $C_{28}H_{26}N_9$ $(M+H)^+$: 488.2; found 488.1.

Example 27. 3-(8-Amino-2-(pyridin-2-ylmethyl)-5-(pyrimidin-4-yl)-[1,2,4]triazolo[1,5-a]pyrazin-6-yl)benzonitrile

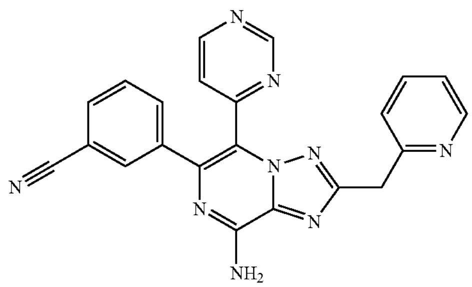 [SMILES: N#Cc1cccc(-c2nc(N)c3nc(Cc4ccccn4)nn3c2-c2ccncn2)c1]

Step 1: Methyl 3-bromo-1-(2-(3-cyanophenyl)-2-oxoethyl)-1H-1,2,4-triazole-5-carboxylate

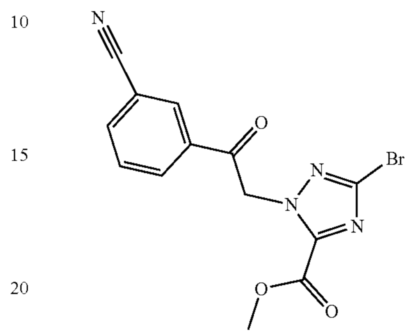

To a solution of methyl 3-bromo-1H-1,2,4-triazole-5-carboxylate (5.0 g, 24.3 mmol), 3-(2-bromoacetyl)benzonitrile (5.44 g, 24.3 mmol) in DMF (100 mL) was added potassium carbonate (3.35 g, 24.3 mmol). The reaction mixture was stirred at ambient temperature for 2 h. The reaction mixture was then diluted with water and DCM. The organic layer was separated, washed with brine, dried over $Na_2SO_4$, filtered and concentrated. The resulting residue was purified via flash chromatography to give the desired product as a white solid (5.2 g, 61%). LC-MS calculated for $C_{13}H_{10}BrN_4O_3$ $(M+H)^+$: m/z=349.0; found 349.0.

Step 2: 3-(2-Bromo-8-oxo-7,8-dihydro-[1,2,4]triazolo[1,5-a]pyrazin-6-yl)benzonitrile

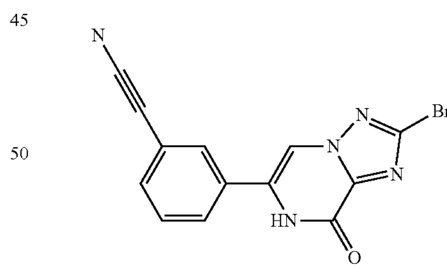

Methyl 3-bromo-1-(2-(3-cyanophenyl)-2-oxoethyl)-1H-1,2,4-triazole-5-carboxylate (10.5 g, 30.1 mmol) was dissolved in acetic acid (100 mL), and ammonium acetate (23.18 g, 301 mmol) was added. The mixture was stirred at 110° C. for 12 h. After cooling to room temperature, the reaction mixture was diluted with water. The resulting precipitate was collected via filtration, washed with water, and dried under vacuum to afford the product (8.4 g, 88%). LC-MS calculated for $C_{12}H_7BrN_5O$ $(M+H)^+$: m/z=316.0; found 316.0.

Step 3: 3-(2-Bromo-8-chloro-[1,2,4]triazolo[1,5-a]pyrazin-6-yl)benzonitrile

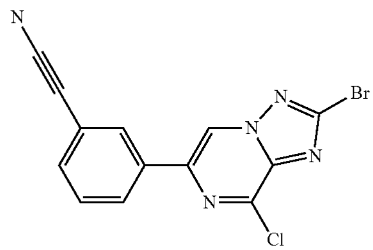 [SMILES: NC#Cc1cccc(-c2cn3nc(Br)nc3c(Cl)n2)c1]

A mixture of 3-(2-bromo-8-oxo-7,8-dihydro-[1,2,4]triazolo[1,5-a]pyrazin-6-yl)benzonitrile (8.4 g, 26.6 mmol) and $POCl_3$ (49.5 mL, 531 mmol) was stirred at 110° C. overnight. After cooling to room temperature, the reaction mixture was slowly added to a flask containing ice and sodium bicarbonate. The resulting precipitate was collected, washed with water, and dried to afford the product (8.8 g, 99%). LC-MS calculated for $C_{12}H_6BrClN_5$ $(M+H)^+$: m/z=333.9; found 334.0.

Step 4. 3-(8-(Bis(4-methoxybenzyl)amino)-2-bromo-[1,2,4]triazolo[1,5-a]pyrazin-6-yl)benzonitrile

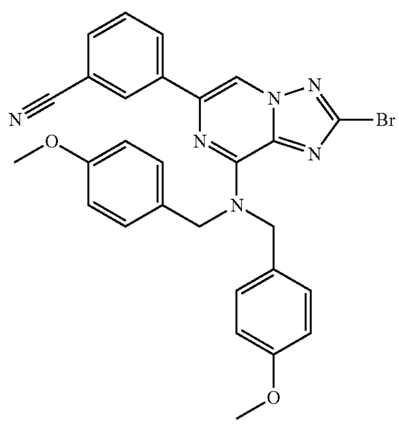 [SMILES: COc1ccc(CN(Cc2ccc(OC)cc2)c2nc(-c3cccc(C#N)c3)cn3nc(Br)nc23)cc1]

A mixture of 3-(2-bromo-8-chloro-[1,2,4]triazolo[1,5-a]pyrazin-6-yl)benzonitrile (8.99 g, 26.9 mmol), bis(4-methoxybenzyl)amine (10.37 g, 40.3 mmol), and DIPEA (9.4 mL, 53.7 mmol) in DMF (134 mL) was stirred at 85° C. overnight. The reaction mixture was cooled to room temperature, and diluted with water. The resulting precipitate was collected via filtration, and dried to afford the product (14.1 g, 94%). LC-MS calculated for $C_{28}H_{24}BrN_6O_2$ $(M+H)^+$: m/z=555.1; found 555.1.

Step 5: 3-(8-(Bis(4-methoxybenzyl)amino)-2-(pyridin-2-ylmethyl)-[1,2,4]triazolo[1,5-a]pyrazin-6-yl)benzonitrile

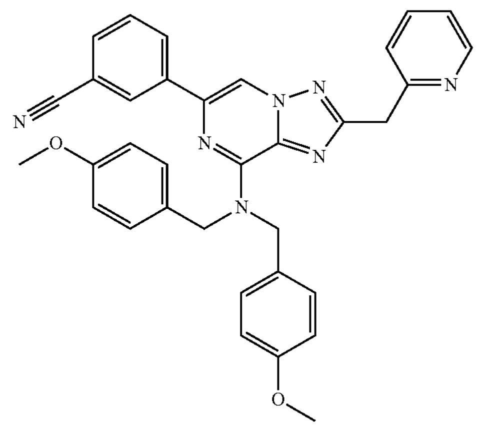 [SMILES: COc1ccc(CN(Cc2ccc(OC)cc2)c2nc(-c3cccc(C#N)c3)cn3nc(Cc4ccccn4)nc23)cc1]

To a solution of 2-methylpyridine (0.050 g, 0.540 mmol) in THE (0.5 mL) was added 2.5 M n-butyllithium (0.216 mL, 0.540 mmol) at −78° C. The resulting solution was stirred at the same temperature for 1 h, before 1.9 M zinc chloride in 2-methyltetrahydrofuran (0.284 mL, 0.540 mmol) was added, and the resulting mixture was stirred at room temperature for 10 min.

A microwave vial charge with 3-(8-(bis(4-methoxybenzyl)amino)-2-bromo-[1,2,4]triazolo[1,5-a]pyrazin-6-yl)benzonitrile (0.15 g, 0.270 mmol), palladium acetate (1.1 mg, 4.7 μmol), and 2'-(dicyclohexylphosphino)-N,N,N',N'-tetramethylbiphenyl-2,6-diamine (4.1 mg, 9.5 μmol) was evacuated under high vacuum and backfilled with nitrogen. THE (2.0 mL) and toluene (0.5 mL) was then added to the reaction vial. The mixture was cooled to 0° C. and the zinc reagent prepared from previous step was added slowly via a syringe. The reaction mixture was then stirred at 60° C. overnight, cooled to room temperature, and partitioned between ethylacetate and saturated $NH_4Cl$ solution. The layers were separated and the aqueous layer was extracted with ethylacetate. The combined organic layers were washed with water and brine, dried over $MgSO_4$, and concentrated. The resulting residue was purified via flash chromatography to afford the product (0.11 g, 71%). LC-MS calculated for $C_{34}H_{30}N_7O_2$ $(M+H)^+$: m/z=568.2; found 568.3.

Step 6. 3-(8-Amino-2-(pyridin-2-ylmethyl)-[1,2,4]triazolo[1,5-a]pyrazin-6-yl)benzonitrile

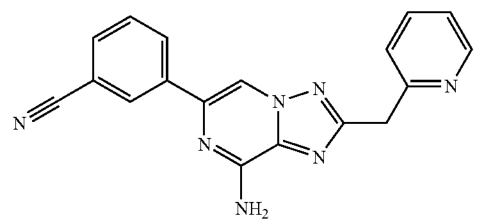 [SMILES: N#Cc1cccc(-c2cn3nc(Cc4ccccn4)nc3c(N)n2)c1]

A mixture of 3-(8-(bis(4-methoxybenzyl)amino)-2-(pyridin-2-ylmethyl)-[1,2,4]triazolo[1,5-a]pyrazin-6-yl)benzonitrile (110 mg, 0.194 mmol) and TFA (746 μL, 9.69 mmol)

was stirred at 80° C. for 30 min, cooled to room temperature, and concentrated. The resulting residue was purified via prep-LCMS (pH 2) to give the product as a white solid (TFA salt) (57 mg, 90%). LC-MS calculated for $C_{18}H_{14}N_7$ $(M+H)^+$: m/z=328.1; found 328.1.

Step 7. 3-(8-Amino-5-bromo-2-(pyridin-2-ylmethyl)-[1,2,4]triazolo[1,5-a]pyrazin-6-yl)benzonitrile

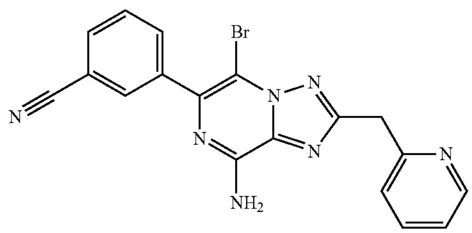

To a solution of 3-(8-amino-2-(pyridin-2-ylmethyl)-[1,2,4]triazolo[1,5-a]pyrazin-6-yl)benzonitrile (TFA salt) (35 mg, 0.079 mmol) in DMF (0.5 mL)/DCM (0.5 mL) was added NBS (14.1 mg, 0.079 mmol). The reaction mixture was then stirred at room temperature for 1 h, and concentrated to afford the crude product, which was used in the next step without further purification. LC-MS calculated for $C_{18}H_{13}BrN_7$ $(M+H)^+$: m/z=406.0; found 406.0.

Step 8. 3-(8-Amino-2-(pyridin-2-ylmethyl)-5-(pyrimidin-4-yl)-[1,2,4]triazolo[1,5-a]pyrazin-6-yl)benzonitrile A mixture of 3-(8-amino-5-bromo-2-(pyridin-2-ylmethyl)-[1,2,4]triazolo[1,5-a]pyrazin-6-yl)benzonitrile (15 mg, 0.037 mmol), 4-(tributylstannyl)pyrimidine (20 mg, 0.055 mmol), and copper(I) chloride (4.4 mg, 0.044 mmol), lithium chloride (1.9 mg, 0.044 mmol) and tetrakis(triphenylphosphine)palladium(0) (4.3 mg, 3.7 μmol) in THE (1 mL) was purged with $N_2$, and stirred at 90° C. for 2 h. The reaction mixture was then cooled to room temperature, diluted with methanol, and purified via prep-LCMS (pH 2, acetonitrile/water with TFA) to give the desired product as a TFA salt. LC-MS calculated for $C_{22}H_{16}N_9$ $(M+H)^+$: m/z=406.2; found 406.2.

Example 28. 3-(8-Amino-5-(1-methyl-6-oxo-1,6-dihydropyridin-3-yl)-2-(pyridin-2-ylmethyl)-[1,2,4]triazolo[1,5-a]pyrazin-6-yl)benzonitrile

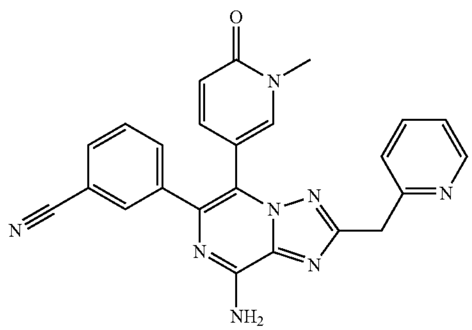 [SMILES: Cn1cc(-c2c(-c3cccc(C#N)c3)nc(N)c3nc(Cc4ccccn4)nn23)ccc1=O]

A mixture of 3-(8-Amino-5-bromo-2-(pyridin-2-ylmethyl)-[1,2,4]triazolo[1,5-a]pyrazin-6-yl)benzonitrile (Example 27, Step 7; 10 mg, 0.025 mmol), 1-methyl-5-(4,4,5,5-tetramethyl-1,3,2-dioxaborolan-2-yl)pyridin-2(1H)-one (10 mg, 0.042 mmol), cesium carbonate (37.6 mg, 0.116 mmol), chloro(2-dicyclohexylphosphino-2',4',6'-triisopropyl-1,1'-biphenyl)[2-(2'-amino-1,1'-biphenyl)]palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated and purified by preparative LCMS (pH 2, acetonitrile/water with TFA) to afford the desired product as TFA salt. LCMS calculated for $C_{24}H_{19}N_8O$ $(M+H)^+$: 435.2; found 435.2.

Example 29. 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile

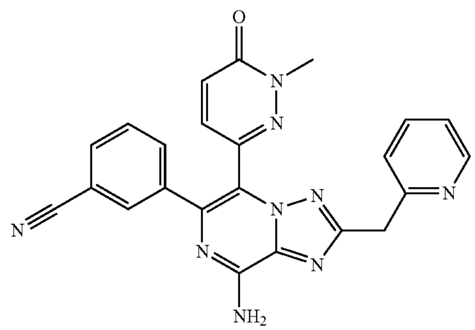 [SMILES: Cn1nc(-c2c(-c3cccc(C#N)c3)nc(N)c3nc(Cc4ccccn4)nn23)ccc1=O]

A mixture of 6-chloro-2-methylpyridazin-3(2H)-one (30 mg, 0.21 mmol), bis(pinacolato)diboron (53 mg, 0.21 mmol), chloro(2-dicyclohexylphosphino-2',4',6'-triisopropyl-1,1'-biphenyl)[2-(2'-amino-1,1'-biphenyl)]palladium(II) (15.7 mg, 0.02 mmol) (XPhos Pd G2) and potassium acetate (61.7 mg, 0.63 mmol) in 1,4-dioxane (1 mL) was stirred at 100° C. for 1 h. 3-(8-Amino-5-bromo-2-(pyridin-2-ylmethyl)-[1,2,4]triazolo[1,5-a]pyrazin-6-yl)benzonitrile (Example 27, Step 7; 10 mg, 0.025 mmol), cesium carbonate (37.6 mg, 0.116 mmol) and water (0.2 mL) were then added to the reaction mixture. The resulting mixture was heated at 90° C. for 1 h. The mixture was concentrated and purified by preparative LCMS (pH 2, acetonitrile/water with TFA) to afford the desired product as TFA salt. LCMS calculated for $C_{23}H_{18}N_9O$ $(M+H)^+$: 436.2; found 436.2.

$^1H$ NMR (500 MHz, DMSO) δ 8.66-8.62 (d, J=5.1 Hz, 1H), 8.09-8.02 (d, J=1.8 Hz, 1H), 7.88-7.85 (t, J=1.8 Hz, 1H), 7.85-7.81 (m, 3H), 7.78-7.72 (d, J=9.6 Hz, 1H), 7.66-7.51 (m, 4H), 7.10-7.06 (d, J=9.6 Hz, 1H), 4.59-4.48 (s, 2H), 3.53-3.43 (s, 3H).

Example 30. (S)-1-(2-((8-Amino-6-(3-cyanophenyl)-5-(pyrimidin-4-yl)-[1,2,4]triazolo[1,5-a]pyrazin-2-yl)methyl)-3-fluorobenzyl)pyrrolidine-3-carboxylic acid

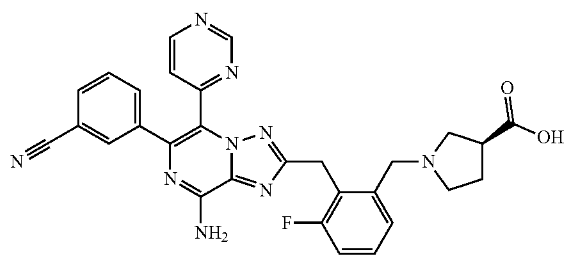 [SMILES: N#Cc1cccc(-c2nc(N)c3nc(Cc4c(F)cccc4CN4CC[C@H](C(=O)O)C4)nn3c2-c2ccncn2)c1]

Step 1: 3-(8-(Bis(4-methoxybenzyl)amino)-2-(2-chloro-6-fluorobenzyl)-[1,2,4]triazolo[1,5-a]pyrazin-6-yl)benzonitrile

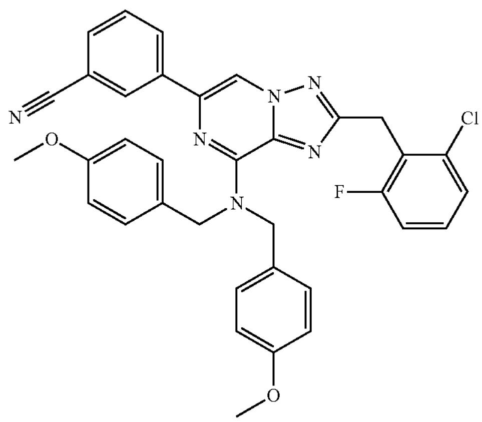 [SMILES: COc1ccc(CN(Cc2ccc(OC)cc2)c2nc(-c3cccc(C#N)c3)cn3nc(Cc4c(F)cccc4Cl)nc23)cc1]

A microwave vial was charged with 3-(8-(bis(4-methoxybenzyl)amino)-2-bromo-[1,2,4]triazolo[1,5-a]pyrazin-6-yl)benzonitrile (Example 27, Step 4; 0.15 g, 0.270 mmol), palladium acetate (1.1 mg, 4.7 μmol), and 2'-(dicyclohexylphosphino)-N,N,N',N'-tetramethylbiphenyl-2,6-diamine (4.1 mg, 9.5 μmol), the vial was then evacuated under high vacuum and backfilled with nitrogen. THE (2.0 mL) was then added to the reaction vial. The mixture was cooled to 0° C. and the (2-chloro-6-fluorobenzyl)zinc(II) chloride (0.5 M THE solution, 1.08 mL) was added slowly via a syringe. The reaction mixture was then stirred at 60° C. for 2 h, cooled to room temperature, and partitioned between ethylacetate and saturated $NH_4Cl$ solution. The layers were separated and the aqueous layer was extracted with ethylacetate. The combined organic layers were washed with water and brine, dried over $MgSO_4$, and concentrated. The resulting residue was purified via flash chromatography to afford the product. LC-MS calculated for $C_{35}H_{29}ClFN_6O_2$ $(M+H)^+$: m/z=619.2; found 619.3.

Step 2: 3-(8-Amino-5-bromo-2-(2-chloro-6-fluorobenzyl)-[1,2,4]triazolo[1,5-a]pyrazin-6-yl)benzonitrile

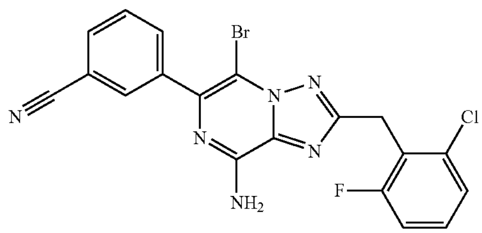 [SMILES: N#Cc1cccc(-c2nc(N)c3nc(Cc4c(F)cccc4Cl)nn3c2Br)c1]

A mixture of 3-(8-(bis(4-methoxybenzyl)amino)-2-(2-chloro-6-fluorobenzyl)-[1,2,4]triazolo[1,5-a]pyrazin-6-yl)benzonitrile (100 mg, 0.161 mmol) and TFA (746 μL, 9.69 mmol) was stirred at 100° C. for 10 min, cooled to room temperature, and concentrated. The resulting residue was dissolved in DMF, and a DMF (0.5 mL) solution of N-bromosuccinimide (28 mg, 0.161 mmol) was added dropwise at 0° C. The resulting mixture was stirred at 0° C. for 10 min. The reaction mixture was diluted with sat. $NaHCO_3$. The mixture was extracted with DCM. The organic phase was washed with brine, dried over $Na_2SO_4$, filtered, and concentrated. The residue was purified with flash chromatography to give the desired product as a light yellow oil. LC-MS calculated for $C_{19}H_{12}BrClFN_6$ $(M+H)^+$: m/z=457.0; found 457.1.

Step 3: 3-(8-Amino-2-(2-chloro-6-fluorobenzyl)-5-(pyrimidin-4-yl)-[1,2,4]triazolo[1,5-a]pyrazin-6-yl)benzonitrile

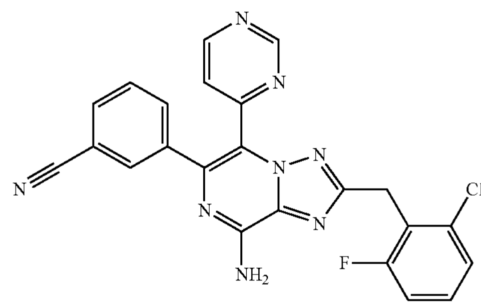 [SMILES: N#Cc1cccc(-c2nc(N)c3nc(Cc4c(F)cccc4Cl)nn3c2-c2ccncn2)c1]

A mixture of 3-(8-amino-5-bromo-2-(2-chloro-6-fluorobenzyl)-[1,2,4]triazolo[1,5-a]pyrazin-6-yl)benzonitrile (51 mg, 0.11 mmol), CuI (4.2 mg, 0.021 mmol), CsF (33 mg, 0.22 mmol), tetrakis(triphenylphosphine)palladium(0) (12 mg, 0.012 mmol), and 4-(tributylstannyl)pyrimidine (49 mg, 0.13 mmol) in 1,4-dioxane (2 mL) was heated at 140° C. for 1 h in a microwave reactor. The reaction mixture was concentrated under vacuum and the resulting residue was purified with flash chromatography to give the desired product as a light yellow oil. LC-MS calculated for $C_{23}H_{15}ClFN_8$ $(M+H)^+$: m/z=457.1 found 457.1.

Step 4: 3-(8-Amino-2-(2-fluoro-6-vinylbenzyl)-5-(pyrimidin-4-yl)-[1,2,4]triazolo[1,5-a]pyrazin-6-yl)benzonitrile

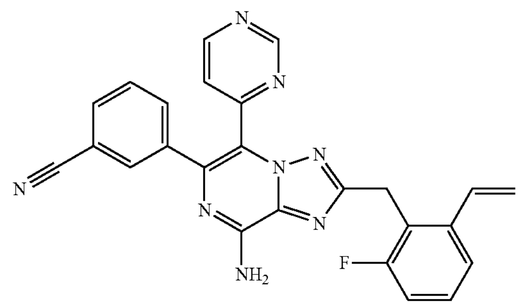 [SMILES: C=Cc1cccc(F)c1Cc1nc2c(N)nc(-c3cccc(C#N)c3)c(-c3ccncn3)n2n1]

A mixture of 3-(8-amino-2-(2-chloro-6-fluorobenzyl)-5-(pyrimidin-4-yl)-[1,2,4]triazolo[1,5-a]pyrazin-6-yl)benzonitrile (50 mg, 0.11 mmol), 4,4,5,5-tetramethyl-2-vinyl-1,3,2-dioxaborolane (34 mg, 0.22 mmol), dicyclohexyl(2',4',6'-triisopropylbiphenyl-2-yl)phosphine-(2'-aminobiphenyl-2-yl)(chloro)palladium (1:1) (8.5 mg, 10.8 μmol) and $K_3PO_4$ (47 mg, 0.22 mmol) in 1,4-dioxane (2 mL)/water (0.4 mL) was stirred at 110° C. for 1 h. The reaction mixture was concentrated under vacuum and the resulting residue was purified with flash chromatography to give the desired product as a light yellow oil. LC-MS calculated for $C_{25}H_{18}FN_8$ (M+H)$^+$: m/z=449.2; found 449.1.

Step 5: 3-(8-Amino-2-(2-fluoro-6-formylbenzyl)-5-(pyrimidin-4-yl)-[1,2,4]triazolo[1,5-a]pyrazin-6-yl)benzonitrile

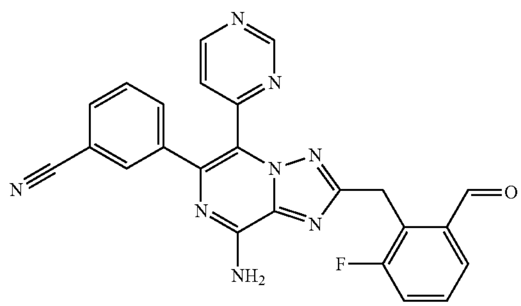 [SMILES: N#Cc1cccc(-c2nc(N)c3nc(Cc4c(F)cccc4C=O)nn3c2-c2ccncn2)c1]

To a solution of 3-(8-amino-2-(2-fluoro-6-vinylbenzyl)-5-(pyrimidin-4-yl)-[1,2,4]triazolo[1,5-a]pyrazin-6-yl)benzonitrile (40 mg, 0.089 mmol) in THF (1 mL) and water (1 mL) was added 0.157 M osmium tetraoxide in water (0.02 mmol). After 2 min, sodium metaperiodate (86 mg, 0.4 mmol) was added. The reaction mixture was heated at 60° C. for 1 h before quenched with sat. $Na_2S_2O_3$. The mixture was extracted with DCM. The organic phase was washed with brine, dried over $Na_2SO_4$, filtered, and concentrated to afford the product as a light yellow oil. LC-MS calculated for $C_{24}H_{16}FN_8O$ (M+H)$^+$: m/z=451.1; found 451.1.

Step 6: (S)-1-(2-((8-amino-6-(3-cyanophenyl)-5-(pyrimidin-4-yl)-[1,2,4]triazolo[1,5-a]pyrazin-2-yl)methyl)-3-fluorobenzyl)pyrrolidine-3-carboxylic acid To a solution of 3-(8-amino-2-(2-fluoro-6-formylbenzyl)-5-(pyrimidin-4-yl)-[1,2,4]triazolo[1,5-a]pyrazin-6-yl)benzonitrile (10 mg, 0.02 mmol) in DCM (0.5 mL) was added (S)-pyrrolidine-3-carboxylic acid (4.6 mg, 0.04 mmol) then acetic acid (4 μL, 0.08 mmol). After 1 h, sodium triacetoxyborohydride (8.5 mg, 0.04 mmol) was added to the reaction. The reaction was stirred overnight and the mixture was concentrated and purified by preparative LCMS (pH 2, acetonitrile/water with TFA) to afford the desired product as TFA salt. LCMS calculated for $C_{29}H_{25}FN_9O_2$ (M+H)$^+$: 550.2 found 550.2.

Example 31. 1-(2-((8-Amino-6-(3-cyanophenyl)-5-(pyrimidin-4-yl)-[1,2,4]triazolo[1,5-a]pyrazin-2-yl)methyl)-3-fluorobenzyl)azetidine-3-carboxylic acid

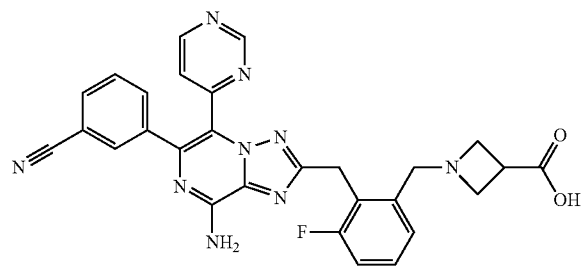 [SMILES: N#Cc1cccc(-c2nc(N)c3nc(Cc4c(F)cccc4CN4CC(C(=O)O)C4)nn3c2-c2ccncn2)c1]

The title compound was prepared using similar procedures as described for Example 30, with azetidine-3-carboxylic acid replacing (S)-pyrrolidine-3-carboxylic acid in Step 6. The reaction mixture was purified by prep-HPLC (pH=2, acetonitrile/water+TFA) to give the desired product as TFA salt. LC-MS calculated for $C_{28}H_{23}FN_9O_2$ (M+H)+. 536.2 found 536.2.

Example 32 and Example 33. 3-(2-((1H-Pyrrolo[2,3-b]pyridin-1-yl)methyl)-8-amino-5-(pyrimidin-4-yl)-[1,2,4]triazolo[1,5-a]pyrazin-6-yl)benzonitrile and 3-(2-((7H-pyrrolo[2,3-b]pyridin-7-yl)methyl)-8-amino-5-(pyrimidin-4-yl)-[1,2,4]triazolo[1,5-a]pyrazin-6-yl)benzonitrile

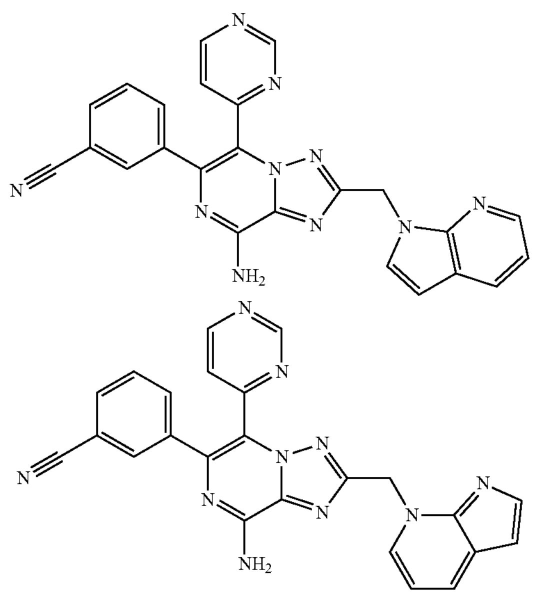

Step 1: 3-(8-(Bis(4-methoxybenzyl)amino)-2-vinyl-[1,2,4]triazolo[1,5-a]pyrazin-6-yl)benzonitrile

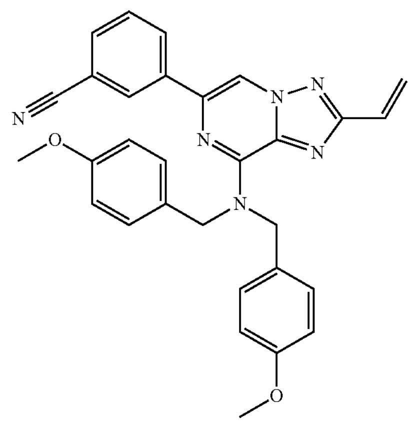 [SMILES: C=Cc1nc2c(N(Cc3ccc(OC)cc3)Cc3ccc(OC)cc3)nc(-c3cccc(C#N)c3)cn2n1]

A mixture of 3-(8-(bis(4-methoxybenzyl)amino)-2-bromo-[1,2,4]triazolo[1,5-a]pyrazin-6-yl)benzonitrile (362 mg, 0.66 mmol) (from Example 27, Step 4), 4,4,5,5-tetramethyl-2-vinyl-1,3,2-dioxaborolane (204 mg, 1.32 mmol), dicyclohexyl(2',4',6'-triisopropylbiphenyl-2-yl)phosphine-(2'-aminobiphenyl-2-yl)(chloro)palladium (1:1) (51 mg, 64.8 μmol) and $K_3PO_4$ (282 mg, 1.32 mmol) in 1,4-dioxane (5 mL)/water (1 mL) was stirred at 80° C. for 1 h. The reaction mixture was concentrated under vacuum and the resulting residue was purified with flash chromatography to give the desired product as a light yellow oil. LC-MS calculated for $C_{30}H_{27}N_6O_2$ $(M+H)^+$: m/z=503.2; found 503.2.

Step 2: 3-(8-(Bis(4-methoxybenzyl)amino)-5-bromo-2-vinyl-[1,2,4]triazolo[1,5-a]pyrazin-6-yl)benzonitrile

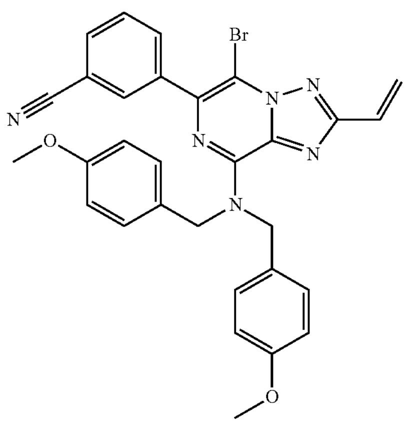 [SMILES: C=Cc1nc2c(N(Cc3ccc(OC)cc3)Cc3ccc(OC)cc3)nc(-c3cccc(C#N)c3)c(Br)n2n1]

To a solution of 3-(8-(bis(4-methoxybenzyl)amino)-2-vinyl-[1,2,4]triazolo[1,5-a]pyrazin-6-yl)benzonitrile (241 mg, 0.48 mmol) in DCM (5 mL) was added NBS (84.6 mg, 0.48 mmol). The reaction mixture was then stirred at room temperature for 1 h, and concentrated to afford the crude product, which was used in the next step without further purification. LC-MS calculated for $C_{30}H_{26}BrN_6O_2$ $(M+H)^+$: m/z=581.1; found 581.1.

Step 3: 3-(8-(Bis(4-methoxybenzyl)amino)-5-bromo-2-(hydroxymethyl)-[1,2,4]triazolo[1,5-a]pyrazin-6-yl)benzonitrile

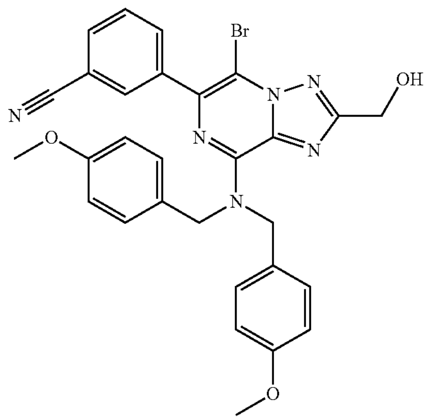 [SMILES: COc1ccc(CN(Cc2ccc(OC)cc2)c2nc(-c3cccc(C#N)c3)c(Br)n3nc(CO)nc23)cc1]

To a solution of 3-(8-(bis(4-methoxybenzyl)amino)-5-bromo-2-vinyl-[1,2,4]triazolo[1,5-a]pyrazin-6-yl)benzonitrile (203 mg, 0.35 mmol) in THE (4 mL) and water (4 mL) was added 0.157 M osmium tetraoxide in water (0.1 mmol). After 2 min, sodium metaperiodate (430 mg, 2 mmol) was added. The reaction mixture was heated at 60° C. for 1 h before quenched with sat. $Na_2S_2O_3$. The mixture was extracted with DCM. The organic phase was washed with brine, dried over $Na_2SO_4$, filtered, and concentrated. The crude material was dissolved in DCM (1 mL) and MeOH (3 mL), which was cooled to −78° C. before $NaBH_4$ (13 mg, 0.35 mmol) was added. The resulting mixture was warmed to 0° C. and stirred at this temperature for 10 min. Water (10 mL) was then added and the mixture was extracted with DCM. The organic phase was washed with brine, dried over $Na_2SO_4$, filtered, and concentrated to afford the product as a light yellow oil. LC-MS calculated for $C_{29}H_{26}BrN_6O_3$ $(M+H)^+$: m/z=585.1; found 585.1.

Step 4: 3-(8-(Bis(4-methoxybenzyl)amino)-2-(hydroxymethyl)-5-(pyrimidin-4-yl)-[1,2,4]triazolo[1,5-a]pyrazin-6-yl)benzonitrile

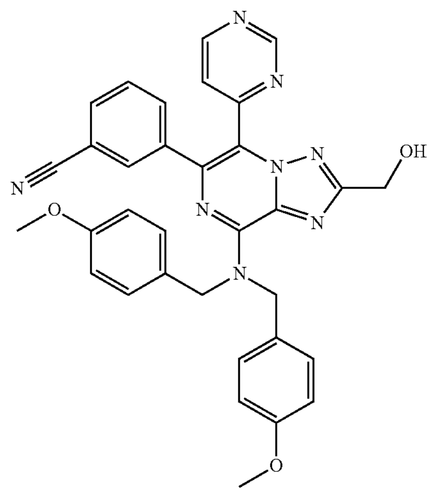 [SMILES: COc1ccc(CN(Cc2ccc(OC)cc2)c2nc(-c3cccc(C#N)c3)c(-c3ccncn3)n3nc(CO)nc23)cc1]

A mixture of 3-(8-(bis(4-methoxybenzyl)amino)-5-bromo-2-(hydroxymethyl)-[1,2,4]triazolo[1,5-a]pyrazin-6-yl)benzonitrile (257 mg, 0.44 mmol), CuI (17 mg, 0.084 mmol), CsF (132 mg, 0.88 mmol), tetrakis(triphenylphosphine)palladium(0) (48 mg, 0.048 mmol), and 4-(tributylstannyl)pyrimidine (196 mg, 0.52 mmol) in 1,4-dioxane (4 mL) was heated at 140° C. for 1 h in a microwave reactor. The reaction mixture was concentrated under vacuum and the resulting residue was purified with flash chromatography to give the desired product as a light yellow oil. LC-MS calculated for $C_{33}H_{29}N_8O_3$ $(M+H)^+$: m/z=585.2 found 585.2.

Step 5: 3-(8-(Bis(4-methoxybenzyl)amino)-2-(bromomethyl)-5-(pyrimidin-4-yl)-[1,2,4]triazolo[1,5-a]pyrazin-6-yl)benzonitrile

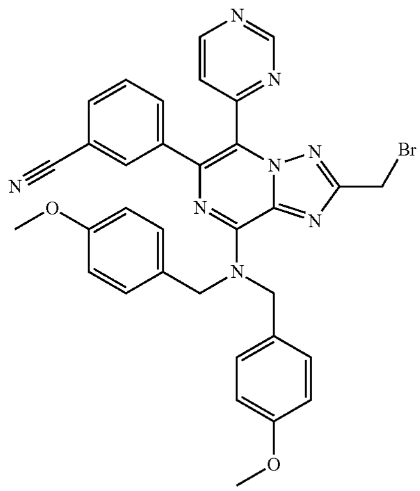 [SMILES: COc1ccc(CN(Cc2ccc(OC)cc2)c2nc(-c3cccc(C#N)c3)c(-c3ccncn3)n3nc(CBr)nc23)cc1]

3-(8-(Bis(4-methoxybenzyl)amino)-2-(hydroxymethyl)-5-(pyrimidin-4-yl)-[1,2,4]triazolo[1,5-a]pyrazin-6-yl)benzonitrile (234 mg, 0.4 mmol) was dissolved in THE (5 mL), and $PBr_3$ (0.077 mL, 0.8 mmol) was added. The mixture was stirred at 60° C. for 4 h. After completion, the reaction was quenched by adding sat. $NaHCO_3$, the mixture was then extracted with EtOAc. The organic phase was washed with brine, dried over $Na_2SO_4$, filtered, and concentrated. The residue was purified with flash chromatography to give the desired product as white solid. LC-MS calculated for $C_{33}H_{28}BrN_8O_2$ $(M+H)^+$: m/z=647.1; found 647.2.

Step 6: 3-(2-((1H-pyrrolo[2,3-b]pyridin-1-yl)methyl)-8-amino-5-(pyrimidin-4-yl)-[1,2,4]triazolo[1,5-a]pyrazin-6-yl)benzonitrile and 3-(2-((7H-pyrrolo[2,3-b]pyridin-7-yl)methyl)-8-amino-5-(pyrimidin-4-yl)-[1,2,4]triazolo[1,5-a]pyrazin-6-yl)benzonitrile 3-(8-(Bis(4-methoxybenzyl)amino)-2-(bromomethyl)-5-(pyrimidin-4-yl)-[1,2,4]triazolo[1,5-a]pyrazin-6-yl)benzonitrile (20 mg, 0.031 mmol) was dissolved in MeCN (2 mL), $K_2CO_3$ (8.6 mg, 0.062 mmol) and 1H-pyrrolo[2,3-b]pyridine (7.3 mg, 0.062) were added. The mixture was stirred at 70° C. for 6 h. After completion, the solvent was removed under vacuum and 1 mL of TFA was added to the residue. The mixture was heated at 100° C. for 10 min. The reaction mixture was concentrated under vacuum and the resulting residue was dissolved in methanol, and purified with prep-LCMS (pH 2, acetonitrile/water+TFA). The first peak was isolated as Example 32 as a TFA salt. LC-MS calculated for $C_{24}H_{17}N_{10}$ $(M+H)^+$: m/z=445.2 found 445.1. The second peak was isolated as Example 33, also as a TFA salt. LC-MS calculated for $C_{24}H_{17}N_{10}$ $(M+H)^+$: m/z=445.2 found 445.1.

Example 34. 3-(4-Amino-7-(4-(1-hydroxyethyl)-2-methyloxazol-5-yl)-2-(pyridin-2-ylmethyl)pyrazolo[1,5-a]pyrazin-6-yl)benzonitrile

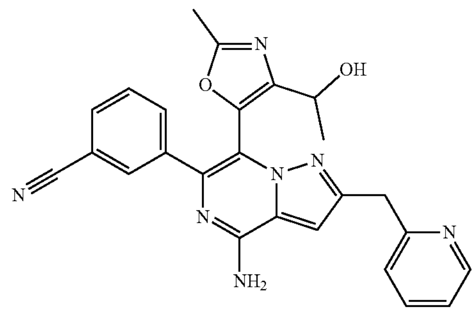 [SMILES: Cc1nc(C(C)O)c(-c2c(-c3cccc(C#N)c3)nc(N)c3cc(Cc4ccccn4)nn23)o1]

Step 1: 4-(1-((tert-Butyldimethylsilyl)oxy)ethyl)-2-methyloxazole

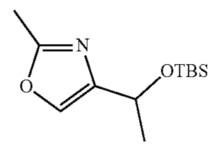 [SMILES: Cc1nc(C(C)O[Si](C)(C)C(C)(C)C)co1]

In a flame dried round-bottomed flask equipped with a magnetic stir bar, a solution of 1-(2-methyloxazol-4-yl)ethan-1-ol (1 g, 7.87 mmol) in DCM (10 mL) was treated at rt with tert-butylchlorodimethylsilane (1.3 g, 7.88 mmol) followed by imidazole (0.54 g, 7.87 mmol) and the resulting suspension was stirred for 1 h at rt. Water was added. The aq. layer was extracted with DCM and the combined org. layers were dried over $Na_2SO_4$, filtered and the solvent was removed under reduced pressure. The residue was purified with flash chromatography to give the desired product. LC-MS calculated for $C_{12}H_{24}NO_2Si$ $(M+H)^+$: m/z=242.2; found 242.2.

Step 2: 4-(1-((tert-Butyldimethylsilyl)oxy)ethyl)-2-methyl-5-(4,4,5,5-tetramethyl-1,3,2-dioxaborolan-2-yl)oxazole

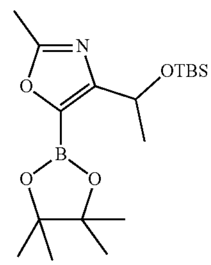 [SMILES: Cc1nc(C(C)O[Si](C)(C)C(C)(C)C)c(B2OC(C)(C)C(C)(C)O2)o1]

In a flame dried round-bottomed flask equipped with a magnetic stir bar, was charged with (1,5-cyclooctadiene)(methoxy)iridium(I) dimer (30 mg, 0.045 mmol), 4,4,5,5-tetramethyl-1,3,2-dioxaborolane (190 mg, 1.5 mmol), and pentane (2.0 mL). The mixture was stirred at rt for 10 min.

Then 4,4'-di-tert-butyl-2,2'-dipyridyl (24 mg, 0.09 mmol) was added to this mixture and reaction stirred for additional 20 min. 4-(1-((tert-butyldimethylsilyl)oxy)ethyl)-2-methyloxazole (300 mg, 1.24 mmol) dissolved in $Et_2O$ (2 mL) was added to the active catalyst mixture. The reaction was stirred at room temperature until completion. Solvent was removed under reduced pressure, and the crude material was purified with flash chromatography to give the desired product. LC-MS calculated for the corresponding boronic acid $C_{12}H_{25}BNO_4Si$ $(M+H)^+$: m/z=286.2; found 286.2.

Step 3: 3-(4-Amino-7-(4-(1-hydroxyethyl)-2-methyloxazol-5-yl)-2-(pyridin-2-ylmethyl)pyrazolo[1,5-a]pyrazin-6-yl)benzonitrile A mixture of 3-(4-amino-7-bromo-2-(pyridin-2-ylmethyl)pyrazolo[1,5-a]pyrazin-6-yl)benzonitrile (Example 17, Step 1; 15 mg, 0.037 mmol), 4-(1-((tert-butyldimethylsilyl)oxy)ethyl)-2-methyl-5-(4,4,5,5-tetramethyl-1,3,2-dioxaborolan-2-yl)oxazole (29 mg, 0.08 mmol), dicyclohexyl(2',4',6'-triisopropylbiphenyl-2-yl)phosphine-(2'-aminobiphenyl-2-yl)(chloro)palladium (1:1) (2.86 mg, 3.63 μmol) and $Cs_2CO_3$ (23.2 mg, 0.071 mmol) in 1,4-dioxane (1 mL)/water (0.200 mL) was stirred at 90° C. for 1 h. The reaction mixture was cooled down to room temperature before 6 N HCl (1 mL) was added and resulting reaction mixture was stirred at 60° C. for 30 min. The reaction was then diluted with methanol and purified with prep-LCMS (pH 2, acetonitrile/water+TFA) to give the desired product as a racemic material. Chiral separation was then conducted with chiral HPLC using AM-1 column and 30% EtOH in hexanes (20 ml/min) solvent system. Peak 2 was collected as the desired product. LC-MS calculated for $C_{25}H_{22}N_7O_2$ $(M+H)^+$: m/z=452.2; found 452.2.

Example 35. 3-(4-Amino-7-(4-(2,2-difluoro-1-hydroxyethyl)-2-methyloxazol-5-yl)-2-(pyridin-2-ylmethyl)pyrazolo[1,5-a]pyrazin-6-yl)benzonitrile

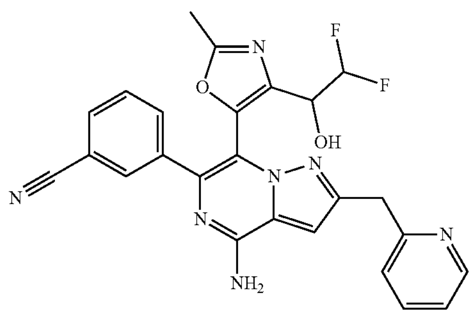 [SMILES: Cc1nc(C(O)C(F)F)c(-c2c(-c3cccc(C#N)c3)nc(N)c3cc(Cc4ccccn4)nn23)o1]

Step 1: 2,2-Difluoro-1-(2-methyloxazol-4-yl)ethan-1-ol

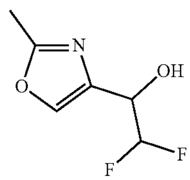

To a solution of (bromodifluoromethyl)trimethylsilane (2.4 ml, 15.07 mmol) in dry acetonitrile (10.1 ml) was added 3-bromo-4-methylbenzaldehyde (2 g, 10.05 mmol) and triphenylphosphine (3.16 g, 12.06 mmol). The resulting suspension was cooled to 0° C. and 1,3-dimethyl-3,4,5,6-tetrahydro-2(1H)-pyrimidinone (2.4 ml, 20.10 mmol) [DMPU] was added dropwise. The cooling bath was removed and the reaction mixture was warmed to rt and stirred for 1 h. With the reaction flask in a rt water bath, aqueous 3 M KOH (1.7 g, 30.1 mmol) was added dropwise via addition funnel. The bath was removed, and the reaction mixture was stirred rapidly for 1.5 h. The reaction was then neutralized by aqueous 2 M HCl (10.1 ml, 20.10 mmol), and the mixture was extracted with MTBE (2×75 ml). The combined organic layers were washed with Sat. NaCl solution, dried over $Na_2SO_4$, filtered, and concentrated to afford the crude product as a brown oil, which was purified with flash chromatography to give the desired product. LC-MS calculated for $C_6H_8F_2NO_2$ $(M+H)^+$: m/z=164.0; found 164.0.

Step 2: 4-(1-((tert-butyldimethylsilyl)oxy)-2,2-difluoroethyl)-2-methyloxazole

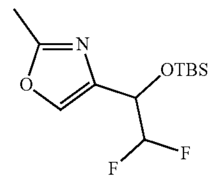 [SMILES: Cc1nc(C(O[Si](C)(C)C(C)(C)C)C(F)F)co1]

In a flame dried round-bottomed flask equipped with a magnetic stir bar, a solution of 2,2-difluoro-1-(2-methyloxazol-4-yl)ethan-1-ol (1.29 g, 7.87 mmol) in DCM (10 mL) was treated at rt with tert-butylchlorodimethylsilane (1.3 g, 7.88 mmol) followed by imidazole (0.54 g, 7.87 mmol) and the resulting suspension was stirred for 1 h at rt. Water was added. The aq. layer was extracted with and the combined org. layers were dried over $Na_2SO_4$, filtered and the solvent was removed under reduced pressure. The residue was purified with flash chromatography to give the desired product. LC-MS calculated for $C_{12}H_{22}F_2NO_2Si$ $(M+H)^+$: m/z=278.1; found 278.1.

Step 3: 4-(1-((tert-Butyldimethylsilyl)oxy)-2,2-difluoroethyl)-2-methyl-5-(4,4,5,5-tetramethyl-4,3,2-dioxaborolan-2-yl)oxazole

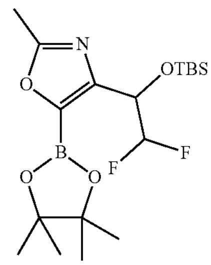 [SMILES: Cc1nc(C(O[Si](C)(C)C(C)(C)C)C(F)F)c(B2OC(C)(C)C(C)(C)O2)o1]

In a flame dried round-bottomed flask equipped with a magnetic stir bar, was charged with (1,5-cyclooctadiene)(methoxy)iridium(I) dimer (60 mg, 0.09 mmol), 4,4,5,5- tetramethyl-1,3,2-dioxaborolane (834 mg, 3.0 mmol), and pentane (4.0 mL). The mixture was stirred at room temperature for 10 min. Then 4,4'-di-tert-butyl-2,2'-dipyridyl (48 mg, 0.18 mmol) was added to this mixture and reaction stirred for additional 20 min. 4-(1-((tert-butyldimethylsilyl)oxy)ethyl)-2-methyloxazole (600 mg, 2.4 mmol) dissolved in $Et_2O$ (4 mL) was added to the active catalyst mixture. The reaction was stirred at room temperature until completion. Solvent was removed under reduced pressure, and the crude material was purified with flash chromatography to give the desired product. LC-MS calculated for the corresponding boronic acid $C_{12}H_{22}BF_2NO_4Si$ $(M+H)^+$: m/z=322.2; found 322.1.

Step 4: 3-(4-Amino-7-(4-(2,2-difluoro-1-hydroxyethyl)-2-methyloxazol-5-yl)-2-(pyridin-2-ylmethyl)pyrazolo[1,5-a]pyrazin-6-yl)benzonitrile A mixture of 3-(4-amino-7-bromo-2-(pyridin-2-ylmethyl)pyrazolo[1,5-a]pyrazin-6-yl)benzonitrile (Example 17, Step 1; 15 mg, 0.037 mmol), 4-(1-((tert-butyldimethylsilyl)oxy)-2,2-difluoroethyl)-2-methyl-5-(4,4,5,5-tetramethyl-1,3,2-dioxaborolan-2-yl)oxazole (32 mg, 0.08 mmol), dicyclohexyl(2',4',6'-triisopropylbiphenyl-2-yl)phosphine-(2'-aminobiphenyl-2-yl)(chloro)palladium (1:1) (2.86 mg, 3.63 μmol) and $Cs_2CO_3$ (23.2 mg, 0.071 mmol) in 1,4-dioxane (1 mL)/water (0.200 mL) was stirred at 90° C. for 1 h. The reaction mixture was cooled down to room temperature before 6 N HCl (1 mL) was added and resulting reaction mixture was stirred at 60° C. for 30 min. The reaction was then diluted with methanol and purified with prep-LCMS (pH 2, acetonitrile/water+TFA) to give the desired product as a racemic material. Chiral separation was then conducted with chiral HPLC using Phenomenex LUX Amylose-1 column and 45% EtOH in hexanes (20 ml/min) solvent system. Peak 1 was collected as the desired product. LC-MS calculated for $C_{25}H_{20}F_2N_7O_2$ $(M+H)^+$: m/z=488.2; found 488.2.

Example 36. 3-(4-Amino-7-(1-ethyl-1H-1,2,3-triazol-5-yl)-2-(pyridin-2-ylmethyl)pyrazolo[1,5-a]pyrazin-6-yl)benzonitrile

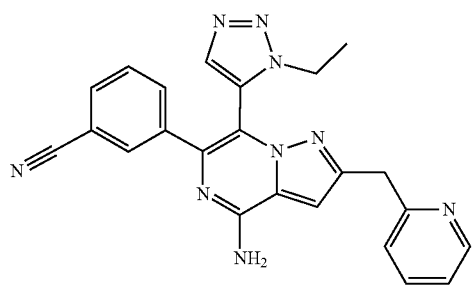 [SMILES: CCn1nncc1-c1c(-c2cccc(C#N)c2)nc(N)c2cc(Cc3ccccn3)nn12]

Step 1: 1-Ethyl-5-(trimethylstannyl)-1H-1,2,3-triazole

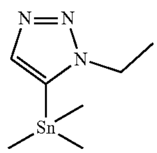

To a stirred solution of 1-ethyl-1H-1,2,3-triazole (0.58 g, 6.0 mmol) in anhydrous tetrahydrofuran (50 mL) at −78° C. under an atmosphere of nitrogen was added n-butyllithium (2.5M solution in hexanes, 2.6 mL, 6.6 mmol) dropwise over ten minutes. On complete addition the reaction was allowed to warm to −30° C. and stirred for 2 h. A solution of chlorotrimethylstannane (1.3 g, 6.6 mmol) in tetrahydrofuran (2 mL) was added dropwise over 10 minutes then the reaction mixture was allowed to warm to room temperature over 2 h. The reaction was quenched by the addition of saturated ammonium chloride solution (5 mL) then diluted with water (20 mL). The solvent was evaporated in vacuo and the aqueous phase extracted with ethyl acetate (2×30 mL). The combined organic layer was dried over sodium sulfate, filtered and concentrated to afford the desired product as a pale oil. LC-MS calculated for $C_7H_{16}N_3Sn$ $(M+H)^+$: m/z=262.0; found 262.0.

Step 2: 3-(4-Amino-7-(1-ethyl-1H-1,2,3-triazol-5-yl)-2-(pyridin-2-ylmethyl)pyrazolo[1,5-a]pyrazin-6-yl)benzonitrile A mixture of 3-(4-amino-7-bromo-2-(pyridin-2-ylmethyl)pyrazolo[1,5-a]pyrazin-6-yl)benzonitrile (Example 17, Step 1; 15 mg, 0.037 mmol), CuI (17 mg, 0.084 mmol), CsF (132 mg, 0.88 mmol), tetrakis(triphenylphosphine)palladium(0) (48 mg, 0.048 mmol), and 1-ethyl-5-(trimethylstannyl)-1H-1,2,3-triazole (135 mg, 0.52 mmol) in 1,4-dioxane (4 mL) was heated at 140° C. for 1 h in a microwave reactor. The reaction mixture was concentrated under vacuum and the resulting residue was dissolved in methanol, and purified with preparative LCMS (pH 2, acetonitrile/water with TFA) to afford the desired product as TFA salt. LCMS calculated for $C_{23}H_{20}N_9$ $(M+H)^+$: m/z=422.2 found 422.2.

Example 37. 3-(4-Amino-7-(1-methyl-1H-1,2,3-triazol-5-yl)-2-(pyridin-2-ylmethyl)pyrazolo[1,5-a]pyrazin-6-yl)benzonitrile

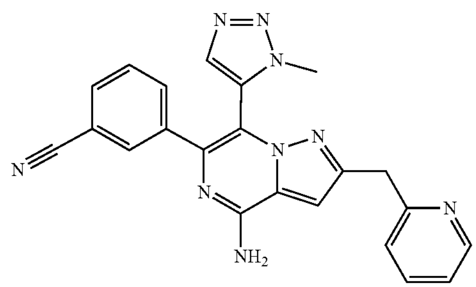 [SMILES: Cn1nncc1-c1c(-c2cccc(C#N)c2)nc(N)c2cc(Cc3ccccn3)nn12]

The title compound was prepared using similar procedures as described for Example 36, with 1-methyl-5-(tributylstannyl)-1H-1,2,3-triazole replacing 1-ethyl-5-(trimethylstannyl)-1H-1,2,3-triazole in Step 2. The reaction mixture was purified with preparative LCMS (pH 2, acetonitrile/water with TFA) to afford the desired product as TFA salt. LCMS calculated for $C_{22}H_{18}N_9$ $(M+H)^+$: m/z=408.2 found 408.1.

Example 38. 3-(4-Amino-2-((2-fluorophenyl)(hydroxy)methyl)-7-(pyrimidin-4-yl)pyrazolo[1,5-a]pyrazin-6-yl)benzonitrile

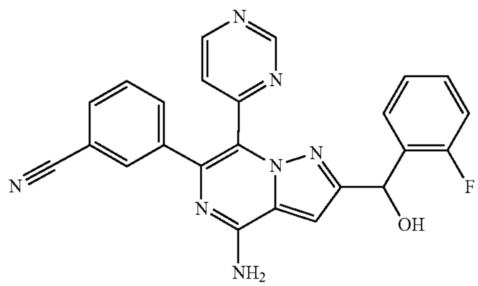 [SMILES: N#Cc1cccc(-c2nc(N)c3cc(C(O)c4ccccc4F)nn3c2-c2ccncn2)c1]

The title compound, an enantiomeric pure compound, was prepared by separating a racemic mixture of Example 23. The chiral separation was conducted with chiral HPLC using Phenomenex Lux Cellulose-4, 21.2×250 mm, 5 um column and 40% EtOH in hexanes (20 ml/min) solvent system. Peak 1 was collected as the title compound. LC-MS calculated for $C_{24}H_{17}FN_7O$ $(M+H)^+$: m/z=438.2 found 438.2.

Example 39. 3-(8-Amino-2-(2-fluorophenoxy)-5-(pyrimidin-4-yl)-[1,2,4]triazolo[1,5-a]pyrazin-6-yl)benzonitrile

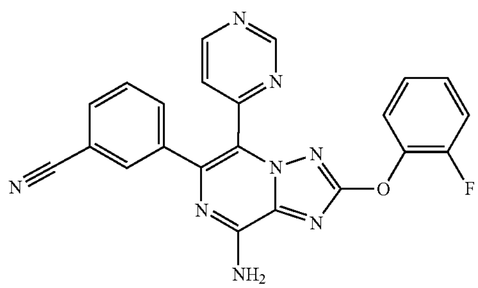 [SMILES: N#Cc1cccc(-c2nc(N)c3nc(Oc4ccccc4F)nn3c2-c2ccncn2)c1]

Step 1: 3-(8-(Bis(4-methoxybenzyl)amino)-2-(3-fluorophenoxy)-[1,2,4]triazolo[1,5-a]pyrazin-6-yl)benzonitrile

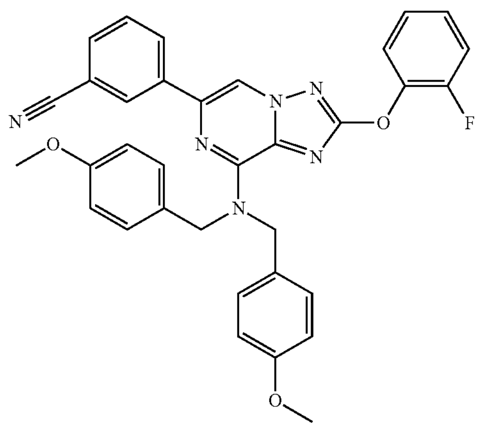 [SMILES: COc1ccc(CN(Cc2ccc(OC)cc2)c2nc(-c3cccc(C#N)c3)cn3nc(Oc4ccccc4F)nc23)cc1]

A reaction vial was charged with 3-(8-(bis(4-methoxybenzyl)amino)-2-bromo-[1,2,4]triazolo[1,5-a]pyrazin-6-yl)benzonitrile (25 mg, 0.045 mmol) (from Example 27, Step 4), 3-fluorophenol (7.6 mg, 0.068 mmol), dimethylglycine (4.2 mg, 0.041 mmol), CuI (2.6 mg, 0.014 mmol), cesium carbonate (29 mg, 0.090 mmol) and dioxane (1 mL). The reaction mixture was purged with nitrogen for 5 min before heating to 100° C. and stirring for 15 h. The reaction mixture was then diluted with water and ethyl acetate. The organic layer was separated, washed with brine, dried over $Na_2SO_4$, filtered and concentrated. The resulting residue was purified via flash chromatography to give the desired product as a white solid (18 mg, 56%). LC-MS calculated for $C_{34}H_{28}FN_6O_3$ $(M+H)^+$: m/z=587.2; found 587.2.

Step 2: 3-(8-(Bis(4-methoxybenzyl)amino)-2-(2-fluorophenoxy)-5-(pyrimidin-4-yl)-[1,2,4]triazolo[1,5-a]pyrazin-6-yl)benzonitrile

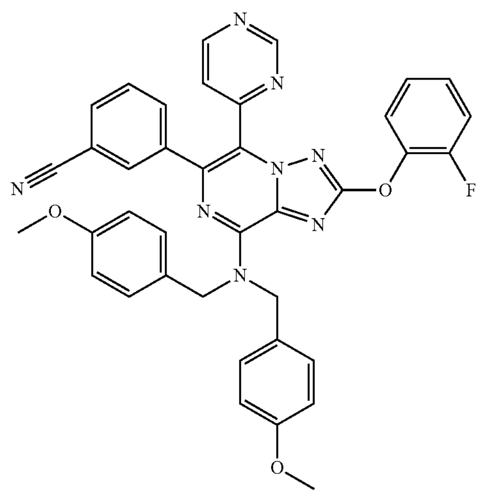 [SMILES: COc1ccc(CN(Cc2ccc(OC)cc2)c2nc(-c3cccc(C#N)c3)c(-c3ccncn3)n3nc(Oc4ccccc4F)nc23)cc1]

3-(8-(Bis(4-methoxybenzyl)amino)-2-(3-fluorophenoxy)-[1,2,4]triazolo[1,5-a]pyrazin-6-yl)benzonitrile (18 mg, 0.025 mmol) was dissolved dichloromethane (1 mL), and NBS (8 mg, 0.045 mmol) was added. The mixture was stirred at rt for 0.5 h before quenching by the addition of aqueous $Na_2SO_3$ solution. The organic layer was separated, dried over $Na_2SO_4$, filtered and concentrated. The crude brominated product was added LiCl (1.3 mg, 0.030 mmol), CuI (5.8 mg, 0.030 mmol), $Pd_2(dba)_3$ (2.3 mg, 0.003 mmol), $PPh_3$ (1.3 mg, 0.005 mmol) and 4-(tributylstannyl)pyrimidine (14 mg, 0.038 mmol). The reaction mixture was dissolved in dioxane, and purged with nitrogen for 5 min, before heating to 100° C. for 15 h. The reaction mixture was then cooled to rt, filtered, concentrated, and purified via flash chromatography to give the desired product as a white solid (10 mg, 60%). LC-MS calculated for $C_{38}H_{30}FN_8O_3$ $(M+H)^+$: m/z=665.2; found 665.2.

Step 3: 3-(8-Amino-2-(2-fluorophenoxy)-5-(pyrimidin-4-yl)-[1,2,4]triazolo[1,5-a]pyrazin-6-yl)benzonitrile 3-(8-(Bis(4-methoxybenzyl)amino)-2-(2-fluorophenoxy)-5-(pyrimidin-4-yl)-[1,2,4]triazolo[1,5-a]pyrazin-6-yl)benzonitrile (10 mg, 0.015 mmol) was added TFA (0.5 mL), and stirred at 100° C. for 5 min. The reaction mixture was then cooled to room temperature, solvent removed, diluted with methanol, and purified via prep-LCMS (pH 2, acetonitrile/water with TFA) to give the desired product as a TFA salt. LC-MS calculated for $C_{22}H_{14}FN_8O$ $(M+H)^+$: m/z=425.1; found 425.2.

Example 40. 3-(8-Amino-2-(hydroxy(pyridin-2-yl)methyl)-5-(4-methyloxazol-5-yl)-[1,2,4]triazolo[1,5-a]pyrazin-6-yl)benzonitrile

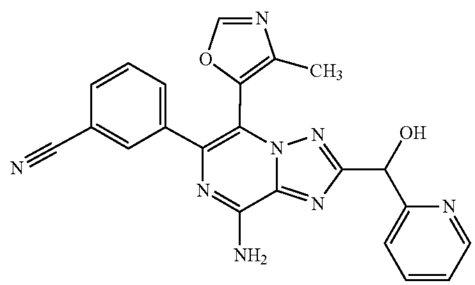 [SMILES: Cc1ncoc1-c1c(-c2cccc(C#N)c2)nc(N)c2nc(C(O)c3ccccn3)nn12]

Step 1: 3-(8-(Bis(4-methoxybenzyl)amino)-2-formyl-[1,2,4]triazolo[1,5-a]pyrazin-6-yl)benzonitrile

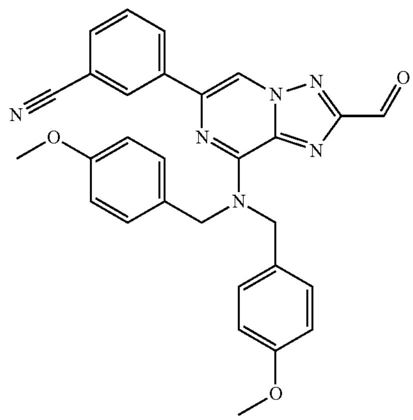 [SMILES: COc1ccc(CN(Cc2ccc(OC)cc2)c2nc(-c3cccc(C#N)c3)cn3nc(C=O)nc23)cc1]

To a solution of 3-(8-(bis(4-methoxybenzyl)amino)-2-vinyl-[1,2,4]triazolo[1,5-a]pyrazin-6-yl)benzonitrile (1.00 g, 1.99 mmol) (From Example 32, Step 1) and sodium periodate (1.92 g, 8.95 mmol) in THE (10 mL) and water (10 mL) was added osmium tetroxide (4% solution in water, 1.21 mL, 0.20 mmol). The reaction mixture was stirred at 60° C. for 1 h. The reaction mixture was then diluted with water and DCM. The layers were separated, the aqueous layer was extracted with DCM, and the combined organic fractions were dried over $MgSO_4$, filtered and concentrated. The resulting residue was purified using flash chromatography to give the desired product (0.74 g, 74%). LC-MS calculated for $C_{29}H_{25}N_6O_3$ $(M+H)^+$: m/z=505.2; found 505.2.

Step 2: 3-(8-(Bis(4-methoxybenzyl)amino)-2-(hydroxy(pyridin-2-yl)methyl)-[1,2,4]triazolo[1,5-a]pyrazin-6-yl)benzonitrile

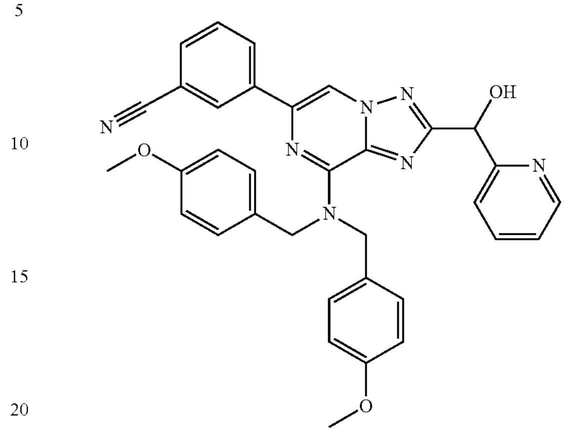

To a solution of 2-iodopyridine (0.40 g, 1.95 mmol) in THE (2 mL) was added isopropylmagnesium chloride lithium chloride complex solution (1.3 M, 1.3 mL, 1.71 mmol) dropwise at 0° C. The reaction mixture was stirred at 0° C. for 30 minutes. A solution of 3-(8-(bis(4-methoxybenzyl)amino)-2-formyl-[1,2,4]triazolo[1,5-a]pyrazin-6-yl)benzonitrile (0.25 g, 0.49 mmol) in THE (2 mL) was added dropwise and the reaction mixture was stirred at 0° C. for 1 h. The reaction mixture was then quenched with saturated aqueous $NH_4Cl$ solution and diluted with DCM. The layers were separated, the aqueous layer was extracted with DCM, and the combined organic fractions were dried over $MgSO_4$, filtered and concentrated. The resulting residue was purified using flash chromatography to give the desired product (0.19 g, 67%). LC-MS calculated for $C_{34}H_{30}N_7O_3$ $(M+H)^+$: m/z=584.2; found 584.3.

Step 3: 3-(8-(Bis(4-methoxybenzyl)amino)-5-bromo-2-(hydroxy(pyridin-2-yl)methyl)-[1,2,4]triazolo[1,5-a]pyrazin-6-yl)benzonitrile

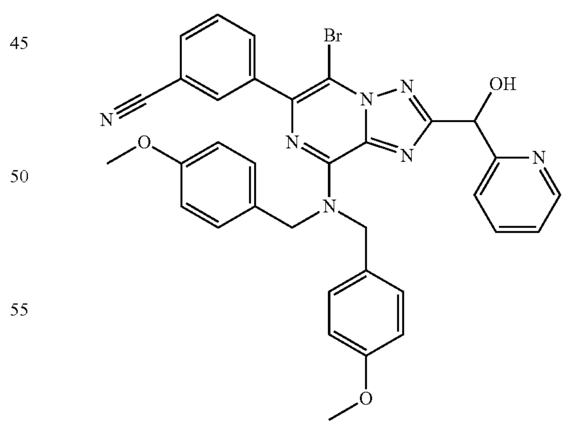

To a solution of 3-(8-(bis(4-methoxybenzyl)amino)-2-(hydroxy(pyridin-2-yl)methyl)-[1,2,4]triazolo[1,5-a]pyrazin-6-yl)benzonitrile (0.17 g, 0.29 mmol) in DCM (3 mL) was added a solution of NBS (0.052 g, 0.29 mmol) in DCM (3 mL) dropwise at 0° C. The reaction mixture was stirred at 0° C. for 1 h. The reaction mixture was concentrated, and the resulting residue was purified using flash chromatography to give the desired product (0.15 g, 78%). LC-MS calculated for $C_{34}H_{29}BrN_7O_3$ (M+H)$^+$: m/z=662.2; found 662.2.

Step 4: 3-(8-Amino-2-(hydroxy(pyridin-2-yl)methyl)-5-(4-methyloxazol-5-yl)-[1,2,4]triazolo[1,5-a]pyrazin-6-yl)benzonitrile To a solution of 3-(8-(bis(4-methoxybenzyl)amino)-5-bromo-2-(hydroxy(pyridin-2-yl)methyl)-[1,2,4]triazolo[1,5-a]pyrazin-6-yl)benzonitrile (0.010 g, 0.015 mmol), 4-methyl-5-(4,4,5,5-tetramethyl-1,3,2-dioxaborolan-2-yl)oxazole (0.013 g, 0.060 mmol), and dicyclohexyl(2',4',6'-triisopropylbiphenyl-2-yl)phosphine-(2'-aminobiphenyl-2-yl)(chloro)palladium (1:1) (0.004 g, 0.005 mmol) in dioxane (0.250 mL) and water (0.050 mL) was added potassium phosphate tribasic (0.016 g, 0.075 mmol). The reaction mixture was stirred at 100° C. for 1 h. The reaction mixture was then diluted with water and DCM. The layers were separated, the aqueous layer was extracted with DCM, and the combined organic fractions were dried over $MgSO_4$, filtered and concentrated. The crude material was dissolved in TFA (1 mL) and heated to 80° C. for 20 minutes. The solution was diluted with DMF (4 mL) and purified with prep-LCMS (pH=2, acetonitrile/water+TFA) to give the desired product as a pair of enantiomers, and as a TFA salt (3.5 mg, 43%). LC-MS calculated for $C_{22}H_{17}N_8O_2$ (M+H)$^+$: m/z=425.2; found 425.3.

Example 41. 3-(8-Amino-2-(2-(1-methyl-1H-pyrazol-4-yl)benzyl)-5-(pyrimidin-4-yl)-[1,2,4]triazolo[1,5-a]pyrazin-6-yl)benzonitrile

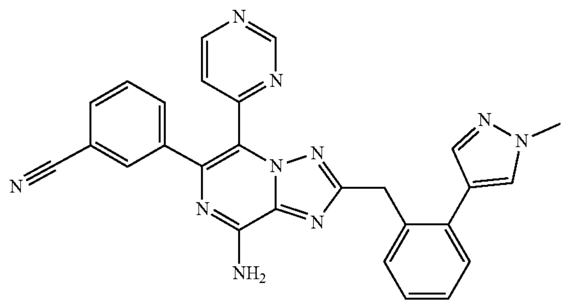 [SMILES: Cn1cc(-c2ccccc2Cc2nc3c(N)nc(-c4cccc(C#N)c4)c(-c4ccncn4)n3n2)cn1]

Step 1: 3-(8-(Bis(4-methoxybenzyl)amino)-2-(2-chlorobenzyl)-[1,2,4]triazolo[1,5-a]pyrazin-6-yl)benzonitrile

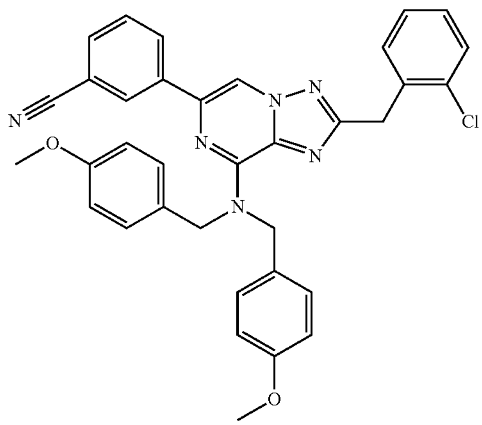 [SMILES: COc1ccc(CN(Cc2ccc(OC)cc2)c2nc(-c3cccc(C#N)c3)cn3nc(Cc4ccccc4Cl)nc23)cc1]

A microwave vial was charge with 3-(8-(bis(4-methoxybenzyl)amino)-2-bromo-[1,2,4]triazolo[1,5-a]pyrazin-6-yl)benzonitrile (350 mg, 0.630 mmol) (from example 27 step 4), palladium acetate (7.07 mg, 0.032 mmol), and 2'-(dicyclohexylphosphino)-N,N,N',N'-tetramethylbiphenyl-2,6-diamine (27.5 mg, 0.063 mmol) was evacuated under high vacuum and backfilled with nitrogen. (2-chlorobenzyl)zinc (II) chloride (1386 µl, 0.693 mmol) was added via syringe. After addition, the reaction was heated to 60° C. for 1 h. The reaction solution was partitioned between EtOAc and sat. $NH_4Cl$ solution. The layers were separated and the aqueous extracted further with EtOAc (2×). The combined organics were washed with water and brine, dried over $MgSO_4$, and concentrated. The residue was purified with flash chromatography to give the desired product (0.32 g, 82%). LC-MS calculated for $C_{35}H_{30}ClN_6O_2$ (M+H)$^+$: m/z=601.2; found 601.2.

Step 2. 3-(8-(Bis(4-methoxybenzyl)amino)-5-bromo-2-(2-chlorobenzyl)-[1,2,4]triazolo[1,5-a]pyrazin-6-yl)benzonitrile

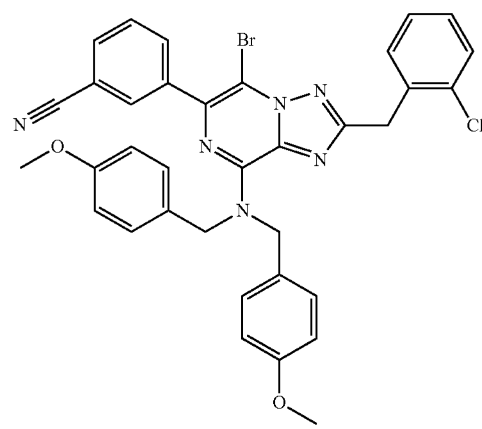 [SMILES: COc1ccc(CN(Cc2ccc(OC)cc2)c2nc(-c3cccc(C#N)c3)c(Br)n3nc(Cc4ccccc4Cl)nc23)cc1]

To a solution of 3-(8-(bis(4-methoxybenzyl)amino)-2-(2-chlorobenzyl)-[1,2,4]triazolo[1,5-a]pyrazin-6-yl)benzonitrile (0.379 g, 0.631 mmol) in DCM (6.3 ml) was added 1-bromopyrrolidine-2,5-dione (0.107 g, 0.599 mmol) at 0° C. After stirring at room temperature for 1 h, the reaction mixture was diluted with water. The organic layer was separated, dried over $Na_2SO_4$, filtered and concentrated. The residue was purified with silica gel column to give the desired product (0.38 g, 89%). LC-MS calculated for $C_{35}H_{29}BrClN_6O_2$ (M+H)$^+$: m/z=679.1, 681.1; found 679.2, 681.2.

Step 3. 3-(8-(Bis(4-methoxybenzyl)amino)-2-(2-chlorobenzyl)-5-(pyrimidin-4-yl)-[1,2,4]triazolo[1,5-a]pyrazin-6-yl)benzonitrile

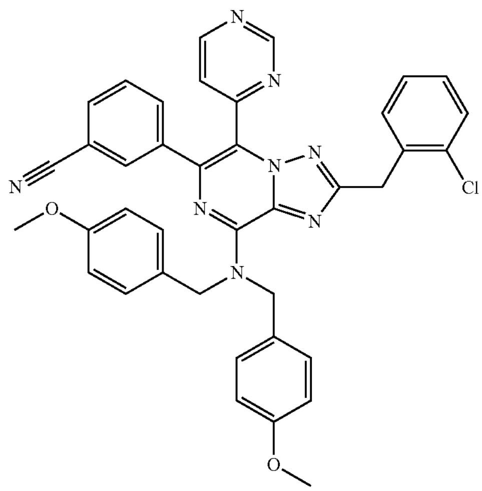 [SMILES: COc1ccc(CN(Cc2ccc(OC)cc2)c2nc(-c3cccc(C#N)c3)c(-c3ccncn3)n3nc(Cc4ccccc4Cl)nc23)cc1]

A mixture of 3-(8-(bis(4-methoxybenzyl)amino)-5-bromo-2-(2-chlorobenzyl)-[1,2,4]triazolo[1,5-a]pyrazin-6-yl)benzonitrile (381 mg, 0.560 mmol), 4-(tributylstannyl) pyrimidine (310 mg, 0.840 mmol), and copper(I) chloride (66.6 mg, 0.672 mmol), lithium chloride (28.5 mg, 0.672 mmol) and tetrakis(triphenylphosphine)palladium(0) (64.7 mg, 0.056 mmol) in THE (6 ml) was first purged with $N_2$, and then heated and stirred at 90° C. for 2 h. The reaction mixture was diluted with ethyl acetate and water. The reaction mixture was filtered through a pad of Celite®. The organic layer was separated and dried over $Na_2SO_4$, filtered and concentrated. The residue was purified with flash chromatography to give the desired product (0.31 g, 83%). LC-MS calculated for $C_{39}H_{32}ClN_8O_2$ $(M+H)^+$: m/z=679.2; found 679.2.

Step 4. 3-(8-Amino-2-(2-(1-methyl-1H-pyrazol-4-yl)benzyl)-5-(pyrimidin-4-yl)-[1,2,4]triazolo[1,5-a]pyrazin-6-yl)benzonitrile A mixture of 3-(8-(bis(4-methoxybenzyl)amino)-2-(2-chlorobenzyl)-5-(pyrimidin-4-yl)-[1,2,4]triazolo[1,5-a] pyrazin-6-yl)benzonitrile (10 mg, 0.015 mmol), 1-methyl-4-(4,4,5,5-tetramethyl-1,3,2-dioxaborolan-2-yl)-1H-pyrazole (3.68 mg, 0.018 mmol), dicyclohexyl(2',4',6'-triisopropylbiphenyl-2-yl)phosphine-(2'-aminobiphenyl-2-yl)(chloro)palladium (1:1) (1.158 mg, 1.472 μmol) and tripotassium phosphate hydrate (7.46 mg, 0.032 mmol) in 1,4-dioxane (1.0 mL)/water (0.3 mL) was stirred at 80° C. for 1 h. The reaction mixture was diluted with EtOAc and water, the organic layer was separated and concentrated. The residue was treated with TFA (1 mL) at 80° C. for 20 min. The solvent was removed, the residue was dissolved in methanol and DMSO, then purified with prep-LCMS (pH 2, acetonitrile/water+TFA) to give the desired product as TFA salt. LC-MS calculated for $C_{27}H_{21}N_{10}$ $(M+H)^+$: m/z=485.2; found 485.2.

Example 42. 3-(8-Amino-5-(4-methyloxazol-5-yl)-2-(pyridin-2-ylmethyl)-[1,2,4]triazolo[1,5-a]pyrazin-6-yl)benzonitrile

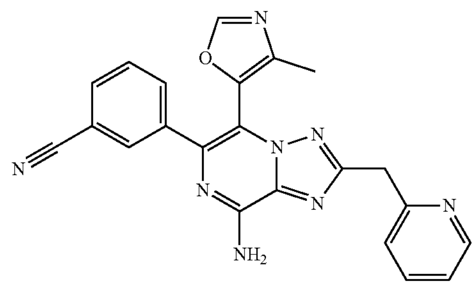 [SMILES: Cc1ncoc1-c1c(-c2cccc(C#N)c2)nc(N)c2nc(Cc3ccccn3)nn12]

Step 1: 3-(8-(Bis(4-methoxybenzyl)amino)-5-bromo-2-(pyridin-2-ylmethyl)-[1,2,4]triazolo[1,5-a] pyrazin-6-yl)benzonitrile

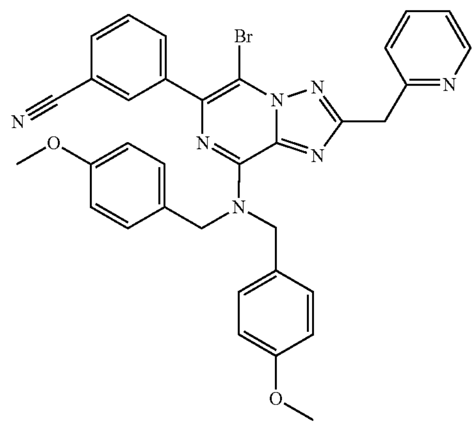 [SMILES: COc1ccc(CN(Cc2ccc(OC)cc2)c2nc(-c3cccc(C#N)c3)c(Br)n3nc(Cc4ccccn4)nc23)cc1]

To a solution of 3-(8-(bis(4-methoxybenzyl)amino)-2-(pyridin-2-ylmethyl)-[1,2,4]triazolo[1,5-a]pyrazin-6-yl) benzonitrile (0.697 g, 1.228 mmol) (From Example 27, Step 5) in DCM (12 ml) was added 1-bromopyrrolidine-2,5-dione (0.219 g, 1.228 mmol) at 0° C. After stirring at room temperature for 1 h, the reaction mixture was diluted with water. The organic layer was separated, dried over $Na_2SO_4$, filtered and concentrated. The residue was purified with silica gel column to give the desired product (0.74 g, 93%). LC-MS calculated for $C_{34}H_{29}BrN_7O_2$ $(M+H)^+$: m/z=646.2, 648.2; found 646.2, 648.2.

Step 2. 3-(8-(Bis(4-methoxybenzyl)amino)-2-(pyridin-2-ylmethyl)-5-vinyl-[1,2,4]triazolo[1,5-a]pyrazin-6-yl)benzonitrile

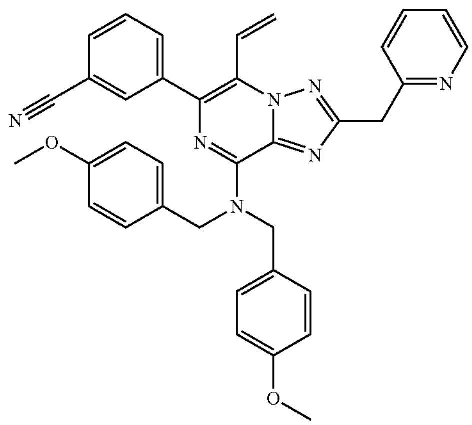 [SMILES: C=Cc1c(-c2cccc(C#N)c2)nc(N(Cc2ccc(OC)cc2)Cc2ccc(OC)cc2)c2nc(Cc3ccccn3)nn12]

A mixture of 3-(8-(bis(4-methoxybenzyl)amino)-5-bromo-2-(pyridin-2-ylmethyl)-[1,2,4]triazolo[1,5-a]pyrazin-6-yl)benzonitrile (390 mg, 0.603 mmol), 4,4,5,5-tetramethyl-2-vinyl-1,3,2-dioxaborolane (111 mg, 0.724 mmol), dicyclohexyl(2',4',6'-triisopropylbiphenyl-2-yl)phosphine-(2'-aminobiphenyl-2-yl)(chloro)palladium (1:1) (47.5 mg, 0.060 mmol) and tripotassium phosphate hydrate (306 mg, 1.327 mmol) in 1,4-dioxane (5.0 mL)/water (1.7 mL) was stirred at 80° C. for 1 h. The reaction mixture was diluted with EtOAc and water. The organic layer was separated, dried over $Na_2SO_4$, filtered and concentrated. The residue was purified with silica gel column to give the desired product (0.28 g, 77%). LC-MS calculated for $C_{36}H_{32}N_7O_2$ $(M+H)^+$: m/z=594.3; found 594.3.

Step 3. 3-(8-(Bis(4-methoxybenzyl)amino)-5-formyl-2-(pyridin-2-ylmethyl)-[1,2,4]triazolo[1,5-a]pyrazin-6-yl)benzonitrile

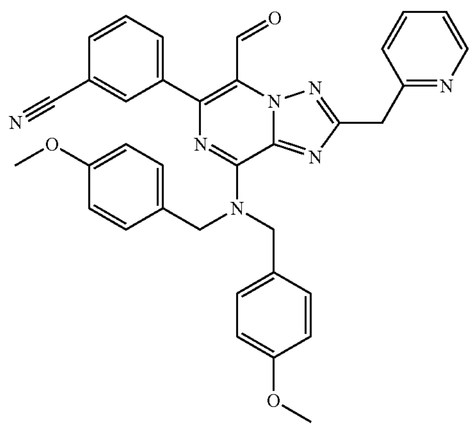 [SMILES: COc1ccc(CN(Cc2ccc(OC)cc2)c2nc(-c3cccc(C#N)c3)c(C=O)n3nc(Cc4ccccn4)nc23)cc1]

To a solution of 3-(8-(bis(4-methoxybenzyl)amino)-2-(pyridin-2-ylmethyl)-5-vinyl-[1,2,4]triazolo[1,5-a]pyrazin-6-yl)benzonitrile (277 mg, 0.467 mmol) in THE (2.3 mL) and water (2.3 mL) was added 4% osmium tetraoxide in water (233 µl, 0.037 mmol) and sodium metaperiodate (449 mg, 2.1 mmol). The reaction mixture was stirred at 60° C. for 1 h. The mixture was filtered through a plug of Celite®, rinsed with THF. The organic layer was concentrated under vacuum. The residue was purified with flash chromatography to give the desired product (0.21 g, 76%). LC-MS calculated for $C_{35}H_{30}N_7O_3$ $(M+H)^+$: m/z=596.2; found 596.2.

Step 4. 3-(8-Amino-5-(4-methyloxazol-5-yl)-2-(pyridin-2-ylmethyl)-[1,2,4]triazolo[1,5-a]pyrazin-6-yl)benzonitrile To a solution of 3-(8-(bis(4-methoxybenzyl)amino)-5-(4-methyloxazol-5-yl)-2-(pyridin-2-ylmethyl)-[1,2,4]triazolo[1,5-a]pyrazin-6-yl)benzonitrile (38 mg, 0.064 mmol) in methanol (0.3 mL) and 1,2-dichloroethane (0.3 mL) was added 1-((1-isocyanoethyl)sulfonyl)-4-methylbenzene (13.35 mg, 0.064 mmol). The resulting mixture was heated at 70° C. overnight. The reaction mixture was diluted with DCM and water, the organic layer was separated and concentrated. The residue was treated with TFA (1 mL) at 80° C. for 20 min. The solvent was removed, the residue was dissolved in methanol and DMSO, then purified with prep-LCMS (pH 2, acetonitrile/water+TFA) to give the desired product as TFA salt. LC-MS calculated for $C_{22}H_{17}N_8O$ $(M+H)^+$: m/z=409.2; found 409.1.

Example 43. 3-(8-Amino-5-(4-ethyloxazol-5-yl)-2-(pyridin-2-ylmethyl)-[1,2,4]triazolo[1,5-a]pyrazin-6-yl)benzonitrile

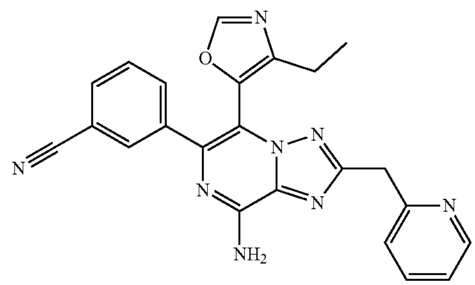 [SMILES: CCc1ncoc1-c1c(-c2cccc(C#N)c2)nc(N)c2nc(Cc3ccccn3)nn12]

The title compound was prepared using similar procedures as described for Example 42 with 1-((1-isocyanopropyl)sulfonyl)-4-methylbenzene replacing 1-((1-isocyanoethyl)sulfonyl)-4-methylbenzene in Step 4. The reaction mixture was purified by prep-HPLC (pH=2, acetonitrile/water+TFA) to give the desired product as TFA salt. LC-MS calculated for $C_{23}H_{19}N_8O$ $(M+H)^+$: m/z=423.2; found 423.2.

Example 44. 3-(8-Amino-5-(3-methylpyridin-4-yl)-2-(pyridin-2-ylmethyl)-[1,2,4]triazolo[1,5-a]pyrazin-6-yl)benzonitrile

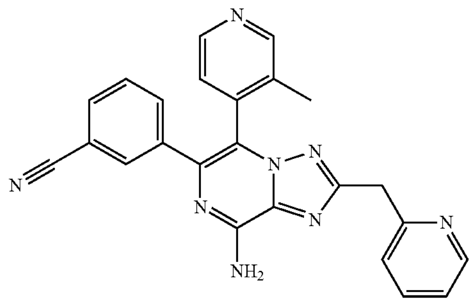 [SMILES: Cc1cnccc1-c1c(-c2cccc(C#N)c2)nc(N)c2nc(Cc3ccccn3)nn12]

A mixture of 3-(8-amino-5-bromo-2-(pyridin-2-ylmethyl)-[1,2,4]triazolo[1,5-a]pyrazin-6-yl)benzonitrile (Example 27, Step 7; 10 mg, 0.025 mmol), (3-methylpyridin-4-yl)boronic acid (4.1 mg, 0.030 mmol), dicyclohexyl(2',4',6'-triisopropylbiphenyl-2-yl)phosphine-(2'-aminobiphenyl-2-yl)(chloro)palladium (1:1) (1.9 mg, 2.5 μmol) and tripotassium phosphate hydrate (12.5 mg, 0.054 mmol) in 1,4-dioxane (1.0 mL)/water (0.3 mL) was stirred at 80° C. for 1 h. The reaction mixture was diluted with DCM and water, the organic layer was separated and concentrated. The resulting residue was dissolved in methanol and DMSO, then purified with prep-LCMS (pH 2, acetonitrile/water+TFA) to give the desired product as TFA salt. LC-MS calculated for $C_{24}H_{19}N_8$ $(M+H)^+$: m/z=419.2; found 419.2.

Example 45. 3-(8-Amino-2-(imidazo[1,2-a]pyridin-8-ylmethyl)-5-(pyrimidin-4-yl)-[1,2,4]triazolo[1,5-a]pyrazin-6-yl)benzonitrile

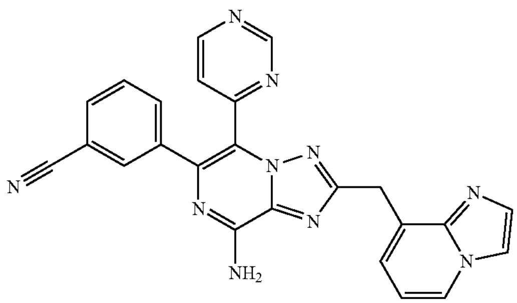 [SMILES: N#Cc1cccc(-c2nc(N)c3nc(Cc4cccn5ccnc45)nn3c2-c2ccncn2)c1]

A microwave vial charged with 3-(8-(bis(4-methoxybenzyl)amino)-2-(bromomethyl)-5-(pyrimidin-4-yl)-[1,2,4]triazolo[1,5-a]pyrazin-6-yl)benzonitrile (20 mg, 0.031 mmol) (from Example 32, Step 5), 8-(4,4,5,5-tetramethyl-1,3,2-dioxaborolan-2-yl)imidazo[1,2-a]pyridine (15.08 mg, 0.062 mmol), dicyclohexyl(2',4',6'-triisopropylbiphenyl-2-yl)phosphine-(2'-aminobiphenyl-2-yl)(chloro)palladium (1:1) (2.430 mg, 3.09 μmol) and cesium carbonate (30.2 mg, 0.093 mmol) was sealed and evacuated under high vacuum and refilled with nitrogen (repeated three times). 1,4-Dioxane (2.0 mL) and water (0.67 mL) was stirred at 90° C. overnight. The reaction mixture was diluted with ethyl acetate and water. The organic layer was separated and concentrated. The residue was treated with TFA (1 mL) at 80° C. for 20 min. After removal of the volatile, the residue was dissolved in methanol and DMSO and purified with prep-LCMS (pH 2, acetonitrile/water+TFA) to give the desired product as TFA salt. LC-MS calculated for $C_{24}H_{17}N_{10}$ $(M+H)^+$: m/z=445.2; found 445.2.

Example 46. 3-(8-Amino-2-(pyrazolo[1,5-a]pyridin-7-ylmethyl)-5-(pyrimidin-4-yl)-[1,2,4]triazolo[1,5-a]pyrazin-6-yl)benzonitrile

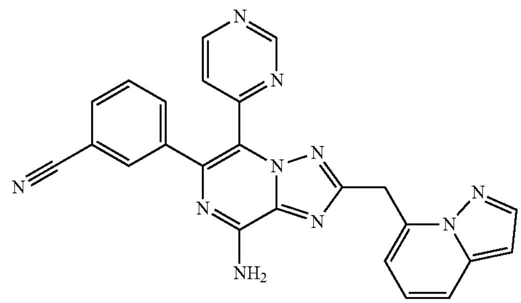 [SMILES: N#Cc1cccc(-c2nc(N)c3nc(Cc4cccc5ccnn45)nn3c2-c2ccncn2)c1]

The title compound was prepared using similar procedures as described for Example 45 with 7-(4,4,5,5-tetramethyl-1,3,2-dioxaborolan-2-yl)pyrazolo[1,5-a]pyridine replacing 8-(4,4,5,5-tetramethyl-1,3,2-dioxaborolan-2-yl)imidazo[1,2-a]pyridine. The reaction mixture was purified by prep-HPLC (pH=2, acetonitrile/water+TFA) to give the desired product as TFA salt. LC-MS calculated for $C_{24}H_{17}N_{10}$ $(M+H)^+$: m/z=445.2; found 445.2.

Example 47 and Example 48. 3-(2-((2H-Indazol-2-yl)methyl)-8-amino-5-(pyrimidin-4-yl)-[1,2,4]triazolo[1,5-a]pyrazin-6-yl)benzonitrile and 3-(2-((1H-Indazol-1-yl)methyl)-8-amino-5-(pyrimidin-4-yl)-[1,2,4]triazolo[1,5-a]pyrazin-6-yl)benzonitrile

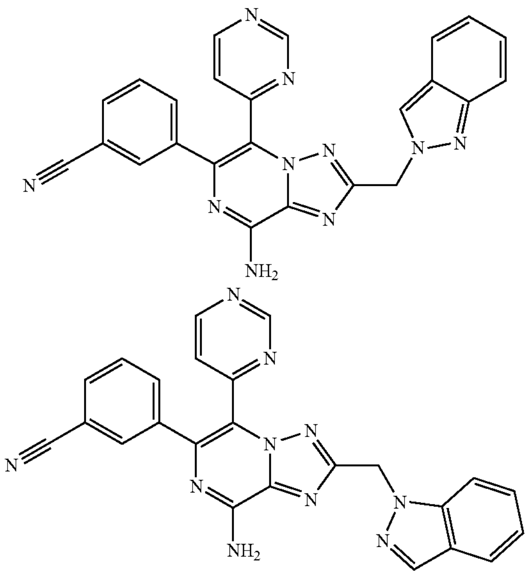

A mixture of 3-(8-(bis(4-methoxybenzyl)amino)-2-(bromomethyl)-5-(pyrimidin-4-yl)-[1,2,4]triazolo[1,5-a]

pyrazin-6-yl)benzonitrile (15 mg, 0.023 mmol) (from Example 32, Step 5), 1H-indazole (4.1 mg, 0.035 mmol), cesium carbonate (22.64 mg, 0.069 mmol) in DMF (300 μl) was stirred at 50° C. for 15 min. The reaction was diluted with EtOAc and water. The organic layer was separated and concentrated. The residue was treated with TFA (1 mL) at 80° C. for 20 min. The volatile was removed in vacuo, the residue was dissolved in methanol and DMSO and purified with prep-HPLC (pH=2, acetonitrile/water+TFA) to give the two products both as TFA salts. LC-MS calculated for both compounds $C_{24}H_{17}N_{10}$ $(M+H)^+$: m/z=445.2; found 445.2.

Example 49. 3-(8-Amino-2-((2,6-difluorophenyl)(hydroxy)methyl)-5-(pyrimidin-4-yl)-[1,2,4]triazolo[1,5-a]pyrazin-6-yl)benzonitrile, Peak 1

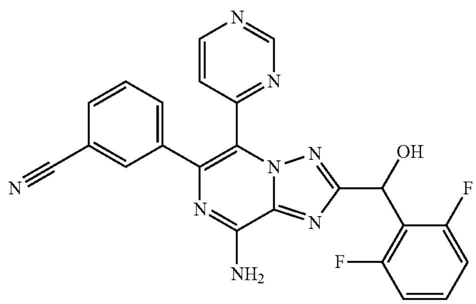 [SMILES: N#Cc1cccc(-c2nc(N)c3nc(C(O)c4c(F)cccc4F)nn3c2-c2ccncn2)c1]

Step 1: Methyl 3-bromo-1-(2-(3-cyanophenyl)-2-oxoethyl)-1H-1,2,4-triazole-5-carboxylate

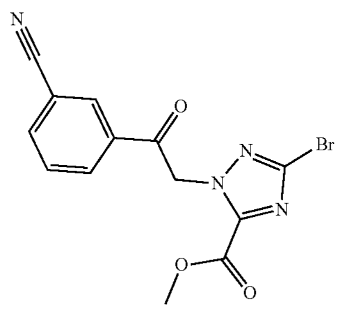 [SMILES: COC(=O)c1nc(Br)nn1CC(=O)c1cccc(C#N)c1]

To a solution of methyl 3-bromo-1H-1,2,4-triazole-5-carboxylate (5.0 g, 24.3 mmol), 3-(2-bromoacetyl)benzonitrile (5.44 g, 24.3 mmol) in DMF (100 mL) was added potassium carbonate (3.35 g, 24.3 mmol). The reaction mixture was stirred at ambient temperature for 2 h. The reaction mixture was then diluted with water and DCM. The organic layer was separated, washed with brine, dried over $Na_2SO_4$, filtered and concentrated. The resulting residue was purified via flash chromatography to give the desired product as a white solid (5.2 g, 61%). LC-MS calculated for $C_{13}H_{10}BrN_4O_3$ $(M+H)^+$: m/z=349.0; found 349.0.

Step 2: 3-(2-Bromo-8-oxo-7,8-dihydro-[1,2,4]triazolo[1,5-a]pyrazin-6-yl)benzonitrile

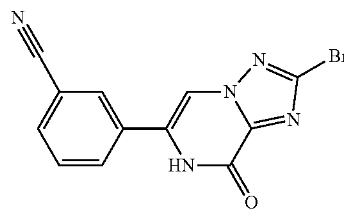

Methyl 3-bromo-1-(2-(3-cyanophenyl)-2-oxoethyl)-1H-1,2,4-triazole-5-carboxylate (10.5 g, 30.1 mmol) was dissolved in acetic acid (100 mL), and ammonium acetate (23.18 g, 301 mmol) was added. The mixture was stirred at 110° C. for 12 h. After cooling to room temperature, the reaction mixture was diluted with water. The resulting precipitate was collected via filtration, washed with water, and dried under vacuum to afford the product (8.4 g, 88%). LC-MS calculated for $C_{12}H_7BrN_5O$ $(M+H)^+$: m/z=316.0; found 316.0.

Step 3: 3-(2-Bromo-8-chloro-[1,2,4]triazolo[1,5-a]pyrazin-6-yl)benzonitrile

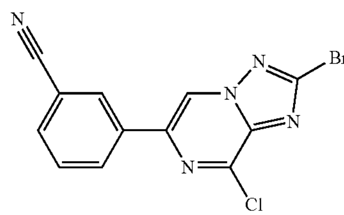

A mixture of 3-(2-bromo-8-oxo-7,8-dihydro-[1,2,4]triazolo[1,5-a]pyrazin-6-yl)benzonitrile (8.4 g, 26.6 mmol) and $POCl_3$ (49.5 mL, 531 mmol) was stirred at 110° C. overnight. After cooling to room temperature, the reaction mixture was slowly added to a flask containing ice and sodium bicarbonate. The resulting precipitate was collected via filtration, washed with water, and dried to afford the product (8.8 g, 99%). LC-MS calculated for $C_{12}H_6BrClN_5$ $(M+H)^+$: m/z=336.0; found 336.0.

Step 4: 3-(8-(Bis(4-methoxybenzyl)amino)-2-bromo-[1,2,4]triazolo[1,5-a]pyrazin-6-yl)benzonitrile

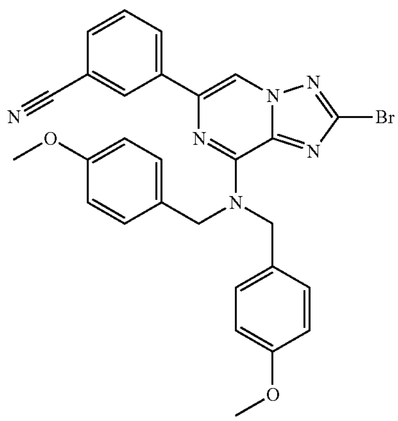 [SMILES: COc1ccc(CN(Cc2ccc(OC)cc2)c2nc(-c3cccc(C#N)c3)cn3nc(Br)nc23)cc1]

A mixture of 3-(2-bromo-8-chloro-[1,2,4]triazolo[1,5-a]pyrazin-6-yl)benzonitrile (8.99 g, 26.9 mmol), bis(4-methoxybenzyl)amine (10.37 g, 40.3 mmol), and DIPEA (9.4 mL, 53.7 mmol) in DMF (134 mL) was stirred at 65° C. overnight. The reaction mixture was cooled to room temperature, and diluted with water. The resulting precipitate was collected via filtration, and dried to afford the product (14.1 g, 94%). LC-MS calculated for $C_{28}H_{24}BrN_6O_2$ (M+H)$^+$: m/z=555.1; found 555.1.

Step 5: 3-(8-(Bis(4-methoxybenzyl)amino)-2-vinyl-[1,2,4]triazolo[1,5-a]pyrazin-6-yl)benzonitrile

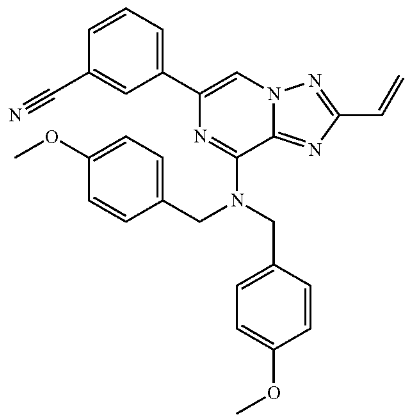 [SMILES: C=Cc1nc2c(N(Cc3ccc(OC)cc3)Cc3ccc(OC)cc3)nc(-c3cccc(C#N)c3)cn2n1]

A mixture of 3-(8-(bis(4-methoxybenzyl)amino)-2-bromo-[1,2,4]triazolo[1,5-a]pyrazin-6-yl)benzonitrile (10.0 g, 18.0 mmol), 4,4,5,5-tetramethyl-2-vinyl-1,3,2-dioxaborolane (3.88 g, 25.2 mmol), potassium phosphate tribasic (9.55 g, 45.0 mmol) and chloro(2-dicyclohexylphosphino-2',4',6'-triisopropyl-1,1'-biphenyl)[2-(2'-amino-1,1'-biphenyl)]palladium(II) (567 mg, 0.72 mmol) in 1,4-dioxane (200 mL) and water (50 mL) was stirred at 85° C. for 2 hrs. The reaction mixture was cooled to room temperature, and most of 1,4-dioxane was removed. The resulting precipitate was collected via filtration, washed with water and dried to afford the crude product (9.1 g), which was used in the next step directly. LC-MS calculated for $C_{30}H_{27}N_6O_2$ (M+H)$^+$: m/z=503.2; found 503.1.

Step 6. 3-(8-(Bis(4-methoxybenzyl)amino)-5-bromo-2-vinyl-[1,2,4]triazolo[1,5-a]pyrazin-6-yl)benzonitrile

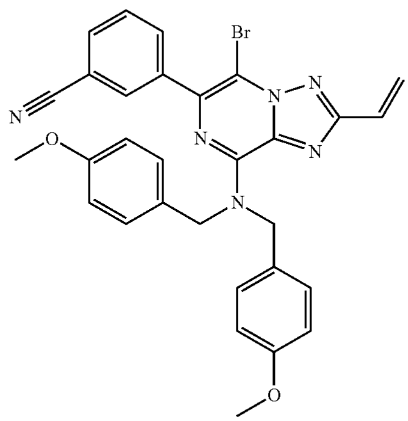 [SMILES: C=Cc1nc2c(N(Cc3ccc(OC)cc3)Cc3ccc(OC)cc3)nc(-c3cccc(C#N)c3)c(Br)n2n1]

To a solution of 3-(8-(bis(4-methoxybenzyl)amino)-2-vinyl-[1,2,4]triazolo[1,5-a]pyrazin-6-yl)benzonitrile (717 mg, 1.43 mmol) in 10 mL of dichloromethane, 1-bromopyrrolidine-2,5-dione (254 mg, 1.43 mmol) was added at 0° C. The resulting mixture was stirred for 4 hrs, and directly purified by a silica gel column to afford the desired product (780 mg, 94%). LC-MS calculated for $C_{30}H_{26}BrN_6O_2$ (M+H)$^+$: m/z=581.1; found 581.2.

Step 7: 3-(8-(Bis(4-methoxybenzyl)amino)-5-(pyrimidin-4-yl)-2-vinyl-[1,2,4]triazolo[1,5-a]pyrazin-6-yl)benzonitrile

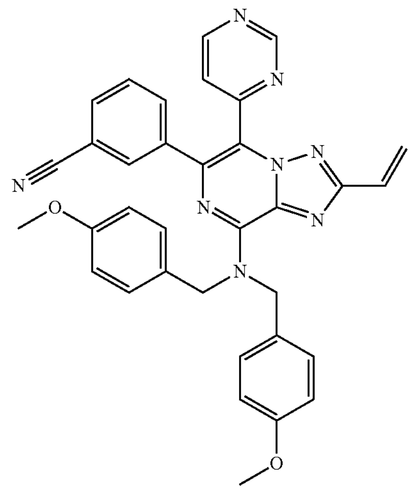 [SMILES: C=Cc1nc2c(N(Cc3ccc(OC)cc3)Cc3ccc(OC)cc3)nc(-c3cccc(C#N)c3)c(-c3ccncn3)n2n1]

A mixture of 3-(8-(bis(4-methoxybenzyl)amino)-5-bromo-2-vinyl-[1,2,4]triazolo[1,5-a]pyrazin-6-yl)benzonitrile (260 mg, 0.45 mmol), 4-(tributylstannyl)pyrimidine (215 mg, 0.58 mmol), lithium chloride (28.4 mg, 0.67 mmol), copper(I) chloride (67 mg, 0.67 mmol), and Tetrakis (triphenylphosphine)palladium(0) (52 mg, 0.045 mmol) in THE (5 mL) was stirred at 90° C. for 45 mins. The reaction mixture was quenched with water and extracted with dichloromethane. The combined organic layers were concentrated, and purified by a silica gel column to afford the desired product (176 mg, 67%). LC-MS calculated for $C_{34}H_{29}N_8O_2$ (M+H)$^+$: m/z=581.2; found 581.1.

Step 8: 3-(8-(Bis(4-methoxybenzyl)amino)-2-formyl-5-(pyrimidin-4-yl)-[1,2,4]triazolo[1,5-a]pyrazin-6-yl)benzonitrile

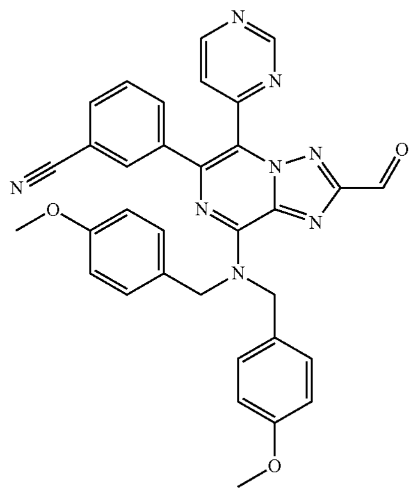 [SMILES: COc1ccc(CN(Cc2ccc(OC)cc2)c2nc(-c3cccc(C#N)c3)c(-c3ccncn3)n3nc(C=O)nc23)cc1]

A mixture of 3-(8-(bis(4-methoxybenzyl)amino)-5-(pyrimidin-4-yl)-2-vinyl-[1,2,4]triazolo[1,5-a]pyrazin-6-yl)benzonitrile (176 mg, 0.3 mmol), osmium(VIII) oxide (3 mg in 0.3 mL water, 0.015 mmol), and sodium periodate (292 mg, 1.36 mmol) in THF/water (1:1, 6 mL) was stirred at 65° C. for 1 h. The reaction mixture was cooled to room temperature, and extracted with dichloromethane. The combined organic layers were concentrated, and purified by silica gel column to afford the desired product (130 mg, 74%). LC-MS calculated for $C_{33}H_{27}N_8O_3$ $(M+H)^+$: m/z=583.2; found 583.2.

Step 9: 3-(8-Amino-2-((2,6-difluorophenyl)(hydroxy)methyl)-5-(pyrimidin-4-yl)-[1,2,4]triazolo[1,5-a]pyrazin-6-yl)benzonitrile Preparation of the Grignard reagent: To a solution of 1,3-difluoro-2-iodobenzene (142 mg, 0.6 mmol) in tetrahydrofuran (1 mL), isopropylmagnesium chloride solution (296 μl, 2 M) was added at −10° C. The resulting mixture was stirred for 1 h, and used directly in the following step.

To a solution of 3-(8-(bis(4-methoxybenzyl)amino)-2-formyl-5-(pyrimidin-4-yl)-[1,2,4]triazolo[1,5-a]pyrazin-6-yl)benzonitrile (120 mg, 0.2 mmol) in THF (2 mL), the freshly prepared Grignard reagent from previous step was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and basified by adding aqeuous $NaHCO_3$ solution. The crude material was directly purified by a silica gel column to afford the desired product (60 mg, 64%) as a racemic mixture. The product was then separated with chiral HPLC using a chiral column (Phenomenex Lux 5 um Cellulose-4, 21.2×250 mm) and 75% EtOH in hexanes (20 mL/min) solvent system.

Peak 1 was isolated, and further purified via preparative LC/MS (pH=2, acetonitrile/water with TFA) to give the desired product as a TFA salt. LC-MS calculated for $C_{23}H_{15}F_2N_8O$ $(M+H)^+$: m/z=457.1; found 457.0.

Example 50. 3-(8-Amino-2-((2,6-difluorophenyl)(hydroxy)methyl)-5-(pyrimidin-4-yl)-[1,2,4]triazolo[1,5-a]pyrazin-6-yl)benzonitrile, Peak 2

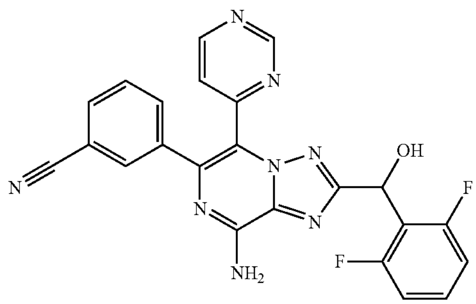 [SMILES: N#Cc1cccc(-c2nc(N)c3nc(C(O)c4c(F)cccc4F)nn3c2-c2ccncn2)c1]

This compound was prepared using the same procedure as described for Example 49. The product was separated with chiral HPLC using a chiral column (Phenomenex Lux Sum Cellulose-4, 21.2×250 mm) and 75% EtOH in hexanes (20 mL/min) solvent system. Peak 2 was isolated, and further purified via preparative LC/MS (pH=2, acetonitrile/water with TFA) to give the desired product as a TFA salt. LC-MS calculated for $C_{23}H_{15}F_2N_8O$ $(M+H)^+$: m/z=457.1; found 457.0.

$^1H$ NMR (600 MHz, DMSO-$d_6$) δ 9.14 (d, J=1.3 Hz, 1H), 8.95 (d, J=5.2 Hz, 1H), 7.90 (dd, J=5.2, 1.4 Hz, 1H), 7.88 (s, 1H), 7.78 (dt, J=7.6, 1.4 Hz, 1H), 7.74 (t, J=1.4 Hz, 1H), 7.54 (dt, J=7.9, 1.3 Hz, 1H), 7.51-7.40 (m, 2H), 7.09 (t, J=8.4 Hz, 2H), 6.27 (s, 1H).

Example 51. 3-(8-Amino-2-((2,5-difluorophenyl)(hydroxy)methyl)-5-(pyrimidin-4-yl)-[1,2,4]triazolo[1,5-a]pyrazin-6-yl)benzonitrile, Peak 1

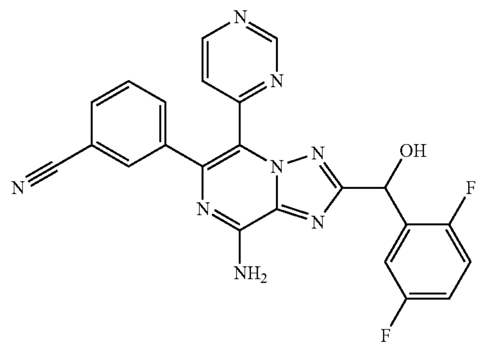 [SMILES: N#Cc1cccc(-c2nc(N)c3nc(C(O)c4cc(F)ccc4F)nn3c2-c2ccncn2)c1]

To a solution of 3-(8-(bis(4-methoxybenzyl)amino)-2-formyl-5-(pyrimidin-4-yl)-[1,2,4]triazolo[1,5-a]pyrazin-6-yl)benzonitrile (115 mg, 0.2 mmol) in THF (1 mL), the freshly prepared Grignard reagent (prepared using a similar procedure as described in Example 49, Step 9, using 1,4-difluoro-2-iodobenzene instead of 1,3-difluoro-2-iodobenzene) was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and basified by adding aqeuous $NaHCO_3$ solution. The crude material was directly purified by a silica gel column to afford the desired product (70 mg, 77%) as a racemic mixture. The product was then separated with chiral HPLC using a chiral column (Phenomenex Lux Sum Cellulose-4, 21.2×250 mm) and 40% EtOH in hexanes (20 mL/min) as the mobile phase. Peak 1 was isolated, and further purified via preparative LC/MS (pH=2, acetonitrile/water with TFA) to give the desired product as a TFA salt. LC-MS calculated for $C_{23}H_{15}F_2N_8O$ $(M+H)^+$: m/z=457.1; found 457.0.

Example 52. 3-(8-Amino-2-((2,5-difluorophenyl)(hydroxy)methyl)-5-(pyrimidin-4-yl)-[1,2,4]triazolo[1,5-a]pyrazin-6-yl)benzonitrile, Peak 2

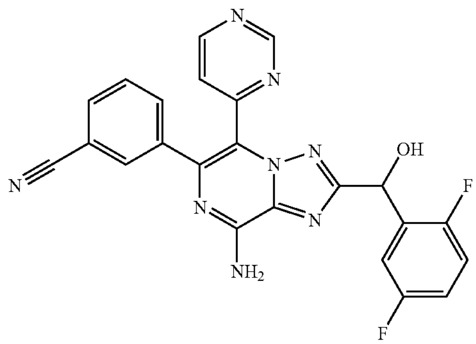 [SMILES: N#Cc1cccc(-c2nc(N)c3nc(C(O)c4cc(F)ccc4F)nn3c2-c2ccncn2)c1]

This compound was prepared using the same procedure as described for Example 51. The product was separated with chiral HPLC using a chiral column (Phenomenex Lux Sum Cellulose-4, 21.2×250 mm) and 40% EtOH in hexanes (20 mL/min) as the mobile phase. Peak 2 was isolated, and further purified via preparative LC/MS (pH=2, acetonitrile/water with TFA) to give the desired product as a TFA salt. LC-MS calculated for $C_{23}H_{15}F_2N_8O$ $(M+H)^+$: m/z=457.1; found 457.0.

Example 53. 3-(8-Amino-2-((2,3-difluorophenyl)(hydroxy)methyl)-5-(pyrimidin-4-yl)-[1,2,4]triazolo[1,5-a]pyrazin-6-yl)benzonitrile, Peak 1

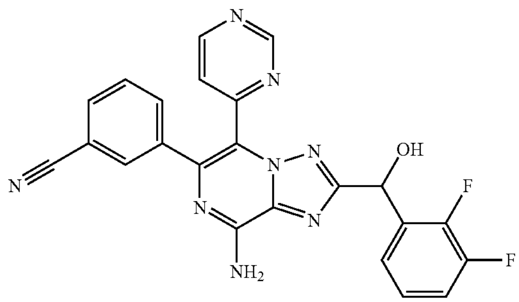 [SMILES: N#Cc1cccc(-c2nc(N)c3nc(C(O)c4cccc(F)c4F)nn3c2-c2ccncn2)c1]

To a solution of 1,2-difluoro-3-iodobenzene (70 mg, 0.3 mmol) in tetrahydrofuran (1 mL), isopropylmagnesium chloride (150 μl, 2 M solution) was added at −10° C., and the resulting mixture was stirred for 1 h before a solution of 3-(8-(bis(4-methoxybenzyl)amino)-2-formyl-5-(pyrimidin-4-yl)-[1,2,4]triazolo[1,5-a]pyrazin-6-yl)benzonitrile (60 mg, 0.1 mmol) in THE (1 mL) was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and basified by adding aqeuous $NaHCO_3$ solution. The crude material was directly purified by a silica gel column to afford the desired product (30 mg, 70%) as a racemic mixture. The resulting product was then separated with chiral HPLC using a chiral column (Phenomenex Lux 5 um Cellulose-4, 21.2×250 mm) and 40% EtOH in hexanes (20 mL/min) as the mobile phase. Peak 1 was isolated, and further purified via preparative LC/MS (pH=2, acetonitrile/water with TFA) to give the desired product as a TFA salt. LC-MS calculated for $C_{23}H_{15}F_2N_8O$ $(M+H)^+$: m/z=457.1; found 457.0.

Example 54. 3-(8-Amino-2-((2,3-difluorophenyl)(hydroxy)methyl)-5-(pyrimidin-4-yl)-[1,2,4]triazolo[1,5-a]pyrazin-6-yl)benzonitrile, Peak 2

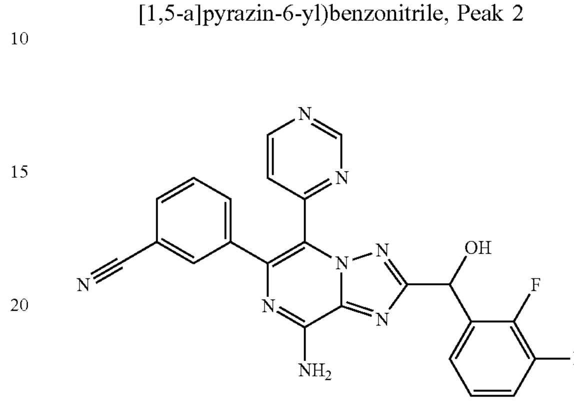

This compound was prepared using the same procedure as described for Example 53. The product was separated with chiral HPLC using a chiral column (Phenomenex Lux Sum Cellulose-4, 21.2×250 mm) and 40% EtOH in hexanes (20 mL/min) as the mobile phase. Peak 2 was isolated, and further purified via preparative LC/MS (pH=2, acetonitrile/water with TFA) to give the desired product as a TFA salt. LC-MS calculated for $C_{23}H_{15}F_2N_8O$ $(M+H)^+$: m/z=457.1; found 457.0.

Example 55. 3-(8-Amino-2-((2-fluorophenyl)(hydroxy)methyl)-5-(pyrimidin-4-yl)-[1,2,4]triazolo[1,5-a]pyrazin-6-yl)benzonitrile, Peak 1

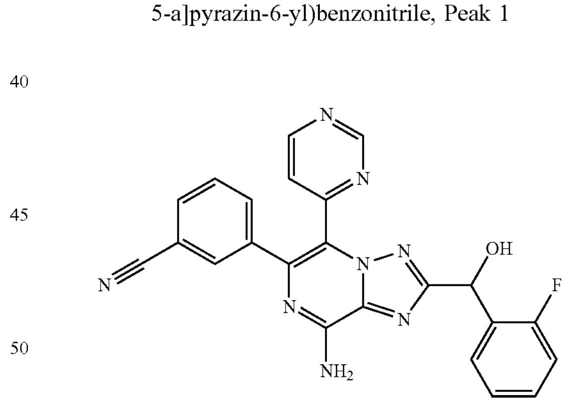

To a solution of 3-(8-(bis(4-methoxybenzyl)amino)-2-formyl-5-(pyrimidin-4-yl)-[1,2,4]triazolo[1,5-a]pyrazin-6-yl)benzonitrile (100 mg, 0.17 mmol) in THE (2 mL), the corresponding Grignard reagent (freshly prepared using a similar procedure as described in Example 49, Step 9, using 1-fluoro-2-iodobenzene instead of 1,3-difluoro-2-iodobenzene) was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and basified by adding aqeuous $NaHCO_3$ solution. The crude material was directly purified by a silica gel column to afford the desired product (60 mg, 50%) as a racemic mixture. The resulting product was then separated with chiral HPLC using a chiral column (Phenomenex Lux 5 um Cellulose-4, 21.2×250 mm) and 60% EtOH in hexanes (20 mL/min) as the mobile phase. Peak 1 was isolated, and further purified via preparative LC/MS (pH=2, acetonitrile/water with TFA) to give the desired product as a TFA salt. LC-MS calculated for $C_{23}H_{16}FN_8O$ $(M+H)^+$: m/z=439.1; found 439.0.

Example 56. 3-(8-Amino-2-((2-fluorophenyl)(hydroxy)methyl)-5-(pyrimidin-4-yl)-[1,2,4]triazolo[1,5-a]pyrazin-6-yl)benzonitrile, Peak 2

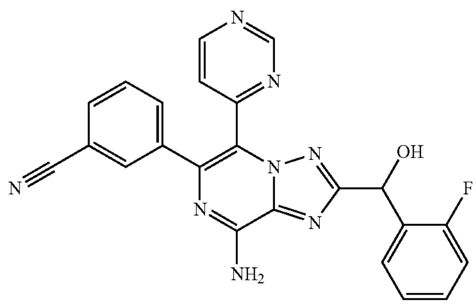 [SMILES: N#Cc1cccc(-c2nc(N)c3nc(C(O)c4ccccc4F)nn3c2-c2ccncn2)c1]

This compound was prepared using the same procedure as described for Example 55. The product was separated with chiral HPLC using a chiral column (Phenomenex Lux Sum Cellulose-4, 21.2×250 mm) and 60% EtOH in hexanes (20 mL/min) as the mobile phase. Peak 2 was isolated, and further purified via preparative LC/MS (pH=2, acetonitrile/water with TFA) to give the desired product as a TFA salt. LC-MS calculated for $C_{23}H_{16}FN_8O$ $(M+H)^+$: m/z=439.1; found 439.0.

Example 57. 3-(8-Amino-2-((2-chlorophenyl)(hydroxy)methyl)-5-(pyrimidin-4-yl)-[1,2,4]triazolo[1,5-a]pyrazin-6-yl)benzonitrile, Peak 1

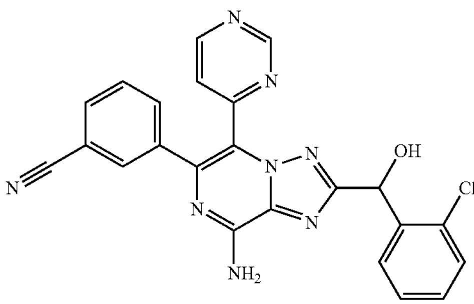 [SMILES: N#Cc1cccc(-c2nc(N)c3nc(C(O)c4ccccc4Cl)nn3c2-c2ccncn2)c1]

To a solution of 3-(8-(bis(4-methoxybenzyl)amino)-2-formyl-5-(pyrimidin-4-yl)-[1,2,4]triazolo[1,5-a]pyrazin-6-yl)benzonitrile (100 mg, 0.17 mmol) in THE (2 mL), the corresponding Grignard reagent (freshly prepared using a similar procedure as described in Example 49, Step 9, using 1-chloro-2-iodobenzene instead of 1,3-difluoro-2-iodobenzene) was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and basified by adding aqeuous $NaHCO_3$ solution. The crude material was directly purified by a silica gel column to afford the desired product (50 mg, 64%) as a racemic mixture. The resulting product was then separated with chiral HPLC using a chiral column (Phenomenex Lux 5 um Cellulose-4, 21.2×250 mm) and 45% EtOH in hexanes (20 mL/min) as the mobile phase. Peak 1 was isolated, and further purified via preparative LC/MS (pH=2, acetonitrile/water with TFA) to give the desired product as a TFA salt. LC-MS calculated for $C_{23}H_{16}ClN_8O$ $(M+H)^+$: m/z=455.1; found 455.1.

Example 58. 3-(8-Amino-2-((2-chlorophenyl)(hydroxy)methyl)-5-(pyrimidin-4-yl)-[1,2,4]triazolo[1,5-a]pyrazin-6-yl)benzonitrile, Peak 2

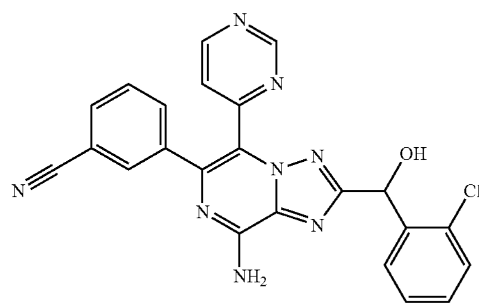 [SMILES: N#Cc1cccc(-c2nc(N)c3nc(C(O)c4ccccc4Cl)nn3c2-c2ccncn2)c1]

This compound was prepared using the same procedure as described for Example 57. The product was separated with chiral HPLC using a chiral column (Phenomenex Lux 5 um Cellulose-4, 21.2×250 mm) and 45% EtOH in hexanes (20 mL/min) as the mobile phase. Peak 2 was isolated, and further purified via preparative LC/MS (pH=2, acetonitrile/water with TFA) to give the desired product as a TFA salt. LC-MS calculated for $C_{23}H_{16}ClN_8O$ $(M+H)^+$: m/z=455.1; found 455.1.

Example 59. 3-(8-Amino-2-(hydroxy(phenyl)methyl)-5-(pyrimidin-4-yl)-[1,2,4]triazolo[1,5-a]pyrazin-6-yl)benzonitrile

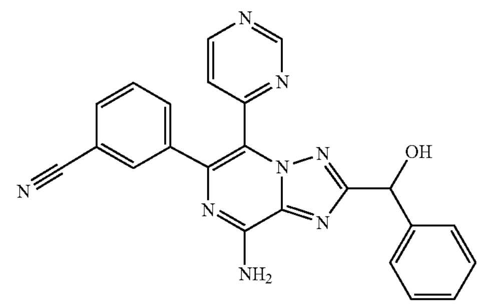 [SMILES: N#Cc1cccc(-c2nc(N)c3nc(C(O)c4ccccc4)nn3c2-c2ccncn2)c1]

To a solution of 3-(8-(bis(4-methoxybenzyl)amino)-2-formyl-5-(pyrimidin-4-yl)-[1,2,4]triazolo[1,5-a]pyrazin-6-yl)benzonitrile (20 mg, 0.17 mmol) in THF (2 mL), phe nylmagnesium chloride (3 M solution in ethyl ether, 0.17 mL) was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and purified with preparative LC/MS (pH=2, acetonitrile/water with TFA) to give the product as a TFA salt. LC-MS calculated for $C_{23}H_{17}N_8O$ $(M+H)^+$: m/z=421.2; found 421.1.

Example 60. 3-(8-Amino-2-(phenylsulfonyl)-5-(pyrimidin-4-yl)-[1,2,4]triazolo[1,5-a]pyrazin-6-yl)benzonitrile

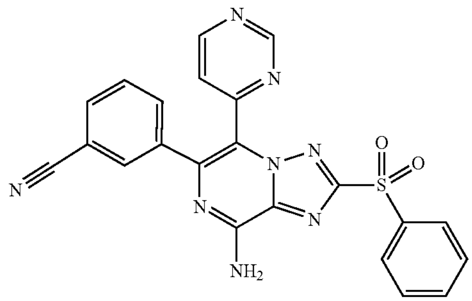 [SMILES: N#Cc1cccc(-c2nc(N)c3nc(S(=O)(=O)c4ccccc4)nn3c2-c2ccncn2)c1]

Step 1: 3-(8-Amino-2-(phenylsulfonyl)-[1,2,4]triazolo[1,5-a]pyrazin-6-yl)benzonitrile

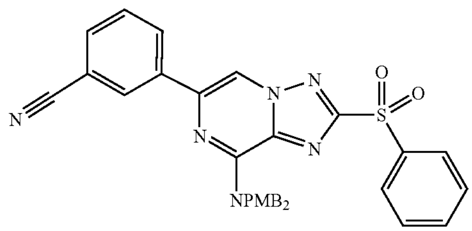

A mixture of 3-(8-(bis(4-methoxybenzyl)amino)-2-bromo-[1,2,4]triazolo[1,5-a]pyrazin-6-yl)benzonitrile (33 mg, 0.06 mmol) (from Example 27, Step 4) and sodium benzenesulfinate (100 mg, 0.6 mmol) in 1 mL DMSO was stirred at 110° C. for 48 hrs, the reaction was quenched with ammonium chloride and extracted with dichloromethane. The combined organic layers were concentrated and purified with silica gel column to afford the desired Product (18 mg, 50%), LC-MS calculated for $C_{34}H_{29}N_6O_4S$ $(M+H)^+$: m/z=617.2; found 617.2.

Step 2: 3-(8-(Bis(4-methoxybenzyl)amino)-5-bromo-2-(phenylsulfonyl)-[1,2,4]triazolo[1,5-a]pyrazin-6-yl)benzonitrile

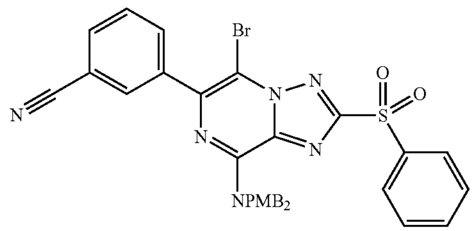

To a solution of 3-(8-Amino-2-(phenylsulfonyl)-[1,2,4]triazolo[1,5-a]pyrazin-6-yl)benzonitrile (20 mg, 0.032 mmol) in 1 mL dichloromethane, 1-bromopyrrolidine-2,5-dione (6 mg, 0.032 mmol) was added at 0° C. The resulting mixture was stirred for 16 hrs before being purified by silica gel column to afford the desired product (18 mg, 80%). LC-MS calculated for $C_{34}H_{28}BrN_6O_4S$ $(M+H)^+$: m/z=695.1; found 695.2.

Step 3: 3-(8-Amino-2-(phenylsulfonyl)-5-(pyrimidin-4-yl)-[1,2,4]triazolo[1,5-a]pyrazin-6-yl)benzonitrile A mixture of 3-(8-(Bis(4-methoxybenzyl)amino)-5-bromo-2-(phenylsulfonyl)-[1,2,4]triazolo[1,5-a]pyrazin-6-yl)benzonitrile (10 mg, 0.014 mmol), 4-(tributylstannyl)pyrimidine (11 mg, 0.029 mmol), lithium chloride (1.0 mg, 0.022 mmol), copper(I) chloride (2.1 mg, 0.022 mmol), and tetrakis(triphenylphosphine)palladium(0) (3.3 mg, 2.88 umol) in THF (2 mL) was stirred at 90° C. for 45 mins. The reaction mixture was filtered and the organic solvent was removed by vacuo, the crude product was dissolved in 3 mL TFA and stirred at 80° C. for 20 mins. After TFA being removed, the crude product was purified by preparative LC/MS (pH=2, acetonitrile/water with TFA) to afford the desired product as a TFA salt. LC-MS calculated for $C_{22}H_{15}N_8O_2S$ $(M+H)^+$: m/z=455.1; found 455.1.

Example 61. 3-(8-Amino-2-(azetidine-1-carbonyl)-5-(4-methyloxazol-5-yl)-[1,2,4]triazolo[1,5-a]pyrazin-6-yl)benzonitrile

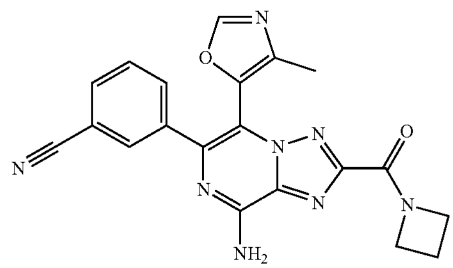 [SMILES: Cc1ncoc1-c1c(-c2cccc(C#N)c2)nc(N)c2nc(C(=O)N3CCC3)nn12]

Step 1: 3-(2-(Azetidine-1-carbonyl)-8-(bis(4-methoxybenzyl)amino)-[1,2,4]triazolo[1,5-a]pyrazin-6-yl)benzonitrile

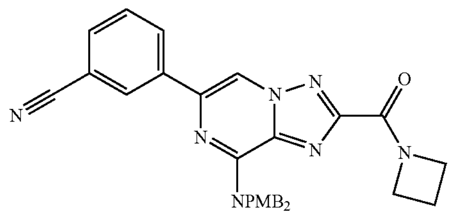

A mixture of 3-(8-(bis(4-methoxybenzyl)amino)-2-bromo-[1,2,4]triazolo[1,5-a]pyrazin-6-yl)benzonitrile (99 mg, 0.18 mmol) and azetidine (50 mg, 0.89 mmol), $PdCl_2$(dppf) (26 mg, 0.036 mmol) and $Na_2CO_3$ (57 mg, 0.48 mmol) in 5 mL 1,4-dioxane and 1 mL water was stirred at 80° C. for 18 hrs under CO balloon atmosphere, the reaction was quenched with ammonium chloride and extracted with dichloromethane. The combined organic layers were concentrated and purified with silica gel column to afford the desired Product (44 mg, 44%), LC-MS calculated for $C_{32}H_{30}N_7O_3$ $(M+H)^+$: m/z=560.2; found 560.2.

Step 2: 3-(2-(Azetidine-1-carbonyl)-8-(bis(4-methoxybenzyl)amino)-5-bromo-[1,2,4]triazolo[1,5-a]pyrazin-6-yl)benzonitrile

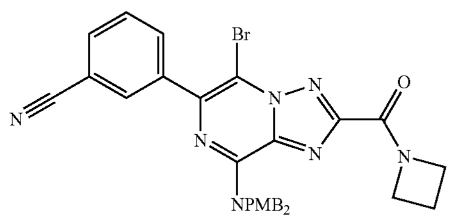

To a solution of 3-(2-(azetidine-1-carbonyl)-8-(bis(4-methoxybenzyl)amino)-[1,2,4]triazolo[1,5-a]pyrazin-6-yl) benzonitrile (40 mg, 0.125 mmol) in 3 mL dichloromethane, 1-bromopyrrolidine-2,5-dione (23 mg, 0.125 mmol) was added at 0° C. The resulting mixture was stirred for 16 hrs before being purified by silica gel column to afford the desired product (50 mg, 100%). LC-MS calculated for $C_{32}H_{29}BrN_7O_3$ $(M+H)^+$: m/z=638.1; found 638.2.

Step 3: 3-(8-Amino-2-(azetidine-1-carbonyl)-5-(4-methyloxazol-5-yl)-[1,2,4]triazolo[1,5-a]pyrazin-6-yl)benzonitrile A mixture of 3-(2-(azetidine-1-carbonyl)-8-(bis(4-methoxybenzyl)amino)-5-bromo-[1,2,4]triazolo[1,5-a]pyrazin-6-yl)benzonitrile (10 mg, 0.016 mmol), 4-methyl-5-(4,4,5,5-tetramethyl-1,3,2-dioxaborolan-2-yl)oxazole (7 mg, 0.032 mmol), sodium carbonate (5 mg, 0.048 mmol) and chloro(2-dicyclohexylphosphino-2',4',6'-triisopropyl-1,1'-biphenyl)[2-(2'-amino-1,1'-biphenyl)]palladium(II) (5 mg, 0.006 mmol) in 4:1 THF/Water (2 mL) was stirred at 100° C. for 75 mins. The reaction mixture was filtered and the organic solvent was removed by vacuo, the crude product was dissolved in 3 mL TFA and stirred at 80° C. for 20 mins. After TFA being removed, the crude product was purified by preparative LC/MS (pH=2, acetonitrile/water with TFA) to afford the desired product as a TFA salt. LC-MS calculated for $C_{20}H_{17}N_8O_2$ $(M+H)^+$: m/z=401.2; found 401.1.

Example 62. 3-(8-amino-5-(6-hydroxypyridin-3-yl)-2-(pyridin-2-ylmethyl)-[1,2,4]triazolo[1,5-a]pyrazin-6-yl)benzonitrile

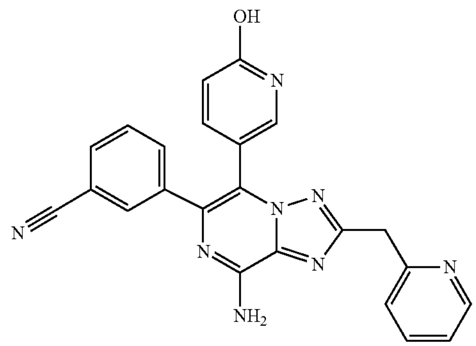 [SMILES: N#Cc1cccc(-c2nc(N)c3nc(Cc4ccccn4)nn3c2-c2ccc(O)nc2)c1]

A mixture of 3-(8-Amino-5-bromo-2-(pyridin-2-ylmethyl)-[1,2,4]triazolo[1,5-a]pyrazin-6-yl)benzonitrile (Example 27, Step 7; 10 mg, 0.025 mmol), (6-methoxypyridin-3-yl)boronic acid (10 mg, 0.042 mmol), cesium carbonate (17.7 mg, 0.116 mmol), chloro(2-dicyclohexylphosphino-2',4',6'-triisopropyl-1,1'-biphenyl)[2-(2'-amino-1,1'-biphenyl)]palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated and added MeCN (0.5 mL) and TMSCl (0.5 mL), the mixture was heated at 80° C. for 30 min before concentrated and purified by preparative LCMS (pH 2, acetonitrile/water with TFA) to afford the desired product as TFA salt. LCMS calculated for $C_{23}H_{17}N_8O$ $(M+H)^+$: 421.1; found 421.2.

Example 63. 3-(8-amino-2-(benzo[d]oxazol-4-ylmethyl)-5-(pyrimidin-4-yl)-[1,2,4]triazolo[1,5-a]pyrazin-6-yl)benzonitrile

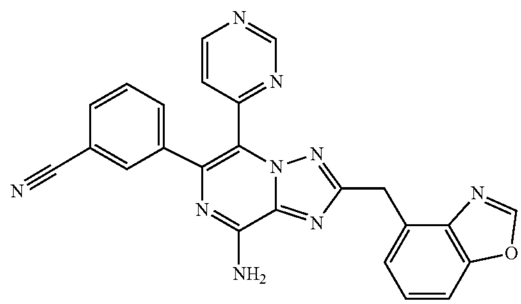 [SMILES: N#Cc1cccc(-c2nc(N)c3nc(Cc4cccc5ocnc45)nn3c2-c2ccncn2)c1]

A mixture of 3-(8-(bis(4-methoxybenzyl)amino)-2-(bromomethyl)-5-(pyrimidin-4-yl)-[1,2,4]triazolo[1,5-a]pyrazin-6-yl)benzonitrile (Example 32, Step 5; 10 mg, 0.022 mmol), 4-(4,4,5,5-tetramethyl-1,3,2-dioxaborolan-2-yl)benzo[d]oxazole (11 mg, 0.044 mmol), cesium carbonate (17.7 mg, 0.116 mmol), chloro(2-dicyclohexylphosphino-2',4',6'-triisopropyl-1,1'-biphenyl)[2-(2'-amino-1,1'-biphenyl)]

palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated and added TFA (1 mL), the mixture was heated at 100° C. for 30 min before concentrated and purified by preparative LCMS (pH 2, acetonitrile/water with TFA) to afford the desired product as TFA salt. LCMS calculated for $C_{24}H_{16}N_9O$ $(M+H)^+$: 446.1; found 446.1.

Example 64. 3-(8-amino-2-(2-fluoro-6-(1-methyl-1H-pyrazol-5-yl)benzyl)-5-(pyrimidin-4-yl)-[1,2,4]triazolo[1,5-a]pyrazin-6-yl)benzonitrile

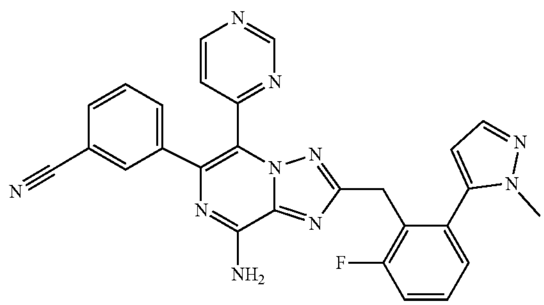 [SMILES: Cn1nccc1-c1cccc(F)c1Cc1nc2c(N)nc(-c3cccc(C#N)c3)c(-c3ccncn3)n2n1]

A mixture of 3-(8-Amino-2-(2-chloro-6-fluorobenzyl)-5-(pyrimidin-4-yl)-[1,2,4]triazolo[1,5-a]pyrazin-6-yl)benzonitrile (Example 30, Step 3; 10 mg, 0.022 mmol), 1-methyl-5-(4,4,5,5-tetramethyl-1,3,2-dioxaborolan-2-yl)-1H-pyrazole (9.2 mg, 0.044 mmol), cesium carbonate (17.7 mg, 0.116 mmol), chloro(2-dicyclohexylphosphino-2',4',6'-triisopropyl-1,1'-biphenyl)[2-(2'-amino-1,1'-biphenyl)]palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated and purified by preparative LCMS (pH 2, acetonitrile/water with TFA) to afford the desired product as TFA salt. LCMS calculated for $C_{27}H_{20}N_{10}F$ $(M+H)^+$: 503.2; found 503.1.

Example 65. (R)-1-(2-((8-amino-6-(3-cyanophenyl)-5-(pyrimidin-4-yl)-[1,2,4]triazolo[1,5-a]pyrazin-2-yl)methyl)-3-fluorobenzyl)-3-methylpyrrolidine-3-carboxylic acid

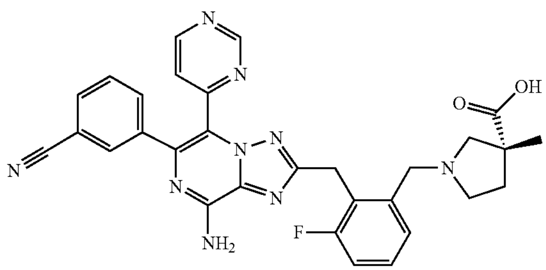 [SMILES: C[C@@]1(C(=O)O)CCN(Cc2cccc(F)c2Cc2nc3c(N)nc(-c4cccc(C#N)c4)c(-c4ccncn4)n3n2)C1]

The title compound was prepared using similar procedures as described for Example 30 with (R)-3-methylpyrrolidine-3-carboxylic acid replacing (S)-pyrrolidine-3-carboxylic acid. The reaction mixture was purified by prep-HPLC (pH=2, acetonitrile/water+TFA) to give the desired product as TFA salt. LC-MS calculated for $C_{30}H_{27}N_9O_2F$ $(M+H)^+$: m/z=564.2; found 564.2.

Example 66. 3-(8-amino-2-(2-fluoro-6-((6-methyl-5-oxo-2,6-diazaspiro[3.4]octan-2-yl)methyl)benzyl)-5-(pyrimidin-4-yl)-[1,2,4]triazolo[1,5-a]pyrazin-6-yl)benzonitrile

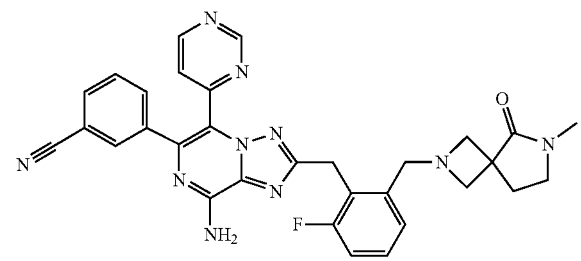 [SMILES: CN1CCC2(CN(Cc3cccc(F)c3Cc3nc4c(N)nc(-c5cccc(C#N)c5)c(-c5ccncn5)n4n3)C2)C1=O]

The title compound was prepared using similar procedures as described for Example 30 with 6-methyl-2,6-diazaspiro[3.4]octan-5-one replacing (S)-pyrrolidine-3-carboxylic acid. The reaction mixture was purified by prep-HPLC (pH=2, acetonitrile/water+TFA) to give the desired product as TFA salt. LC-MS calculated for $C_{31}H_{28}N_{10}OF$ $(M+H)^+$: m/z=575.2; found 575.2.

Example 67. 3-(8-amino-2-(2-fluoro-6-((6-oxohexahydropyrrolo[1,2-a]pyrazin-2(1H)-yl)methyl)benzyl)-5-(pyrimidin-4-yl)-[1,2,4]triazolo[1,5-a]pyrazin-6-yl)benzonitrile

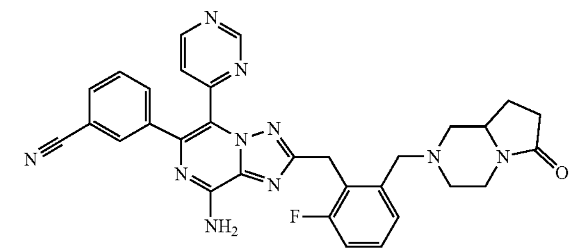 [SMILES: N#Cc1cccc(-c2nc(N)c3nc(Cc4c(F)cccc4CN4CCN5C(=O)CCC5C4)nn3c2-c2ccncn2)c1]

The title compound was prepared using similar procedures as described for Example 30 with hexahydropyrrolo[1,2-a]pyrazin-6(2H)-one replacing (S)-pyrrolidine-3-carboxylic acid. The reaction mixture was purified by prep-HPLC (pH=2, acetonitrile/water+TFA) to give the desired product as TFA salt. LC-MS calculated for $C_{31}H_{28}N_{10}OF$ $(M+H)^+$: m/z=575.2; found 575.2.

Example 68. (S)-3-(8-amino-2-(2-fluoro-6-(((2-oxopyrrolidin-3-yl)amino)methyl)benzyl)-5-(pyrimidin-4-yl)-[1,2,4]triazolo[1,5-a]pyrazin-6-yl)benzonitrile

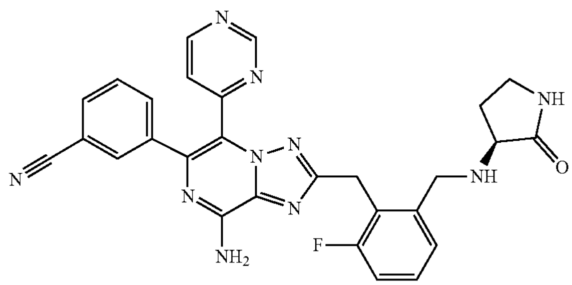 [SMILES: N#Cc1cccc(-c2nc(N)c3nc(Cc4c(F)cccc4CN[C@H]4CCNC4=O)nn3c2-c2ccncn2)c1]

The title compound was prepared using similar procedures as described for Example 30 with (S)-3-aminopyrrolidin-2-one replacing (S)-pyrrolidine-3-carboxylic acid. The reaction mixture was purified by prep-HPLC (pH=2, acetonitrile/water+TFA) to give the desired product as TFA salt. LC-MS calculated for $C_{28}H_{24}N_{10}OF$ $(M+H)^+$: m/z=535.2; found 535.2.

Example 69. 2-((2-((8-amino-6-(3-cyanophenyl)-5-(pyrimidin-4-yl)-[1,2,4]triazolo[1,5-a]pyrazin-2-yl)methyl)-3-fluorobenzyl)amino)acetamide

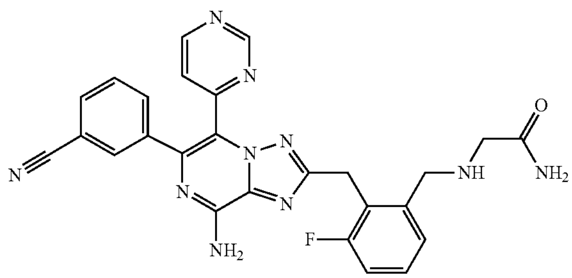 [SMILES: N#Cc1cccc(-c2nc(N)c3nc(Cc4c(F)cccc4CNCC(N)=O)nn3c2-c2ccncn2)c1]

The title compound was prepared using similar procedures as described for Example 30 with 2-aminoacetamide replacing (S)-pyrrolidine-3-carboxylic acid. The reaction mixture was purified by prep-HPLC (pH=2, acetonitrile/water+TFA) to give the desired product as TFA salt. LC-MS calculated for $C_{26}H_{22}N_{10}OF$ $(M+H)^+$: m/z=509.2; found 509.2.

Example 70. 3-(8-amino-2-(2-fluoro-6-((3-oxopiperazin-1-yl)methyl)benzyl)-5-(pyrimidin-4-yl)-[1,2,4]triazolo[1,5-a]pyrazin-6-yl)benzonitrile

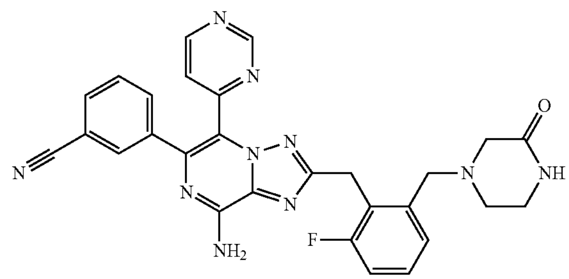 [SMILES: N#Cc1cccc(-c2nc(N)c3nc(Cc4c(F)cccc4CN4CCNC(=O)C4)nn3c2-c2ccncn2)c1]

The title compound was prepared using similar procedures as described for Example 30 with piperazin-2-one replacing (S)-pyrrolidine-3-carboxylic acid. The reaction mixture was purified by prep-HPLC (pH=2, acetonitrile/water+TFA) to give the desired product as TFA salt. LC-MS calculated for $C_{28}H_{24}N_{10}OF$ $(M+H)^+$: m/z=535.2; found 535.2.

Example 71. (1S,3S)-3-((2-((8-amino-6-(3-cyanophenyl)-5-(pyrimidin-4-yl)-[1,2,4]triazolo[1,5-a]pyrazin-2-yl)methyl)-3-fluorobenzyl)amino)cyclobutane-1-carboxylic acid

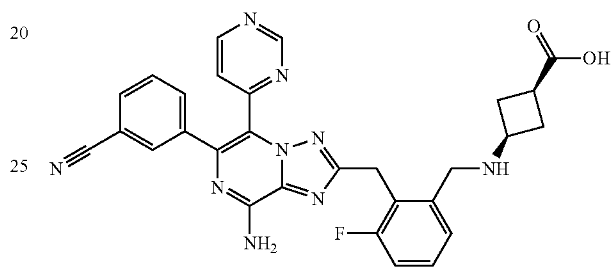

The title compound was prepared using similar procedures as described for Example 30 with (1s,3s)-3-aminocyclobutane-1-carboxylic acid replacing (S)-pyrrolidine-3-carboxylic acid. The reaction mixture was purified by prep-HPLC (pH=2, acetonitrile/water+TFA) to give the desired product as TFA salt. LC-MS calculated for $C_{29}H_{25}N_9O_2F$ $(M+H)^+$: m/z=550.2; found 550.2.

Example 72. 3-(8-amino-2-(2-fluoro-6-(((1-methyl-2-oxopyrrolidin-3-yl)amino)methyl)benzyl)-5-(pyrimidin-4-yl)-[1,2,4]triazolo[1,5-a]pyrazin-6-yl)benzonitrile

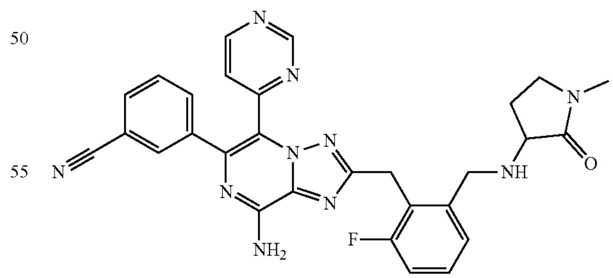

The title compound was prepared using similar procedures as described for Example 30 with 3-amino-1-methylpyrrolidin-2-one replacing (S)-pyrrolidine-3-carboxylic acid. The reaction mixture was purified by prep-HPLC (pH=2, acetonitrile/water+TFA) to give the desired product as TFA salt. LC-MS calculated for $C_{29}H_{26}N_{10}OF$ $(M+H)^+$: m/z=549.2; found 549.2.

Example 73. 1-(2-((8-amino-6-(3-cyanophenyl)-5-(pyrimidin-4-yl)-[1,2,4]triazolo[1,5-a]pyrazin-2-yl)methyl)-3-fluorobenzyl)azetidine-3-carbonitrile

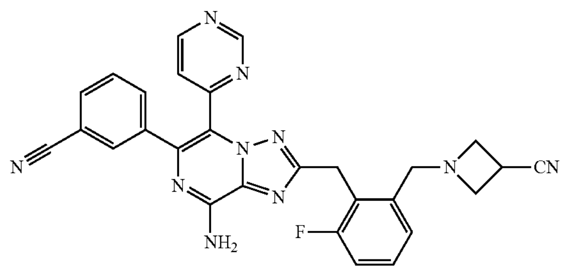 [SMILES: N#Cc1cccc(-c2nc(N)c3nc(Cc4c(F)cccc4CN4CC(C#N)C4)nn3c2-c2ccncn2)c1]

The title compound was prepared using similar procedures as described for Example 30 with azetidine-3-carbonitrile replacing (S)-pyrrolidine-3-carboxylic acid. The reaction mixture was purified by prep-HPLC (pH=2, acetonitrile/water+TFA) to give the desired product as TFA salt. LC-MS calculated for $C_{28}H_{22}N_{10}F$ $(M+H)^+$: m/z=517.2; found 517.2.

Example 74. 3-(8-amino-2-(2-fluoro-6-(((2-methyl-2H-1,2,3-triazol-4-yl)amino)methyl)benzyl)-5-(pyrimidin-4-yl)-[1,2,4]triazolo[1,5-a]pyrazin-6-yl)benzonitrile

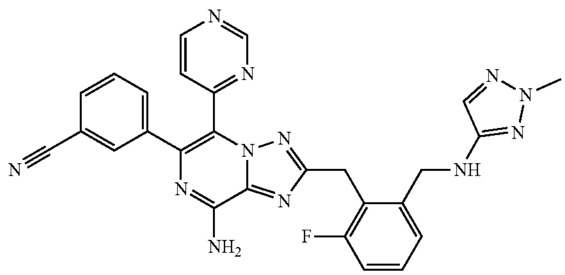 [SMILES: Cn1ncc(NCc2cccc(F)c2Cc2nc3c(N)nc(-c4cccc(C#N)c4)c(-c4ccncn4)n3n2)n1]

To a solution of 3-(8-amino-2-(2-fluoro-6-formylbenzyl)-5-(pyrimidin-4-yl)-[1,2,4]triazolo[1,5-a]pyrazin-6-yl)benzonitrile (Example 30, step 5; 10 mg, 0.02 mmol) in DCM (0.5 mL) was added 2-methyl-2H-1,2,3-triazol-4-amine (4.0 mg, 0.04 mmol) then TFA (4 μL, 0.08 mmol). After 1 h, sodium triacetoxyborohydride (8.5 mg, 0.04 mmol) was added to the reaction. The reaction was stirred overnight and the mixture was concentrated and purified by preparative LCMS (pH 2, acetonitrile/water with TFA) to afford the desired product as TFA salt. LCMS calculated for $C_{27}H_{22}FN_{12}$ $(M+H)^+$: 533.2 found 533.2.

Example 75. (S)-3-(8-amino-2-(2-(((2-oxopyrrolidin-3-yl)amino)methyl)benzyl)-5-(pyrimidin-4-yl)-[1,2,4]triazolo[1,5-a]pyrazin-6-yl)benzonitrile

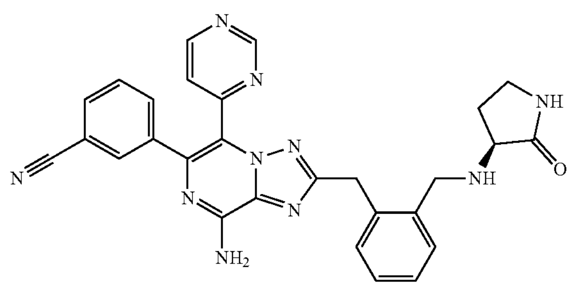 [SMILES: N#Cc1cccc(-c2nc(N)c3nc(Cc4ccccc4CN[C@H]4CCNC4=O)nn3c2-c2ccncn2)c1]

Step 1: 3-(8-(bis(4-methoxybenzyl)amino)-5-(pyrimidin-4-yl)-2-(2-vinylbenzyl)-[1,2,4]triazolo[1,5-a]pyrazin-6-yl)benzonitrile

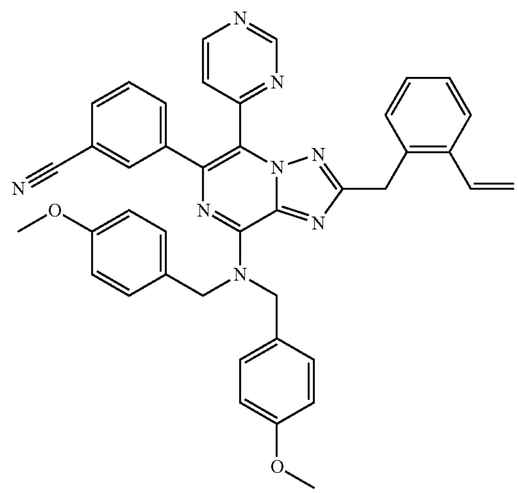 [SMILES: C=Cc1ccccc1Cc1nc2c(N(Cc3ccc(OC)cc3)Cc3ccc(OC)cc3)nc(-c3cccc(C#N)c3)c(-c3ccncn3)n2n1]

A mixture of 3-(8-(bis(4-methoxybenzyl)amino)-2-(2-chlorobenzyl)-5-(pyrimidin-4-yl)-[1,2,4]triazolo[1,5-a]pyrazin-6-yl)benzonitrile (Example 41, step 3; 149 mg, 0.22 mmol), 4,4,5,5-tetramethyl-2-vinyl-1,3,2-dioxaborolane (68 mg, 0.44 mmol), dicyclohexyl(2',4',6'-triisopropylbiphenyl-2-yl)phosphine-(2'-aminobiphenyl-2-yl)(chloro)palladium (1:1) (17 mg, 21.6 μmol) and $K_3PO_4$ (94 mg, 0.44 mmol) in 1,4-dioxane (4 mL)/water (0.8 mL) was stirred at 110° C. for 1 h. The reaction mixture was concentrated under vacuum and the resulting residue was purified with flash chromatography to give the desired product as a light yellow oil. LC-MS calculated for $C_{41}H_{35}N_8O_2$ $(M+H)^+$: m/z=671.3; found 671.2.

Step 2: 3-(8-(bis(4-methoxybenzyl)amino)-2-(2-formylbenzyl)-5-(pyrimidin-4-yl)-[1,2,4]triazolo[1,5-a]pyrazin-6-yl)benzonitrile

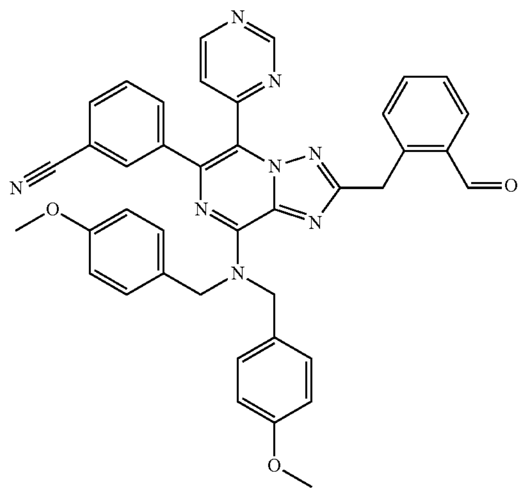 [SMILES: COc1ccc(CN(Cc2ccc(OC)cc2)c2nc(-c3cccc(C#N)c3)c(-c3ccncn3)n3nc(Cc4ccccc4C=O)nc23)cc1]

To a solution of 3-(8-(bis(4-methoxybenzyl)amino)-5-(pyrimidin-4-yl)-2-(2-vinylbenzyl)-[1,2,4]triazolo[1,5-a]pyrazin-6-yl)benzonitrile (60 mg, 0.089 mmol) in THE (1 mL) and water (1 mL) was added 0.157 M osmium tetraoxide in water (0.02 mmol). After 2 min, sodium metaperiodate (86 mg, 0.4 mmol) was added. The reaction mixture was heated at 60° C. for 1 h before quenched with sat. $Na_2S_2O_3$. The mixture was extracted with DCM. The organic phase was washed with brine, dried over $Na_2SO_4$, filtered, and concentrated to afford the product as a light yellow oil. LC-MS calculated for $C_{40}H_{33}N_8O_3$ $(M+H)^+$: m/z=673.3; found 673.3.

Step 3: (S)-3-(8-amino-2-(2-(((2-oxopyrrolidin-3-yl)amino)methyl)benzyl)-5-(pyrimidin-4-yl)-[1,2,4]triazolo[1,5-a]pyrazin-6-yl)benzonitrile To a solution of 3-(8-(bis(4-methoxybenzyl)amino)-2-(2-formylbenzyl)-5-(pyrimidin-4-yl)-[1,2,4]triazolo[1,5-a]pyrazin-6-yl)benzonitrile (13.4 mg, 0.02 mmol) in DCM (0.5 mL) was added (S)-3-aminopyrrolidin-2-one (4.1 mg, 0.04 mmol) then acetic acid (4 μL, 0.08 mmol). After 1 h, sodium triacetoxyborohydride (8.5 mg, 0.04 mmol) was added to the reaction. The reaction was stirred overnight and the mixture was concentrated, then 0.5 mL of TFA was added to the mixture and the mixture was heated at 100° C. for 10 min. The reaction was concentrated and purified by preparative LCMS (pH 2, acetonitrile/water with TFA) to afford the desired product as TFA salt. LCMS calculated for $C_{28}H_{25}N_{10}O$ $(M+H)^+$: 517.2 found 517.2.

Example 76. (R)-1-(2-((8-amino-6-(3-cyanophenyl)-5-(4-methyloxazol-5-yl)-[1,2,4]triazolo[1,5-a]pyrazin-2-yl)methyl)-3-fluorobenzyl)-3-methylpyrrolidine-3-carboxylic acid

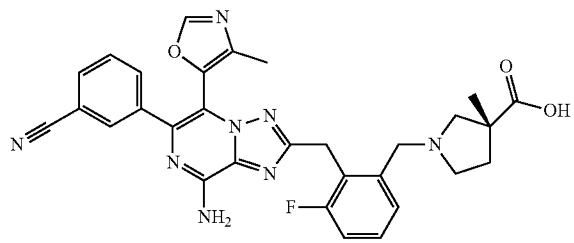 [SMILES: Cc1ncoc1-c1c(-c2cccc(C#N)c2)nc(N)c2nc(Cc3c(F)cccc3CN3CC[C@@](C)(C(=O)O)C3)nn12]

Step 1: 4-methyl-5-(4,4,5,5-tetramethyl-1,3,2-dioxaborolan-2-yl)oxazole

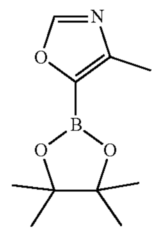

To a solution of 4-methyloxazole (0.654 g, 7.87 mmol) in heptane (3 mL) and $Et_2O$ (1 mL) was added (1,5-cyclooctadiene)(methoxy)iridium(I) dimer (0.221 g, 0.393 mmol), 4,4'-Di-tert-butyl-2,2'-dipyridyl (0.211 g, 0.787 mmol) and 4,4,5,5-tetramethyl-1,3,2-dioxaborolane (1.841 ml, 11.80 mmol). The vial was then evacuated under high vacuum and backfilled with nitrogen. The reaction was stirred overnight, then concentrated and purified via flash chromatography to afford the desired product as a colorless oil. LC-MS calculated for $C_{10}H_{17}BNO_3$ $(M+H)^+$: m/z=210.1; found 128.0 (as the corresponding boronic acid).

Step 2: 3-(8-amino-2-(2-chloro-6-fluorobenzyl)-5-(4-methyloxazol-5-yl)-[1,2,4]triazolo[1,5-a]pyrazin-6-yl)benzonitrile

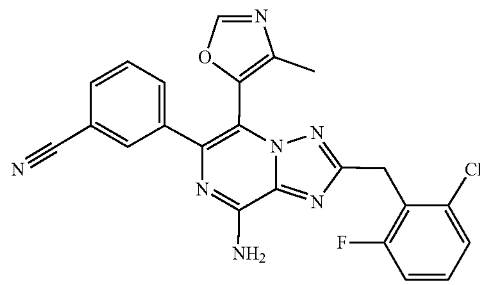 [SMILES: Cc1ncoc1-c1c(-c2cccc(C#N)c2)nc(N)c2nc(Cc3c(F)cccc3Cl)nn12]

A mixture of 3-(8-amino-5-bromo-2-(2-chloro-6-fluorobenzyl)-[1,2,4]triazolo[1,5-a]pyrazin-6-yl)benzonitrile (Example 30, Step 2; 500 mg, 1.09 mmol), 4-methyl-5-(4,4,5,5-tetramethyl-1,3,2-dioxaborolan-2-yl)oxazole (274 mg, 1.31 mmol), tetrakis(triphenylphosphine)palladium(0) (126 mg, 0.11 mmol) and $Cs_2CO_3$ (712 mg, 2.185 mmol) in 1,4-dioxane (2 mL) and water (200 µl) was purged with $N_2$ and heated at 95° C. for 7 h. The mixture was concentrated and purified via flash chromatography to afford the desired product as a white solid. LCMS calculated for $C_{23}H_{16}N_7OClF$ $(M+H)^+$: 460.1; found 460.1.

Step 3: 3-(8-amino-2-(2-fluoro-6-vinylbenzyl)-5-(4-methyloxazol-5-yl)-[1,2,4]triazolo[1,5-a]pyrazin-6-yl)benzonitrile

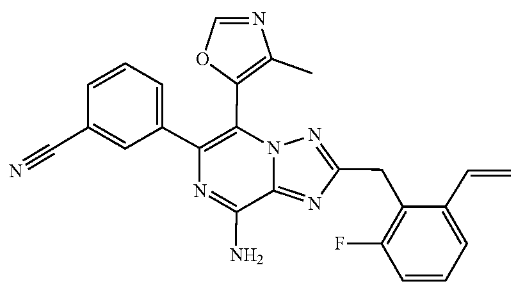 [SMILES: C=Cc1cccc(F)c1Cc1nc2c(N)nc(-c3cccc(C#N)c3)c(-c3ocnc3C)n2n1]

A mixture of 3-(8-amino-2-(2-chloro-6-fluorobenzyl)-5-(4-methyloxazol-5-yl)-[1,2,4]triazolo[1,5-a]pyrazin-6-yl) benzonitrile (101 mg, 0.22 mmol), 4,4,5,5-tetramethyl-2-vinyl-1,3,2-dioxaborolane (68 mg, 0.44 mmol), dicyclohexyl(2',4',6'-triisopropylbiphenyl-2-yl)phosphine-(2'-aminobiphenyl-2-yl)(chloro)palladium (1:1) (17 mg, 21.6 µmol) and $K_3PO_4$ (94 mg, 0.44 mmol) in 1,4-dioxane (2 mL)/water (0.4 mL) was stirred at 110° C. for 1 h. The reaction mixture was concentrated under vacuum and the resulting residue was purified with flash chromatography to give the desired product as a colorless oil. LC-MS calculated for $C_{25}H_{19}FN_7O$ $(M+H)^+$: m/z=452.1; found 452.2.

Step 4: 3-(8-amino-2-(2-fluoro-6-formylbenzyl)-5-(4-methyloxazol-5-yl)-[1,2,4]triazolo[1,5-a]pyrazin-6-yl)benzonitrile

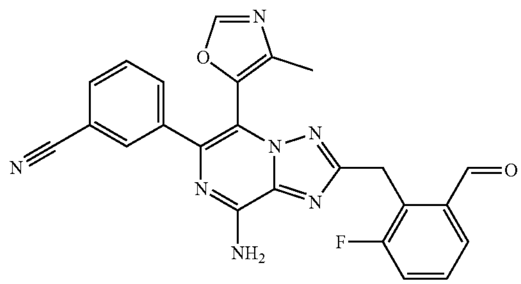 [SMILES: Cc1ncoc1-c1c(-c2cccc(C#N)c2)nc(N)c2nc(Cc3c(F)cccc3C=O)nn12]

To a solution of 3-(8-amino-2-(2-fluoro-6-vinylbenzyl)-5-(4-methyloxazol-5-yl)-[1,2,4]triazolo[1,5-a]pyrazin-6-yl) benzonitrile (40 mg, 0.089 mmol) in THF (1 mL) and water (1 mL) was added 0.157 M osmium tetraoxide in water (0.02 mmol). After 2 min, sodium metaperiodate (86 mg, 0.4 mmol) was added. The reaction mixture was heated at 60° C. for 1 h before quenched with sat. $Na_2S_2O_3$. The mixture was extracted with DCM. The organic phase was washed with brine, dried over $Na_2SO_4$, filtered, and concentrated to afford the product as a light yellow oil. LC-MS calculated for $C_{24}H_{17}FN_7O_2$ $(M+H)^+$: m/z=454.1; found 454.1.

Step 5: (R)-1-(2-((8-amino-6-(3-cyanophenyl)-5-(4-methyloxazol-5-yl)-[1,2,4]triazolo[1,5-a]pyrazin-2-yl)methyl)-3-fluorobenzyl)-3-methylpyrrolidine-3-carboxylic acid To a solution of 3-(8-amino-2-(2-fluoro-6-formylbenzyl)-5-(4-methyloxazol-5-yl)-[1,2,4]triazolo[1,5-a]pyrazin-6-yl) benzonitrile (10 mg, 0.02 mmol) in DCM (0.5 mL) was added (R)-3-methylpyrrolidine-3-carboxylic acid (4.8 mg, 0.04 mmol) then acetic acid (4 µL, 0.08 mmol). After 1 h, sodium triacetoxyborohydride (8.5 mg, 0.04 mmol) was added to the reaction. The reaction was stirred overnight and the mixture was concentrated and purified by preparative LCMS (pH 2, acetonitrile/water with TFA) to afford the desired product as TFA salt. LCMS calculated for $C_{30}H_{28}FN_8O_3$ $(M+H)^+$: 567.2 found 567.2.

Example 77. 3-(8-amino-2-(amino(2,6-difluorophenyl)methyl)-5-(4-methyloxazol-5-yl)-[1,2,4]triazolo[1,5-a]pyrazin-6-yl)benzonitrile

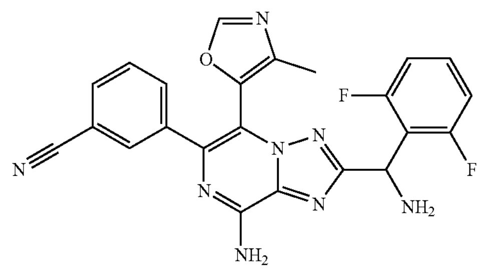 [SMILES: Cc1ncoc1-c1c(-c2cccc(C#N)c2)nc(N)c2nc(C(N)c3c(F)cccc3F)nn12]

Step 1: 3-(8-(bis(4-methoxybenzyl)amino)-5-bromo-2-formyl-[1,2,4]triazolo[1,5-a]pyrazin-6-yl)benzonitrile

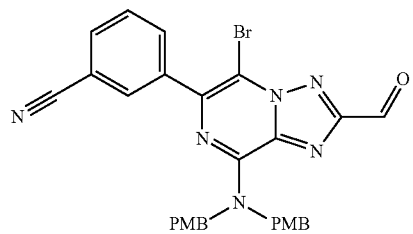

A mixture of 3-(8-(bis(4-methoxybenzyl)amino)-5-bromo-2-vinyl-[1,2,4]triazolo[1,5-a]pyrazin-6-yl)benzonitrile (Example 32, step 2; 174 mg, 0.3 mmol), osmium(VIII) oxide (3 mg in 0.3 mL water, 0.015 mmol), and sodium periodate (292 mg, 1.36 mmol) in THF/water (1:1, 6 mL) was stirred at 65° C. for 1 h. The reaction mixture was cooled to room temperature, and extracted with dichloromethane. The combined organic layers were concentrated, and purified by silica gel column to afford the desired product. LC-MS calculated for $C_{29}H_{24}N_6O_3Br$ $(M+H)^+$: m/z=583.1; found 583.1.

Step 2: 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile

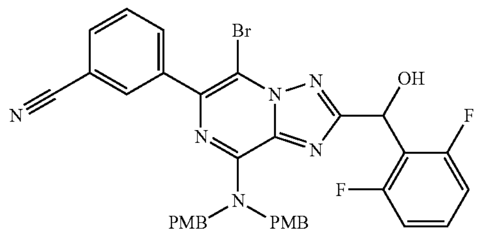

Preparation of the Grignard reagent: To a solution of 1,3-difluoro-2-iodobenzene (142 mg, 0.6 mmol) in tetrahydrofuran (1 mL), isopropylmagnesium chloride solution (296 µl, 2 M) was added at −10° C. The resulting mixture was stirred for 1 h, and used directly in the following step.

To a solution of 3-(8-(bis(4-methoxybenzyl)amino)-5-bromo-2-formyl-[1,2,4]triazolo[1,5-a]pyrazin-6-yl)benzonitrile (120 mg, 0.2 mmol) in THE (2 mL), the freshly prepared Grignard reagent from previous step was added at −10° C. The reaction mixture was stirred for 30 min, quenched with ammonium chloride solution (4 mL), and extracted with dichloromethane. The combined organic layers were concentrated under vacuum and purified by a silica gel column to afford the desired product as a racemic mixture. LC-MS calculated for $C_{35}H_{28}N_6O_3BrF_2$ $(M+H)^+$: m/z=697.1; found 697.1.

Step 3: 3-(8-(bis(4-methoxybenzyl)amino)-2-((2,6-difluorophenyl)(hydroxy)methyl)-5-(4-methyloxazol-5-yl)-[1,2,4]triazolo[1,5-a]pyrazin-6-yl)benzonitrile

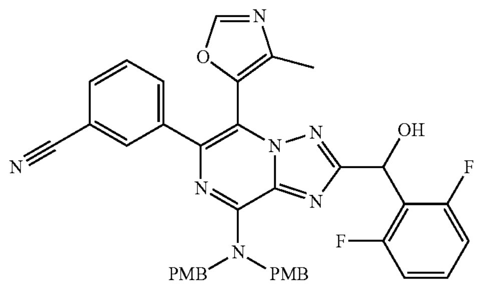

A mixture of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (382 mg, 0.55 mmol), 4-methyl-5-(4,4,5,5-tetramethyl-1,3,2-dioxaborolan-2-yl)oxazole (137 mg, 0.65 mmol), dicyclohexyl(2',4',6'-triisopropylbiphenyl-2-yl)phosphine-(2'-aminobiphenyl-2-yl)(chloro)palladium (1:1) (17 mg, 21.6 µmol) and $Cs_2CO_3$ (356 mg, 1.09 mmol) in 1,4-dioxane (2 mL) and water (200 µl) was purged with $N_2$ and heated at 95° C. for 7 h. The mixture was concentrated and purified via flash chromatography to afford the desired product as a colorless oil. LCMS calculated for $C_{39}H_{32}N_7O_4F_2$ $(M+H)^+$: 700.2; found 700.2.

Step 4: 3-(8-(bis(4-methoxybenzyl)amino)-2-(chloro(2,6-difluorophenyl)methyl)-5-(4-methyloxazol-5-yl)-[1,2,4]triazolo[1,5-a]pyrazin-6-yl)benzonitrile

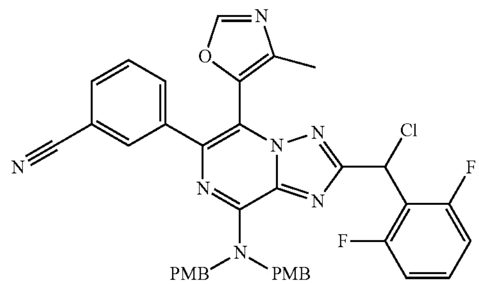

To a solution of 3-(8-(bis(4-methoxybenzyl)amino)-2-((2,6-difluorophenyl)(hydroxy)methyl)-5-(4-methyloxazol-5-yl)-[1,2,4]triazolo[1,5-a]pyrazin-6-yl)benzonitrile (201 mg, 0.29 mmol) in 2 mL of dichloromethane, thionyl chloride (105 µl, 1.435 mmol) was added at rt. The resulting mixture was stirred for 4 h, concentrated and used in next step without any further purification. LC-MS calculated for $C_{39}H_{31}N_7O_3ClF_2$ $(M+H)^+$: m/z=718.2; found 718.2.

Step 5: 3-(8-amino-2-(amino(2,6-difluorophenyl)methyl)-5-(4-methyloxazol-5-yl)-[1,2,4]triazolo[1,5-a]pyrazin-6-yl)benzonitrile To a solution of 3-(8-(bis(4-methoxybenzyl)amino)-2-(chloro(2,6-difluorophenyl)methyl)-5-(4-methyloxazol-5-yl)-[1,2,4]triazolo[1,5-a]pyrazin-6-yl)benzonitrile (40 mg, 0.084 mmol) in 1 mL of DMSO was added ammonia solution (1 mL). The mixture was heated with microwave condition at 100° C. for 10 h before diluted with water and extracted with EtOAc. The combined organic layers were washed with water and brine, dried over $MgSO_4$, and concentrated. The resulting residue was dissolved in TFA (1 mL), and stirred at 80° C. for 20 min. The reaction mixture was then cooled to room temperature, concentrated, and basified by adding aq. $NaHCO_3$ solution. The crude material was directly purified by a silica gel column to afford the desired product as a racemic mixture. The product was then separated with chiral HPLC using a chiral column (AM-1) and 45% EtOH in hexanes (20 mL/min) solvent system. Peak 1 was isolated, and further purified via preparative LC/MS (pH=2, acetonitrile/water with TFA) to give the desired product as a TFA salt. LC-MS calculated for $C_{23}H_{17}F_2N_8O$ $(M+H)^+$: m/z=459.1; found 459.0.

Example 78. 3-(8-amino-2-((2,6-difluorophenyl)(methylamino)methyl)-5-(4-methyloxazol-5-yl)-[1,2,4]triazolo[1,5-a]pyrazin-6-yl)benzonitrile

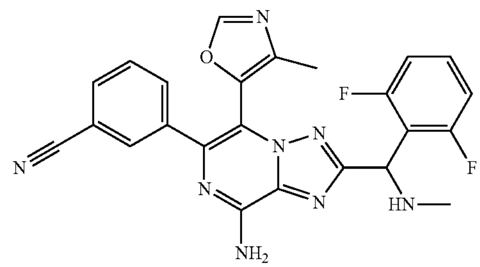 [SMILES: CNC(c1nc2c(N)nc(-c3cccc(C#N)c3)c(-c3ocnc3C)n2n1)c1c(F)cccc1F]

The title compound was prepared using similar procedures as described for Example 77 with methyl amine (2M THE solution) replacing ammonia solution in step 5. In addition, the replacement reaction was conducted at 70° C. for 1 h with 2 equivalents of $K_2CO_3$. After deprotection, the racemic product was separated with chiral HPLC using a chiral column (C2) and 30% EtOH in hexanes (20 mL/min) solvent system. Peak 2 was isolated, and further purified via preparative LC/MS (pH=2, acetonitrile/water with TFA) to give the desired product as a TFA salt. LC-MS calculated for $C_{24}H_{19}F_2N_8O$ $(M+H)^+$: m/z=473.2; found 473.2.

Example 79. 3-(8-amino-2-((2,6-difluorophenyl)((2-hydroxyethyl)amino)methyl)-5-(4-methyloxazol-5-yl)-[1,2,4]triazolo[1,5-a]pyrazin-6-yl)benzonitrile

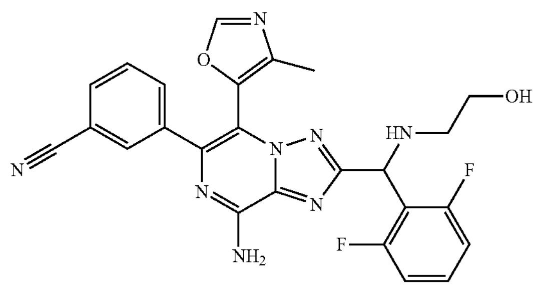 [SMILES: Cc1ncoc1-c1c(-c2cccc(C#N)c2)nc(N)c2nc(C(NCCO)c3c(F)cccc3F)nn12]

The title compound was prepared using similar procedures as described for Example 77 with 2-aminoethan-1-ol replacing ammonia solution in step 5. In addition, the replacement reaction was conducted at 70° C. for 1 h with 2 equivalents of $K_2CO_3$. After deprotection, the reaction mixture was purified by prep-HPLC (pH=2, acetonitrile/water+TFA) to give the desired product as TFA salt. LC-MS calculated for $C_{25}H_{21}N_8O_2F_2$ $(M+H)^+$: m/z=503.2; found 503.2.

Example 80. 3-(8-amino-2-(amino(2-fluorophenyl)methyl)-5-(4-methyloxazol-5-yl)-[1,2,4]triazolo[1,5-a]pyrazin-6-yl)benzonitrile

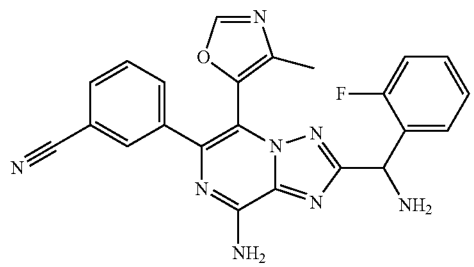 [SMILES: Cc1ncoc1-c1c(-c2cccc(C#N)c2)nc(N)c2nc(C(N)c3ccccc3F)nn12]

The title compound was prepared using similar procedures as described for Example 77 with 1-fluoro-2-iodobenzene replacing 1,3-difluoro-2-iodobenzene in step 2. The final reaction mixture was purified by prep-HPLC (pH=2, acetonitrile/water+TFA) to give the desired product as TFA salt. LC-MS calculated for $C_{23}H_{18}N_8OF$ $(M+H)^+$: m/z=441.1; found 441.2.

Example 81. 3-(8-amino-2-(amino(2,6-difluorophenyl)methyl)-5-(1-methyl-6-oxo-1,6-dihydropyridazin-3-yl)-[1,2,4]triazolo[1,5-a]pyrazin-6-yl)benzonitrile

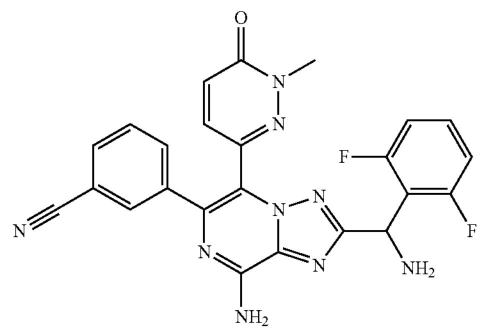 [SMILES: Cn1nc(-c2c(-c3cccc(C#N)c3)nc(N)c3nc(C(N)c4c(F)cccc4F)nn23)ccc1=O]

The title compound was prepared using similar procedures as described for Example 77 with 2-methyl-6-(4,4,5,5-tetramethyl-1,3,2-dioxaborolan-2-yl)pyridazin-3(2H)-one replacing 4-methyl-5-(4,4,5,5-tetramethyl-1,3,2-dioxaborolan-2-yl)oxazole in step 3. The final reaction mixture was purified by prep-HPLC (pH=2, acetonitrile/water+TFA) to give the desired product as TFA salt. LC-MS calculated for $C_{24}H_{18}N_9OF_2$ $(M+H)^+$: m/z=486.1; found 486.2.

Example 82. 3-(8-amino-2-((3-(oxazol-5-yl)pyridin-2-yl)methyl)-5-(pyrimidin-4-yl)-[1,2,4]triazolo[1,5-a]pyrazin-6-yl)benzonitrile

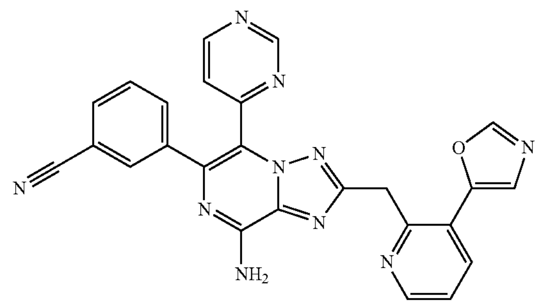 [SMILES: N#Cc1cccc(-c2nc(N)c3nc(Cc4ncccc4-c4cnco4)nn3c2-c2ccncn2)c1]

The title compound was prepared using similar procedures as described for Example 122 with 5-(4,4,5,5-tetramethyl-1,3,2-dioxaborolan-2-yl)oxazole replacing 1-methyl-4-(4,4,5,5-tetramethyl-1,3,2-dioxaborolan-2-yl)-1H-pyrazole in step 4. The reaction mixture was purified by prep-HPLC (pH=2, acetonitrile/water+TFA) to give the desired product as TFA salt. LC-MS calculated for $C_{25}H_{17}N_{10}O$ $(M+H)^+$: m/z=473.1; found 473.2.

Example 83. 3-(8-amino-2-(2-fluoro-6-(1-methyl-1H-pyrazol-4-yl)benzyl)-[1,2,4]triazolo[1,5-a]pyrazin-6-yl)-2-fluorobenzonitrile

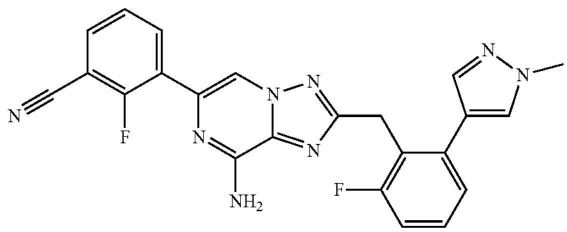 [SMILES: Cn1cc(-c2cccc(F)c2Cc2nc3c(N)nc(-c4cccc(C#N)c4F)cn3n2)cn1]

A mixture of 3-(8-(bis(4-methoxybenzyl)amino)-2-(2-chloro-6-fluorobenzyl)-[1,2,4]triazolo[1,5-a]pyrazin-6-yl)-2-fluorobenzonitrile (13 mg, 0.022 mmol) (from Example 99, step 4), 1-methyl-4-(4,4,5,5-tetramethyl-1,3,2-dioxaborolan-2-yl)-1H-pyrazole (9.5 mg, 0.044 mmol), cesium carbonate (17.7 mg, 0.116 mmol), chloro(2-dicyclohexylphosphino-2',4',6'-triisopropyl-1,1'-biphenyl)[2-(2'-amino-1,1'-biphenyl)]palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated and dissolved in TFA (1 mL) and stirred at 100° C. for 20 min. The reaction mixture was then cooled to room temperature, concentrated, and purified via preparative LC/MS (pH=2, acetonitrile/water with TFA) to give the desired product as a TFA salt. LC-MS calculated for $C_{23}H_{17}F_2N_8$ $(M+H)^+$: m/z=443.1; found 443.2.

Example 84. (S)-3-(8-amino-2-(2-fluoro-6-(((1-methyl-2-oxopyrrolidin-3-yl)amino)methyl)benzyl)-[1,2,4]triazolo[1,5-a]pyrazin-6-yl)-2-fluorobenzonitrile

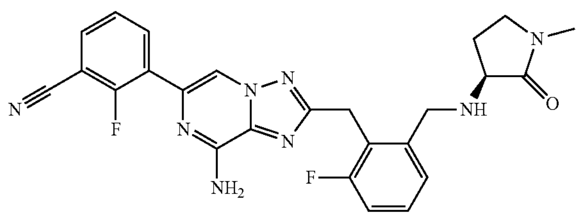 [SMILES: CN1CC[C@H](NCc2cccc(F)c2Cc2nc3c(N)nc(-c4cccc(C#N)c4F)cn3n2)C1=O]

Step 1: 3-(8-(bis(4-methoxybenzyl)amino)-2-(2-fluoro-6-vinylbenzyl)-[1,2,4]triazolo[1,5-a]pyrazin-6-yl)-2-fluorobenzonitrile

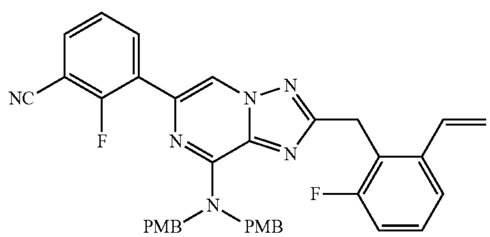

A mixture of 3-(8-(bis(4-methoxybenzyl)amino)-2-(2-chloro-6-fluorobenzyl)-[1,2,4]triazolo[1,5-a]pyrazin-6-yl)-2-fluorobenzonitrile (Example 99, step 4; 70 mg, 0.11 mmol), 4,4,5,5-tetramethyl-2-vinyl-1,3,2-dioxaborolane (34 mg, 0.22 mmol), dicyclohexyl(2',4',6'-triisopropylbiphenyl-2-yl)phosphine-(2'-aminobiphenyl-2-yl)(chloro)palladium (1:1) (8.5 mg, 10.8 μmol) and $K_3PO_4$ (47 mg, 0.22 mmol) in 1,4-dioxane (2 mL)/water (0.4 mL) was stirred at 110° C. for 1 h. The reaction mixture was concentrated under vacuum and the resulting residue was purified with flash chromatography to give the desired product as a light yellow oil. LC-MS calculated for $C_{37}H_{31}F_2N_6O_2$ $(M+H)^+$: m/z=629.2; found 629.3.

Step 2: 3-(8-(bis(4-methoxybenzyl)amino)-2-(2-fluoro-6-formylbenzyl)-[1,2,4]triazolo[1,5-a]pyrazin-6-yl)-2-fluorobenzonitrile

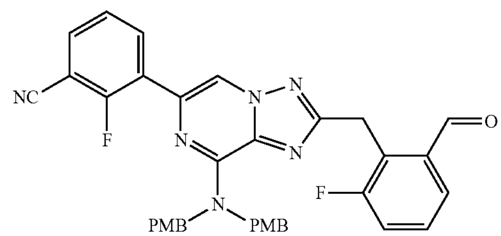

To a solution of 3-(8-(bis(4-methoxybenzyl)amino)-2-(2-fluoro-6-vinylbenzyl)-[1,2,4]triazolo[1,5-a]pyrazin-6-yl)-2-fluorobenzonitrile (56 mg, 0.089 mmol) in THF (1 mL) and water (1 mL) was added 0.157 M osmium tetraoxide in water (0.02 mmol). After 2 min, sodium metaperiodate (86 mg, 0.4 mmol) was added. The reaction mixture was heated at 60° C. for 1 h before quenched with sat. $Na_2S_2O_3$. The mixture was extracted with DCM. The organic phase was washed with brine, dried over $Na_2SO_4$, filtered, and concentrated to afford the product as a light yellow oil. LC-MS calculated for $C_{36}H_{29}F_2N_6O_3$ $(M+H)^+$: m/z=631.2; found 631.1.

Step 3: (S)-3-(8-amino-2-(2-fluoro-6-(((1-methyl-2-oxopyrrolidin-3-yl)amino)methyl)benzyl)-[1,2,4]triazolo[1,5-a]pyrazin-6-yl)-2-fluorobenzonitrile To a solution of 3-(8-(bis(4-methoxybenzyl)amino)-2-(2-fluoro-6-formylbenzyl)-[1,2,4]triazolo[1,5-a]pyrazin-6-yl)-2-fluorobenzonitrile (10 mg, 0.02 mmol) in DCM (0.5 mL) was added (S)-3-amino-1-methylpyrrolidin-2-one (4.6 mg, 0.04 mmol) then acetic acid (4 μL, 0.08 mmol). After 1 h, sodium triacetoxyborohydride (8.5 mg, 0.04 mmol) was added to the reaction. The reaction was stirred overnight and the mixture was concentrated, then 0.5 mL of TFA was added to the mixture and the mixture was heated at 100° C. for 10 min. The reaction was concentrated and purified by preparative LCMS (pH 2, acetonitrile/water with TFA) to afford the desired product as TFA salt. LCMS calculated for $C_{25}H_{23}N_8OF_2$ $(M+H)^+$: 489.2 found 489.2.

Example 85. 3-(8-amino-2-(2-fluoro-6-((6-methyl-5-oxo-2,6-diazaspiro[3.4]octan-2-yl)methyl)benzyl)-[1,2,4]triazolo[1,5-a]pyrazin-6-yl)-2-fluorobenzonitrile

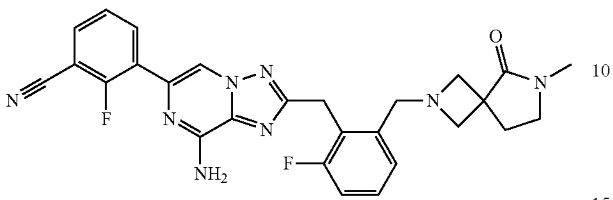

The title compound was prepared using similar procedures as described for Example 84 with 6-methyl-2,6-diazaspiro[3.4]octan-5-one replacing (S)-3-amino-1-methylpyrrolidin-2-one in step 3. The reaction mixture was purified by prep-HPLC (pH=2, acetonitrile/water+TFA) to give the desired product as TFA salt. LC-MS calculated for $C_{27}H_{25}N_8OF_2$ $(M+H)^+$: m/z=515.2; found 515.2.

Example 86. 3-(8-amino-5-(4-methyloxazol-5-yl)-2-(pyridin-2-ylmethyl)-[1,2,4]triazolo[1,5-a]pyrazin-6-yl)-2-fluorobenzonitrile

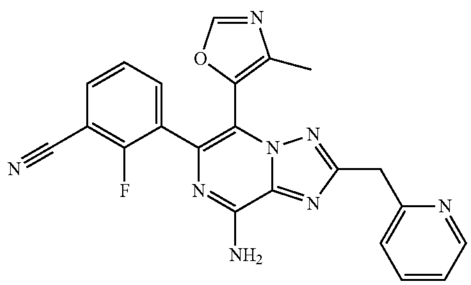 [SMILES: Cc1ncoc1-c1c(-c2cccc(C#N)c2F)nc(N)c2nc(Cc3ccccn3)nn12]

Step 1: 6-bromo-N,N-bis(4-methoxybenzyl)-2-(pyridin-2-ylmethyl)-[1,2,4]triazolo[1,5-a]pyrazin-8-amine

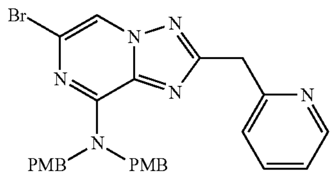

To a flask charged with 2-(pyridin-2-yl)acetic acid (164 mg, 1.2 mmol), HATU (708 mg, 1.9 mmol) in $CH_2C_{12}$ (10 ml) was added 1,2-diamino-3-(bis(4-methoxybenzyl) amino)-5-bromopyrazin-1-ium 2,4,6-trimethylbenzenesulfonate (400 mg, 0.62 mmol), followed by DIEA (0.65 ml, 3.72 mmol). After stirring at room temperature for 6 h, LCMS showed completion of reaction. The reaction mixture was diluted with DCM and water. The organic layer was washed with brine, dried over $Na_2SO_4$, filtered and concentrated. The crude product was purified with flash chromatography to give the desired product. LC-MS calculated for $C_{27}H_{26}BrN_6O_2$ $(M+H)^+$: m/z=545.1; found 545.2.

Step 2: 3-(8-(bis(4-methoxybenzyl)amino)-2-(pyridin-2-ylmethyl)-[1,2,4]triazolo[1,5-a]pyrazin-6-yl)-2-fluorobenzonitrile

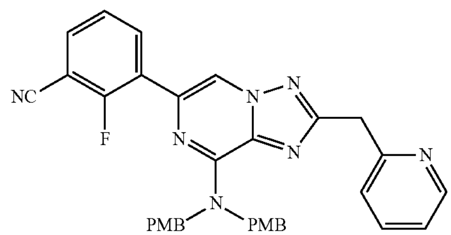

A flask charged with 6-bromo-N,N-bis(4-methoxybenzyl)-2-(pyridin-2-ylmethyl)-[1,2,4]triazolo[1,5-a]pyrazin-8-amine (108 mg, 0.2 mmol), (3-cyano-2-fluorophenyl)boronic acid (49.7 mg, 0.35 mmol), $Cs_2CO_3$ (134 mg, 0.41 mmol), Pd-tetrakis (23 mg, 0.02 mmol), 1,4-dioxane (2 ml) and water (0.2 ml) was evacuated under vacuum and refilled with $N_2$ (repeated three times). The mixture was heated at 100° C. for 8 h. LCMS showed total completion of reaction. The reaction mixture was diluted with DCM and water. The organic layer was washed with brine, dried over $Na_2SO_4$, filtered and concentrated. The crude product was purified with flash chromatography to give the desired product. LC-MS calculated for $C_{34}H_{29}FN_7O_2$ $(M+H)^+$: m/z=586.2; found 586.2.

Step 3: 3-(8-(bis(4-methoxybenzyl)amino)-5-bromo-2-(pyridin-2-ylmethyl)-[1,2,4]triazolo[1,5-a]pyrazin-6-yl)-2-fluorobenzonitrile

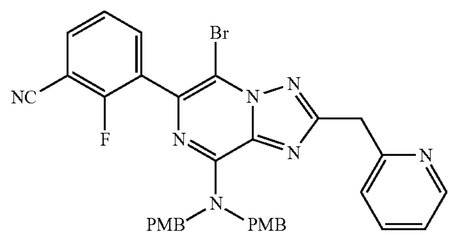

To a solution of 3-(8-(bis(4-methoxybenzyl)amino)-2-(pyridin-2-ylmethyl)-[1,2,4]triazolo[1,5-a]pyrazin-6-yl)-2-fluorobenzonitrile (146 mg, 0.25 mmol) in 3 mL of dichloromethane, 1-bromopyrrolidine-2,5-dione (46 mg, 0.25 mmol) was added at 0° C. The resulting mixture was stirred for 16 h before concentrated and purified by silica gel column to afford the desired product. LC-MS calculated for $C_{34}H_{28}FBrN_7O_2$ $(M+H)^+$: m/z=664.1; found 664.2.

Step 4: 3-(8-amino-5-(4-methyloxazol-5-yl)-2-(pyridin-2-ylmethyl)-[1,2,4]triazolo[1,5-a]pyrazin-6-yl)-2-fluorobenzonitrile A mixture of 3-(8-(bis(4-methoxybenzyl)amino)-5-bromo-2-(pyridin-2-ylmethyl)-[1,2,4]triazolo[1,5-a]pyrazin-6-yl)-2-fluorobenzonitrile (15 mg, 0.022 mmol), 4-methyl-5-(4,4,5,5-tetramethyl-1,3,2-dioxaborolan-2-yl)

oxazole (Example 76, step 1; 9.1 mg, 0.044 mmol), cesium carbonate (17.7 mg, 0.116 mmol), chloro(2-dicyclohexylphosphino-2',4',6'-triisopropyl-1,1'-biphenyl)[2-(2'-amino-1,1'-biphenyl)]palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated, then 0.5 mL of TFA was added to the mixture and the mixture was heated at 100° C. for 10 min. The reaction was concentrated and purified by preparative LCMS (pH 2, acetonitrile/water with TFA) to afford the desired product as TFA salt. LCMS calculated for $C_{22}H_{16}N_8OF$ $(M+H)^+$: 427.1; found 427.1.

Example 87. 3-(8-amino-5-(4-(2,2-difluoro-1-hydroxyethyl)-2-methyloxazol-5-yl)-2-(pyridin-2-ylmethyl)-[1,2,4]triazolo[1,5-a]pyrazin-6-yl)-2-fluorobenzonitrile

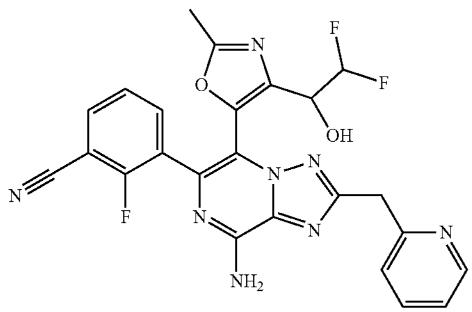 [SMILES: Cc1nc(C(O)C(F)F)c(-c2c(-c3cccc(C#N)c3F)nc(N)c3nc(Cc4ccccn4)nn23)o1]

The title compound was prepared using similar procedures as described for Example 86 with 4-(1-((tert-butyldimethylsilyl)oxy)-2,2-difluoroethyl)-2-methyl-5-(4,4,5,5-tetramethyl-1,3,2-dioxaborolan-2-yl)oxazole (Example 35, step 3) replacing 4-methyl-5-(4,4,5,5-tetramethyl-1,3,2-dioxaborolan-2-yl)oxazole in step 4. The reaction mixture was purified by prep-HPLC (pH=2, acetonitrile/water+TFA) to give the desired product as TFA salt. LC-MS calculated for $C_{24}H_{18}N_8O_2F_3$ $(M+H)^+$: m/z=507.1; found 507.2.

Example 88. 3-(8-amino-5-(2-methyl-4-(2,2,2-trifluoro-1-hydroxyethyl)oxazol-5-yl)-2-(pyridin-2-ylmethyl)-[1,2,4]triazolo[1,5-a]pyrazin-6-yl)-2-fluorobenzonitrile

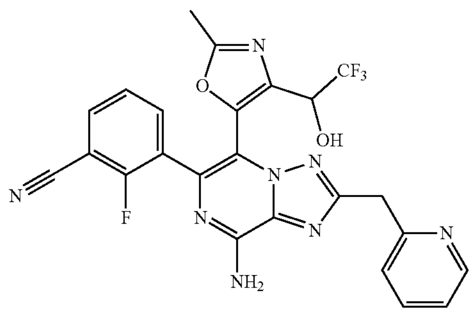 [SMILES: Cc1nc(C(O)C(F)(F)F)c(-c2c(-c3cccc(C#N)c3F)nc(N)c3nc(Cc4ccccn4)nn23)o1]

Step 1: 2,2,2-trifluoro-1-(2-methyloxazol-4-yl)ethan-1-ol

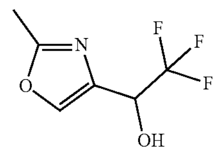

To a solution of 2-methyloxazole-4-carbaldehyde (300 mg, 2.70 mmol) in dry THE (10 ml) was added trimethyl (trifluoromethyl)silane (797 μl, 5.40 mmol) dropwise followed by adding CsF (820 mg, 5.40 mmol). After stirring at rt for 30 min, TBAF (1M THE solution, 2.70 mmol) was added, and the reaction mixture was stirred further for 10 min before quenched with sat. $NH_4Cl$. The mixture was extracted twice with EtOAc, The combined organic layers were washed with sat. NaCl solution, dried over $Na_2SO_4$, filtered, and concentrated to afford the crude product as a brown oil, which was used directly in next step without further purification. LC-MS calculated for $C_6H_7F_3NO_2$ $(M+H)^+$: m/z=182.0; found 182.0.

Step 2: 4-(1-((tert-butyldimethylsilyl)oxy)-2,2,2-trifluoroethyl)-2-methyloxazole

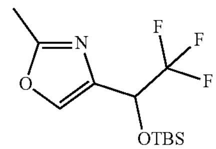 [SMILES: Cc1nc(C(O[Si](C)(C)C(C)(C)C)C(F)(F)F)co1]

In a flame dried round-bottomed flask equipped with a magnetic stir bar, a solution of 2,2,2-trifluoro-1-(2-methyloxazol-4-yl)ethan-1-ol (1.24 g, 6.87 mmol) in DCM (10 mL) was treated at rt with tert-butylchlorodimethylsilane (1.13 g, 6.88 mmol) followed by imidazole (0.47 g, 6.87 mmol) and the resulting suspension was stirred for 1 h at rt. After completion, water was added to quench the reaction. The mixture was then extracted with EtOAc, the organic layers were dried over $Na_2SO_4$, filtered and the solvent was removed under reduced pressure. The residue was purified with flash chromatography to give the desired product. LC-MS calculated for $C_{12}H_{21}F_3NO_2Si$ $(M+H)^+$: m/z=296.1; found 296.1.

Step 3: 4-(1-((tert-butyldimethylsilyl)oxy)-2,2,2-trifluoroethyl)-2-methyl-5-(4,4,5,5-tetramethyl-4,3,2-dioxaborolan-2-yl)oxazole

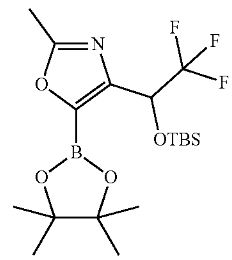 [SMILES: Cc1nc(C(O[Si](C)(C)C(C)(C)C)C(F)(F)F)c(B2OC(C)(C)C(C)(C)O2)o1]

In a flame dried round-bottomed flask equipped with a magnetic stir bar, was charged with (1,5-cyclooctadiene)(methoxy)iridium(I) dimer (60 mg, 0.09 mmol), 4,4,5,5-tetramethyl-1,3,2-dioxaborolane (834 mg, 3.0 mmol), and pentane (4.0 mL). The mixture was stirred at room temperature for 10 min. Then 4,4'-di-tert-butyl-2,2'-dipyridyl (48 mg, 0.18 mmol) was added to this mixture and reaction stirred for additional 20 min. 4-(1-((tert-butyldimethylsilyl)oxy)-2,2,2-trifluoroethyl)-2-methyloxazole (708 mg, 2.4 mmol) dissolved in $Et_2O$ (4 mL) was added to the active catalyst mixture. The reaction was stirred at room temperature until completion. Solvent was removed under reduced pressure, and the crude material was purified with flash chromatography to give the desired product. LC-MS calculated for the corresponding boronic acid $C_{12}H_{22}BF_3NO_4Si$ $(M+H)^+$: m/z=340.2; found 340.1.

Step 4: 3-(8-amino-5-(2-methyl-4-(2,2,2-trifluoro-1-hydroxyethyl)oxazol-5-yl)-2-(pyridin-2-ylmethyl)-[1,2,4]triazolo[1,5-a]pyrazin-6-yl)-2-fluorobenzonitrile A mixture of 3-(8-(bis(4-methoxybenzyl)amino)-5-bromo-2-(pyridin-2-ylmethyl)-[1,2,4]triazolo[1,5-a]pyrazin-6-yl)-2-fluorobenzonitrile (Example 86, step 3; 15 mg, 0.022 mmol), 4-(1-((tert-butyldimethylsilyl)oxy)-2,2,2-trifluoroethyl)-2-methyl-5-(4,4,5,5-tetramethyl-1,3,2-dioxaborolan-2-yl)oxazole (18 mg, 0.044 mmol), cesium carbonate (17.7 mg, 0.116 mmol), chloro(2-dicyclohexylphosphino-2',4',6'-triisopropyl-1,1'-biphenyl)[2-(2'-amino-1,1'-biphenyl)]palladium(II) (2.26 mg, 2.88 μmol) (XPhos Pd G2) in 1,4-dioxane (500 μl) and water (100 μl) was purged with $N_2$ and heated at 95° C. for 1 h. The mixture was concentrated, then 0.5 mL of TFA was added to the mixture and the mixture was heated at 100° C. for 10 min. The reaction was concentrated and purified by preparative LCMS (pH 2, acetonitrile/water with TFA) to afford the desired product as TFA salt. LCMS calculated for $C_{24}H_{17}N_8O_2F_4$ $(M+H)^+$: 525.1; found 525.1.

Example 89. 3-(8-amino-5-(1-methyl-6-oxo-1,6-dihydropyridin-3-yl)-2-(pyridin-2-ylmethyl)-[1,2,4]triazolo[1,5-a]pyrazin-6-yl)-2-fluorobenzonitrile

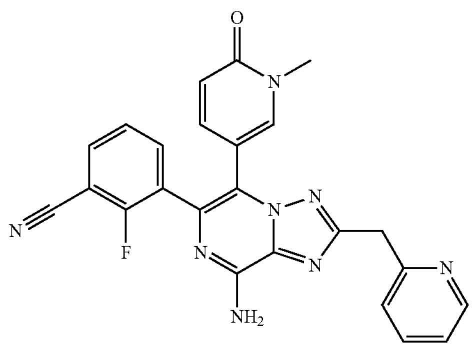 [SMILES: Cn1cc(-c2c(-c3cccc(C#N)c3F)nc(N)c3nc(Cc4ccccn4)nn23)ccc1=O]

The title compound was prepared using similar procedures as described for Example 86 with 1-methyl-5-(4,4,5,5-tetramethyl-1,3,2-dioxaborolan-2-yl)pyridin-2(1H)-one replacing 4-methyl-5-(4,4,5,5-tetramethyl-1,3,2-dioxaborolan-2-yl)oxazole in step 4. The reaction mixture was purified by prep-HPLC (pH=2, acetonitrile/water+TFA) to give the desired product as TFA salt. LC-MS calculated for $C_{24}H_{18}N_8OF$ $(M+H)^+$: m/z=453.1; found 453.2.

Example 90. 3-(8-amino-2-((1-((1-methyl-1H-imidazol-4-yl)sulfonyl)pyrrolidin-2-yl)methyl)-[1,2,4]triazolo[1,5-a]pyrazin-6-yl)-2-fluorobenzonitrile

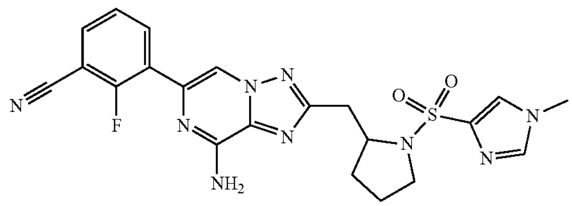 [SMILES: Cn1cnc(S(=O)(=O)N2CCCC2Cc2nc3c(N)nc(-c4cccc(C#N)c4F)cn3n2)c1]

Step 1: tert-butyl 2-((8-(bis(4-methoxybenzyl)amino)-6-bromo-[1,2,4]triazolo[1,5-a]pyrazin-2-yl)methyl)pyrrolidine-1-carboxylate

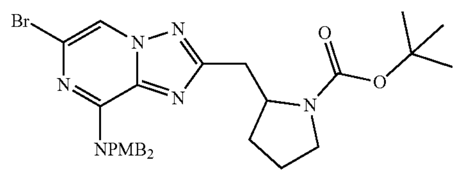

To a solution of 1,2-diamino-3-(bis(4-methoxybenzyl)amino)-5-bromopyrazin-1-ium 2,4,6-trimethylbenzenesulfonate (1.80 g, 2.79 mmol), 2-(1-(tert-butoxycarbonyl)pyrrolidin-2-yl)acetic acid (704 mg, 3.07 mmol), 2-(1H-benzotriazole-1-yl)-1,1,3,3-tetramethylaminium tetrafluoroborate (TBTU, 1.35 g, 4.19 mmol) in dichloromethane (20 mL) was added N,N-diisopropylethylamine (0.980 mL, 5.58 mmol) dropwise. The resultant mixture was stirred at room temp overnight. The resulting mixture was filtered, concentrated under reduced pressure, and purified by Biotage Isolera (with 50 g silica gel column) eluting with 0-50% EtOAc/Hexane to give the product. LCMS calculated for $C_{31}H_{38}BrN_6O_4^+$ $(M+H)^+$: m/z=637.2, 639.2; found: 637.3, 639.3.

Step 2: tert-butyl 2-((8-(bis(4-methoxybenzyl)amino)-6-(3-cyano-2-fluorophenyl)-[1,2,4]triazolo[1,5-a]pyrazin-2-yl)methyl)pyrrolidine-1-carboxylate

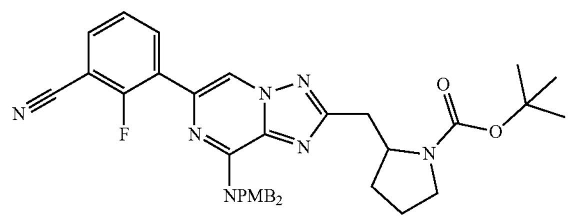

A mixture of tert-butyl 2-((8-(bis(4-methoxybenzyl)amino)-6-bromo-[1,2,4]triazolo[1,5-a]pyrazin-2-yl)methyl)pyrrolidine-1-carboxylate (1.20 g, 1.88 mmol), chloro(2-dicyclohexylphosphino-2',4',6'-triisopropyl-1,1'-biphenyl)[2-(2'-amino-1,1'-biphenyl)]palladium(II) (XPhos Pd G2) (0.148 g, 0.188 mmol), sodium carbonate (0.299 g, 2.82 mmol) and (3-cyano-2-fluorophenyl)boronic acid (0.310 g, 1.88 mmol) in 1,4-dioxane (17 ml)/Water (1.7 ml) in a 40 mL vial was heated at 90° C. overnight. The mixture was diluted with water and extracted with EtOAc (×3). The organic extracts were dried (anhyd. $Na_2SO_4$) and concentrated under reduced pressure. The residue was purified by Biotage Isolera (with 50 g silica gel column) eluting with 0-50% EtOAc/Hexane to give the product. LCMS calculated for $C_{38}H_{41}FN_7O_4^+$ $(M+H)^+$: m/z=678.3; found: 678.4.

Step 3: 3-(8-amino-2-(pyrrolidin-2-ylmethyl)-[1,2,4]triazolo[1,5-a]pyrazin-6-yl)-2-fluorobenzonitrile

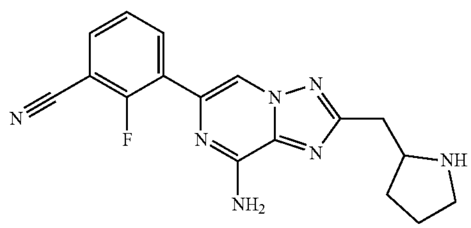 [SMILES: N#Cc1cccc(-c2cn3nc(CC4CCCN4)nc3c(N)n2)c1F]

A mixture of tert-butyl 2-((8-(bis(4-methoxybenzyl)amino)-6-(3-cyano-2-fluorophenyl)-[1,2,4]triazolo[1,5-a]pyrazin-2-yl)methyl)pyrrolidine-1-carboxylate (1.13 g, 1.67 mmol) in TFA (30 mL) was heated at 70° C. for 1 h. After cooling to room temperature, TFA was evaporated, and the residue was diluted with 1 N NaOH (200 mL). The resultant mixture was extracted with DCM (×3) and the combined organic extracts were dried (anhyd. $Na_2SO_4$) and concentrated under reduced pressure to afford the product using without further purification. LCMS calculated for $C_{17}H_{17}FN_7$+$(M+H)^+$: m/z=338.1; found: 338.1.

Step 4: 3-(8-amino-2-((1-((1-methyl-1H-imidazol-4-yl)sulfonyl)pyrrolidin-2-yl)methyl)-[1,2,4]triazolo[1,5-a]pyrazin-6-yl)-2-fluorobenzonitrile A mixture of 3-(8-amino-2-(pyrrolidin-2-ylmethyl)-[1,2,4]triazolo[1,5-a]pyrazin-6-yl)-2-fluorobenzonitrile (14 mg, 0.043 mmol) and 1-methyl-1H-imidazole-4-sulfonyl chloride (6.0 mg, 0.033 mmol) and triethylamine (14 μL, 0.099 mmol) in DCM (0.25 ml) was stirred at room temp for 2 h. The resultant mixture was diluted with acetonitrile, filtered, and purified by preparative LC/MS (pH=2, acetonitrile/water with TFA) to afford the desired product as a TFA salt. LCMS calculated for $C_{21}H_{21}FN_9O_2S^+$ $(M+H)^+$: m/z=482.1; found: 482.0.

Example 91. 3-(2-(2-((1-acetylpiperidin-4-yl)methyl)-6-fluorobenzyl)-8-amino-[1,2,4]triazolo[1,5-a]pyrazin-6-yl)-2-fluorobenzonitrile

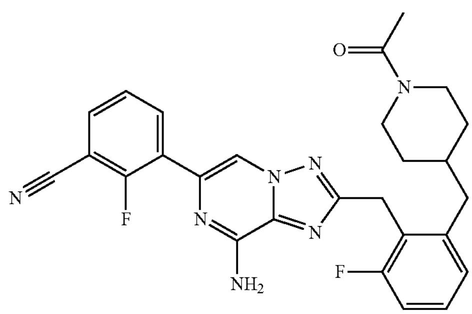 [SMILES: CC(=O)N1CCC(Cc2cccc(F)c2Cc2nc3c(N)nc(-c4cccc(C#N)c4F)cn3n2)CC1]

Step 1: tert-butyl 4-(2-((8-(bis(4-methoxybenzyl)amino)-6-(3-cyano-2-fluorophenyl)-[1,2,4]triazolo[1,5-a]pyrazin-2-yl)methyl)-3-fluorobenzylidene)piperidine-1-carboxylate

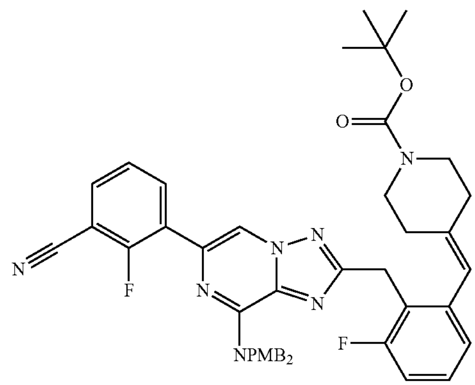

A mixture of 3-(8-(bis(4-methoxybenzyl)amino)-2-(2-chloro-6-fluorobenzyl)-[1,2,4]triazolo[1,5-a]pyrazin-6-yl)-2-fluorobenzonitrile (193 mg, 0.303 mmol) (from Example 99, step 4), XPhos Pd G2 (23.84 mg, 0.030 mmol), potassium phosphate (193 mg, 0.909 mmol) and tert-butyl 4-((4,4,5,5-tetramethyl-1,3,2-dioxaborolan-2-yl)methylene)piperidine-1-carboxylate (98.1 mg, 0.303 mmol) in 1,4-dioxane (2.75 mL)/Water (0.550 mL) in a 40 mL vial was flushed with nitrogen for ca. 2 min and heated at 120° C. for 3 h. After cooling to room temp, the mixture was diluted with water and extracted with DCM (×3). The combined organic extracts were dried (anhyd. $Na_2SO_4$), concentrated under reduced pressure, and purified by Biotage Isolera (with 50 g silica gel column) eluting with 0-100% EtOAc/Hexane to give the product. LCMS calculated for $C_{46}H_{46}F_2N_7O_4^+$ $(M+H)^+$: m/z=798.4; found: 798.4.

Step 2: tert-butyl 4-(2-((8-(bis(4-methoxybenzyl)amino)-6-(3-cyano-2-fluorophenyl)-[1,2,4]triazolo[1,5-a]pyrazin-2-yl)methyl)-3-fluorobenzyl)piperidine-1-carboxylate

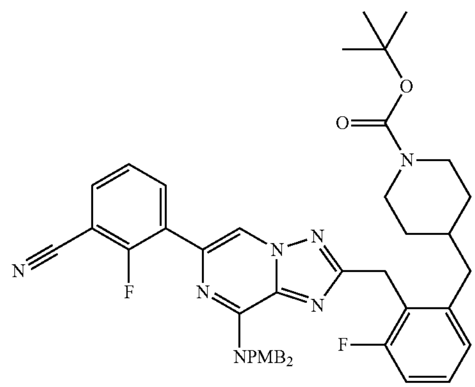

A mixture of tert-butyl 4-(2-((8-(bis(4-methoxybenzyl)amino)-6-(3-cyano-2-fluorophenyl)-[1,2,4]triazolo[1,5-a]pyrazin-2-yl)methyl)-3-fluorobenzylidene)piperidine-1-carboxylate (151 mg, 0.188 mmol) and Pd(OH)2/C (20% wt, 26 mg, 0.038 mmol) in MeOH (2 mL)/DCM (1.000 mL)) in a 20 mL vial was stirred at room temp under $H_2$ balloon overnight. The resultant mixture was filtered, concentrated under reduced pressure, and used without further purification. LCMS calculated for $C_{46}H_{48}F_2N_7O_4^+$ (M+H)$^+$: m/z=800.4; found: 800.5.

Step 3: 2-fluoro-3-(2-(2-fluoro-6-(piperidin-4-ylmethyl)benzyl)-8-((4-methoxybenzyl)amino)-[1,2,4]triazolo[1,5-a]pyrazin-6-yl)benzonitrile

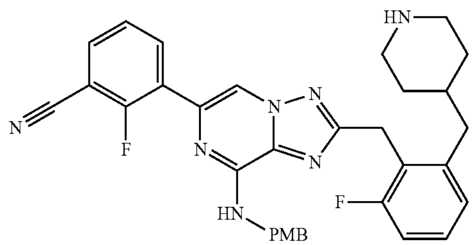

To a solution of tert-butyl 4-(2-((8-(bis(4-methoxybenzyl)amino)-6-(3-cyano-2-fluorophenyl)-[1,2,4]triazolo[1,5-a]pyrazin-2-yl)methyl)-3-fluorobenzyl)piperidine-1-carboxylate (130 mg, 0.163 mmol) in DCM (10 mL) was added TFA (5.0 mL) dropwise. The resultant mixture was stirred and room temp for 30 min and transferred to a separated funnel with DCM and add 1N NaOH (ca. 200 mL) was added. The layers were separated and the aqueous layer was extracted with DCM (×2). The combined organic extracts were dried (anhyd. $Na_2SO_4$), concentrated under reduced pressure, and used without further purification. LCMS calculated for $C_{33}H_{32}F_2N_7O^+$ (M+H)$^+$: m/z=580.3; found: 580.3.

Step 4: 3-(2-(2-((1-acetylpiperidin-4-yl)methyl)-6-fluorobenzyl)-8-((4-methoxybenzyl)amino)-[1,2,4]triazolo[1,5-a]pyrazin-6-yl)-2-fluorobenzonitrile To a solution of 2-fluoro-3-(2-(2-fluoro-6-(piperidin-4-ylmethyl)benzyl)-8-((4-methoxybenzyl)amino)-[1,2,4]triazolo[1,5-a]pyrazin-6-yl)benzonitrile (14 mg, 0.025 mmol) and acetyl chloride (25 μL, 0.025 mmol, 1M in DCM) in DCM (0.5 mL) was added triethylamine (10.5 μL, 0.0750 mmol). The resultant mixture was stirred at room temp for 1 h, filtered, and concentrated under reduced pressure. The residue was added TFA (0.5 mL) stirred 70° C. for 1 h. The resulting mixture was diluted with acetonitrile, filtered, and purified by preparative LC/MS (pH=2, acetonitrile/water with TFA) to afford the desired product as a TFA salt. LCMS calculated for $C_{27}H_{26}F_2N_7O^+$ (M+H)$^+$: m/z=502.2; found: 502.1.

Example 92. 3-(8-amino-2-((2,6-difluorophenyl)(hydroxy)methyl)-5-(1-ethyl-1H-pyrazol-5-yl)-[1,2,4]triazolo[1,5-a]pyrazin-6-yl)benzonitrile, Peak 1

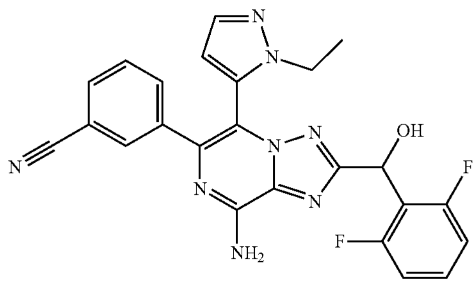 [SMILES: CCn1nccc1-c1c(-c2cccc(C#N)c2)nc(N)c2nc(C(O)c3c(F)cccc3F)nn12]

Step 1: 3-(8-(bis(4-methoxybenzyl)amino)-2-((2,6-difluorophenyl)(hydroxy)methyl)-[1,2,4]triazolo[1,5-a]pyrazin-6-yl)benzonitrile

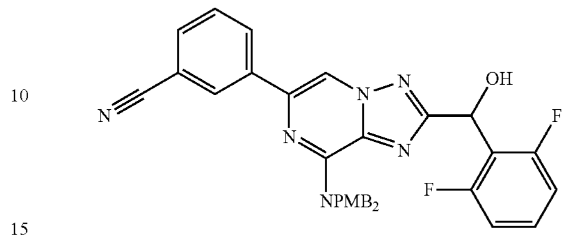

To a solution of 1,3-difluoro-2-iodobenzene (0.822 g, 3.42 mmol) in THF (2 mL) was added isopropylmagnesium chloride lithium chloride complex solution (1.3 M, 2.3 mL, 3.0 mmol) dropwise at 0° C. The reaction mixture was stirred at 0° C. for 30 minutes, A solution of 3-(8-(bis(4-methoxybenzyl)amino)-2-formyl-[1,2,4]triazolo[1,5-a]pyrazin-6-yl)benzonitrile (0.432 g, 0.856 mmol) (from Example 40, step 1) in THE (2 mL) was added dropwise and the reaction mixture was stirred at 0° C. for 1 h. The reaction mixture was then quenched with saturated aqueous $NH_4Cl$ solution and diluted with DCM. The layers were separated, the aqueous layer was extracted with DCM, and the combined organic fractions were dried over $MgSO_4$, filtered and concentrated. The crude residue was purified using flash chromatography to give the desired product (0.301 g, 57%). LC-MS calculated for $C_{35}H_{29}F_2N_6O_3$ (M+H)$^+$: m/z=619.2; found 619.2.

Step 2: 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile

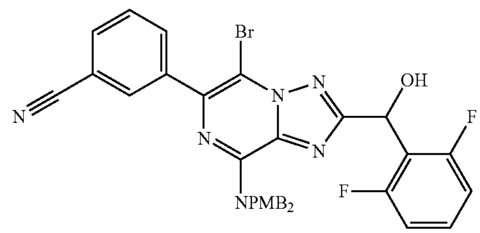

To a solution of 3-(8-(bis(4-methoxybenzyl)amino)-2-((2,6-difluorophenyl)(hydroxy)methyl)-[1,2,4]triazolo[1,5-a]pyrazin-6-yl)benzonitrile (0.301 g, 0.487 mmol) in DCM (2 mL) was added a solution of NBS (0.087 g, 0.487 mmol) in DCM (2 mL) dropwise at 0° C. The reaction mixture was stirred at 0° C. for 1 h. The reaction mixture was concentrated, and the resulting residue was purified using flash chromatography to give the desired product (0.339 g, 99%). LC-MS calculated for $C_{35}H_{28}BrF_2N_6O_3$ (M+H)$^+$: m/z=697.1; found 697.1.

Step 3: 3-(8-amino-2-((2,6-difluorophenyl)(hydroxy)methyl)-5-(1-ethyl-1H-pyrazol-5-yl)-[1,2,4]triazolo[1,5-a]pyrazin-6-yl)benzonitrile To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (0.210 g, 0.301 mmol), 1-ethyl-5-(4,4,5,5-tetramethyl-1,3,2-dioxaborolan- 2-yl)-1H-pyrazole (0.267 g, 1.20 mmol), and dicyclohexyl (2',4',6'-triisopropylbiphenyl-2-yl)phosphine-(2'-aminobiphenyl-2-yl)(chloro)palladium (1:1) (0.071 g, 0.090 mmol) in dioxane (2.50 mL) and water (0.50 mL) was added potassium phosphate tribasic (0.320 g, 1.51 mmol). The reaction mixture was stirred at 100° C. for 2 h. The reaction mixture was then diluted with water and DCM. The layers were separated, the aqueous layer was extracted with DCM, and the combined organic fractions were dried over $MgSO_4$, filtered and concentrated. The crude material was dissolved in TFA (5 mL) and heated to 80° C. for 20 minutes. The reaction mixture was then cooled to room temperature, concentrated, and basified by adding aqueous $NaHCO_3$ solution. The crude material was directly purified by a silica gel column to afford the desired product (110 mg, 77%) as a racemic mixture. The product was then separated with chiral SFC using a chiral column (ES Industries Chromega-Chiral CC4) and 25% MeOH in $CO_2$ (85 mL/min) solvent system. Peak 1 was isolated, and further purified using preparative LC/MS (pH=2, acetonitrile/water with TFA) to give the desired product as a TFA salt. LC-MS calculated for $C_{24}H_{19}F_2N_8O$ $(M+H)^+$: m/z=473.2; found 473.2.

Example 93. 3-(8-amino-2-((2,6-difluorophenyl)(hydroxy)methyl)-5-(1-ethyl-1H-pyrazol-5-yl)-[1,2,4]triazolo[1,5-a]pyrazin-6-yl)benzonitrile, Peak 2

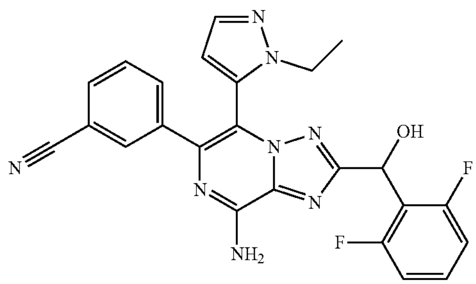 [SMILES: CCn1nccc1-c1c(-c2cccc(C#N)c2)nc(N)c2nc(C(O)c3c(F)cccc3F)nn12]

This compound was prepared using the same procedure as described for Example 92. The product was separated with chiral SFC using a chiral column (ES Industries Chromega-Chiral CC4) and 25% MeOH in $CO_2$ (85 mL/min) solvent system. Peak 2 was isolated, and further purified using preparative LC/MS (pH=2, acetonitrile/water with TFA) to give the desired product as a TFA salt. LC-MS calculated for $C_{24}H_{19}F_2N_8O$ $(M+H)^+$: m/z=473.2; found 473.2.

Example 94. 3-(8-amino-2-((2,6-difluorophenyl)(hydroxy)methyl)-5-(2,6-dimethylpyridin-4-yl)-[1,2,4]triazolo[1,5-a]pyrazin-6-yl)benzonitrile, Peak 1

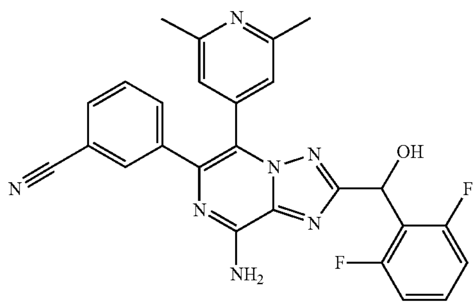 [SMILES: Cc1cc(-c2c(-c3cccc(C#N)c3)nc(N)c3nc(C(O)c4c(F)cccc4F)nn23)cc(C)n1]

To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (0.518 g, 0.638 mmol) (from example 92, step 2), 2,6-dimethyl-4-(4,4,5,5-tetramethyl-1,3,2-dioxaborolan-2-yl)pyridine (0.346 g, 1.48 mmol), and dicyclohexyl(2',4',6'-triisopropylbiphenyl-2-yl)phosphine-(2'-aminobiphenyl-2-yl)(chloro)palladium (1:1) (0.058 g, 0.074 mmol) in dioxane (3.0 mL) and water (0.60 mL) was added potassium phosphate tribasic (0.472 g, 2.23 mmol). The reaction mixture was stirred at 90° C. for 1 h. The reaction mixture was then diluted with water and DCM. The layers were separated, the aqueous layer was extracted with DCM, and the combined organic fractions were dried over $MgSO_4$, filtered and concentrated. The crude material was dissolved in TFA (5 mL) and heated to 80° C. for 20 minutes. The reaction mixture was then cooled to room temperature, concentrated, and basified by adding aqueous $NaHCO_3$ solution. The crude material was directly purified by a silica gel column to afford the desired product (257 mg, 72%) as a racemic mixture. The product was then separated with chiral HPLC using a chiral column (Phenomenex Lux 5 um Cellulose-2, 21.1×250 mm) and 35% EtOH in Hexanes (20 mL/min) solvent system. Peak 1 was isolated, and further purified using preparative LC/MS (pH=2, acetonitrile/water with TFA) to give the desired product as a TFA salt. LC-MS calculated for $C_{26}H_{20}F_2N_7O$ $(M+H)^+$: m/z=484.2; found 484.2. $^1H$ NMR (500 MHz, DMSO-$d_6$) δ 7.92 (s, 2H), 7.85 (s, 1H), 7.83 (d, J=7.6 Hz, 1H), 7.56 (d, J=8.0 Hz, 1H), 7.53-7.40 (m, 4H), 7.10 (t, J=8.4 Hz, 2H), 6.27 (s, 1H), 2.51 (s, 6H).

Example 95. 3-(8-amino-2-((2,6-difluorophenyl)(hydroxy)methyl)-5-(2,6-dimethylpyridin-4-yl)-[1,2,4]triazolo[1,5-a]pyrazin-6-yl)benzonitrile, Peak 2

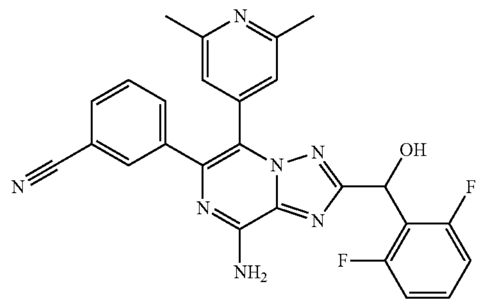 [SMILES: Cc1cc(-c2c(-c3cccc(C#N)c3)nc(N)c3nc(C(O)c4c(F)cccc4F)nn23)cc(C)n1]

This compound was prepared using the same procedure as described for Example 94. The product was then separated with chiral HPLC using a chiral column (Phenomenex Lux Sum Cellulose-2, 21.1×250 mm) and 35% EtOH in Hexanes (20 mL/min) solvent system. Peak 2 was isolated, and further purified using preparative LC/MS (pH=2, acetonitrile/water with TFA) to give the desired product as a TFA salt. LC-MS calculated for $C_{26}H_{20}F_2N_7O$ $(M+H)^+$: m/z=484.2; found 484.2. $^1H$ NMR (500 MHz, DMSO-$d_6$) δ 7.92 (s, 2H), 7.85 (s, 1H), 7.83 (d, J=7.6 Hz, 1H), 7.56 (d, J=8.0 Hz, 1H), 7.53-7.40 (m, 4H), 7.10 (t, J=8.4 Hz, 2H), 6.27 (s, 1H), 2.51 (s, 6H).

Example 96. 3-(2-((1H-pyrrolo[3,2-b]pyridin-3-yl) methyl)-4-amino-7-(pyrimidin-4-yl)pyrazolo[1,5-a] pyrazin-6-yl)benzonitrile

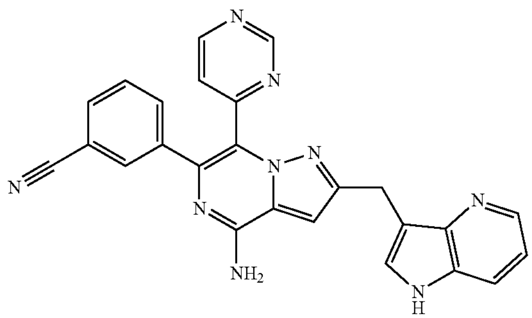 [SMILES: N#Cc1cccc(-c2nc(N)c3cc(Cc4c[nH]c5cccnc45)nn3c2-c2ccncn2)c1]

Step 1: 3-(4-amino-2-(bromomethyl)-7-(pyrimidin-4-yl)pyrazolo[1,5-a]pyrazin-6-yl)benzonitrile

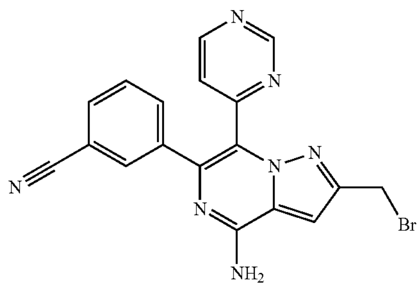 [SMILES: N#Cc1cccc(-c2nc(N)c3cc(CBr)nn3c2-c2ccncn2)c1]

To a solution of 3-(4-amino-2-(hydroxymethyl)-7-(pyrimidin-4-yl)pyrazolo[1,5-a]pyrazin-6-yl)benzonitrile (0.48 g, 1.40 mmol) (from Example 13, step 2) in dry THE (10 ml) was added $PBr_3$ (1.14 g, 4.19 mmol) dropwise at room temperature. The reaction mixture was stirred rapidly at 60° C. for 5 hours. The reaction mixture was cooled and quenched with saturated aqueous $NaHCO_3$ solution. The layers were separated, the aqueous layer was extracted with DCM, and the combined organic fractions were dried over $MgSO_4$, filtered and concentrated. The crude material was directly purified by a silica gel column (0 to 100% ethyl acetate/hexanes) to afford the desired product (0.48 g, 84%). LC-MS calculated for $C_{18}H_{13}BrN_7$ $(M+H)^+$: m/z=406.0; found 406.1.

Step 2: 3-(2-((1H-pyrrolo[3,2-b]pyridin-3-yl) methyl)-4-amino-7-(pyrimidin-4-yl)pyrazolo[1,5-a] pyrazin-6-yl)benzonitrile To a solution of 3-(4-amino-2-(bromomethyl)-7-(pyrimidin-4-yl)pyrazolo[1,5-a]pyrazin-6-yl)benzonitrile (0.015 g, 0.037 mmol), 3-(4,4,5,5-tetramethyl-1,3,2-dioxaborolan-2-yl)-1-tosyl-1H-pyrrolo[3,2-b]pyridine (0.029 g, 0.074 mmol), and dicyclohexyl(2',4',6'-triisopropylbiphenyl-2-yl) phosphine-(2'-aminobiphenyl-2-yl)(chloro)palladium (1:1) (0.006 g, 0.007 mmol) in dioxane (0.3 mL) and water (0.06 mL) was added potassium phosphate tribasic (0.024 g, 0.111 mmol). The reaction mixture was stirred at 90° C. for 1 h. The reaction mixture was then diluted with water (0.3 ml) and THE (0.3 ml). NaOH (25 mg) was added to the vial and the vial was stirred at room temperature for 30 minutes. The reaction mixture was diluted with DMF (4 ml) and purified with prep-LCMS (pH=2, acetonitrile/water+TFA) to give the desired product as TFA salt. LC-MS calculated for $C_{25}H_{18}N_9$ $(M+H)^+$: m/z=444.2; found 444.2.

Example 97. 3-(8-amino-2-((2-(difluoromethoxy)-6-fluorophenyl)(hydroxy)methyl)-5-(pyrimidin-4-yl)-[1,2,4]triazolo[1,5-a]pyrazin-6-yl)benzonitrile, Peak 1

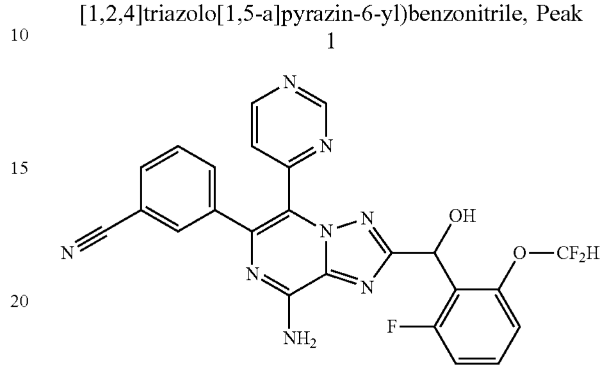

To a solution of 1-(difluoromethoxy)-3-fluoro-2-iodobenzene (74 mg, 0.26 mmol) in tetrahydrofuran (0.2 mL), isopropylmagnesium chloride lithium chloride (0.2 ml, 1.3 M solution) was added at −10° C., and the resulting mixture was stirred for 1 hour before a solution of 3-(8-(bis(4-methoxybenzyl)amino)-2-formyl-5-(pyrimidin-4-yl)-[1,2,4] triazolo[1,5-a]pyrazin-6-yl)benzonitrile (20 mg, 0.034 mmol) (from Example 49 step 8) in THE (0.2 mL) was added at −10° C. The reaction mixture was stirred for 30 min, quenched with ammonium chloride solution (1 mL), and extracted with dichloromethane. The combined organic layers were concentrated under vacuum. The resulting material was dissolved in TFA (1 mL), and stirred at 80° C. for 20 min. The reaction mixture was then cooled to room temperature, concentrated, and basified by adding aqueous $NaHCO_3$ solution. The crude material was directly purified by a silica gel column to afford the desired product (16 mg, 94%) as a racemic mixture. The product was then separated with chiral HPLC using a chiral column (Phenomenex Lux 5 um Cellulose-4, 21.1×250 mm) and 45% EtOH in Hexanes (20 mL/min) solvent system. Peak 1 was isolated, and further purified using preparative LC/MS (pH=2, acetonitrile/water with TFA) to give the desired product as a TFA salt. LC-MS calculated for $C_{24}H_{16}F_3N_8O_2$ $(M+H)^+$: m/z=505.1; found 505.1.

Example 98. 3-(8-amino-2-((2-(difluoromethoxy)-6-fluorophenyl)(hydroxy)methyl)-5-(pyrimidin-4-yl)-[1,2,4]triazolo[1,5-a]pyrazin-6-yl)benzonitrile, Peak 2

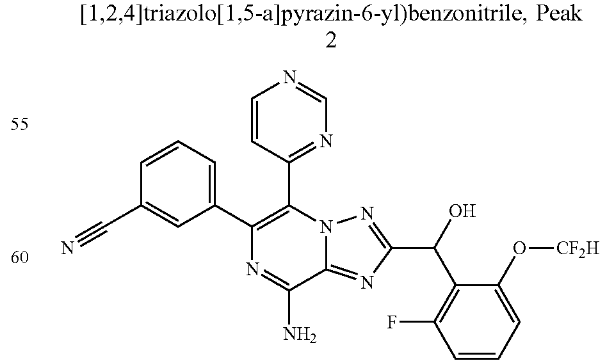

This compound was prepared using the same procedure as described for Example 97. The racemic product was separated with chiral HPLC using a chiral column (Phenomenex Lux Sum Cellulose-4, 21.1×250 mm) and 45% EtOH in Hexanes (20 mL/min) solvent system. Peak 2 was isolated, and further purified using preparative LC/MS (pH=2, acetonitrile/water with TFA) to give the desired product as a TFA salt. LC-MS calculated for $C_{24}H_{16}F_3N_8O_2$ $(M+H)^+$: m/z=505.1; found 505.1.

Example 99. 3-(8-amino-2-(2-fluoro-6-(1-((1-methyl-1H-pyrazol-4-yl)methyl)-1H-pyrazol-4-yl)benzyl)-[1,2,4]triazolo[1,5-a]pyrazin-6-yl)-2-fluorobenzonitrile

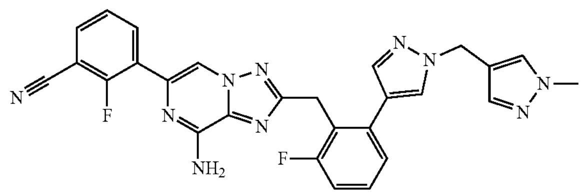 [SMILES: Cn1cc(Cn2cc(-c3cccc(F)c3Cc3nc4c(N)nc(-c5cccc(C#N)c5F)cn4n3)cn2)cn1]

Step 1: 6-bromo-$N^2$,$N^2$-bis(4-methoxybenzyl)pyrazine-2,3-diamine

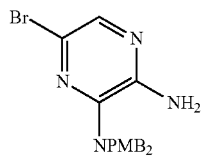

To a stirred suspension of 3,5-dibromopyrazin-2-amine (6 g, 23.25 mmol) and bis(4-methoxybenzyl)amine (6.72 g, 25.6 mmol) in n-butanol (23.25 ml) at room temperature was added N,N-diisopropylethylamine (8.18 ml, 46.5 mmol). The reaction mixture was heated at 120° C. for 72 hours. The reaction mixture was cooled to room temperature. The resulting slurry was stirred at room temperature for 1 hour. The suspension was filtered to remove the excess 3,5-dibromopyrazin-2-amine. The filtrate was concentrated in vacuo. The residue was purified by Biotage Isolera (with 330 g silica gel column) eluting with 0-50% EtOAc/Hexane to give the product as a brown very viscous oil (6.282 g, 77% yield). LC-MS calculated for $C_{20}H_{22}BrN_4O_2$ $(M+H)^+$: m/z=429.1; found 429.4.

Step 2: 1,2-diamino-3-(bis(4-methoxybenzyl)amino)-5-bromopyrazin-1-ium 2,4,6-trimethylbenzenesulfonate

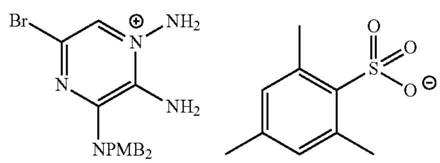

To a solution of O-(mesitylsulfonyl)hydroxylamine (8.88 g, 41.3 mmol) (from Example 14 step 2) in dichloromethane (300 ml) was added 6-bromo-$N^2$,$N^2$-bis(4-methoxybenzyl)pyrazine-2,3-diamine (16.1 g, 37.5 mmol). The resulting solution was stirred at room temperature overnight. The mixture was concentrated and purified with a silica gel column (eluting with a gradient of 0-100% ethyl acetate in hexanes then 0-20% methanol in DCM) to give the desired product (16 g, 66%). LC-MS calculated for $C_{20}H_{23}BrN_5O_2$ $(M-C_9H_{11}O_3S)^+$: m/z=444.1; found 444.1.

Step 3: 6-bromo-2-(2-chloro-6-fluorobenzyl)-N,N-bis(4-methoxybenzyl)-[1,2,4]triazolo[1,5-a]pyrazin-8-amine

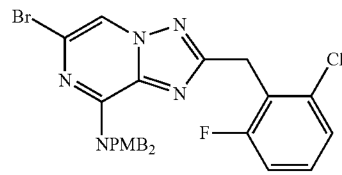

To a solution of 1,2-diamino-3-(bis(4-methoxybenzyl)amino)-5-bromopyrazin-1-ium 2,4,6-trimethylbenzenesulfonate (2.5 g, 3.88 mmol), N,N-diisopropylethylamine (7.52 g, 58.2 mmol), and 2-(2-chloro-6-fluorophenyl)acetic acid (2.93 g, 15.5 mmol) in DMF (20 ml) was added (3-dimethylaminopropyl)-N'-ethylcarbodiimide hydrochloride (0.36 g, 1.86 mmol). The reaction mixture was stirred at room temperature for 1 hour. The solvent was removed under reduced pressure and the crude residue was diluted with water and dichloromethane. The layers were separated and the aqueous layer extracted with dichloromethane. The combined organic fractions were filtered over a plug of magnesium sulfate and concentrated. Purification by automatic flash column chromatography afforded the desired product (1.34 g, 58%). LC-MS calculated for $C_{28}H_{25}BrClFN_5O_2$ $(M+H)^+$: m/z=596.1; found 596.1.

Step 4: 3-(8-(bis(4-methoxybenzyl)amino)-2-(2-chloro-6-fluorobenzyl)-[1,2,4]triazolo[1,5-a]pyrazin-6-yl)-2-fluorobenzonitrile

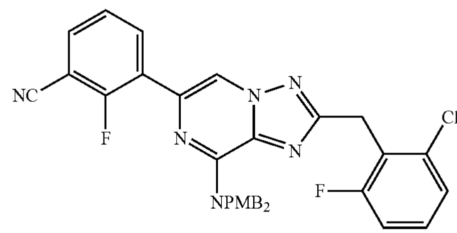

To a solution of 6-bromo-2-(2-chloro-6-fluorobenzyl)-N,N-bis(4-methoxybenzyl)-[1,2,4]triazolo[1,5-a]pyrazin-8-amine (1.34 g, 2.25 mmol), 2-fluoro-3-(4,4,5,5-tetramethyl-1,3,2-dioxaborolan-2-yl)benzonitrile (0.72 g, 2.92 mmol), potassium phosphate tribasic (1.43 g, 6.73 mmol) in dioxane (10 ml) and water (2 ml) was added tetrakis(triphenylphosphine)palladium(0) (0.39 g, 0.38 mmol). The reaction mixture was sparged with nitrogen gas for five minutes, sealed and heated to 90° C. for 1 hour. The reaction mixture was cooled to room temperature, the solvent was removed under reduced pressure, and the crude residue was diluted with water and dichloromethane. The layers were separated and the aqueous layer extracted with dichloromethane. The combined organic fractions were filtered over a plug of magnesium sulfate and concentrated. Purification by automatic flash column chromatography afforded the desired product (0.886 g, 62%). LC-MS calculated for $C_{35}H_{28}ClF_2N_6O_2$ (M+H)$^+$: m/z=637.2; found 637.2.

Step 5: 1-methyl-4-((4-(4,4,5,5-tetramethyl-1,3,2-dioxaborolan-2-yl)-1H-pyrazol-1-yl)methyl)-1H-pyrazole

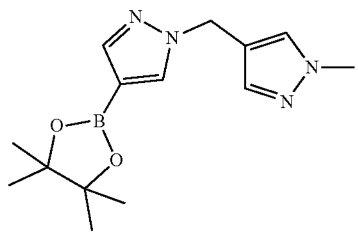

A vial was charged with 4-(4,4,5,5-tetramethyl-1,3,2-dioxaborolan-2-yl)-1H-pyrazole (0.5 g, 2.58 mmol), 4-(bromomethyl)-1-methyl-1H-pyrazole hydrobromide (0.660 g, 2.58 mmol), cesium carbonate (2.52 g, 7.73 mmol), and DMF (6.44 ml). The reaction mixture was stirred at 60° C. for one hour. The solvent was stripped and the crude residue was diluted with water and dichloromethane. The layers were separated and the aqueous layer extracted with dichloromethane. The combined organic fractions were filtered over a plug of magnesium sulfate and concentrated. The crude material was used in the next step without further purification (0.74 g, 99%). LC-MS calculated for $C_{14}H_{22}BN_4O_2$ (M+H)$^+$: m/z=289.2; found 289.1.

Step 6: 3-(8-amino-2-(2-fluoro-6-(1-((1-methyl-1H-pyrazol-4-yl)methyl)-1H-pyrazol-4-yl)benzyl)-[1,2,4]triazolo[1,5-a]pyrazin-6-yl)-2-fluorobenzonitrile To a solution of 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.010 g, 0.016 mmol), 1-methyl-4-((4-(4,4,5,5-tetramethyl-1,3,2-dioxaborolan-2-yl)-1H-pyrazol-1-yl)methyl)-1H-pyrazole (0.009 g, 0.031 mmol), and dicyclohexyl(2',4',6'-triisopropylbiphenyl-2-yl)phosphine-(2'-aminobiphenyl-2-yl)(chloro)palladium (1:1) (0.002 g, 0.003 mmol) in dioxane (0.3 mL) and water (0.06 mL) was added potassium phosphate tribasic (0.010 g, 0.047 mmol). The reaction mixture was stirred at 90° C. for 1 h. The reaction mixture was then diluted with water and dichloromethane. The layers were separated and the aqueous layer extracted with dichloromethane. The combined organic fractions were concentrated under vacuum. The resulting material was dissolved in TFA (1 mL), and stirred at 80° C. for 20 min. The reaction mixture was then cooled to room temperature, diluted with DMF (4 ml) and purified using preparative LC/MS (pH=2, acetonitrile/water with TFA) to give the desired product as a TFA salt. LC-MS calculated for $C_{27}H_{21}F_2N_{10}$ (M+H)$^+$: m/z=523.2; found 523.2.

Example 100. 3-(8-amino-2-((2-((dimethylamino)methyl)-6-fluorophenyl)(hydroxy)methyl)-5-(pyrimidin-4-yl)-[1,2,4]triazolo[1,5-a]pyrazin-6-yl)benzonitrile, Peak 1

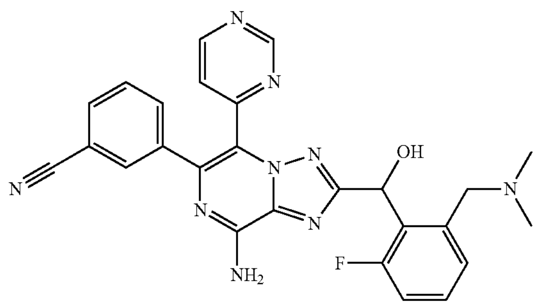 [SMILES: CN(C)Cc1cccc(F)c1C(O)c1nc2c(N)nc(-c3cccc(C#N)c3)c(-c3ccncn3)n2n1]

Step 1: 1-(bromomethyl)-3-fluoro-2-iodobenzene

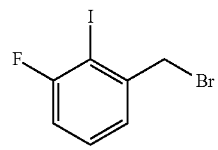

A round bottom flask was charged with (3-fluoro-2-iodophenyl)methanol (0.445 g, 1.766 mmol), carbon tetrabromide (0.703 g, 2.119 mmol), triphenylphosphine (0.556 g, 2.119 mmol), N,N-diisopropylethylamine (0.617 ml, 3.53 mmol), and dichloromethane (17.66 ml). The reaction mixture was stirred overnight at room temperature. The solvent was stripped and the crude residue was purified by automatic flash column chromatography to afford the desired product (0.554 g, 99%).

Step 2: 1-(3-fluoro-2-iodophenyl)-N,N-dimethylmethanamine

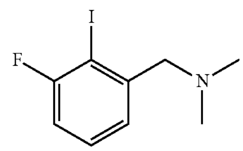

A round bottom flask was charged with 1-(bromomethyl)-3-fluoro-2-iodobenzene (0.554 g, 1.77 mmol), dichloromethane (17 ml), and dimethylamine solution (4.41 ml, 2M in ethanol). The reaction mixture was stirred at room temperature for 1 hour. The solvent was stripped and the crude residue was purified by automatic flash column chromatography to afford the desired product (0.176 g, 36%). LC-MS calculated for $C_9H_{12}FIN$ (M+H)$^+$: m/z=280.0; found 280.1.

Step 3: 3-(8-amino-2-((2-((dimethylamino)methyl)-6-fluorophenyl)(hydroxy)methyl)-5-(pyrimidin-4-yl)-[1,2,4]triazolo[1,5-a]pyrazin-6-yl)benzonitrile, Peak 1

To a solution of 1-(3-fluoro-2-iodophenyl)-N,N-dimethylmethanamine (0.179 g, 0.642 mmol) in tetrahydrofuran (1.5 mL), isopropylmagnesium chloride lithium chloride (0.726 ml, 1.3 M solution) was added at −10° C., and the resulting mixture was stirred for 1 h before a solution of 3-(8-(bis(4-methoxybenzyl)amino)-2-formyl-5-(pyrimidin-4-yl)-[1,2,4]triazolo[1,5-a]pyrazin-6-yl)benzonitrile (0.220 mg, 0.378 mmol) (from Example 49 step 8) in THE (1.5 mL) was added at −10° C. The reaction mixture was stirred for 60 min, then quenched with ammonium chloride solution (3 mL), and extracted with dichloromethane. The combined organic layers were concentrated under vacuum. The resulting material was dissolved in TFA (3 mL), and stirred at 80° C. for 20 min. The reaction mixture was then cooled to room temperature, concentrated, and basified by adding aqueous $NaHCO_3$ solution. The crude material was directly purified by a silica gel column to afford the desired product (87 mg, 47%) as a racemic mixture. The product was then separated with chiral HPLC using a chiral column (Phenomenex Lux Sum Cellulose-1, 21.1×250 mm) and 30% EtOH in Hexanes (20 mL/min) solvent system. Peak 1 was isolated, and further purified using preparative LC/MS (pH=2, acetonitrile/water with TFA) to give the desired product as a TFA salt. LC-MS calculated for $C_{26}H_{23}FN_9O$ $(M+H)^+$: m/z=496.2; found 496.2.

Example 101. 3-(8-amino-2-((2-((dimethylamino)methyl)-6-fluorophenyl)(hydroxy)methyl)-5-(pyrimidin-4-yl)-[1,2,4]triazolo[1,5-a]pyrazin-6-yl)benzonitrile, Peak 2

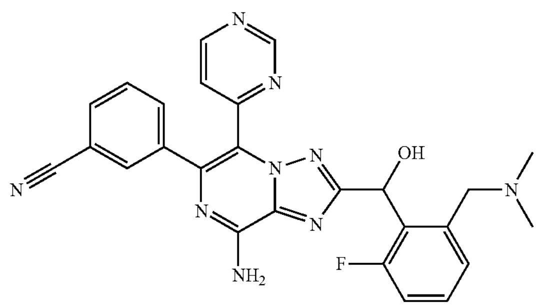 [SMILES: CN(C)Cc1cccc(F)c1C(O)c1nc2c(N)nc(-c3cccc(C#N)c3)c(-c3ccncn3)n2n1]

This compound was prepared using the same procedure as described for Example 100. The product was then separated with chiral HPLC using a chiral column (Phenomenex Lux 5 um Cellulose-1, 21.1×250 mm) and 30% EtOH in Hexanes (20 mL/min) solvent system. Peak 2 was isolated, and further purified using preparative LC/MS (pH=2, acetonitrile/water with TFA) to give the desired product as a TFA salt. LC-MS calculated for $C_{26}H_{23}FN_9O$ $(M+H)^+$: m/z=496.2; found 496.2.

Example 102. 3-(8-amino-2-((2,6-difluorophenyl)(hydroxy)methyl)-5-(3-methyl-1H-pyrazol-4-yl)-[1,2,4]triazolo[1,5-a]pyrazin-6-yl)benzonitrile, Peak 1

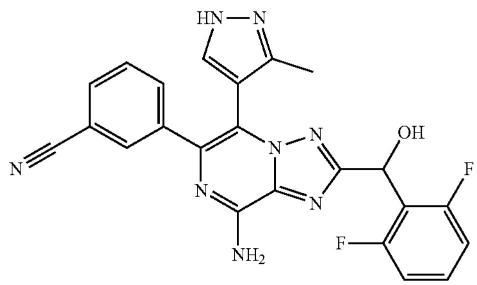 [SMILES: Cc1n[nH]cc1-c1c(-c2cccc(C#N)c2)nc(N)c2nc(C(O)c3c(F)cccc3F)nn12]

To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (0.43 g, 0.062 mmol) (from example 92, step 2), tert-butyl 3-methyl-4-(4,4,5,5-tetramethyl-1,3,2-dioxaborolan-2-yl)-1H-pyrazole-1-carboxylate (0.076 g, 0.246 mmol), and dicyclohexyl(2',4',6'-triisopropylbiphenyl-2-yl)phosphine-(2'-aminobiphenyl-2-yl)(chloro)palladium (1:1) (0.010 g, 0.012 mmol) in dioxane (0.5 mL) and water (0.1 mL) was added potassium phosphate tribasic (0.065 g, 0.308 mmol). The reaction mixture was stirred at 100° C. for 1 hour. The reaction mixture was then diluted with water and DCM. The layers were separated, the aqueous layer was extracted with DCM, and the combined organic fractions were dried over $MgSO_4$, filtered and concentrated. The crude material was dissolved in TFA (2 mL) and heated to 80° C. for 20 minutes. The reaction mixture was then cooled to room temperature, concentrated, and basified by adding aqueous $NaHCO_3$ solution. The crude material was directly purified by a silica gel column to afford the desired product (8 mg, 29%) as a racemic mixture. The product was then separated with chiral HPLC using a chiral column (Phenomenex Lux 5 um Cellulose-4, 21.1×250 mm) and 40% EtOH in Hexanes (20 mL/min) solvent system. Peak 1 was isolated, and further purified using preparative LC/MS (pH=2, acetonitrile/water with TFA) to give the desired product as a TFA salt. LC-MS calculated for $C_{23}H_{17}F_2N_8O$ $(M+H)^+$: m/z=459.1; found 459.2.

Example 103. 3-(8-amino-2-((2,6-difluorophenyl)(hydroxy)methyl)-5-(3-methyl-1H-pyrazol-4-yl)-[1,2,4]triazolo[1,5-a]pyrazin-6-yl)benzonitrile, Peak 2

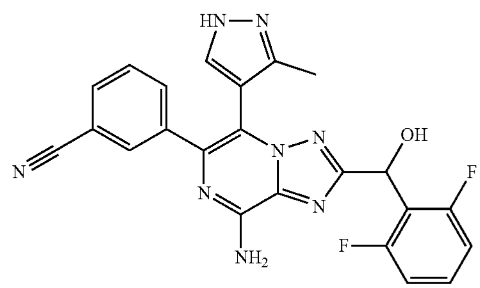 [SMILES: Cc1n[nH]cc1-c1c(-c2cccc(C#N)c2)nc(N)c2nc(C(O)c3c(F)cccc3F)nn12]

This compound was prepared using the same procedure as described for Example 102. The product was separated with chiral HPLC using a chiral column (Phenomenex Lux Sum Cellulose-4, 21.1×250 mm) and 40% EtOH in Hexanes (20 mL/min) solvent system. Peak 2 was isolated, and further purified using preparative LC/MS (pH=2, acetonitrile/water with TFA) to give the desired product as a TFA salt. LC-MS calculated for $C_{23}H_{17}F_2N_8O$ $(M+H)^+$: m/z=459.1; found 459.2.

Example 104. 3-(5-([1,2,4]triazolo[4,3-a]pyridin-6-yl)-8-amino-2-((2,6-difluorophenyl)(hydroxy)methyl)-[1,2,4]triazolo[1,5-a]pyrazin-6-yl)benzonitrile

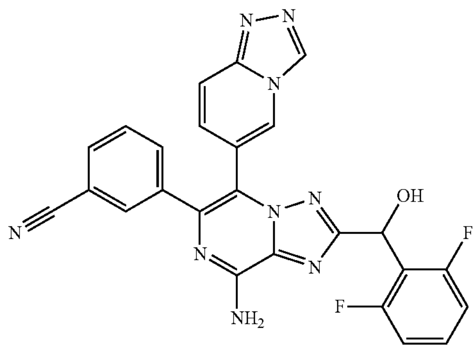 [SMILES: N#Cc1cccc(-c2nc(N)c3nc(C(O)c4c(F)cccc4F)nn3c2-c2ccc3nncn3c2)c1]

To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (0.015 g, 0.022 mmol) (from example 92, step 2), 6-(4,4,5,5-tetramethyl-1,3,2-dioxaborolan-2-yl)-[1,2,4]triazolo[4,3-a]pyridine (0.021 g, 0.086 mmol), and dicyclohexyl(2',4',6'-triisopropylbiphenyl-2-yl)phosphine-(2'-aminobiphenyl-2-yl)(chloro)palladium (1:1) (0.005 g, 0.006 mmol) in dioxane (0.3 mL) and water (0.06 mL) was added potassium phosphate tribasic (0.023 g, 0.108 mmol). The reaction mixture was stirred at 100° C. for 1 hour. The reaction mixture was then diluted with water and DCM. The layers were separated, the aqueous layer was extracted with DCM, and the combined organic fractions were dried over $MgSO_4$, filtered and concentrated. The crude material was dissolved in TFA (1 mL) and heated to 80° C. for 20 minutes. The reaction mixture was then cooled to room temperature, diluted with DMF (4 ml), and purified using preparative LC/MS (pH=2, acetonitrile/water with TFA) to give the desired racemic product as a TFA salt. LC-MS calculated for $C_{25}H_{16}F_2N_9O$ $(M+H)^+$: m/z=496.1; found 496.1.

Example 105. 3-(8-amino-2-((2,6-difluorophenyl)(hydroxy)methyl)-5-(oxazol-5-yl)-[1,2,4]triazolo[1,5-a]pyrazin-6-yl)benzonitrile, Peak 1

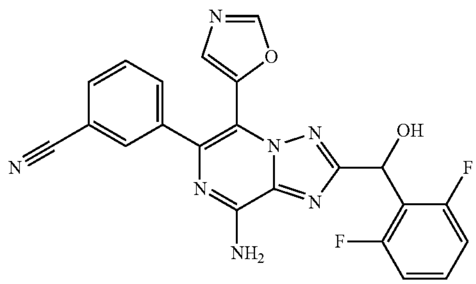 [SMILES: N#Cc1cccc(-c2nc(N)c3nc(C(O)c4c(F)cccc4F)nn3c2-c2cnco2)c1]

To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (0.43 g, 0.062 mmol) (from example 92, step 2), 5-(4,4,5,5-tetramethyl-1,3,2-dioxaborolan-2-yl)oxazole (0.048 g, 0.246 mmol), and dicyclohexyl(2',4',6'-triisopropylbiphenyl-2-yl)phosphine-(2'-aminobiphenyl-2-yl)(chloro)palladium (1:1) (0.010 g, 0.012 mmol) in dioxane (0.5 mL) and water (0.1 mL) was added potassium phosphate tribasic (0.065 g, 0.308 mmol). The reaction mixture was stirred at 100° C. for 1 hour. The reaction mixture was then diluted with water and DCM. The layers were separated, the aqueous layer was extracted with DCM, and the combined organic fractions were dried over $MgSO_4$, filtered and concentrated. The crude material was dissolved in TFA (2 mL) and heated to 80° C. for 20 minutes. The reaction mixture was then cooled to room temperature, concentrated, and basified by adding aqueous $NaHCO_3$ solution. The crude material was directly purified by a silica gel column to afford the desired product (6 mg, 22%) as a racemic mixture. The product was then separated with chiral SFC using a chiral column (ES Industries CC4 5um 20×250 mm) and 35% MeOH in $CO_2$ (65 mL/min) solvent system. Peak 1 was isolated, and further purified using preparative LC/MS (pH=2, acetonitrile/water with TFA) to give the desired product as a TFA salt. LC-MS calculated for $C_{22}H_{14}F_2N_7O_2$ $(M+H)^+$: m/z=446.1; found 446.1.

Example 106. 3-(8-amino-2-((2,6-difluorophenyl)(hydroxy)methyl)-5-(oxazol-5-yl)-[1,2,4]triazolo[1,5-a]pyrazin-6-yl)benzonitrile, Peak 2

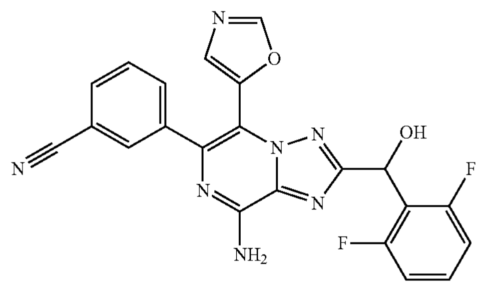 [SMILES: N#Cc1cccc(-c2nc(N)c3nc(C(O)c4c(F)cccc4F)nn3c2-c2cnco2)c1]

This compound was prepared using the same procedure as described for Example 105. The product was then separated with chiral SFC using a chiral column (ES Industries CC4 5 μm 20×250 mm) and 35% MeOH in $CO_2$ (65 mL/min) solvent system. Peak 2 was isolated, and further purified using preparative LC/MS (pH=2, acetonitrile/water with TFA) to give the desired product as a TFA salt. LC-MS calculated for $C_{22}H_{14}F_2N_7O_2$ $(M+H)^+$: m/z=446.1; found 446.1.

Example 107. 3-(8-amino-2-(2-fluoro-6-(1-(pyridin-2-ylmethyl)-1H-pyrazol-4-yl)benzyl)-[1,2,4]triazolo[1,5-a]pyrazin-6-yl)-2-fluorobenzonitrile

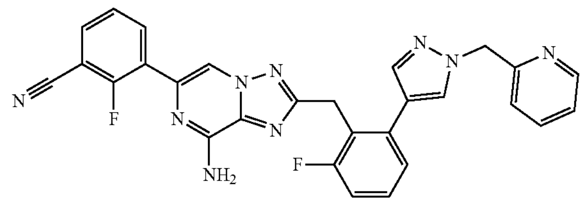 [SMILES: N#Cc1cccc(-c2cn3nc(Cc4c(F)cccc4-c4cnn(Cc5ccccn5)c4)nc3c(N)n2)c1F]

To a solution of 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.01 g, 0.016 mmol) (from Example 99, step 4), 2-((4-(4,4,5,5-tetramethyl-1,3,2-dioxaborolan-2-yl)-1H-pyrazol-1-yl)methyl)pyridine (0.009 g, 0.031 mmol), and dicyclohexyl(2',4',6'-triisopropylbiphenyl-2-yl) phosphine-(2'-aminobiphenyl-2-yl)(chloro)palladium (1:1) (0.002 g, 0.003 mmol) in dioxane (0.3 mL) and water (0.06 mL) was added potassium phosphate tribasic (0.010 g, 0.047 mmol). The reaction mixture was stirred at 90° C. for 1 hour. The reaction mixture was then diluted with water and dichloromethane. The layers were separated and the aqueous layer extracted with dichloromethane. The combined organic fractions were concentrated under vacuum. The resulting material was dissolved in TFA (1 mL), and stirred at 80° C. for 20 min. The reaction mixture was then cooled to room temperature, diluted with DMF (4 ml) and purified using preparative LC/MS (pH=2, acetonitrile/water with TFA) to give the desired product as a TFA salt. LC-MS calculated for $C_{28}H_{20}F_2N_9$ $(M+H)^+$: m/z=520.2; found 520.1.

Example 108. 3-(8-amino-2-((2,6-difluorophenyl)(hydroxy)methyl)-5-(3-methylpyridin-4-yl)-[1,2,4]triazolo[1,5-a]pyrazin-6-yl)benzonitrile, Peak 1

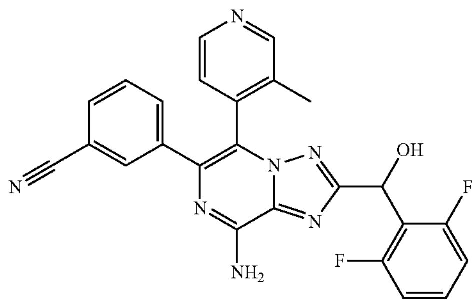 [SMILES: Cc1cnccc1-c1c(-c2cccc(C#N)c2)nc(N)c2nc(C(O)c3c(F)cccc3F)nn12]

To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (0.43 g, 0.062 mmol) (from example 92, step 2), 3-methyl-4-(4,4,5,5-tetramethyl-1,3,2-dioxaborolan-2-yl)pyridine (0.054 g, 0.246 mmol), and dicyclohexyl(2',4',6'-triisopropylbiphenyl-2-yl)phosphine-(2'-aminobiphenyl-2-yl)(chloro)palladium (1:1) (0.010 g, 0.012 mmol) in dioxane (0.5 mL) and water (0.1 mL) was added potassium phosphate tribasic (0.065 g, 0.308 mmol). The reaction mixture was stirred at 100° C. for 1 hour. The reaction mixture was then diluted with water and DCM. The layers were separated, the aqueous layer was extracted with DCM, and the combined organic fractions were dried over $MgSO_4$, filtered and concentrated. The crude material was dissolved in TFA (2 mL) and heated to 80° C. for 20 minutes. The reaction mixture was then cooled to room temperature, concentrated, and basified by adding aqueous $NaHCO_3$ solution. The crude material was directly purified by a silica gel column to afford the desired product (8 mg, 28%) as a racemic mixture. The product was then separated with chiral SFC using a chiral column (ES Industries CC4 Sum 20×250 mm) and 35% MeOH in $CO_2$ (65 mL/min) solvent system. Peak 1 was isolated, and further purified using preparative LC/MS (pH=2, acetonitrile/water with TFA) to give the desired product as a TFA salt. LC-MS calculated for $C_{25}H_{18}F_2N_7O$ $(M+H)^+$: m/z=470.2; found 470.2.

Example 109. 3-(8-amino-2-((2,6-difluorophenyl)(hydroxy)methyl)-5-(3-methylpyridin-4-yl)-[1,2,4]triazolo[1,5-a]pyrazin-6-yl)benzonitrile, Peak 2

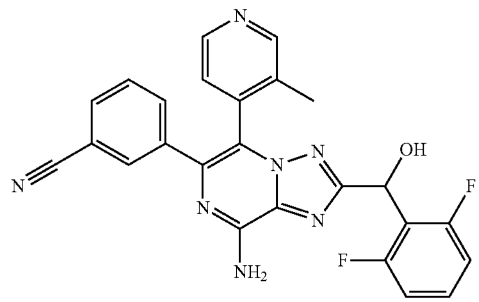 [SMILES: Cc1cnccc1-c1c(-c2cccc(C#N)c2)nc(N)c2nc(C(O)c3c(F)cccc3F)nn12]

This compound was prepared using the same procedure as described for Example 108. The product was then separated with chiral SFC using a chiral column (ES Industries CC4 5 μm 20×250 mm) and 35% MeOH in $CO_2$ (65 mL/min) solvent system. Peak 2 was isolated, and further purified using preparative LC/MS (pH=2, acetonitrile/water with TFA) to give the desired product as a TFA salt. LC-MS calculated for $C_{25}H_{18}F_2N_7O$ $(M+H)^+$: m/z=470.2; found 470.2.

Example 110. 3-(8-amino-2-((2-fluoro-6-(pyrrolidin-1-ylmethyl)phenyl)(hydroxy)methyl)-5-(pyrimidin-4-yl)-[1,2,4]triazolo[1,5-a]pyrazin-6-yl)benzonitrile, Peak 1

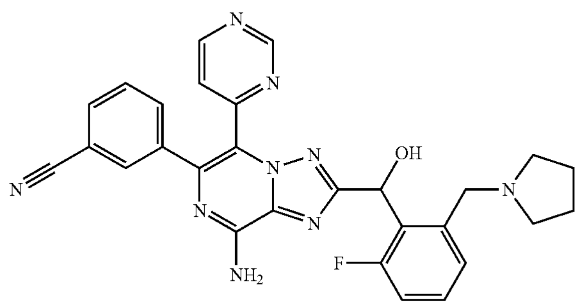 [SMILES: N#Cc1cccc(-c2nc(N)c3nc(C(O)c4c(F)cccc4CN4CCCC4)nn3c2-c2ccncn2)c1]

Step 1: 3-(8-(bis(4-methoxybenzyl)amino)-2-((2-chloro-6-fluorophenyl)(hydroxy)methyl)-5-(pyrimidin-4-yl)-[1,2,4]triazolo[1,5-a]pyrazin-6-yl)benzonitrile

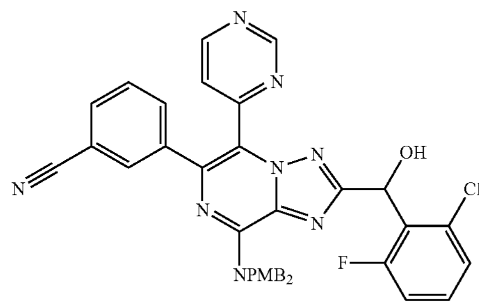

To a solution of 1-chloro-3-fluoro-2-iodobenzene (0.335 g, 1.30 mmol) in tetrahydrofuran (1.5 mL), isopropylmagnesium chloride lithium chloride (0.878 ml, 1.3 M solution) was added at −10° C., and the resulting mixture was stirred for 1 hour before a solution of 3-(8-(bis(4-methoxybenzyl) amino)-2-formyl-5-(pyrimidin-4-yl)-[1,2,4]triazolo[1,5-a] pyrazin-6-yl)benzonitrile (0.190 g, 0.326 mmol) (from Example 49 step 8) in THE (1.5 mL) was added at −10° C. The reaction mixture was stirred for 60 minutes, then quenched with ammonium chloride solution (3 mL), and extracted with dichloromethane. The combined organic layers were concentrated under vacuum. The crude material was directly purified by a silica gel column to afford the desired product (147 mg, 63%) as a racemic mixture. LC-MS calculated for $C_{39}H_{31}ClFN_8O_3$ $(M+H)^+$: m/z=713.2; found 713.3.

Step 2: 3-(8-(bis(4-methoxybenzyl)amino)-2-((2-fluoro-6-vinylphenyl)(hydroxy)methyl)-5-(pyrimidin-4-yl)-[1,2,4]triazolo[1,5-a]pyrazin-6-yl)benzonitrile

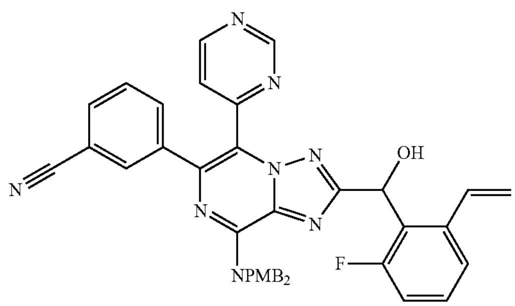

To a solution of 3-(8-(bis(4-methoxybenzyl)amino)-2-((2-chloro-6-fluorophenyl)(hydroxy)methyl)-5-(pyrimidin-4-yl)-[1,2,4]triazolo[1,5-a]pyrazin-6-yl)benzonitrile (0.212 g, 0.297 mmol), 4,4,5,5-tetramethyl-2-vinyl-1,3,2-dioxaborolane (0.055 g, 0.357 mmol), and dicyclohexyl(2',4',6'-triisopropylbiphenyl-2-yl)phosphine-(2'-aminobiphenyl-2-yl) (chloro)palladium (1:1) (0.023 g, 0.030 mmol) in dioxane (2.5 mL) and water (0.5 mL) was added potassium phosphate tribasic (0.126 g, 0.595 mmol). The reaction mixture was stirred at 100° C. for 1 h. The reaction mixture was then diluted with water and DCM. The layers were separated, the aqueous layer was extracted with DCM, and the combined organic fractions were dried over $MgSO_4$, filtered and concentrated. The crude material was directly purified by a silica gel column to afford the desired product (0.195 mg, 93%). LC-MS calculated for $C_{41}H_{34}FN_8O_3$ $(M+H)^+$: m/z=705.3; found 705.4.

Step 3: 3-(8-(bis(4-methoxybenzyl)amino)-2-((2-fluoro-6-formylphenyl)(hydroxy)methyl)-5-(pyrimidin-4-yl)-[1,2,4]triazolo[1,5-a]pyrazin-6-yl)benzonitrile

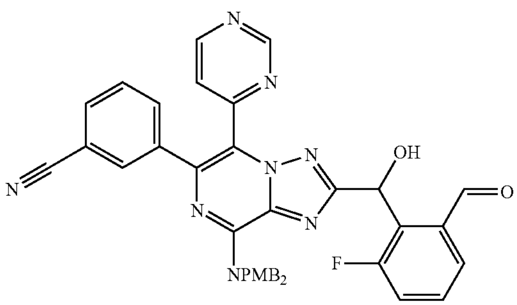

A vial was charged with 3-(8-(bis(4-methoxybenzyl) amino)-2-((2-fluoro-6-vinylphenyl)(hydroxy)methyl)-5-(pyrimidin-4-yl)-[1,2,4]triazolo[1,5-a]pyrazin-6-yl)benzonitrile (0.195 g, 0.277 mmol), THE (2.5 ml), water (2.5 ml), sodium periodate (0.266 g, 1.245 mmol), and osmium tetroxide solution (0.176 ml, 4% in water). The mixture was stirred at room temperature for 30 minutes. The reaction mixture was diluted with water and dichloromethane. The layers were separated and the aqueous layer extracted with dichloromethane. The combined organic fractions were filtered over a plug of magnesium sulfate and purified by automatic flash column chromatography to afford the product (0.135 g, 69%). LC-MS calculated for $C_{40}H_{32}FN_8O_4$ $(M+H)^+$: m/z=707.2; found 707.3.

Step 4: 3-(8-amino-2-((2-fluoro-6-(pyrrolidin-1-ylmethyl)phenyl)(hydroxy)methyl)-5-(pyrimidin-4-yl)-[1,2,4]triazolo[1,5-a]pyrazin-6-yl)benzonitrile, Peak 1

A vial was charged with 3-(8-(bis(4-methoxybenzyl) amino)-2-((2-fluoro-6-formylphenyl)(hydroxy)methyl)-5-(pyrimidin-4-yl)-[1,2,4]triazolo[1,5-a]pyrazin-6-yl)benzonitrile (0.013 g, 0.018 mmol), pyrrolidine (0.013 g, 0.178 mmol), acetic acid (2.041 μl, 0.036 mmol), dichloromethane (0.4 ml), and sodium borohydride (1.3 mg, 0.036 mmol). The reaction mixture was stirred at room temperature for 2 hours. The reaction mixture was quenched with saturated aqueous sodium bicarbonate solution. The solution was diluted with dichloromethane and the layers were separated. The aqueous layer was extracted with dichloromethane and the combined organic fractions were filtered over a plug of magnesium sulfate and concentrated. The crude residue was dissolved into 1 mL TFA and stirred at 80° C. for 20 minutes. The reaction mixture was then cooled to room temperature, concentrated, and basified by adding aqueous $NaHCO_3$ solution. The crude material was directly purified by a silica gel column to afford the desired product (6 mg, 65%) as a racemic mixture. The product was then separated with chiral HPLC using a chiral column (Phenomenex Lux 5 um Cellulose-1, 21.2×250 mm) and 30% EtOH in hexanes (20 mL/min) solvent system. Peak 1 was isolated, and further purified using preparative LC/MS (pH=2, acetonitrile/water with TFA) to give the desired product as a TFA salt. LC-MS calculated for $C_{28}H_{25}FN_9O$ $(M+H)^+$: m/z=522.2; found 522.2.

Example 111. 3-(8-amino-2-((2-fluoro-6-(pyrrolidin-1-ylmethyl)phenyl)(hydroxy)methyl)-5-(pyrimidin-4-yl)-[1,2,4]triazolo[1,5-a]pyrazin-6-yl)benzonitrile, Peak 2

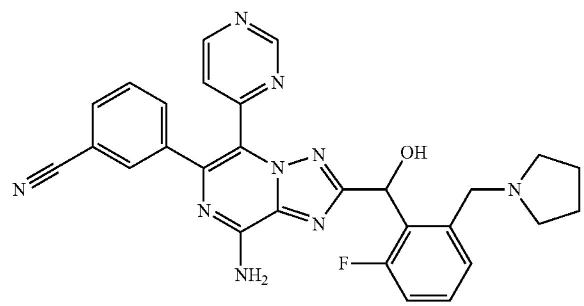 [SMILES: N#Cc1cccc(-c2nc(N)c3nc(C(O)c4c(F)cccc4CN4CCCC4)nn3c2-c2ccncn2)c1]

This compound was prepared using the same procedure as described for Example 110. The product was then separated with chiral HPLC using a chiral column (Phenomenex Lux Sum Cellulose-1, 21.2×250 mm) and 30% EtOH in hexanes (20 mL/min) solvent system. Peak 2 was isolated, and further purified using preparative LC/MS (pH=2, acetonitrile/water with TFA) to give the desired product as a TFA salt. LC-MS calculated for $C_{28}H_{25}FN_9O$ $(M+H)^+$: m/z=522.2; found 522.2.

Example 112. 3-(8-amino-2-(2-fluoro-6-(1-(2-(methylsulfonyl)ethyl)-1H-pyrazol-4-yl)benzyl)-[1,2,4]triazolo[1,5-a]pyrazin-6-yl)-2-fluorobenzonitrile

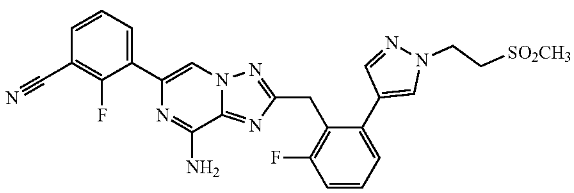 [SMILES: CS(=O)(=O)CCn1cc(-c2cccc(F)c2Cc2nc3c(N)nc(-c4cccc(C#N)c4F)cn3n2)cn1]

To a solution 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.075 g, 0.118 mmol) (from Example 99, step 4), 1-(2-(methylsulfonyl)ethyl)-4-(4,4,5,5-tetramethyl-1,3-dioxolan-2-yl)-1H-pyrazole (0.071 g, 0.235 mmol), and dicyclohexyl(2',4',6'-triisopropylbiphenyl-2-yl)phosphine-(2'-aminobiphenyl-2-yl)(chloro)palladium (1:1) (0.018 g, 0.024 mmol) in dioxane (1.0 mL) and water (0.2 mL) was added potassium phosphate tribasic (0.075 g, 0.353 mmol). The reaction mixture was stirred at 100° C. for 1 h. The reaction mixture was then diluted with water and dichloromethane. The layers were separated and the aqueous layer extracted with dichloromethane. The combined organic fractions were concentrated under vacuum. The resulting material was dissolved in TFA (2 mL), and stirred at 80° C. for 20 minutes. The reaction mixture was then cooled to room temperature, diluted with DMF (3 ml) and purified using preparative LC/MS (pH=2, acetonitrile/water with TFA) to give the desired product as a TFA salt. LC-MS calculated for $C_{25}H_{21}F_2N_8O_2S$ $(M+H)^+$: m/z=535.1; found 535.1.

Example 113. 3-(8-amino-2-((2-fluoro-6-((6-oxohexahydropyrrolo[1,2-a]pyrazin-2(1H)-yl)methyl)phenyl)(hydroxy)methyl)-[1,2,4]triazolo[1,5-a]pyrazin-6-yl)-2-fluorobenzonitrile

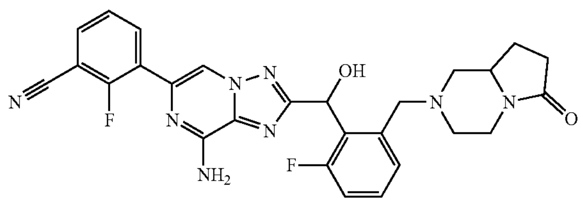 [SMILES: N#Cc1cccc(-c2cn3nc(C(O)c4c(F)cccc4CN4CCN5C(=O)CCC5C4)nc3c(N)n2)c1F]

Step 1: 6-bromo-N,N-bis(4-methoxybenzyl)-2-vinyl-[1,2,4]triazolo[1,5-a]pyrazin-8-amine

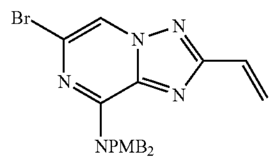

To a solution of 1,2-diamino-3-(bis(4-methoxybenzyl)amino)-5-bromopyrazin-1-ium 2,4,6-trimethylbenzenesulfonate (1.00 g, 1.55 mmol) (from Example 99, step 2) and acryloyl chloride (0.253 ml, 3.10 mmol) in DMF (4 ml) and dichloromethane (4 ml) at 0° C. was added triethylamine (0.540 ml, 3.88 mmol). The reaction mixture was stirred at 0° C. for 2 hours. The solvent was removed under reduced pressure and the crude residue was purified by automatic flash column chromatography to afford the desired product (0.268 g, 36%). LC-MS calculated for $C_{23}H_{23}BrN_5O_2$ $(M+H)^+$: m/z=480.1; found 480.1.

Step 2: 3-(8-(bis(4-methoxybenzyl)amino)-2-vinyl-[1,2,4]triazolo[1,5-a]pyrazin-6-yl)-2-fluorobenzonitrile

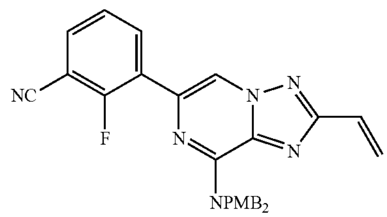

To a solution of 6-bromo-N,N-bis(4-methoxybenzyl)-2-vinyl-[1,2,4]triazolo[1,5-a]pyrazin-8-amine (0.070 g, 0.146 mmol), (3-cyano-2-fluorophenyl)boronic acid (0.048 g, 0.291 mmol), cesium carbonate (0.142 g, 0.437 mmol) in dioxane (1.3 ml) and water (0.15 ml) was added tetrakis(triphenylphosphine)palladium(0) (0.034 g, 0.029 mmol). The reaction mixture was sparged with nitrogen gas for five minutes, sealed and heated to 90° C. for 4 hours. The reaction mixture was cooled to room temperature, the solvent removed under reduced pressure, and the crude residue purified by automatic flash column chromatography to afford the desired product (0.061 g, 80%). LC-MS calculated for $C_{30}H_{26}FN_6O_2$ $(M+H)^+$: m/z=521.2; found 521.1.

Step 3: 3-(8-(bis(4-methoxybenzyl)amino)-2-formyl-[1,2,4]triazolo[1,5-a]pyrazin-6-yl)-2-fluorobenzonitrile

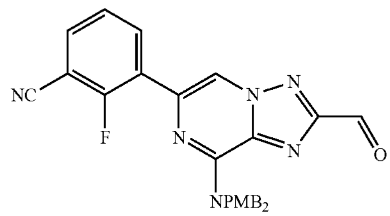

A vial was charged with 3-(8-(bis(4-methoxybenzyl)amino)-2-vinyl-[1,2,4]triazolo[1,5-a]pyrazin-6-yl)-2-fluorobenzonitrile (0.287 g, 0.551 mmol), THE (2.5 ml), water (2.5 ml), sodium periodate (0.531 g, 2.481 mmol), and osmium tetroxide solution (0.433 ml, 4% in water). The mixture was stirred at room temperature overnight. The reaction mixture was adsorbed onto silica gel, and the solvent was removed under reduced pressure. The crude material (adsorbed onto silica gel) was purified by automatic flash column chromatography to afford the product (0.127 g, 44%). LC-MS calculated for $C_{29}H_{24}FN_6O_3$ $(M+H)^+$: m/z=523.2; found 523.1.

Step 4: 3-(8-(bis(4-methoxybenzyl)amino)-2-((2-chloro-6-fluorophenyl)(hydroxy)methyl)-[1,2,4]triazolo[1,5-a]pyrazin-6-yl)-2-fluorobenzonitrile

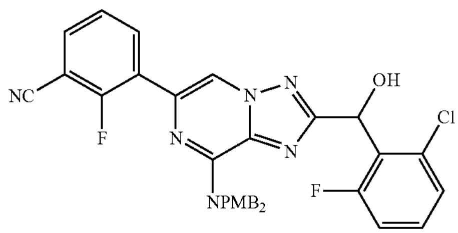

To a solution of 1-chloro-3-fluoro-2-iodobenzene (0.491 g, 1.92 mmol) in tetrahydrofuran (2.5 mL), isopropylmagnesium chloride lithium chloride (1.47 ml, 1.3 M solution) was added at −10° C., and the resulting mixture was stirred for 1 hour before a solution of 3-(8-(bis(4-methoxybenzyl)amino)-2-formyl-[1,2,4]triazolo[1,5-a]pyrazin-6-yl)-2-fluorobenzonitrile (0.143 g, 0.274 mmol) in THE (2.5 mL) was added at −10° C. The reaction mixture was stirred for 60 min, then quenched with ammonium chloride solution (3 mL), and extracted with dichloromethane. The combined organic layers were concentrated under vacuum. The crude material was directly purified by a silica gel column to afford the desired product (116 mg, 65%) as a racemic mixture. LC-MS calculated for $C_{35}H_{28}ClF_2N_6O_3$ $(M+H)^+$: m/z=653.2; found 653.1.

Step 5: 3-(8-(bis(4-methoxybenzyl)amino)-2-((2-fluoro-6-vinylphenyl)(hydroxy)methyl)-[1,2,4]triazolo[1,5-a]pyrazin-6-yl)-2-fluorobenzonitrile

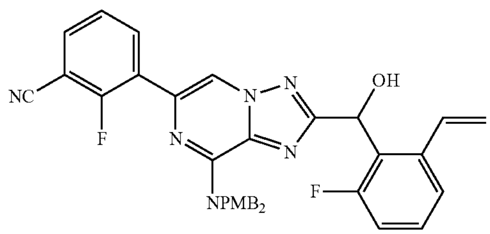

To a solution of 3-(8-(bis(4-methoxybenzyl)amino)-2-((2-chloro-6-fluorophenyl)(hydroxy)methyl)-[1,2,4]triazolo[1,5-a]pyrazin-6-yl)-2-fluorobenzonitrile (0.194 g, 0.297 mmol), 4,4,5,5-tetramethyl-2-vinyl-1,3,2-dioxaborolane (0.093 g, 0.602 mmol), and dicyclohexyl(2',4',6'-triisopropylbiphenyl-2-yl)phosphine-(2'-aminobiphenyl-2-yl)(chloro)palladium (1:1) (0.016 g, 0.021 mmol) in dioxane (1.8 mL) and water (0.2 mL) was added potassium phosphate tribasic (0.170 g, 0.803 mmol). The reaction mixture was stirred at 100° C. for 1 hour. The reaction mixture was then diluted with water and DCM. The layers were separated, the aqueous layer was extracted with DCM, and the combined organic fractions were dried over $MgSO_4$, filtered and concentrated. The crude material was directly purified by a silica gel column to afford the desired product (0.097 mg, 75%). LC-MS calculated for $C_{37}H_{31}F_2N_6O_3$ $(M+H)^+$: m/z=645.2; found 645.3.

Step 6: 3-(8-(bis(4-methoxybenzyl)amino)-2-((tert-butyldimethylsilyloxy)(2-fluoro-6-vinylphenyl)methyl)-[1,2,4]triazolo[1,5-a]pyrazin-6-yl)-2-fluorobenzonitrile

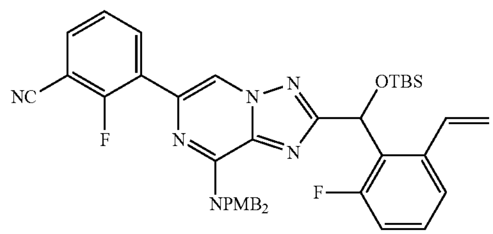

A vial was charged with 3-(8-(bis(4-methoxybenzyl)amino)-2-((2-fluoro-6-vinylphenyl)(hydroxy)methyl)-[1,2,4]triazolo[1,5-a]pyrazin-6-yl)-2-fluorobenzonitrile (0.178 g, 0.276 mmol), DMF (2.76 ml), imidazole (0.150 g, 2.205 mmol), and TBS-Cl (0.166 g, 1.102 mmol). The reaction mixture was stirred at room temperature for 1 hour. The solvent was removed under reduced pressure, and the crude residue was purified by automatic flash column chromatography to afford the desired product (0.166 g, 79%). For the purposes of characterization using LC-MS, the desired product was subjected to deprotection of a single PMB group; an aliquot of pure product was dissolved into 1:1 dichloromethane/trifluoroacetic acid solution (0.1 ml) and allowed to stand at room temperature for 5 minutes, furnishing 3-(2-((tert-butyldimethylsilyloxy)(2-fluoro-6-vinylphenyl)methyl)-8-(4-methoxybenzylamino)-[1,2,4]triazolo[1,5-a]pyrazin-6-yl)-2-fluorobenzonitrile. LC-MS calculated for $C_{35}H_{37}F_2N_6O_2Si$ $(M+H)^+$: m/z=639.3; found 639.3.

Step 7: 3-(8-(bis(4-methoxybenzyl)amino)-2-((tert-butyldimethylsilyloxy)(2-fluoro-6-formylphenyl)methyl)-[1,2,4]triazolo[1,5-a]pyrazin-6-yl)-2-fluorobenzonitrile

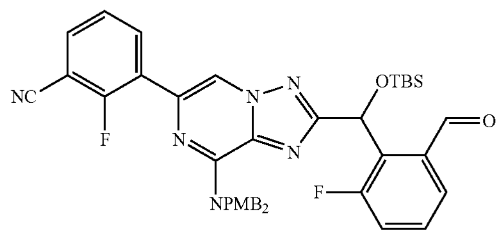

A vial was charged 3-(8-(bis(4-methoxybenzyl)amino)-2-(((tert-butyldimethylsilyl)oxy)(2-fluoro-6-vinylphenyl)

methyl)-[1,2,4]triazolo[1,5-a]pyrazin-6-yl)-2-fluorobenzonitrile (0.109 g, 0.144 mmol), sodium periodate (0.138 g, 0.646 mmol), THE (0.7 ml), water (0.7 ml), and osmium tetroxide solution (0.113 ml, 4% in water). The mixture was stirred at 45° C. overnight. The reaction mixture was adsorbed onto silica gel, and the solvent was removed under reduced pressure. The crude material (adsorbed onto silica gel) was purified by automatic flash column chromatography to afford the product (0.05 g, 46%). LC-MS calculated for $C_{42}H_{43}F_2N_6O_4Si$ $(M+H)^+$: m/z=761.3; found 761.3.

Step 8: 3-(8-amino-2-((2-fluoro-6-((6-oxohexahydropyrrolo[1,2-a]pyrazin-2(1H)-yl)methyl)phenyl)(hydroxy)methyl)-[1,2,4]triazolo[1,5-a]pyrazin-6-yl)-2-fluorobenzonitrile A vial was charged with 3-(8-(bis(4-methoxybenzyl)amino)-2-(((tert-butyldimethylsilyl)oxy)(2-fluoro-6-formylphenyl)methyl)-[1,2,4]triazolo[1,5-a]pyrazin-6-yl)-2-fluorobenzonitrile (0.01 g, 0.013 mmol), hexahydropyrrolo[1,2-a]pyrazin-6(7H)-one (0.018 g, 0.131 mmol), acetic acid (1.505 μl, 0.026 mmol), DCM (0.202 ml), and sodium triacetoxyborohydride (5.57 mg, 0.026 mmol). The reaction mixture was heated to 40° C. and stirred for 2 hours. The reaction mixture was quenched with saturated aqueous sodium bicarbonate solution and diluted with DCM. The layers were separated and the aqueous layer was extracted with DCM. The combined organic fractions were concentrated, and the crude residue was dissolved into 1 mL TFA and 0.1 ml MeOH. The solution was stirred at 80° C. for 20 minutes. The reaction mixture was diluted with DMF (4 mL) and purified by preparative LC/MS (pH=2, acetonitrile/water with TFA) to give the desired racemic product as a TFA salt. LC-MS calculated for $C_{27}H_{25}F_2N_8O_2$ $(M+H)^+$: m/z=531.2; found 531.2.

Example 114. 2-(4-(2-((8-amino-6-(3-cyano-2-fluorophenyl)-[1,2,4]triazolo[1,5-a]pyrazin-2-yl)methyl)-3-fluorophenyl)-1H-pyrazol-1-yl)-N,N-dimethylacetamide

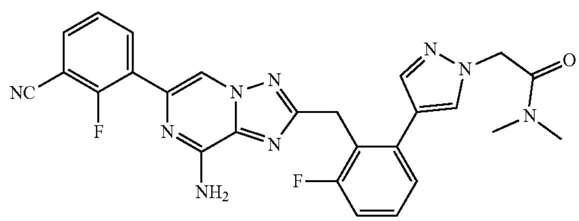 [SMILES: CN(C)C(=O)Cn1cc(-c2cccc(F)c2Cc2nc3c(N)nc(-c4cccc(C#N)c4F)cn3n2)cn1]

Step 1: 2-(4-(2-((8-(bis(4-methoxybenzyl)amino)-6-(3-cyano-2-fluorophenyl)-[1,2,4]triazolo[1,5-a]pyrazin-2-yl)methyl)-3-fluorophenyl)-1H-pyrazol-1-yl)acetic acid

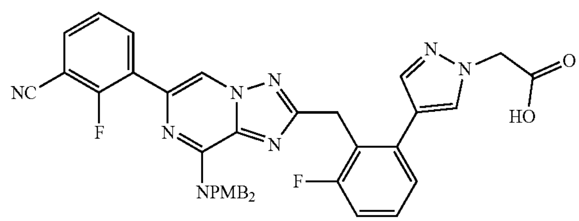

To a solution 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.075 g, 0.118 mmol) (from Example 99, step 4), ethyl 2-(4-(4,4,5,5-tetramethyl-1,3,2-dioxaborolan-2-yl)-1H-pyrazol-1-yl)acetate (0.157 g, 0.559 mmol), and dicyclohexyl(2',4',6'-triisopropylbiphenyl-2-yl)phosphine-(2'-aminobiphenyl-2-yl)(chloro)palladium (1:1) (0.022 g, 0.028 mmol) in dioxane (2.0 mL) and water (0.4 mL) was added potassium phosphate tribasic (0.178 g, 0.838 mmol). The reaction mixture was stirred at 100° C. for 1 b. The reaction mixture was cooled to room temperature, diluted with MeOH (2 ml) and water (2 ml), and into this solution was added lithium hydroxide hydrate (0.176 g, 4.19 mmol). The suspension was stirred at room temperature for 1 hour. The suspension was made neutral by addition of saturated aqueous ammonium chloride solution, and diluted with DCM. The layers were separated and the aqueous layer was extracted with DCM. The combined organic fractions were dried over a plug of magnesium sulfate and concentrated. Purification by automatic flash column chromatography afforded the desired product (0.050 g, 25%). LC-MS calculated for $C_{40}H_{33}F_2N_8O_4$ $(M+H)^+$: m/z=727.3; found 727.2.

Step 2: 2-(4-(2-((8-amino-6-(3-cyano-2-fluorophenyl)-[1,2,4]triazolo[1,5-a]pyrazin-2-yl)methyl)-3-fluorophenyl)-1H-pyrazol-1-yl)-N,N-dimethylacetamide A vial was charged with 2-(4-(2-((8-(bis(4-methoxybenzyl)amino)-6-(3-cyano-2-fluorophenyl)-[1,2,4]triazolo[1,5-a]pyrazin-2-yl)methyl)-3-fluorophenyl)-1H-pyrazol-1-yl)acetic acid (0.01 g, 0.014 mmol), DMF (0.46 ml), dimethylamine solution (0.069 ml, 2M in THF), N,N-diisopropylethylamine (8.89 mg, 0.069 mmol), and 2-(3H-[1,2,3]triazolo[4,5-b]pyridin-3-yl)-1,1,3,3-tetramethylisouronium hexafluorophosphate(V) (10.46 mg, 0.028 mmol). The reaction mixture was stirred at room temperature for 1 hour. The reaction mixture was diluted with dichloromethane and water. The layers were separated and the aqueous layer was extracted with DCM. The combined organic fractions were dried over a plug of magnesium sulfate and concentrated. The combined organic fractions were concentrated, and the crude residue was dissolved into 1 mL TFA. The solution was stirred at 80° C. for 20 minutes. The reaction mixture was diluted with DMF (4 mL) and purified by preparative LC/MS (pH=2, acetonitrile/water with TFA) to give the desired product as a TFA salt. LC-MS calculated for $C_{26}H_{22}F_2N_9O$ $(M+H)^+$: m/z=514.2; found 514.2.

Example 115. 2-(4-(2-((8-amino-6-(3-cyano-2-fluorophenyl)-[1,2,4]triazolo[1,5-a]pyrazin-2-yl)methyl)-3-fluorophenyl)-1H-pyrazol-1-yl)acetamide

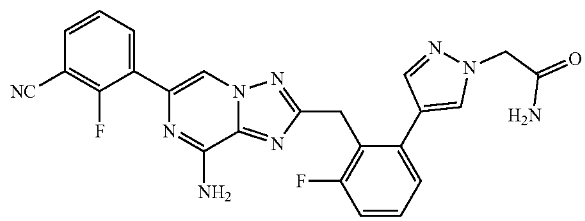 [SMILES: N#Cc1cccc(-c2cn3nc(Cc4c(F)cccc4-c4cnn(CC(N)=O)c4)nc3c(N)n2)c1F]

To a solution 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.075 g, 0.118 mmol) (from Example 99, step 4), 2-(4-(4,4,5,5-tetramethyl-1,3-dioxolan-2-yl)-1H-pyrazol-1-yl)acetamide (0.060 g, 0.235 mmol), and dicyclohexyl(2',4',6'-triisopropylbiphenyl-2-yl)phosphine-(2'-aminobiphenyl-2-yl)(chloro)palladium (1:1) (0.018 g, 0.024 mmol) in dioxane (1.0 mL) and water (0.2 mL) was added potassium phosphate tribasic (0.075 g, 0.353 mmol). The reaction mixture was stirred at 100° C. for 1 h. The reaction mixture was cooled to room temperature and diluted with water and DCM. The layers were separated and the aqueous layer was extracted with DCM. The combined organic fractions were dried over a plug of magnesium sulfate and concentrated. The crude residue was dissolved into TFA (2 ml) and stirred at 80° C. for 20 minutes. The reaction mixture was diluted with DMF (3 mL) and purified by preparative LC/MS (pH=2, acetonitrile/water with TFA) to give the desired product as a TFA salt. LC-MS calculated for $C_{24}H_{18}F_2N_9O$ $(M+H)^+$: m/z=486.2; found 486.1.

Example 116. 3-(8-amino-2-(2-fluoro-6-(1-((trans)-3-(methylamino)cyclobutyl)-1H-pyrazol-4-yl)benzyl)-[1,2,4]triazolo[1,5-a]pyrazin-6-yl)-2-fluorobenzonitrile

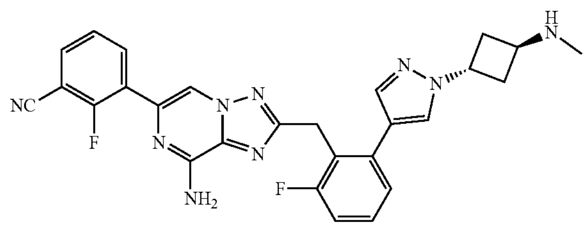 [SMILES: CN[C@H]1C[C@H](n2cc(-c3cccc(F)c3Cc3nc4c(N)nc(-c5cccc(C#N)c5F)cn4n3)cn2)C1]

Step 1: Tert-butyl methyl((trans)-3-(4-(4,4,5,5-tetramethyl-1,3,2-dioxaborolan-2-yl)-1H-pyrazol-1-yl)cyclobutyl)carbamate

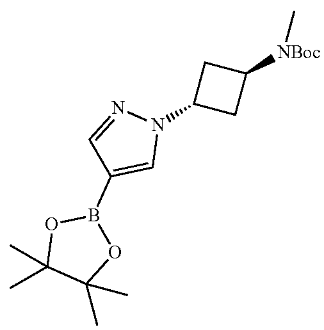

A vial was charged with 4-(4,4,5,5-tetramethyl-1,3,2-dioxaborolan-2-yl)-1H-pyrazole (0.192, 0.988), tert-butyl ((cis)-3-hydroxycyclobutyl)(methyl)carbamate (0.1 g, 0.494 mmol), triphenylphosphine (0.285 g, 1.09 mmol), and THE (1 ml). The solution was cooled to 0° C. and diisopropyl (E)-diazene-1,2-dicarboxylate (0.234 ml, 1.19 mmol) was added dropwise. The reaction mixture was slowly warmed to room temperature and stirred overnight. The solvent was stripped and the crude residue purified by automatic flash column chromatography to afford the desired product (0.112 g, 60%). LC-MS calculated for $C_{19}H_{33}BN_3O_4$ $(M+H)^+$: m/z=378.3; found 378.3.

Step 2: 3-(8-amino-2-(2-fluoro-6-(1-((trans)-3-(methylamino)cyclobutyl)-1H-pyrazol-4-yl)benzyl)-[1,2,4]triazolo[1,5-a]pyrazin-6-yl)-2-fluorobenzonitrile To a solution 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.01 g, 0.016 mmol) (from Example 99, step 4), tert-butyl methyl((trans)-3-(4-(4,4,5,5-tetramethyl-1,3,2-dioxaborolan-2-yl)-1H-pyrazol-1-yl)cyclobutyl)carbamate (0.012 g, 0.031 mmol), and dicyclohexyl(2',4',6'-triisopropylbiphenyl-2-yl)phosphine-(2'-aminobiphenyl-2-yl)(chloro)palladium (1:1) (2.50 mg, 3.14 μmol) in dioxane (0.24 mL) and water (0.06 mL) was added potassium phosphate tribasic (0.010 g, 0.047 mmol). The reaction mixture was stirred at 100° C. for 1 h. The reaction mixture was cooled to room temperature and diluted with water and DCM. The layers were separated and the aqueous layer was extracted with DCM. The combined organic fractions were dried over a plug of magnesium sulfate and concentrated. The crude residue was dissolved into TFA (1 ml) and stirred at 80° C. for 20 minutes. The reaction mixture was diluted with DMF (4 mL) and purified by preparative LC/MS (pH=2, acetonitrile/water with TFA) to give the desired product as a TFA salt. LC-MS calculated for $C_{27}H_{24}F_2N_9$ $(M+H)^+$: m/z=512.2; found 512.1.

Example 117. 3-(8-amino-2-(2-(1-(2-cyanoethyl)-1H-pyrazol-4-yl)-6-fluorobenzyl)-[1,2,4]triazolo[1,5-a]pyrazin-6-yl)-2-fluorobenzonitrile

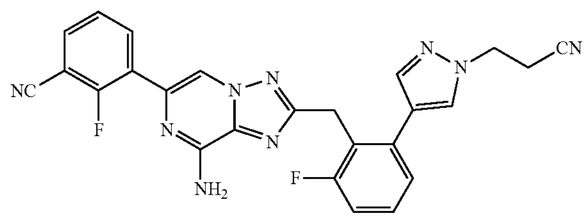 [SMILES: N#CCCn1cc(-c2cccc(F)c2Cc2nc3c(N)nc(-c4cccc(C#N)c4F)cn3n2)cn1]

To a solution 3-(8-(bis(4-methoxybenzyl)amino)-2-(2-chloro-6-fluorobenzyl)-[1,2,4]triazolo[1,5-a]pyrazin-6-yl)-2-fluorobenzonitrile (0.01 g, 0.016 mmol) (from Example 99, step 4), 3-(4-(4,4,5,5-tetramethyl-1,3,2-dioxaborolan-2-yl)-1H-pyrazol-1-yl)propanenitrile (0.008 g, 0.031 mmol), and dicyclohexyl(2',4',6'-triisopropylbiphenyl-2-yl)phosphine-(2'-aminobiphenyl-2-yl)(chloro)palladium (1:1) (2.50 mg, 3.14 μmol) in dioxane (0.24 mL) and water (0.06 mL) was added potassium phosphate tribasic (0.010 g, 0.047 mmol). The reaction mixture was stirred at 100° C. for 1 hour. The reaction mixture was cooled to room temperature and diluted with water and DCM. The layers were separated and the aqueous layer was extracted with DCM. The combined organic fractions were dried over a plug of magnesium sulfate and concentrated. The crude residue was dissolved into TFA (1 ml) and stirred at 80° C. for 20 minutes. The reaction mixture was diluted with DMF (4 mL) and purified by preparative LC/MS (pH=2, acetonitrile/water with TFA) to give the desired product as a TFA salt. LC-MS calculated for $C_{25}H_{18}F_2N_9$ $(M+H)^+$: m/z=482.2; found 482.2.

Example 118. 3-(8-amino-2-(2-fluoro-6-(1-(2-(3-hydroxyazetidin-1-yl)-2-oxoethyl)-1H-pyrazol-4-yl)benzyl)-[1,2,4]triazolo[1,5-a]pyrazin-6-yl)-2-fluorobenzonitrile

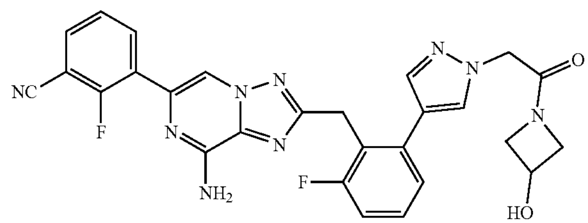 [SMILES: N#Cc1cccc(-c2cn3nc(Cc4c(F)cccc4-c4cnn(CC(=O)N5CC(O)C5)c4)nc3c(N)n2)c1F]

A vial was charged with 2-(4-(2-((8-(bis(4-methoxybenzyl)amino)-6-(3-cyano-2-fluorophenyl)-[1,2,4]triazolo[1,5-a]pyrazin-2-yl)methyl)-3-fluorophenyl)-1H-pyrazol-1-yl)acetic acid (0.01 g, 0.014 mmol) (from Example 114, step 1), DMF (0.46 ml), azetidin-3-ol (10 mg, 0.138 mmol), N,N-diisopropylethylamine (8.89 mg, 0.069 mmol), and 2-(3H-[1,2,3]triazolo[4,5-b]pyridin-3-yl)-1,1,3,3-tetramethylisouronium hexafluorophosphate(V) (10.46 mg, 0.028 mmol). The reaction mixture was stirred at room temperature for 1 hour. The reaction mixture was diluted with dichloromethane and water. The layers were separated and the aqueous layer was extracted with DCM. The combined organic fractions were dried over a plug of magnesium sulfate and concentrated. The combined organic fractions were concentrated, and the crude residue was dissolved into 1 mL TFA. The solution was stirred at 80° C. for 20 minutes. The reaction mixture was diluted with DMF (4 mL) and purified by preparative LC/MS (pH=2, acetonitrile/water with TFA) to give the desired product as a TFA salt. LC-MS calculated for $C_{27}H_{22}F_2N_9O_2$ $(M+H)^+$: m/z=542.2; found 542.1.

Example 119. 3-(8-amino-2-((3-methylpyridin-2-yl)methoxy)-5-(pyrimidin-4-yl)-[1,2,4]triazolo[1,5-a]pyrazin-6-yl)benzonitrile

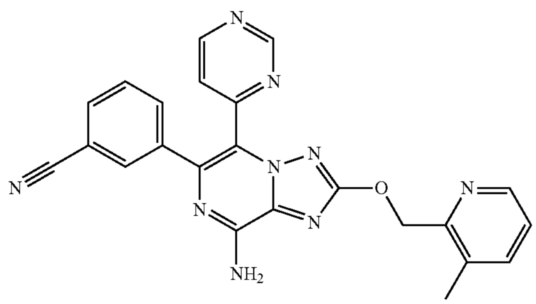 [SMILES: Cc1cccnc1COc1nc2c(N)nc(-c3cccc(C#N)c3)c(-c3ccncn3)n2n1]

Step 1: 3-(8-(bis(4-methoxybenzyl)amino)-2-hydroxy-[1,2,4]triazolo[1,5-a]pyrazin-6-yl)benzonitrile

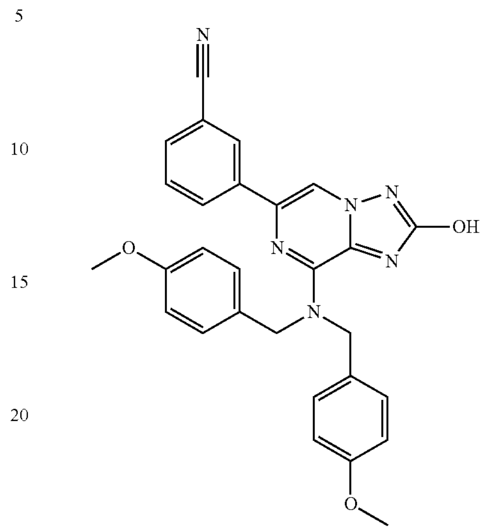

A reaction vial was charged with 3-(8-(bis(4-methoxybenzyl)amino)-2-bromo-[1,2,4]triazolo[1,5-a]pyrazin-6-yl)benzonitrile (50 mg, 0.090 mmol) (from Example 27, Step 4), tBuBrettPhos Pd G3 (3.8 mg, 0.0045 mmol), sodium tert-butoxide (17.3 mg, 0.18 mmol), $H_2O$ (0.1 mL) and dioxane (1 mL). The reaction mixture was purged with nitrogen for 5 min before heating to 110° C. and stirring for 5 h. The reaction mixture was then diluted with water and ethyl acetate. The organic layer was separated, washed with brine, dried over $Na_2SO_4$, filtered and concentrated. The resulting residue was purified via flash chromatography to give the desired product as a white solid (40 mg, 90%). LC-MS calculated for $C_{28}H_{25}N_6O_3$ $(M+H)^+$: m/z=493.2; found 493.3.

Step 2: 3-(8-(bis(4-methoxybenzyl)amino)-2-((3-methylpyridin-2-yl)methoxy)-5-(pyrimidin-4-yl)-[1,2,4]triazolo[1,5-a]pyrazin-6-yl)benzonitrile

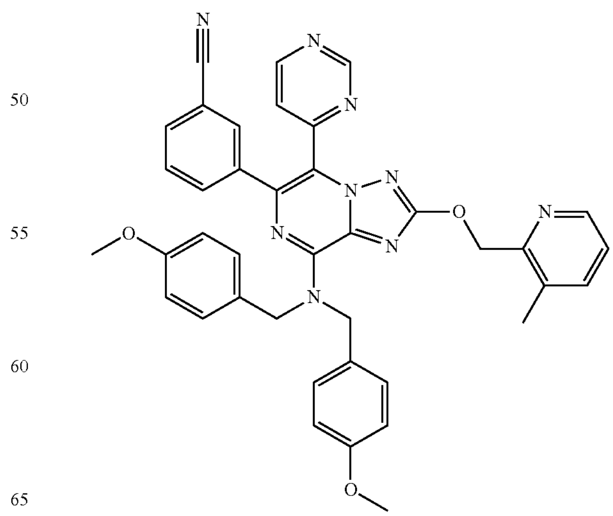

3-(8-(Bis(4-methoxybenzyl)amino)-2-hydroxy-[1,2,4]triazolo[1,5-a]pyrazin-6-yl)benzonitrile (15 mg, 0.030 mmol) was dissolved in acetonitrile (0.5 mL), and 2-(chloromethyl)-3-methylpyridine (13 mg, 0.090 mmol) and potassium carbonate (13 mg, 0.090 mmol) were added. The reaction was stirred at room temperature for 1 h. Upon completion, $NH_4Cl$ saturated aqueous solution was added and the content was extracted with EtOAc (2 mL×3). The combined organic phase was dried over $MgSO_4$, filtered, and the solvents removed. The crude product was re-dissolved in dichloromethane (1 mL). NBS (8 mg, 0.045 mmol) was added. The mixture was stirred at rt for 0.5 h before quenching by the addition of aqueous $Na_2SO_3$ solution. The organic layer was separated, dried over $Na_2SO_4$, filtered and concentrated. The crude brominated product was added LiCl (1.3 mg, 0.030 mmol), CuI (5.8 mg, 0.030 mmol), $Pd_2(dba)_3$ (2.3 mg, 0.003 mmol), $PPh_3$ (1.3 mg, 0.005 mmol) and 4-(tributylstannyl)pyrimidine (14 mg, 0.038 mmol). The reaction mixture was dissolved in dioxane, and purged with nitrogen for 5 min, before heating to 100° C. for 15 h. The reaction mixture was then cooled to rt, filtered, concentrated, and purified via flash chromatography to give the desired product as a white solid (10 mg, 50%). LC-MS calculated for $C_{39}H_{34}N_9O_3$ $(M+H)^+$: m/z=676.3; found 676.3.

Step 3: 3-(8-amino-2-((3-methylpyridin-2-yl)methoxy)-5-(pyrimidin-4-yl)-[1,2,4]triazolo[1,5-a]pyrazin-6-yl)benzonitrile 3-(8-(bis(4-methoxybenzyl)amino)-2-((3-methylpyridin-2-yl)methoxy)-5-(pyrimidin-4-yl)-[1,2,4]triazolo[1,5-a]pyrazin-6-yl)benzonitrile (10 mg, 0.015 mmol) was added TFA (0.5 mL), and stirred at 100° C. for 5 min. The reaction mixture was then cooled to room temperature, solvent removed, diluted with methanol, and purified via prep-LCMS (pH 2, acetonitrile/water with TFA) to give the desired product as a TFA salt. LC-MS calculated for $C_{23}H_{18}N_9O$ $(M+H)^+$: m/z=436.2; found 436.0.

Example 120. 3-(8-Amino-2-((3-((1-(pyridin-4-ylmethyl)-1H-pyrazol-4-yl)amino)pyridin-2-yl)methyl)-[1,2,4]triazolo[1,5-a]pyrazin-6-yl)-2-fluorobenzonitrile

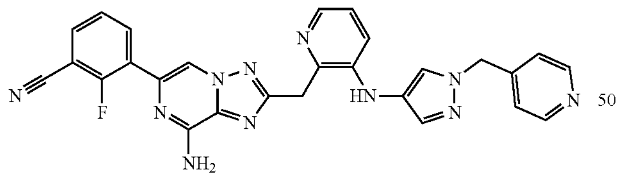

Step 1: Diethyl 2-(3-chloropyridin-2-yl)malonate

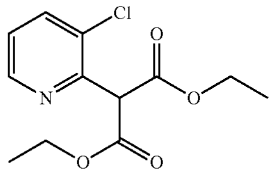 [SMILES: CCOC(=O)C(C(=O)OCC)c1ncccc1Cl]

The mixture of 3-chloro-2-fluoropyridine (6.25 g, 47.5 mmol), diethyl malonate (18.27 g, 114 mmol), cesium carbonate (37.2 g, 114 mmol) and DMSO (55.9 ml) was heated at 100° C. for 10 h. The mixture was poured onto ice, diluted with ethyl acetate. The organic layer was separated, washed with water, and brine, dried over $Na_2SO_4$, filtered and concentrated. The residue was purified with silica gel column (eluting with a gradient 0-30% ethyl acetate in hexane) to give the desired product (12.9 g, 100%). LC-MS calculated for $C_{12}H_{15}ClNO_4$ $(M+H)^+$: m/z=272.1; found 272.1.

Step 2: ethyl 2-(3-chloropyridin-2-yl)acetate

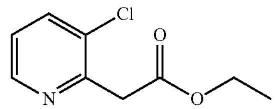

A mixture of diethyl 2-(3-chloropyridin-2-yl)malonate (12.9 g, 47.5 mmol), sodium chloride (3.05 ml, 52.2 mmol), water (1.711 ml, 95 mmol) in DMSO (68 ml) was heated at 145° C. for 5 h. LCMS showed completion of reaction. The reaction mixture was diluted with ethyl acetate and washed with water (2×), brine, dried over $MgSO_4$, filtered and concentrated. The residue was purified with silica gel column (eluting with a gradient 0-30% ethyl acetate in hexane) to give the desired product (7.8 g, 82%). LC-MS calculated for $C_9H_{11}ClNO_2$ $(M+H)^+$: m/z=200.0; found 200.0.

Step 3: 2-(3-chloropyridin-2-yl)acetic acid

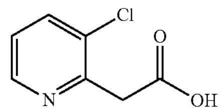 [SMILES: O=C(O)Cc1ncccc1Cl]

To a solution of ethyl 2-(3-chloropyridin-2-yl)acetate (7.8 g, 39.1 mmol) in THE (130 ml) was added 1.0 M sodium hydroxide solution (78 ml, 78 mmol). The resulting mixture was stirred at rt for 1 h. LCMS showed the completion of reaction. pH of the reaction mixture was adjusted with 1 N HCl to pH 3. The organic solvent was removed in vacuo. The resulting precipitate was collected via filtration, washed with water and ethyl acetate and dried under vacuum to give the product as white solid (5.5 g, 82%). LC-MS calculated for $C_7H_7ClNO_2$ $(M+H)^+$: m/z=172.0; found 172.0.

Step 4: 6-Bromo-2-((3-chloropyridin-2-yl)methyl)-N,N-bis(4-methoxybenzyl)-[1,2,4]triazolo[1,5-a]pyrazin-8-amine

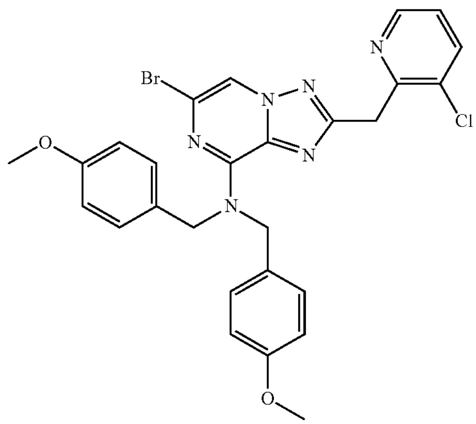 [SMILES: COc1ccc(CN(Cc2ccc(OC)cc2)c2nc(Br)cn3nc(Cc4ncccc4Cl)nc23)cc1]

To a flask charged with 2-(3-chloropyridin-2-yl)acetic acid (0.372 g, 2.168 mmol), HATU (0.907 g, 2.385 mmol) in CH2Cl2 (21.68 ml) was added 1,2-diamino-3-(bis(4-methoxybenzyl)amino)-5-bromopyrazin-1-ium 2,4,6-trimethylbenzenesulfonate (1.398 g, 2.168 mmol) (from Example 99, Step 2), followed by DIEA (0.757 ml, 4.34 mmol). After stirring at room temperature for 6 h, LCMS showed completion of reaction. The reaction mixture was diluted with DCM and water. The organic layer was washed with brine, dried over $Na_2SO_4$, filtered and concentrated. The crude was purified with flash chromatography (eluting with a gradient 0-40% ethyl acetate in hexanes with 10% DCM) to give the desired product (1.0 g, 80%). LC-MS calculated for $C_{27}H_{25}BrClN_6O_2$ $(M+H)^+$: m/z=579.1, 581.1; found 579.1, 581.1.

Step 5: 3-(8-(bis(4-methoxybenzyl)amino)-2-((3-chloropyridin-2-yl)methyl)-[1,2,4]triazolo[1,5-a]pyrazin-6-yl)-2-fluorobenzonitrile

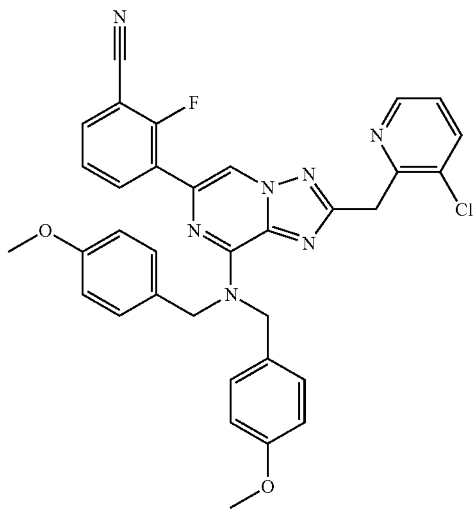 [SMILES: COc1ccc(CN(Cc2ccc(OC)cc2)c2nc(-c3cccc(C#N)c3F)cn3nc(Cc4ncccc4Cl)nc23)cc1]

A flask charged with 6-bromo-2-((3-chloropyridin-2-yl)methyl)-N,N-bis(4-methoxybenzyl)-[1,2,4]triazolo[1,5-a]pyrazin-8-amine (4.70 g, 8.11 mmol), (3-cyano-2-fluorophenyl)boronic acid (1.871 g, 11.35 mmol), $Cs_2CO_3$ (5.28 g, 16.21 mmol), tetrakis (0.937 g, 0.811 mmol), 1,4-dioxane (73.7 ml) and water (7.37 ml) was evacuated under vacuum and refilled with N2 (repeated three times). The mixture was heated at 90° C. for 4 h. Another 0.3 equivalent (3-cyano-2-fluorophenyl)boronic acid (1.871 g, 11.35 mmol) was added and heated at 90° C. for 2 h. LCMS showed total completion of reaction. The reaction mixture was diluted with DCM and water. The organic layer was washed with brine, dried over $Na_2SO_4$, filtered and concentrated. The crude was triturated with hexanes and ethyl acetate, the resulting precipitate was collected vial filtration and washed with methanol, dried under vacuum to give the desired product as white solid (4.4 g, 88%). LC-MS calculated for $C_{34}H_{28}ClFN_7O_2$ $(M+H)^+$: m/z=620.2; found 620.2.

Step 6: 3-(8-Amino-2-((3-((1-(pyridin-4-ylmethyl)-1H-pyrazol-4-yl)amino)pyridin-2-yl)methyl)-[1,2,4]triazolo[1,5-a]pyrazin-6-yl)-2-fluorobenzonitrile To a vial 3-(8-(bis(4-methoxybenzyl)amino)-2-((3-chloropyridin-2-yl)methyl)-[1,2,4]triazolo[1,5-a]pyrazin-6-yl)-2-fluorobenzonitrile (15 mg, 0.024 mmol), 1-(pyridin-4-ylmethyl)-1H-pyrazol-4-amine (4.21 mg, 0.024 mmol), Brettphos palladacycle (3.29 mg, 3.63 μmol), and cesium carbonate (12.44 μl, 0.073 mmol) were added. The vial was sealed with a teflon screw-cap, evacuated and backfilled with nitrogen (this process was repeated a total of three times). Anhydrous t-butanol (1 ml) was added. The mixture was heated to 90° C. for 2 h. The reaction mixture was filtered through a SiliaPrep-Thiol funnel, the filtrate was concentrated. The residue was treated with TFA (1 mL) at 80° C. for 20 min. The volatile was removed, the crude was dissolved in methanol and purified with prep-LCMS (pH 2, acetonitrile/water+TFA) to give the desired product as TFA salt (4 mg, 33%). LC-MS calculated for $C_{27}H_{21}FN_{11}$ $(M+H)^+$: m/z=518.2; found 518.2.

Example 121. 3-(8-amino-2-((3-((1-(tetrahydro-2H-pyran-4-yl)-1H-pyrazol-4-yl)amino)pyridin-2-yl)methyl)-[1,2,4]triazolo[1,5-a]pyrazin-6-yl)-2-fluorobenzonitrile

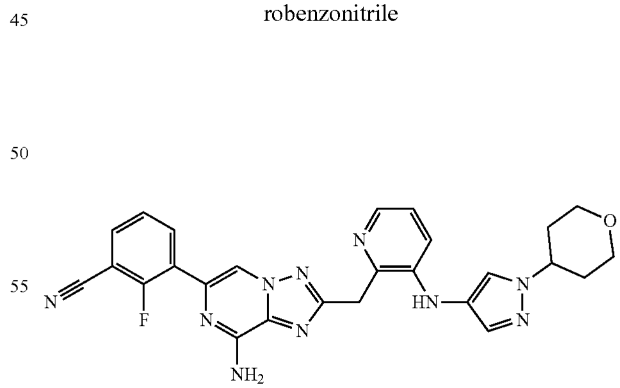

The title compound was prepared using similar procedures as described for Example 120 with 1-(tetrahydro-2H-pyran-4-yl)-1H-pyrazol-4-amine replacing 1-(pyridin-4-ylmethyl)-1H-pyrazol-4-amine in Step 9. The reaction mixture was purified by prep-HPLC (pH=2, acetonitrile/water+TFA) to give the desired product as TFA salt. LC-MS calculated for $C_{26}H_{24}FN_{10}O$ $(M+H)^+$: m/z=511.2; found 511.2.

Example 122. 3-(8-Amino-2-((3-(1-methyl-1H-pyrazol-4-yl)pyridin-2-yl)methyl)-5-(pyrimidin-4-yl)-[1,2,4]triazolo[1,5-a]pyrazin-6-yl)benzonitrile

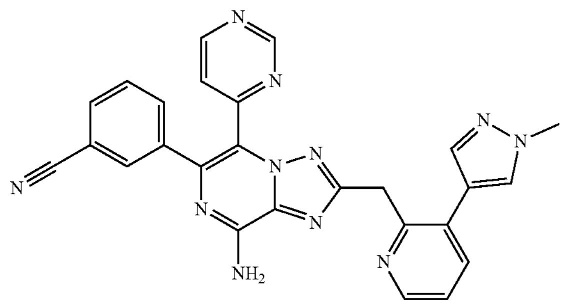 [SMILES: Cn1cc(-c2cccnc2Cc2nc3c(N)nc(-c4cccc(C#N)c4)c(-c4ccncn4)n3n2)cn1]

Step 1: 3-(8-(bis(4-methoxybenzyl)amino)-2-((3-chloropyridin-2-yl)methyl)-[1,2,4]triazolo[1,5-a]pyrazin-6-yl)benzonitrile

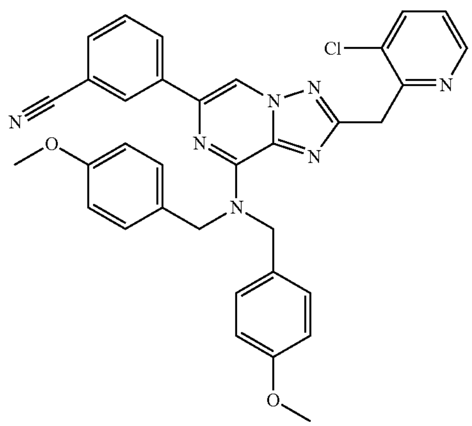 [SMILES: COc1ccc(CN(Cc2ccc(OC)cc2)c2nc(-c3cccc(C#N)c3)cn3nc(Cc4ncccc4Cl)nc23)cc1]

To a solution of 3-chloro-2-methylpyridine (0.367 g, 2.88 mmol) in THE (10 mL) was added 0.65 M (2,2,6,6-tetramethylpiperidin-1-yl)zinc(II) lithium chloride (6.65 ml, 4.32 mmol) at rt. The resulting yellow solution was stirred at same temperature for 1 h, scandium trifluoromethanesulfonate (0.057 g, 0.115 mmol) was added and stirred at room temperature for 15 min. A microwave vial was charge with 3-(8-(bis(4-methoxybenzyl)amino)-2-bromo-[1,2,4]triazolo[1,5-a]pyrazin-6-yl)benzonitrile (0.64 g, 1.152 mmol), palladium acetate (0.021 g, 0.092 mmol), and 2'-(dicyclohexylphosphino)-N,N,N',N'-tetramethylbiphenyl-2,6-diamine (0.080 g, 0.184 mmol) was evacuated under high vacuum and backfilled with nitrogen. The mixture was cooled to 0° C. and the zinc reagent was added slowly via syringe. After addition, the reaction was heated to 60° C. for 1 h. The reaction solution was partitioned between EtOAc and sat. $NH_4Cl$ solution. The layers were separated and the aqueous extracted further with EtOAc (2×). The combined organics were washed with water and brine, dried over $MgSO_4$, and concentrated. The resulting residue was purified via flash chromatography to afford the product. LC-MS calculated for $C_{34}H_{29}ClN_7O_2$ $(M+H)^+$: m/z=602.2; found 602.2.

Step 2: 3-(8-(bis(4-methoxybenzyl)amino)-5-bromo-2-((3-chloropyridin-2-yl)methyl)-[1,2,4]triazolo[1,5-a]pyrazin-6-yl)benzonitrile

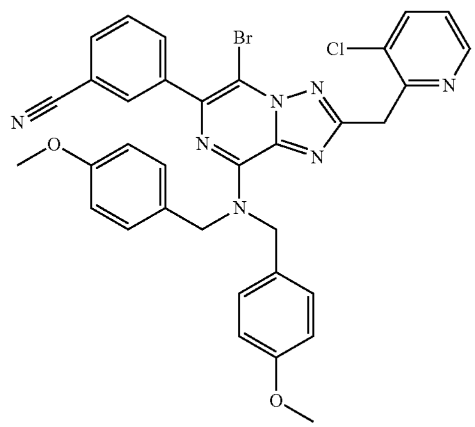 [SMILES: COc1ccc(CN(Cc2ccc(OC)cc2)c2nc(-c3cccc(C#N)c3)c(Br)n3nc(Cc4ncccc4Cl)nc23)cc1]

A mixture of 3-(8-(bis(4-methoxybenzyl)amino)-2-((3-chloropyridin-2-yl)methyl)-[1,2,4]triazolo[1,5-a]pyrazin-6-yl)benzonitrile (0.218 g, 0.362 mmol), 1-bromopyrrolidine-2,5-dione (0.061 g, 0.344 mmol) and CH2Cl2 (4 ml); was stirred at 0° C. for 30 min, The reaction mixture was diluted with sat. $NaHCO_3$. The mixture was extracted with DCM. The organic phase was washed with brine, dried over $Na_2SO_4$, filtered, and concentrated. The residue was purified with flash chromatography to give the desired product as a light yellow oil. LC-MS calculated for $C_{34}H_{28}BrClN_7O_2$ $(M+H)^+$: m/z=680.1, 682.1; found 680.1, 682.1.

Step 3: 3-(8-Amino-2-((3-chloropyridin-2-yl)methyl)-5-(pyrimidin-4-yl)-[1,2,4]triazolo[1,5-a]pyrazin-6-yl)benzonitrile

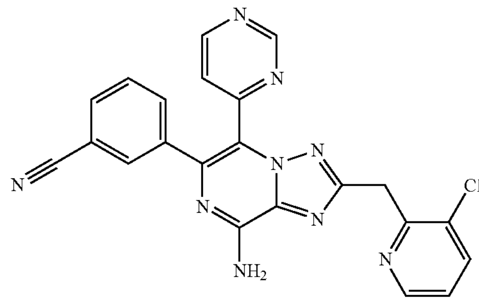 [SMILES: N#Cc1cccc(-c2nc(N)c3nc(Cc4ncccc4Cl)nn3c2-c2ccncn2)c1]

A mixture of 3-(8-(bis(4-methoxybenzyl)amino)-5-bromo-2-((3-chloropyridin-2-yl)methyl)-[1,2,4]triazolo[1,5-a]pyrazin-6-yl)benzonitrile (86 mg, 0.126 mmol), 4-(tributylstannyl)pyrimidine (69.9 mg, 0.189 mmol), and copper(I) chloride (15.00 mg, 0.152 mmol), lithium chloride (6.42 mg, 0.152 mmol) and tetrakis(triphenylphosphine) palladium(0) (14.59 mg, 0.013 mmol) in THE (3 ml) was first purged with $N_2$, and then heated and stirred at 90 C for 2 h. The reaction was dilute with methanol and purified with prep-LCMS (pH 2, acetonitrile/water with TFA) to give coupling product, that was treated with TFA (1 mL) at 80 C for 20 min, The volatile was removed and the resulting residue was dissolved in methanol and purified with prep- LCMS (pH 2, acetonitrile/water with TFA) to give the desired product. LC-MS calculated for $C_{22}H_{15}ClN_9$ $(M+H)^+$: m/z=440.1 found 440.1.

Step 4: 3-(8-amino-2-((3-(1-methyl-1H-pyrazol-4-yl)pyridin-2-yl)methyl)-5-(pyrimidin-4-yl)-[1,2,4]triazolo[1,5-a]pyrazin-6-yl)benzonitrile A mixture of 3-(8-amino-2-((3-chloropyridin-2-yl)methyl)-5-(pyrimidin-4-yl)-[1,2,4]triazolo[1,5-a]pyrazin-6-yl)benzonitrile (10 mg, 0.023 mmol), 1-methyl-4-(4,4,5,5-tetramethyl-1,3,2-dioxaborolan-2-yl)-1H-pyrazole (5.7 mg, 0.027 mmol), dicyclohexyl(2',4',6'-triisopropylbiphenyl-2-yl)phosphine-(2'-aminobiphenyl-2-yl)(chloro)palladium (1:1) (1.8 mg, 2.3 μmol) and tripotassium phosphate hydrate (11.5 mg, 0.050 mmol) in 1,4-dioxane (2.0 mL)/Water (0.65 mL) was stirred at 80° C. for 1 h. The mixture was diluted in methanol and DMSO and purified with prep-LCMS (pH 2, acetonitrile/water with TFA) to afford the desired product as TFA salt. LCMS calculated for $C_{26}H_{20}N_{11}$ $(M+H)^+$: 486.2 found 486.2.

Example 123. (S)-3-(8-Amino-2-(2-((3-hydroxypyrrolidin-1-yl)methyl)benzyl)-5-(pyrimidin-4-yl)-[1,2,4]triazolo[1,5-a]pyrazin-6-yl)benzonitrile

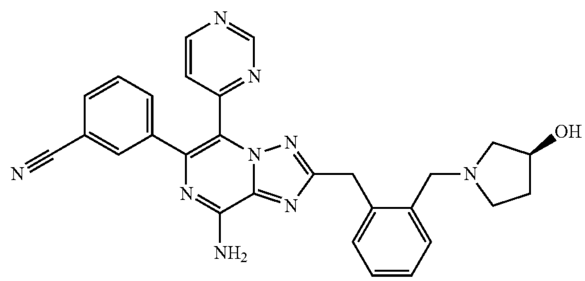 [SMILES: N#Cc1cccc(-c2nc(N)c3nc(Cc4ccccc4CN4CC[C@H](O)C4)nn3c2-c2ccncn2)c1]

Step 1: 3-(8-(Bis(4-methoxybenzyl)amino)-2-(2-chlorobenzyl)-[1,2,4]triazolo[1,5-a]pyrazin-6-yl)benzonitrile

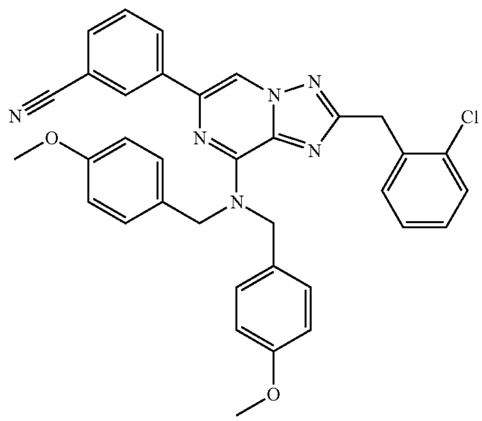 [SMILES: COc1ccc(CN(Cc2ccc(OC)cc2)c2nc(-c3cccc(C#N)c3)cn3nc(Cc4ccccc4Cl)nc23)cc1]

A microwave vial was charge with 3-(8-(bis(4-methoxybenzyl)amino)-2-bromo-[1,2,4]triazolo[1,5-a]pyrazin-6-yl)benzonitrile (350 mg, 0.630 mmol), palladium acetate (7.07 mg, 0.032 mmol), and 2'-(dicyclohexylphosphino)-N,N,N',N'-tetramethylbiphenyl-2,6-diamine (27.5 mg, 0.063 mmol) was evacuated under high vacuum and backfilled with nitrogen. (2-chlorobenzyl)zinc(II) chloride (1.4 mL, 0.693 mmol) was added via syringe. After addition, the reaction was heated to 60° C. for 1 h. The reaction solution was partitioned between EtOAc and sat. $NH_4Cl$ solution. The layers were separated and the aqueous extracted further with EtOAc (2×). The combined organics were washed with water and brine, dried over $MgSO_4$, and concentrated. The residue was purified with flash chromatography to give the desired product (0.32 g, 82%). LC-MS calculated for $C_{35}H_{30}ClN_6O_2$ $(M+H)^+$: m/z=601.2; found 601.2.

Step 2: 3-(8-(Bis(4-methoxybenzyl)amino)-5-bromo-2-(2-chlorobenzyl)-[1,2,4]triazolo[1,5-a]pyrazin-6-yl)benzonitrile

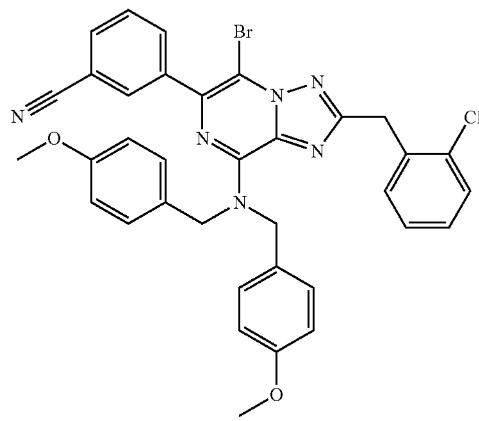 [SMILES: COc1ccc(CN(Cc2ccc(OC)cc2)c2nc(-c3cccc(C#N)c3)c(Br)n3nc(Cc4ccccc4Cl)nc23)cc1]

To a solution of 3-(8-(bis(4-methoxybenzyl)amino)-2-(2-chlorobenzyl)-[1,2,4]triazolo[1,5-a]pyrazin-6-yl)benzonitrile (0.379 g, 0.631 mmol) in DCM (6.3 ml) was add 1-bromopyrrolidine-2,5-dione (0.107 g, 0.599 mmol) at 0° C. The resulting mixture was stirred at 0° C. for 30 min. The reaction mixture was diluted with sat. $NaHCO_3$. The mixture was extracted with DCM. The organic phase was washed with brine, dried over $Na_2SO_4$, filtered, and concentrated. The residue was purified with flash chromatography to give the desired product as a light yellow oil (0.38 g, 89%). LC-MS calculated for $C_{35}H_{29}BrClN_6O_2$ $(M+H)^+$: m/z=679.1, 681.1; found 679.1, 681.1.

Step 3: 3-(8-(Bis(4-methoxybenzyl)amino)-2-(2-chlorobenzyl)-5-(pyrimidin-4-yl)-[1,2,4]triazolo[1,5-a]pyrazin-6-yl)benzonitrile

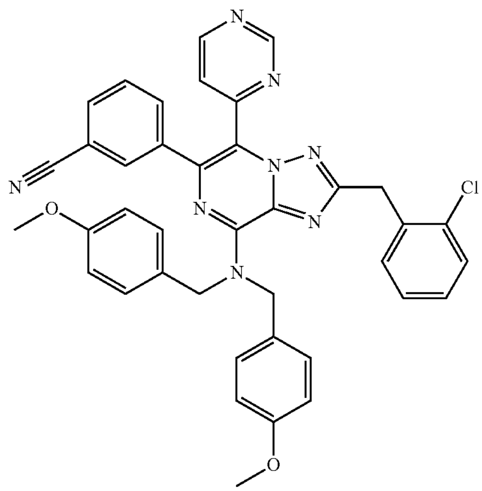 [SMILES: COc1ccc(CN(Cc2ccc(OC)cc2)c2nc(-c3cccc(C#N)c3)c(-c3ccncn3)n3nc(Cc4ccccc4Cl)nc23)cc1]

A mixture of 3-(8-(bis(4-methoxybenzyl)amino)-5-bromo-2-(2-chlorobenzyl)-[1,2,4]triazolo[1,5-a]pyrazin-6-yl)benzonitrile (381 mg, 0.560 mmol), 4-(tributylstannyl) pyrimidine (310 mg, 0.840 mmol), and copper(I) chloride (66.6 mg, 0.672 mmol), lithium chloride (28.5 mg, 0.672 mmol) and tetrakis(triphenylphosphine)palladium(0) (64.7 mg, 0.056 mmol) in THE (6 ml) was first purged with $N_2$, and then heated and stirred at 90° C. for 2 h. The reaction mixture was concentrated under vacuum and the resulting residue was purified with flash chromatography to give the desired product as a light yellow oil (0.31 g, 83%). LC-MS calculated for $C_{39}H_{32}ClN_8O_2$ $(M+H)^+$: m/z=679.2 found 679.2.

Step 4: 3-(8-(Bis(4-methoxybenzyl)amino)-5-(pyrimidin-4-yl)-2-(2-vinylbenzyl)-[1,2,4]triazolo[1,5-a]pyrazin-6-yl)benzonitrile

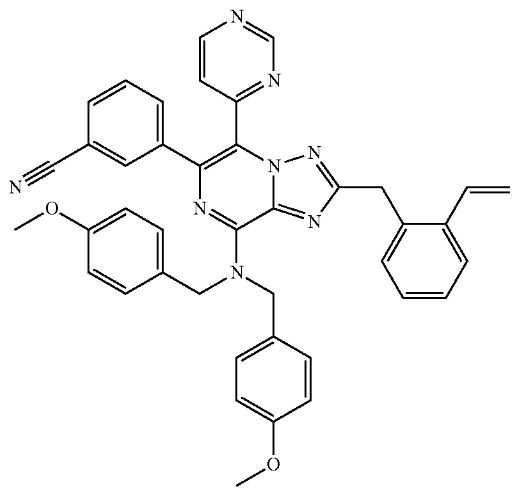 [SMILES: C=Cc1ccccc1Cc1nc2c(N(Cc3ccc(OC)cc3)Cc3ccc(OC)cc3)nc(-c3cccc(C#N)c3)c(-c3ccncn3)n2n1]

A mixture of 3-(8-(bis(4-methoxybenzyl)amino)-2-(2-chlorobenzyl)-5-(pyrimidin-4-yl)-[1,2,4]triazolo[1,5-a] pyrazin-6-yl)benzonitrile (300 mg, 0.442 mmol), 4,4,5,5-tetramethyl-2-vinyl-1,3,2-dioxaborolane (82 mg, 0.530 mmol), dicyclohexyl(2',4',6'-triisopropylbiphenyl-2-yl) phosphine-(2'-aminobiphenyl-2-yl)(chloro)palladium (1:1) (34.8 mg, 0.044 mmol) and tripotassium phosphate hydrate (224 mg, 0.972 mmol) in 1,4-dioxane (5.0 mL)/water (1.7 mL) was stirred at 80° C. for 1 h. The reaction mixture was concentrated under vacuum and the resulting residue was purified with flash chromatography to give the desired product as a light yellow oil. LC-MS calculated for $C_{41}H_{35}N_8O_2$ $(M+H)^+$: m/z=671.3; found 671.3.

Step 5: 3-(8-(Bis(4-methoxybenzyl)amino)-2-(2-formylbenzyl)-5-(pyrimidin-4-yl)-[1,2,4]triazolo[1,5-a]pyrazin-6-yl)benzonitrile

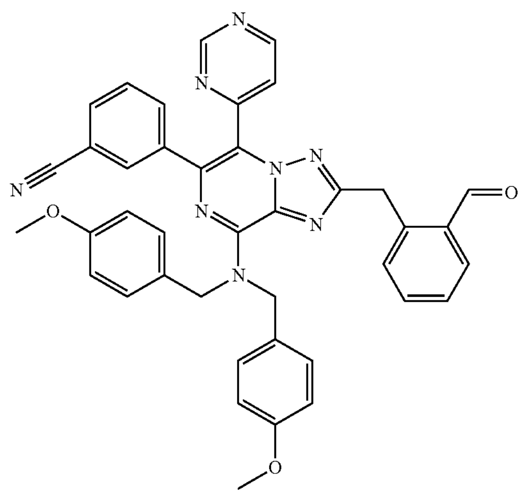 [SMILES: COc1ccc(CN(Cc2ccc(OC)cc2)c2nc(-c3cccc(C#N)c3)c(-c3ccncn3)n3nc(Cc4ccccc4C=O)nc23)cc1]

3-(8-(bis(4-methoxybenzyl)amino)-5-(pyrimidin-4-yl)-2-(2-vinylbenzyl)-[1,2,4]triazolo[1,5-a]pyrazin-6-yl)benzonitrile (296 mg, 0.441 mmol) was mixed with tetrahydrofuran (2.2 mL), 0.16 M osmium tetraoxide in water (220 μL, 0.035 mmol), sodium metaperiodate (425 mg, 1.986 mmol) and water (2.2 mL). The reaction was stirred at 60° C. for 1 h before quenched with sat. $Na_2S_2O_3$. The mixture was extracted with DCM. The organic phase was washed with brine, dried over $Na_2SO_4$, filtered, and concentrated to afford the product as a light yellow oil. LC-MS calculated for $C_{40}H_{33}N_8O_3$ $(M+H)^+$: m/z=673.3; found 673.3.

Step 6: (S)-3-(8-Amino-2-(2-((3-hydroxypyrrolidin-1-yl)methyl)benzyl)-5-(pyrimidin-4-yl)-[1,2,4]triazolo[1,5-a]pyrazin-6-yl)benzonitrile A mixture of (3-(8-(bis(4-methoxybenzyl)amino)-2-(2-formylbenzyl)-5-(pyrimidin-4-yl)-[1,2,4]triazolo[1,5-a] pyrazin-6-yl)benzonitrile (12 mg, 0.018 mmol), (S)-pyrrolidin-3-ol (1.6 mg, 0.018 mmol) in DCM (0.5 mL) and MeOH (0.5 mL) was added sodium triacetoxyborohydride (7.6 mg, 0.036 mmol). After stirring at room temperature overnight, solvent was removed in vacuo. The residue was treated with TFA (1 mL) at 80° C. for 20 min. After removal of volatile. The residue was dissolved in methanol and purified with preparative LCMS (pH 2, acetonitrile/water with TFA) to afford the desired product as TFA salt. LCMS calculated for $C_{28}H_{26}N_9O$ $(M+H)^+$: 504.2 found 504.2.

Example 124. 3-(8-Amino-5-(imidazo[1,2-a]pyridin-6-yl)-[1,2,4]triazolo[1,5-a]pyrazin-6-yl)benzonitrile

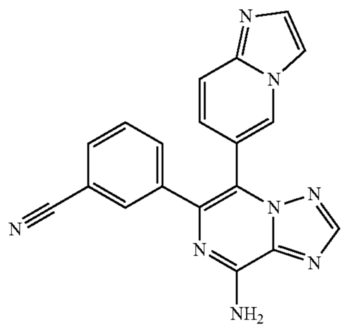 [SMILES: N#Cc1cccc(-c2nc(N)c3ncnn3c2-c2ccc3nccn3c2)c1]

The title compound was prepared using similar procedures as described for Example 15 with 6-(4,4,5,5-tetramethyl-1,3,2-dioxaborolan-2-yl)imidazo[1,2-a]pyridine replacing (6-methoxypyridin-3-yl)boronic acid in Step 5. The reaction mixture was purified by prep-HPLC (pH=2, acetonitrile/water+TFA) to give the desired product as TFA salt. LC-MS calculated for $C_{19}H_{13}N_8$ $(M+H)^+$: m/z=353.1; found 353.1.

Example 125. 3-(8-amino-2-(azetidine-1-carbonyl)-5-(3-fluoropyridin-4-yl)-[1,2,4]triazolo[1,5-a]pyrazin-6-yl)benzonitrile

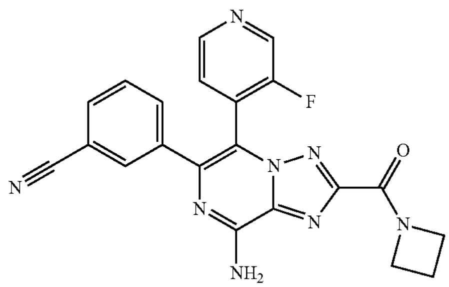 [SMILES: N#Cc1cccc(-c2nc(N)c3nc(C(=O)N4CCC4)nn3c2-c2ccncc2F)c1]

A mixture of 3-(2-(azetidine-1-carbonyl)-8-(bis(4-methoxybenzyl)amino)-5-bromo-[1,2,4]triazolo[1,5-a]pyrazin-6-yl)benzonitrile (20 mg, 0.032 mmol) (from Example 61, Step 2), 3-fluoropyridine-4-boronic acid (16 mg, 0.13 mmol), sodium carbonate (34 mg, 0.32 mmol) and chloro(2-dicyclohexylphosphino-2',4',6'-triisopropyl-1,1'-biphenyl)[2-(2'-amino-1,1'-biphenyl)]palladium(II) (5 mg, 0.006 mmol) in 4:1 dioxane/Water (1.3 mL) was stirred at 100° C. for 1.5 hours. The reaction mixture was diluted with dichloromethane and water, and the organic solvent was concentrated in vacuo, the crude product was dissolved in 3 mL TFA and stirred at 80° C. for 20 mins. After TFA being removed, the crude product was purified by preparative LC/MS (pH=2, acetonitrile/water with TFA) to afford the desired product as a TFA salt. LC-MS calculated for $C_{21}H_{16}FN_8O$ $(M+H)^+$: m/z=415.2; found 415.1.

Example 126. 3-(8-amino-2-((2,6-difluorophenyl)(hydroxy)methyl)-5-(2,6-dimethylpyridin-4-yl)-[1,2,4]triazolo[1,5-a]pyrazin-6-yl)-2-fluorobenzonitrile

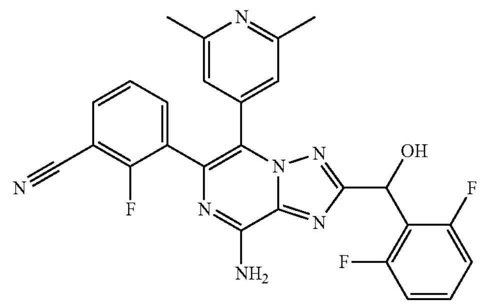 [SMILES: Cc1cc(-c2c(-c3cccc(C#N)c3F)nc(N)c3nc(C(O)c4c(F)cccc4F)nn23)cc(C)n1]

Step 1: 2-((tert-butyldimethylsilyl)oxy)-2-(2,6-difluorophenyl)acetonitrile

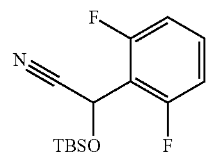 [SMILES: CC(C)(C)[Si](C)(C)OC(C#N)c1c(F)cccc1F]

To a stirred solution of 2,6-difluorobenzaldehyde (0.987 ml, 8.97 mmol) in acetonitrile (9 ml) at rt was added tert-Butyldimethylsilyl cyanide (1.959 g, 13.45 mmol) (1.5 eq) and cesium fluoride (0.272 g, 1.793 mmol) (0.2 eq). The reaction mixture was stirred at rt overnight (16 h). The reaction mixture was filtered to remove CsF. The filtrate was concentrated in vacuo. The residue was purified by Biotage Isolera (with 40 g silica gel column) eluting with 0-10% EtOAc/Hexane to give the product as a colorless oil (2.468 g, 97%). LCMS calculated for $C_{14}H_{20}F_2NOSi$ $(M+H)^+$: m/z=284.1; found: 284.1.

Step 2: 2-((tert-butyldimethylsilyl)oxy)-N-(3,5-dibromopyrazin-2-yl)-2-(2,6-difluorophenyl)acetimidamide

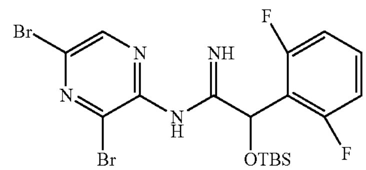 [SMILES: CC(C)(C)[Si](C)(C)OC(C(=N)Nc1ncc(Br)nc1Br)c1c(F)cccc1F]

To a stirred solution of 2-((tert-butyldimethylsilyl)oxy)-2-(2,6-difluorophenyl)acetonitrile (2.0 g, 7.06 mmol) in anhydrous 1,2-Dichloroethane (10 ml) (5 volume) at rt was added 3,5-dibromopyrazin-2-amine (2.73 g, 10.59 mmol) (1.5 eq) and Tin(IV) chloride (1.264 ml, 10.59 mmol) (1.5 eq). The resulting suspension was heated at 110° C. overnight (15 h). The reaction mixture was cooled to rt. It was diluted with dichloromethane (20 mL), basified with 1N NaOH to pH 10. It was extracted with dichloromethane (50 mL). The dichloromethane layer was dried over $Na_2SO_4$, filtered and concentrated in vacuo. The residue was purified by Biotage Isolera (with 120 g silica gel column) eluting with 0-30% EtOAc/Hexane to give the product as a light yellow solid (2.681 g, 70%). LCMS calculated for $C_{18}H_{23}Br_2F_2N4OSi$ $(M+H)^+$: m/z=534.9; found: 534.9.

Step 3: 6,8-dibromo-2-(((tert-butyldimethylsilyl)oxy)(2,6-difluorophenyl)methyl)-[1,2,4]triazolo[1,5-a]pyrazine

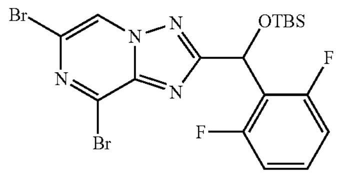 [SMILES: CC(C)(C)[Si](C)(C)OC(c1nc2c(Br)nc(Br)cn2n1)c1c(F)cccc1F]

To a stirred solution of 2-((tert-butyldimethylsilyl)oxy)-N-(3,5-dibromopyrazin-2-yl)-2-(2,6-difluorophenyl)acetimidamide (1.0 g, 1.831 mmol) in Hexafluoroisopropanol (18 ml) (HFIPA, 18 volume) at rt was added (Bis(trifluoroacetoxy)iodo)benzene (1.623 g, 3.66 mmol) (2 eq) and Triethylamine (1.023 ml, 7.32 mmol) (4 eq). The reaction mixture was stirred at rt for 2 hours. The reaction was quenched with saturated aqueous $NaHCO_3$ (20 mL). It was extracted with dichloromethane (50 mL). Dichloromethane layer was dried over $Na_2SO_4$, filtered and concentrated in vacuo. The residue purified by Biotage Isolera (with 120 g silica gel column) eluting with 0-20% EtOAc/Hexane to give the product as a viscous light yellow oil (0.98 g, 95%). LCMS calculated for $C_{18}H_{21}Br_2F_2N_4OSi$ $(M+H)^+$: m/z=533.0; found 532.8.

Step 4: 6-bromo-2-(((tert-butyldimethylsilyl)oxy)(2,6-difluorophenyl)methyl)-N,N-bis(4-methoxybenzyl)-[1,2,4]triazolo[1,5-a]pyrazin-8-amine

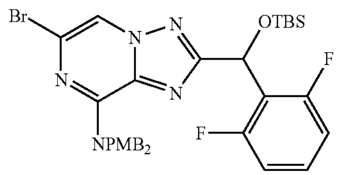

To a stirred solution of 6,8-dibromo-2-(((tert-butyldimethylsilyl)oxy)(2,6-difluorophenyl)methyl)-[1,2,4]triazolo[1,5-a]pyrazine (0.98 g, 1.741 mmol) in 2-Propanol (10 ml) at rt was added bis(4-methoxybenzyl)amine (0.594 g, 2.264 mmol) and N,N-Diisopropylethylamine (0.613 ml, 3.48 mmol). The reaction mixture was heated at 80° C. for 2 hours. The reaction mixture was cooled to rt, and concentrated in vacuo. The residue was purified by Biotage Isolera (with 120 g silica gel column) eluting with 0-30% EtOAc/Hexane to give the product as a white foamy solid (1.190 g, 96%). LCMS calculated for $C_{34}H_{39}BrF_2N_5O_3Si$: m/z=710.2, found 710.3.

Step 5: 3-(8-(bis(4-methoxybenzyl)amino)-2-(((tert-butyldimethylsilyl)oxy)(2,6-difluorophenyl)methyl)-[1,2,4]triazolo[1,5-a]pyrazin-6-yl)-2-fluorobenzonitrile

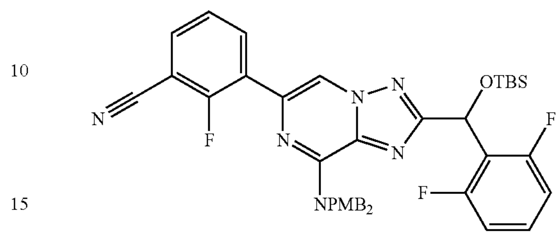

To a stirred solution of 6-bromo-2-(((tert-butyldimethylsilyl)oxy)(2,6-difluorophenyl)methyl)-N,N-bis(4-methoxybenzyl)-[1,2,4]triazolo[1,5-a]pyrazin-8-amine (1.37 g, 1.93 mmol) in 1,4-dioxane/H2O (4:1, 13 mL), (3-cyano-2-fluorophenyl)boronic acid (0.413 g, 2.5 mmol), chloro(2-dicyclohexylphosphino-2',4',6'-triisopropyl-1,1'-biphenyl)[2-(2'-amino-1,1'-biphenyl)]palladium(II) (78 mg, 0.1 mmol) (XPhos Pd G2) and sodium carbonate (0.613 mg, 5.78 mmol) were added at rt. The reaction mixture was heated at 90° C. for 2 hours. The reaction mixture was cooled to rt, extracted with dichloromethane and concentrated in vacuo. The residue was purified by Biotage Isolera eluting with 0-30% EtOAc/Hexane to give the product as a foamy solid (1.3 g, 90%). LCMS calculated for $C_{41}H_{42}F_3N_6O_3Si$: m/z=751.3, found 751.2.

Step 6: 3-(8-(bis(4-methoxybenzyl)amino)-5-bromo-2-(((tert-butyldimethylsilyl)oxy)(2,6-difluorophenyl)methyl)-[1,2,4]triazolo[1,5-a]pyrazin-6-yl)-2-fluorobenzonitrile

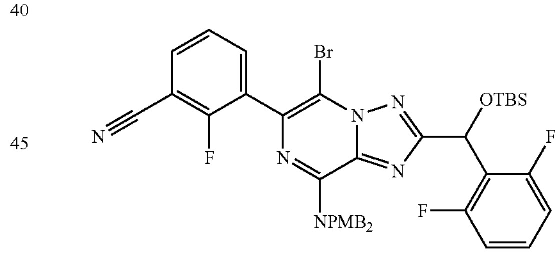

To a solution of 3-(8-(bis(4-methoxybenzyl)amino)-2-(((tert-butyldimethylsilyl)oxy)(2,6-difluorophenyl)methyl)-[1,2,4]triazolo[1,5-a]pyrazin-6-yl)-2-fluorobenzonitrile (690 mg, 0.92 mmol) in 5 mL dichloromethane, 1-bromopyrrolidine-2,5-dione (180 mg, 1.0 mmol) was added at rt The reaction mixture was stirred for overnight before it was purified by Biotage Isolera eluting with 0-30% EtOAc/Hexane to give the product as a foamy solid (700 mg, 92%). LCMS calculated for $C_{41}H_{41}BrF_3N_6O_3Si$: m/z=829.2, found 829.3.

Step 7: 3-(8-amino-2-((2,6-difluorophenyl)(hydroxy)methyl)-5-(2,6-dimethylpyridin-4-yl)-[1,2,4]triazolo[1,5-a]pyrazin-6-yl)-2-fluorobenzonitrile A mixture of 3-(8-(bis(4-methoxybenzyl)amino)-5-bromo-2-(((tert-butyldimethylsilyl)oxy)(2,6-difluorophenyl)methyl)-[1,2,4]triazolo[1,5-a]pyrazin-6-yl)-2-fluorobenzonitrile (350 mg, 0.42 mmol), (2,6-dimethylpyridin-4-yl)boronic acid (96 mg, 0.63 mmol), sodium carbonate (134 mg, 1.26 mmol) and chloro(2-dicyclohexylphosphino-2',4',6'-triisopropyl-1,1'-biphenyl)[2-(2'-amino-1,1'-biphenyl)]palladium(II) (16 mg, 0.02 mmol) in 4:1 dioxane/Water (5 mL) was stirred at 90° C. for 75 mins. The reaction mixture was diluted with dichloromethane and water and the organic solvent was removed in vacuo, the crude product was dissolved in 10 mL TFA and stirred at 80° C. for 1 hour. After TFA being removed in vacuo, the crude product was basified by sodium bicarbonate solution, and extracted with dichloromethane. The dichloromethane layer was concentrated in vacuo, and purified by Biotage Isolera to give the desired product as a racemic mixture (140 mg, 66%) The product was then separated with chiral HPLC using a chiral column (Phenomenex Lux Sum Cellulose-4, 21.2×250 mm) and 75% EtOH in hexanes (20 mL/min) solvent system. Peak 2 was isolated, and further purified by preparative LC/MS (pH=2, acetonitrile/water with TFA) to give the desired product as a TFA salt. LC-MS calculated for $C_{26}H_{19}F_3N_7O$ $(M+H)^+$: m/z=502.2; found 502.2.

Example 127. 3-(8-amino-5-(1-(methyl-d3)-6-oxo-1,6-dihydropyridazin-3-yl)-2-(pyridin-2-ylmethyl)-[1,2,4]triazolo[1,5-a]pyrazin-6-yl)benzonitrile

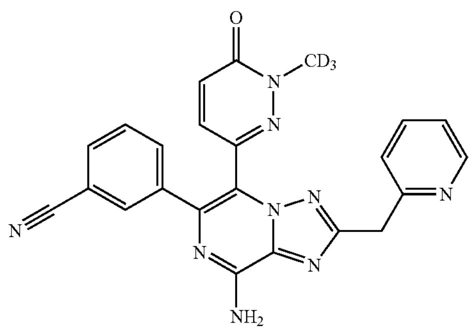 [SMILES: [2H]C([2H])([2H])n1nc(-c2c(-c3cccc(C#N)c3)nc(N)c3nc(Cc4ccccn4)nn23)ccc1=O]

Step 1: 6-bromo-2-(methyl-d3)pyridazin-3(2H)-one

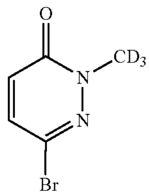 [SMILES: [2H]C([2H])([2H])n1nc(Br)ccc1=O]

To a solution of 6-bromopyridazin-3(2H)-one (1.1 g, 6.3 mmol) in 9 mL DMF, iodomethane-d3 (1.0 g, 6.91 mmol) and potassium carbonate (1.3 g, 9.4 mmol) were added at rt and stirred overnight. The resulting mixture was quenched with ammonium chloride solution and extracted with dichloromethane, after concentrated in vacuo, the crude product was purified by Biotage Isolera to afford the desired product (0.96 g, 80%) as white solid. LC-MS calculated for $C_5H_3D_3BrN_2O$ $(M+H)^+$: m/z=192.0; found 192.1.

Step 2: 2-(methyl-d3)-6-(4,4,5,5-tetramethyl-1,3,2-dioxaborolan-2-yl)pyridazin-3(2H)-one

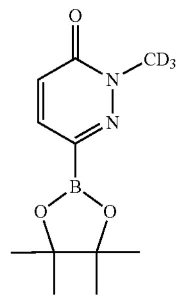 [SMILES: [2H]C([2H])([2H])n1nc(B2OC(C)(C)C(C)(C)O2)ccc1=O]

To a mixture of 6-bromo-2-(methyl-d3)pyridazin-3(2H)-one (300 mg, 1.56 mmol), potassium acetate (460 mg, 4.69 mmol), and 4,4,4',4',5,5,5',5'-octamethyl-2,2'-bi(1,3,2-dioxaborolane) (440 mg, 1.7 mmol) in dioxane (5 mL), Tetrakis(triphenylphosphine)palladium(0) (90 mg, 0.08 mmol) was added at rt, the resulting mixture was stirred at 100° C. overnight. The reaction mixture was then quenched with ammonium chloride solution and extracted with dichloromethane, after being concentrated in vacuo, the crude product was purified by Biotage Isoler, and the desired product (0.17 g, 46%) was obtained as a white solid. LC-MS calculated for $C_{11}H_{15}D_3BN_2O_3$ $(M+H)^+$: m/z=240.2; found 240.2.

Step 3: 3-(8-amino-5-(1-(methyl-d3)-6-oxo-1,6-dihydropyridazin-3-yl)-2-(pyridin-2-ylmethyl)-[1,2,4]triazolo[1,5-a]pyrazin-6-yl)benzonitrile To a mixture of 3-(8-amino-5-bromo-2-(pyridin-2-ylmethyl)-[1,2,4]triazolo[1,5-a]pyrazin-6-yl)benzonitrile (Example 27, Step 7; 20 mg, 0.05 mmol), 2-(methyl-d3)-6-(4,4,5,5-tetramethyl-1,3,2-dioxaborolan-2-yl)pyridazin-3(2H)-one (24 mg, 0.1 mmol), and sodium carbonate (20 mg, 0.2 mmol) in dioxane/water (4:1, 1.5 mL), chloro(2-dicyclohexylphosphino-2',4',6'-triisopropyl-1,1'-biphenyl)[2-(2'-amino-1,1'-biphenyl)]palladium(II) (4 mg, 0.005 mmol) (XPhos Pd G2) was added. The resulting mixture was heated at 90° C. for 1 hour. The mixture was concentrated and purified by preparative LCMS (pH 2, acetonitrile/water with TFA) to afford the desired product as TFA salt. LCMS calculated for $C_{23}H_{15}D_3N_9O$ $(M+H)^+$: m/z=439.2; found 439.2.

Example 128. 3-(8-amino-2-((6-methoxypyridin-2-yl)methyl)-5-(1-methyl-6-oxo-1,6-dihydropyridazin-3-yl)-[1,2,4]triazolo[1,5-a]pyrazin-6-yl)benzonitrile

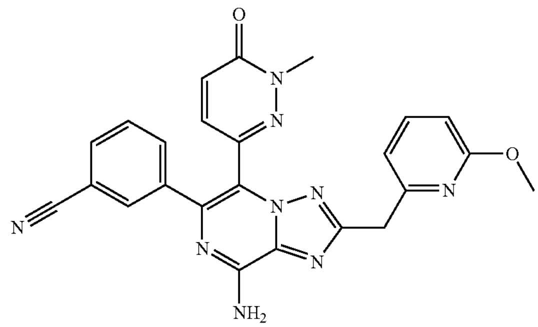 [SMILES: COc1cccc(Cc2nc3c(N)nc(-c4cccc(C#N)c4)c(-c4ccc(=O)n(C)n4)n3n2)n1]

Step 1: 6-bromo-N,N-bis(4-methoxybenzyl)-2-((6-methoxypyridin-2-yl)methyl)-[1,2,4]triazolo[1,5-a]pyrazin-8-amine

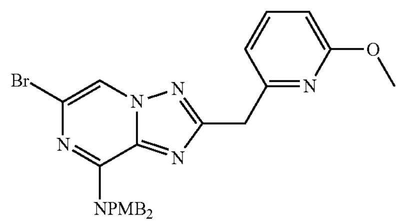

To a vial charged with 2-(6-methoxypyridin-2-yl)acetic acid (47 mg, 0.28 mmol), HATU (133 mg, 0.35 mmol) in dichloromethane 2 mL was added 1,2-diamino-3-(bis(4-methoxybenzyl)amino)-5-bromopyrazin-1-ium 2,4,6-trimethylbenzenesulfonate (example 99, step 2, 150 mg, 0.23 mmol), followed by N-ethyl-N-isopropylpropan-2-amine (90 mg, 0.7 mmol). After stirring at room temperature for 6 hours, the reaction mixture was diluted with dichloromethane and water. The organic layer was washed with brine, dried over $Na_2SO_4$, filtered and concentrated. The crude was purified with flash chromatography (eluting with a gradient 0-10% ethyl acetate in dichloromethane) to give the desired product (100 mg, 75%). LC-MS calculated for $C_{28}H_{28}BrN_6O_2$ $(M+H)^+$: m/z=575.1, 577.1; found 575.1, 577.1.

Step 2: 3-(8-(bis(4-methoxybenzyl)amino)-2-((6-methoxypyridin-2-yl)methyl)-[1,2,4]triazolo[1,5-a]pyrazin-6-yl)benzonitrile

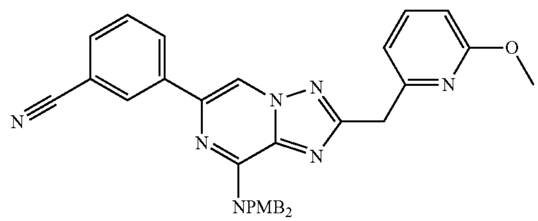

To a solution of 6-bromo-N,N-bis(4-methoxybenzyl)-2-((6-methoxypyridin-2-yl)methyl)-[1,2,4]triazolo[1,5-a]pyrazin-8-amine (75 mg, 0.13 mmol) and (3-cyanophenyl)boronic acid (29 mg, 0.2 mmol) in 2 mL 1,4-dioxane/$H_2O$=4:1, sodium carbonate (42 mg, 0.4 mmol) and chloro(2-dicyclohexylphosphino-2',4',6'-triisopropyl-1,1'-biphenyl)[2-(2'-amino-1,1'-biphenyl)]palladium(II) (3 mg, 0.004 mmol) (XPhos Pd G2) were added. The reaction mixture was heated to 90° C. and stirred for 1 hour before being diluted with dichloromethane and water. The organic layer was washed with brine, dried over $Na_2SO_4$, filtered and concentrated. The crude was purified with flash chromatography (eluting with a gradient 0-10% ethyl acetate in dichloromethane) to give the desired product (60 mg, 77%). LC-MS calculated for $C_{35}H_{32}N_7O_3$ $(M+H)^+$: m/z=598.2; found 598.2.

Step 3: 3-(8-amino-5-(1-(methyl-d3)-6-oxo-1,6-dihydropyridazin-3-yl)-2-(pyridin-2-ylmethyl)-[1,2,4]triazolo[1,5-a]pyrazin-6-yl)benzonitrile

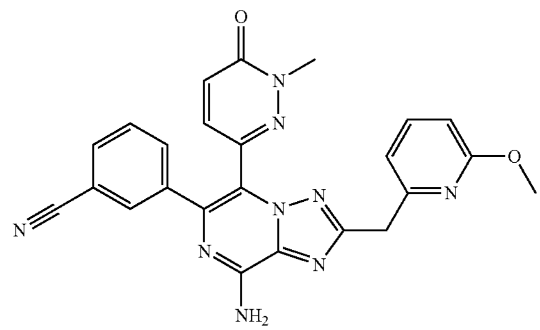 [SMILES: COc1cccc(Cc2nc3c(N)nc(-c4cccc(C#N)c4)c(-c4ccc(=O)n(C)n4)n3n2)n1]

A solution of 3-(8-(bis(4-methoxybenzyl)amino)-2-((6-methoxypyridin-2-yl)methyl)-[1,2,4]triazolo[1,5-a]pyrazin-6-yl)benzonitrile (60 mg, 0.1 mmol) in 4 mL TFA was heated to 80° C. and stirred for 20 mins. The reaction mixture was then concentrated in vacuo, basified with sodium bicarbonate solution and extracted with dichloromethane. The organic layer was concentrated to get crude product for next step. To a solution of above product in 3 mL dichloromethane, 1-bromopyrrolidine-2,5-dione (23 mg, 0.13 mmol) was added at rt and the reaction mixture was stirred for overnight before being concentrated in vacuo. The crude product was then used for next step directly without any further purification.

To a solution of the above crude product in dioxane/water (4:1, 2.0 mL), 2-methyl-6-(4,4,5,5-tetramethyl-1,3,2-dioxaborolan-2-yl)pyridazin-3(2H)-one (35 mg, 1.5 mmol), sodium carbonate (30 mg, 0.3 mmol) chloro(2-dicyclohexylphosphino-2',4',6'-triisopropyl-1,1'-biphenyl)[2-(2'-amino-1,1'-biphenyl)]palladium(II) (4 mg, 0.005 mmol) (XPhos Pd G2) was added. The resulting mixture was heated at 90° C. for 1 hour before being diluted with acetonitrile and methanol and purified by preparative LCMS (pH 2, acetonitrile/water with TFA) to afford the desired product as TFA salt. LCMS calculated for $C_{24}H_{20}N_9O_2$ $(M+H)^+$: m/z=466.2; found 466.2.

Example A. Adenosine A2A Receptor Cyclic AMP GS Assay

Stably transfected HEK-293 cells expressing the human adenosine A2A receptor (Perkin Elmer) are maintained in MEM culture medium with 10% FBS and 400 μg/mL Geneticin (Life Technologies). 18 to 24 hours prior to assay, geneticin is removed from culture. The cisbio cAMP-GS Dynamic kit utilizing the FRET (Fluorescence Resonance Energy Transfer) technology is used to measure cAMP accumulation in the cells. Compounds of the present disclosure at an appropriate concentration are mixed with 10000 cells/well in white 96 well half area plates (Perkin Elmer) for 30 min at rt gently shaking. Agonist, CGS21680 (R&D Technologies) at 4 nM is added to each well for 60 min at room temperature gently shaking. Detection reagents, d2-labeled cAMP (acceptor) and anti-cAMP cryptate (donor) are added to each well for 60 min at room temperature gently shaking. Plates are read on Pherastar (BMG Labtech), fluorescence ratio 665/620 is calculated and $EC_{50}$ determination is performed by fitting the curve of percent of control versus the log of the compound concentration using GraphPad Prism.

Example B. Adenosine A2B Receptor Cyclic AMP GS Assay

Stably transfected HEK-293 cells expressing the human adenosine A2B receptor (Perkin Elmer) were maintained in MEM culture medium with 10% FBS and 100 μg/mL Geneticin (Life Technologies). 18 to 24 hours prior to assay, geneticin was removed from culture. The cisbio cAMP-GS Dynamic kit utilizing the FRET (Fluorescence Resonance Energy Transfer) technology was used to measure cAMP accumulation in the cells. Compounds of the present disclosure at an appropriate concentration were mixed with 10000 cells/well in white 96 well half area plates (Perkin Elmer) for 30 min at room temperature gently shaking. Agonist, NECA (R&D Technologies) at 12 nM was added to each well for 60 min at room temperature gently shaking. Detection reagents, d2-labeled cAMP (acceptor) and anti-cAMP cryptate (donor) were added to each well for 60 min at rt gently shaking. Plates were read on Pherastar (BMG Labtech), fluorescence ratio 665/620 was calculated and $EC_{50}$ determination was performed by fitting the curve of percent of control versus the log of the compound concentration using GraphPad Prism. The $EC_{50}$ data for the Examples obtained via this method are shown in Table 1.

Example C. A2A Tag-Lite® HTRF Assay

Assays were conducted in black low volume 384-well polystyrene plates (Greiner 784076-25) in a final volume of 10 μL. Test compounds were first serially diluted in DMSO and 100 nl added to the plate wells before the addition of other reaction components. The final concentration of DMSO was 1%. Tag-Lite® Adenosine A2A labeled cells (CisBio C1TT1A2A) were diluted 1:5 into Tag-lite buffer (CisBio LABMED) and spun 1200 g for 5 mins. The pellet was resuspended at a volume 10.4× the initial cell suspension volume in Tag-lite buffer, and Adenosine A2A Receptor Red antagonist fluorescent ligand (CisBio L0058RED) added at 12.5 nM final concentration. 10 ul of the cell and ligand mix was added to the assay wells and incubated at room temperature for 45 minutes before reading on a PHERAstar FS plate reader (BMG Labtech) with HTRF 337/620/665 optical module. Percent binding of the fluorescent ligand was calculated; where 100 nM of A2A antagonist control ZM 241385 (Tocris 1036) displaces the ligand 100% and 1% DMSO has 0% displacement. The % binding data versus the log of the inhibitor concentration was fitted to a one-site competitive binding model (GraphPad Prism version 7.02) where the ligand constant=12.5 nM and the ligand Kd=1.85 nM. The $K_i$ data for the Examples obtained via this method are shown in Table 1.

Example D. A2B Filter Binding Assay

Assays are conducted in deep well polypropylene plates (Greiner 786201) in a final volume of 550 μL. Test compounds are first serially diluted in DMSO and 5.5 ul is then added to the plate wells before the addition of other reaction components. The final concentration of DMSO is 3%. HEK293 cell membranes overexpressing the human adenosine receptor A2B (Perkin Elmer ES-113-M400UA) are diluted to 40 μg/mL in 50 mM HEPES pH 7.0, 5 mM $MgCl_2$, 1 mM EDTA (Assay buffer). [3H] 8-cyclopentyl-1,3-dipropylxanthine (Perkin Elmer NET974001MC) is diluted in assay buffer+22% DMSO to 24.2 nM, and then further diluted to 1 nM by addition to the diluted membranes. 545 μl of the membrane and ligand mix is added to the assay wells and incubated on a shaker at room temperature for 1 hour. The membrane mix is then filtered over a UniFilter GF/C filter plate (Perkin Elmer 6005174) pre-soaked in 50 mM HEPES pH 6.5, 5 mM $MgCl_2$, 1 mM EDTA 0.5% BSA and then washed with 5 mL ice cold 50 mM HEPES pH 6.5, 5 mM $MgCl_2$, 1 mM EDTA 0.2% BSA. 50 μl MicroScint™ cocktail (Perkin Elmer 6013621) is added and plates are read on a Topcount NXT FS (Perkin Elmer). Percent binding of the [3H] ligand is calculated, where 1000 nM of LUF 5834 (Tocris 4603) control displaces the ligand 100% and 3% DMSO has 0% displacement. The % binding data versus the log of the inhibitor concentration is fitted to a one-site competitive binding model (GraphPad Prism version 7.02) where the ligand constant=2 nM and the ligand Kd=13 nM.

Example E. A1 and A3 SPA Binding Assays

Both assays are conducted in white 384-well polystyrene plates (Greiner 781075) in a final volume of 50 μL. Inhibitors are first serially diluted in DMSO and 100 nL is added to the plate wells before the addition of other reaction components. The final concentration of DMSO is 2%.

Wheatgerm agglutinin-coated yttrium silicate SPA beads (Perkin Elmer RPNQ0023) and CHO-K1 cell membranes overexpressing each human adenosine receptor are incubated in 50 mM HEPES pH 7.0, 5 mM $MgCl_2$, 1 mM EDTA (Assay buffer) on a rotary stirrer for 2 hours at 4° C. The beads are pelleted by centrifugation at 6000 g for one minute, and then the supernatant with unbound membrane is discarded. The beads are re-suspended to the original volume in assay buffer. Each radioligand is diluted in assay buffer+22% DMSO at 12.2× the final concentration, and then added to the SPA bead suspension. 50 μl of the SPA bead reaction mix is added to the assay wells and the plates shaken at 600 rpm for 1 hour at room temperature. The beads are then allowed to settle for 1 hour before reading on a Topcount NXT FS (Perkin Elmer). Percent binding of the radiolabeled ligand is calculated, where a control at >100× Ki displaces the ligand 100% and 2% DMSO has 0% displacement. The % binding data versus the log of the inhibitor concentration is fitted to a one-site competitive binding model (GraphPad Prism version 7.02). Assay conditions are provided in Table A below.

TABLE A

| Assay Component | A1 | A3 |
|---|---|---|
| SPA beads in Hepes buffer | 3 mg/mL | 1.25 mg/mL |
| Membrane | 60 μg/mL Perkin Elmer ES-010 | 20 μg/mL Perkin Elemer ES-012 |
| Radioligand | 1 nM [3H] DP-CPX (Perkin Elmer NET974) $K_D$ = 1 nM | 0.1 nM [125I] MECA (Perkin Elmer NEX312) $K_D$ = 0.8 nM |
| Control | 1 μM DPCPX (Tocris 0439) | 0.1 μM IB-MECA (Tocris 1066) |

The $A_{2A}$_Ki data and $A_{2B}$_cAMP_$EC_{50}$ data are provided below. The symbol "†" indicates $A_{2A}$_Ki or $A_{2B}$_cAMP_$EC_{50}$≤10 nM, "††" indicates $A_{2A}$_Ki or $A_{2B}$_cAMP_$EC_{50}$>10 nM but ≤100 nM. "†††" indicates $A_{2A}$_Ki or $A_{2B}$_cAMP_$EC_{50}$>100 nM but ≤1 μM; and "††††" indicates $A_{2A}$_Ki or $A_{2B}$_cAMP_$EC_{50}$ is greater than 1 μM.

TABLE 1

| Ex. No. | $A_{2A}$_Ki (nM) | $A_{2B}$_cAMP_$EC_{50}$ (nM) |
|---|---|---|
| 1 | † | †† |
| 2 | † | †† |
| 3 | † | ††† |
| 4 | † | †† |
| 5 | † | ††† |
| 6 | †† | †††† |
| 7 | † | † |
| 8 | † | †† |
| 9 | † | †† |
| 10 | † | † |
| 11 | † | † |
| 12 | † | †† |
| 13 | †† | ††† |
| 14 | †† | †††† |
| 15 | † | † |
| 16 | † | † |
| 17 | † | † |
| 18 | † | † |
| 19 | † | †† |
| 20 | † | † |
| 21 | † | ††† |
| 22 | † | ††† |
| 23 | † | † |
| 24 | † | †† |
| 25 | † | †† |
| 26 | † | †† |
| 27 | † | † |
| 28 | † | †† |
| 29 | † | † |
| 30 | † | †† |
| 31 | † | †† |
| 32 | † | † |
| 33 | † | † |
| 34 | † | †† |
| 35 | † | † |
| 36 | † | † |
| 37 | † | † |
| 38 | † | † |
| 39 | † | † |
| 40 | † | † |
| 41 | † | † |
| 42 | † | † |
| 43 | † | † |
| 44 | † | † |
| 45 | † | † |
| 46 | † | † |
| 47 | † | †† |
| 48 | † | †† |
| 49 | † | † |
| 50 | † | † |
| 51 | † | † |
| 52 | † | † |
| 53 | † | † |
| 54 | † | † |
| 55 | † | † |
| 56 | † | † |
| 57 | † | † |
| 58 | † | † |
| 59 | † | †† |
| 60 | † | †† |
| 61 | † | † |
| 62 | † | † |
| 63 | † | † |
| 64 | † | † |
| 65 | † | †† |
| 66 | † | † |
| 67 | † | † |
| 68 | † | †† |
| 69 | † | † |
| 70 | † | †† |
| 71 | † | † |
| 72 | † | † |
| 73 | † | † |
| 74 | † | † |
| 75 | † | † |
| 76 | † | †† |
| 77 | † | † |
| 78 | † | † |
| 79 | † | † |
| 80 | † | † |
| 81 | † | † |
| 82 | † | † |
| 83 | † | † |
| 84 | † | † |
| 85 | † | †† |
| 86 | † | † |
| 87 | † | †† |
| 88 | † | †† |
| 89 | † | †† |
| 90 | † | ††† |
| 91 | † | †† |
| 92 | † | † |
| 93 | † | † |
| 94 | † | †† |
| 95 | † | †† |
| 96 | † | †† |
| 97 | † | † |
| 98 | † | † |
| 99 | † | †† |
| 100 | † | ††† |
| 101 | † | † |
| 102 | † | † |
| 103 | † | † |
| 104 | † | †† |
| 105 | † | † |
| 106 | † | † |
| 107 | † | †† |
| 108 | † | † |
| 109 | † | † |
| 110 | † | ††† |
| 111 | † | † |
| 112 | † | † |
| 113 | † | †† |
| 114 | † | †† |
| 115 | † | † |
| 116 | † | †† |
| 117 | † | † |
| 118 | † | † |
| 119 | † | † |
| 120 | † | †† |
| 121 | † | †† |
| 122 | † | †† |
| 123 | † | †† |
| 124 | † | † |
| 125 | † | †† |
| 126 | † | †† |
| 127 | † | † |
| 128 | † | †† |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

(I)

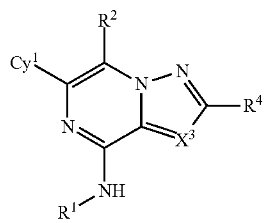

or a pharmaceutically acceptable salt thereof, wherein:

$R^1$ is selected from H, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, and $C_{1-6}$ haloalkyl of $R^1$ are each optionally substituted with 1, 2, 3, or 4 independently selected $R^{1A}$ substituents;

each $R^{a1}$, $R^{b1}$, $R^{e1}$, and $R^{d1}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl of $R^{a1}$, $R^{b1}$, $R^{e1}$, and $R^{d1}$ are each optionally substituted with 1, 2, 3, or 4 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{1A}$ is independently selected from OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

$X^3$ is N or $CR^3$;

$R^3$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl) carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$Cy^1$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^1$ are each optionally substituted with 1, 2, 3, 4, 5, or 6 independently selected $R^7$ substituents;

each $R^7$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NOH)R^{b7}$, $C(=NCN)R^{b7}$, $C(=NR^{e7})NR^{c7}R^{d7}$, $NR^{c7}C(=NR^{e7})NR^{c7}R^{d7}$, $NR^{c7}C(=NOH)NR^{c7}R^{d7}$, $NR^{c7}C(=NCN)NR^{c7}R^{d7}$, $NR^{c7}C(=NR^{e7})R^{b7}$, $NR^{c7}S(O)NR^{c7}R^{d7}$, $NR^{c7}S(O)R^{b7}$, $NR^{c7}S(O)_2R^{b7}$ $NR^{c7}S(O)(=NR^{e7})R^{b7}$, $NR^{c7}S(O)_2NR^{c7}R^{47}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^7$ are each optionally substituted with 1, 2, 3, or 4 independently selected $R^{7A}$ substituents;

each $R^{a7}$, $R^{b7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a7}$, $R^{b7}$, $R^{c7}$ and $R^{d7}$ are each optionally substituted with 1, 2, 3, or 4 independently selected $R^{7A}$ substituents;

or, any $R^{c7}$ and $R^{d7}$, attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy- $C_{1-6}$ alkyl, $C_{3-5}$ cycloalkyl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-4}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, C(O) $NR^{e2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})\ R^{b2}$, C(=NOH) $R^{b2}$, C(=NCN) $R^{b2}$, $C(=NR^{e2})\ NR^{c2}R^{d2}$, $NR^{c2}C(=NR^{e2})\ NR^{c2}R^{d2}$, $NR^{c2}C(=NOH)NR^{c2}R^{d2}$, $NR^{c2}C(=NCN)NR^{c2}R^{d2}$, $NR^{c2}C(=NR^{e2})\ R^{b2}$, $NR^{c2}S(O)\ NR^{c2}R^{d2}$, $NR^{c2}S(O)\ R^{b2}$, $NR^{c2}S(O)_2R^{b2}$, $NR^{c2}S(O)\ (=NR^{e2})\ R^{b2}$, $NR^{c2}S(O)_2NR^{c2}R^{d2}$, S(O) $R^{b2}$, S(O) $NR^{c2}R^{d2}$, $S(O)_2R^{b2}$, $S(O)_2NR^{c2}R^{d2}$, OS(O) $(=NR^{e2})\ R^{b2}$, $OS(O)_2R^{b2}$, $SF_5$, P(O) $R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, or 6 independently selected $R^{2A}$ substituents;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, C(O) $NR^{c4}\ (OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)\ R^{b4}$, $NR^{c4}C(O)OR^{a4}$, $NR^{c4}C(O)NR^{c4}R^{d4}$, $C(=NR^{e4})\ R^{b4}$, C(=NOH) $R^{b4}$, C(=NCN) $R^{b4}$, $C(=NR^{e4})\ NR^{c4}R^{d4}$, $NR^{c4}C(=NR^{e4})NR^{c4}R^{d4}$, $NR^{c4}C(=NOH)NR^{c4}R^{d4}$, $NR^{c4}C(=NCN)\ NR^{c4}R^{d4}$, $NR^{c4}C(=NR^{e4})\ R^{b4}$, $NR^{c4}S(O)\ NR^{c4}R^{d4}$, $NR^{c4}S(O)\ R^{b4}$, $NR^{c4}S(O)_2R^{b4}$, $NR^{c4}S(O)\ (=NR^{e4})\ R^{b4}$, $NR^{c4}S(O)_2NR^{c4}R^{d4}$, S(O) $R^{b4}$, S(O) $NR^{c4}R^{d4}$, $S(O)_2R^{b4}$, $S(O)_2NR^{c4}R^{d4}$, OS(O) $(=NR^{e4})\ R^{b4}$, $OS(O)_2R^{b4}$, $SF_5$, P(O) $R^{f4}R^{g4}$, $OP(O)(OR^{h4})(OR^{i4})$, P(O) $(OR^{h4})\ (OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents;

provided that:

(a) when $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, 4, 5, or 6 independently selected $R^{2A}$ substituents;

then $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$ $SR^{a4}$, $NHOR^{a4}$, $C(O)R^{b4}$, $C(O)NR^{c4}R^{d4}$, $C(O)NR^{c4}\ (OR^{a4})$, $C(O)OR^{a4}$, $OC(O)R^{b4}$ $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)\ OR^{a4}$, $NR^{c4}C(O)NR^{c4}R^{d4}$, $C(=NR^{e4})\ R^{b4}$, C(=NOH) $R^{b4}$, C(=NCN) $R^{b4}$, $C(=NR^{e4})\ NR^{c4}R^{d4}$, $NR^{c4}C(=NR^{e4})\ NR^{c4}R^{d4}$, $NR^{c4}C(=NOH)NR^{c4}R^{d4}$, $NR^{c4}C(=NCN)\ NR^{c4}R^{d4}$, $NR^{c4}C(=NR^{e4})\ R^{b4}$, $NR^{c4}S(O)\ NR^{c4}R^{d4}$, $NR^{c4}S(O)\ R^{b4}$, $NR^{c4}S(O)_2R^{b4}$, $NR^{c4}S(O)\ (=NR^{e4})\ R^{b4}$, $NR^{c4}S(O)_2NR^{c4}R^{d4}$, S(O) $R^{b4}$, S(O) $NR^{c4}R^{d4}$, $S(O)_2R^{b4}$, $S(O)_2NR^{c4}R^{d4}$, OS(O) $(=NR^{e4})\ R^{b4}$, $OS(O)_2R^{b4}$, $SF_5$, P(O) $R^{f4}R^{g4}$, OP(O) $(OR^{h4})\ (OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents;

or, alternatively, (b) when $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})\ R^{b2}$, C(=NOH) $R^{b2}$, C(=NCN) $R^{b2}$, $C(=NR^{e2})\ NR^{c2}R^{d2}$, $NR^{c2}C(=NR^{e2})\ NR^{c2}R^{d2}$, $NR^{c2}C(=NOH)NR^{c2}R^{d2}$, $NR^{c2}C(=NCN)\ NR^{c2}R^{d2}$ $NR^{c2}C(=NR^{c2})\ R^{b2}$, $NR^{c2}S(O)\ NR^{c2}R^{d2}$, $NR^{c2}S(O)\ R^{b2}$, $NR^{c2}S(O)_2R^{b2}$, $NR^{c2}S(O)\ (=NR^{e2})\ R^{b2}$, $NR^{c2}S(O)_2NR^{c2}R^{d2}$, S(O) $R^{b2}$, S(O) $NR^{c2}R^{d2}$, $S(O)_2R^{b2}$, $S(O)_2NR^{c2}R^{d2}$, OS(O) $(=NR^{e2})\ R^{b2}$, $OS(O)_2R^{b2}$, $SF_5$, P(O) $R^{f2}R^{g2}$, OP(O) $(OR^{h2})\ (OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, or 6 independently selected $R^{2A}$ substituents;

then $R^4$ is selected from halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}\ (OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)\ R^{b4}$, $NR^{c4}C(O)OR^{a4}$, $NR^{c4}C(O)\ NR^{c4}R^{d4}$, $C(=NR^{e4})\ R^{b4}$, C(=NOH) $R^{b4}$, C(=NCN) $R^{b4}$, $C(=NR^{e4})\ NR^{c4}R^{d4}$, $NR^{c4}C(=NR^{e4})\ NR^{c4}R^{d4}$, $NR^{c4}C(=NOH)NR^{c4}R^{d4}$, $NR^{c4}C(=NCN)\ NR^{c4}R^{d4}$, $NR^{c4}C(=NR^{e4})\ R^{b4}$, $NR^{c4}S(O)\ NR^{c4}R^{d4}$, $NR^{c4}S(O)\ R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{84}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, or 6 independently selected $R^{4A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$ and $R^{d2}$ are each optionally substituted with 1, 2, 3, 4, 5, or 6 independently selected $R^{2A}$ substituents;

or, any $R^{c2}$ and $R^{d2}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$ $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NOH)R^{b21}$, $C(=NCN)R^{b21}$, $C(=NR^{e21})NR^{c21}R^{d21}$, $NR^{c21}C(=NR^{e21})$ $NR^{c21}R^{d21}$, $NR^{c21}C(=NOH)NR^{c21}R^{d21}$, $NR^{c21}C(=NCN)NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{e21}R^{d21}$, $OS(O)(=NR^{e21})R^{b21}$, $OS(O)_2R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{b21}$, $R^{c21}$ and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$ and $R^{d21}$ are each optionally substituted with 1, 2, 3, or 4 independently selected $R^{2B}$ substituents;

or, any $R^{c21}$ and $R^{d21}$, attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f21}$ and $R^{g21}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}$ ($OR^{a22}$), C(O) $OR^{a22}$, $OC(O)R^{b22}$, $OC(O)NR^{e22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, C(=$NR^{e22}$) $R^{b22}$, C(=NOH) $R^{b22}$, C(=NCN) $R^{b22}$, C(=$NR^{e22}$) $NR^{c22}R^{d22}$, $NR^{c22}$C(=$NR^{e22}$) $NR^{c22}R^{d22}$, $NR^{c22}$C(=NOH) $NR^{c22}R^{d22}$, $NR^{c22}$C(=NCN) $NR^{c22}R^{d22}$, $NR^{c22}$C (=$NR^{e22}$) $R^{b22}$, $NR^{c22}$S(O) $NR^{c22}R^{422}$, $NR^{c22}$S(O) $R^{b22}$, $NR^{c22}S(O)_2R^{b22}$, $NR^{c22}$S(O) (=$NR^{e22}$) $R^{b22}$, $NR^{c22}S(O)_2NR^{c22}R^{d22}$, S(O) $R^{b22}$, S(O) $NR^{c22}R^{d22}$, $S(O)_2R^{b22}$, $S(O)_2NR^{c22}R^{d22}$, OS(O) (=$NR^{c22}$) $R^{b22}$, $OS(O)_2R^{b22}$, $SF_5$, P(O) $R^{f22}R^{g22}$, OP(O) ($OR^{h22}$) ($OR^{i22}$), P(O) ($OR^{h22}$) ($OR^{i22}$), and $BR^{j22}R^{k22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{b22}$, $R^{c22}$ and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{b22}$, $R^{c22}$ and $R^{d22}$ are each optionally substituted with 1, 2, 3, or 4 independently selected $R^{2C}$ substituents;

or, any $R^{c22}$ and $R^{d22}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f22}$ and $R^{g22}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h22}$ and $R^{i22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, each $R^{j22}$ and $R^{k22}$ is independently selected from OH, $C_{1-6}$ alkoxy, and $C_{1-6}$ haloalkoxy;

or any $R^{j22}$ and $R^{k22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2C}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl) carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$ and $R^{d4}$ are each optionally substituted with 1, 2, 3, 4, 5, or 6 independently selected $R^{4A}$ substituents;

or, any $R^{c4}$ and $R^{d4}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}$ $(OR^{a41})$, C(O) $OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})$ $R^{b41}$, C(=NOH) $R^{b41}$, C(=NCN) $R^{b41}$, $C(=NR^{e41})$ $NR^{c41}R^{d41}$, $NR^{c41}C(=NR^{e41})$ $NR^{c41}R^{d41}$, $NR^{c41}C(=NOH)$ $NR^{c41}R^{d41}$, $NR^{c41}C(=NCN)$ $NR^{c41}R^{d41}$, $NR^{c41}C$ $(=NR^{e41})$ $R^{b41}$, $NR^{c41}S(O)$ $NR^{c41}R^{d41}$, $NR^{c41}S(O)$ $R^{b41}$, $NR^{c41}S(O)_2R^{b41}$, $NR^{c41}S(O)$ $(=NR^{e41})$ $R^{b41}$ $NR^{c41}S(O)_2NR^{c41}R^{d41}$, S(O) $R^{b41}$, S(O) $NR^{c41}R^{d41}$, $S(O)_2R^{b41}$, $S(O)_2NR^{c41}R^{d41}$, OS(O) $(=NR^{e41})$ $R^{b41}$, $OS(O)_2R^{b41}$, $SF_5$, P(O) $R^{f41}R^{g41}$, OP(O) $(OR^{h41})$ $(OR^{i41})$, P(O) $(OR^{h41})$ $(OR^{i41})$, and $BR^{j41}R^{k41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, 4, 5, or 6 independently selected $R^{4B}$ substituents;

each $R^{a41}$, $R^{b41}$, $R^{c41}$ and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{b41}$, $R^{c41}$ and $R^{d41}$ are each optionally substituted with 1, 2, 3, 4, 5, or 6 independently selected $R^{4B}$ substituents;

or, any $R^{c41}$ and $R^{d41}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f41}$ and $R^{g41}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h41}$ and $R^{i41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j41}$ and $R^{k41}$ is independently selected from OH, $C_{1-6}$ alkoxy, and $C_{1-6}$ haloalkoxy;

or any $R^{j41}$ and $R^{k41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}$ $(OR^{a42})$, C(O) $OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})$ $R^{b42}$, C(=NOH) $R^{b42}$, C(=NCN) $R^{b42}$, $C(=NR^{e42})$ $NR^{c42}R^{d42}$, $NR^{c42}C(=NR^{e42})$ $NR^{c42}R^{d42}$, $NR^{c42}C(=NOH)$ $NR^{c42}R^{d42}$, $NR^{c42}C(=NCN)$ $NR^{c42}R^{d42}$, $NR^{c42}C$ $(=NR^{e42})$ $R^{b42}$, $NR^{c42}S(O)$ $NR^{c42}R^{d42}$, $NR^{c42}S(O)$ $R^{b42}$, $NR^{c42}S(O)_2R^{b42}$, $NR^{c42}S(O)$ $(=NR^{e42})$ $R^{b42}$, $NR^{c42}S(O)_2NR^{c42}R^{d42}$, S(O) $R^{b42}$, S(O) $NR^{c42}R^{d42}$, $S(O)_2R^{b42}$, $S(O)_2NR^{c42}R^{d42}$, OS(O) $(=NR^{e42})$ $R^{b42}$, $OS(O)_2R^{b42}$, $SF_5$, P(O) $R^{f42}R^{g42}$, OP(O) $(OR^{h42})$ $(OR^{i42})$, P(O) $(OR^{h42})$ $(OR^{i42})$, and $BR^{j42}R^{k42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, or 4 independently selected $R^{4C}$ substituents;

each $R^{a42}$, $R^{b42}$, $R^{c42}$ and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{b42}$, $R^{e42}$ and $R^{d42}$ are each optionally substituted with 1, 2, 3, or 4 independently selected $R^{4C}$ substituents;

or, any $R^{c42}$ and $R^{d42}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f42}$ and $R^{g42}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h42}$ and $R^{i42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j42}$ and $R^{k42}$ is independently selected from OH, $C_{1-6}$ alkoxy, and $C_{1-6}$ haloalkoxy;

or any $R^{j42}$ and $R^{k42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}$ $(OR^{a43})$, $C(O)OR^{a43}$, $OC(O)R^{b43}$, $OC(O)NR^{c43}R^{d43}$, $NR^{c43}R^{d43}$, $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})$ $R^{b43}$, $C(=NOH)$ $R^{b43}$, $C(=NCN)$ $R^{b43}$, $C(=NR^{e43})$ $NR^{c43}R^{d43}$, $NR^{c43}C(=NR^{e43})$ $NR^{c43}R^{d43}$, $NR^{c43}C(=NOH)$ $NR^{c43}R^{d43}$, $NR^{c43}C(=NCN)$ $NR^{c43}R^{d43}$, $NR^{c43}C$ $(=NR^{e43})$ $R^{b43}$, $NR^{c43}S(O)$ $NR^{c43}R^{d43}$, $NR^{c43}S(O)$ $R^{b43}$, $NR^{c43}S(O)_2R^{b43}$, $NR^{c43}S(O)$ $(=NR^{e43})$ $R^{b43}$ $NR^{c43}S(O)_2NR^{c43}R^{d43}$, $S(O)$ $R^{b43}$, $S(O)$ $NR^{c43}R^{d43}$, $S(O)_2R^{b43}$, $S(O)_2NR^{c43}R^{d43}$, $OS(O)$ $(=NR^{e43})$ $R^{b43}$, $OS(O)_2R^{b43}$, $SF_5$, $P(O)$ $R^{f43}R^{g43}$, $OP(O)$ $(OR^{h43})$ $(OR^{i43})$, $P(O)$ $(OR^{h43})$ $(OR^{i43})$, and $BR^{j43}R^{k43}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4C}$ are each optionally substituted with 1, 2, 3, or 4 independently selected $R^{4D}$ substituents;

each $R^{a43}$, $R^{b43}$, $R^{c43}$ and $R^{d43}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a43}$, $R^{b43}$, $R^{c43}$ and $R^{d43}$ are each optionally substituted with 1, 2, 3, or 4 independently selected $R^{4D}$ substituents;

or, any $R^{c43}$ and $R^{d43}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{4D}$ substituents;

each $R^{e43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f43}$ and $R^{g43}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h43}$ and $R^{i43}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j43}$ and $R^{k43}$ is independently selected from OH, $C_{1-6}$ alkoxy, and $C_{1-6}$ haloalkoxy;

or any $R^{j43}$ and $R^{k43}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4D}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, (4-7 membered heterocycloalkyl)-$C_{1-6}$ alkyl-, CN, $NO_2$, $OR^{a44}$, $SR^{a44}$, $NHOR^{a44}$, $C(O)R^{b44}$, $C(O)NR^{c44}R^{d44}$, $C(O)NR^{c44}$ $(OR^{a44})$, $C(O)OR^{a44}$, $OC(O)R^{b44}$, $OC(O)NR^{c44}R^{d44}$, $NR^{c44}R^{d44}$, $NR^{c44}NR^{c44}R^{d44}$, $NR^{c44}C(O)R^{b44}$, $NR^{c44}C(O)OR^{a44}$, $NR^{c44}C(O)NR^{c44}R^{d44}$, $C(=NR^{e44})$ $R^{b44}$, $C(=NOH)$ $R^{b44}$, $C(=NCN)$ $R^{b44}$, $C(=NR^{e44})$ $NR^{c44}R^{d44}$, $NR^{c44}C$ $(=NR^{e44})$ $NR^{c44}R^{d44}$, $NR^{c44}C(=NOH)NR^{c44}R^{d44}$, $NR^{c44}C(=NCN)$ $NR^{c44}R^{d44}$, $NR^{c44}C(=NR^{e44})$ $R^{b44}$, $NR^{c44}S(O)$ $NR^{c44}R^{d44}$, $NR^{c44}S(O)$ $R^{b44}$, $NR^{c44}S(O)_2R^{b44}$, $NR^{c44}S(O)$ $(=NR^{e44})$ $R^{b44}$, $NR^{c44}S(O)_2NR^{c44}R^{d44}$, $S(O)$ $R^{b44}$, $S(O)$ $NR^{c44}R^{d44}$, $S(O)_2R^{b44}$, $S(O)_2NR^{c44}R^{d44}$, $OS(O)$ $(=NR^{e44})$ $R^{b44}$, $OS(O)_2R^{b44}$, $SF_5$, $P(O)$ $R^{f44}R^{844}$, $OP(O)$ $(OR^{h44})$ $(OR^{i44})$, $P(O)$ $(OR^{h44})$ $(OR^{i44})$, and $BR^{j44}R^{k44}$, wherein the $C_{1-6}$ alkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl- of $R^{4D}$ are each optionally substituted with 1, 2, 3, or 4 independently selected $R^{4E}$ substituents;

each $R^{a44}$, $R^{b44}$, $R^{c44}$ and $R^{d44}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl- of $R^{a44}$, $R^{b44}$, $R^{c44}$ and $R^{d44}$ are each optionally substituted with 1, 2, 3, or 4 independently selected $R^{4E}$ substituents;

or, any $R^{c44}$ and $R^{d44}$, attached to the same N atom, together with the N atom to which they are attached, form a 4-, 5-, 6-, or 7-membered heterocycloalkyl group, wherein the 4-, 5-, 6-, or 7-membered heterocycloalkyl group is optionally substituted with 1, 2, 3, or 4 independently selected $R^{4E}$ substituents;

each $R^{e44}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f44}$ and $R^{g44}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl-;

each $R^{h44}$ and $R^{i44}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl-, and (4-7 membered heterocycloalkyl)-$C_{1-6}$ alkyl-;

each $R^{j44}$ and $R^{k44}$ is independently selected from OH, $C_{1-6}$ alkoxy, and $C_{1-6}$ haloalkoxy;

or any $R^{j44}$ and $R^{k44}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{4E}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl) carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_1$-3 alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

2. The compound of claim 1, or a pharmaceutically acceptable salt thereof, wherein 1, 2, 3, 4, 5, 6, 7, or 8 hydrogen atoms, attached to carbon atoms of any alkyl, alkenyl, alkynyl, aryl, cycloalkyl, heterocycloalkyl, or heteroaryl substituents or —$C_{1-6}$ alkyl-, alkylene, alkenylene, and alkynylene linking groups, are each optionally replaced by a deuterium atom.

3. The compound of claim 1, which is a compound of Formula (IIa):

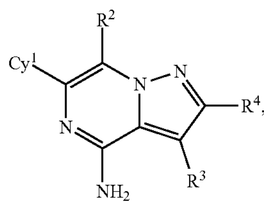

(IIa)

or a pharmaceutically acceptable salt thereof.

4. The compound of claim 1, or a pharmaceutically acceptable salt thereof, wherein $R^3$ is CN or H.

5. The compound of claim 1, or a pharmaceutically acceptable salt thereof, wherein $R^3$ is H.

6. The compound of claim 1, or a pharmaceutically acceptable salt thereof, wherein $R^2$ is selected from phenyl, $C_{3-7}$ cycloalkyl, 5-6 membered heteroaryl and 4-7 membered heterocycloalkyl, wherein the phenyl, $C_{3-7}$ cycloalkyl, 5-6 membered heteroaryl and 4-7 membered heterocycloalkyl of $R^2$ are each optionally substituted with 1, 2, or 3 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a21}$, $SR^{a21}$, $NHOR^{a21}$, $C(O)R^{b21}$, $C(O)NR^{e21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{e21}R^{d21}$, $S(O)R^{b21}$, and $S(O)_2R^{b21}$, wherein said phenyl, $C_{3-7}$ cycloalkyl, 5-6 membered heteroaryl and 4-7 membered heterocycloalkyl of $R^{2A}$ are optionally substituted with 1, 2, or 3 independently selected $R^{2B}$ substituents;

each $R^{a21}$, $R^{b21}$, $R^{c21}$, and $R^{d21}$ is independently selected from H, $C_{1-6}$ alkyl, and $C_{1-6}$ haloalkyl; and each $R^{2B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

7. The compound of claim 1, or a pharmaceutically acceptable salt thereof, wherein $R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents;

each $R^{2A}$ is independently selected from halo, $C_{1-4}$ alkyl, $C_{1-4}$ haloalkyl, and $C(O)NR^{c21}R^{d21}$, wherein said $C_{1-4}$ alkyl of $R^{2A}$ is optionally substituted with 1, 2, or 3 independently selected $R^{2B}$ substituents;

each $R^{a21}$, $R^{b21}$, $R^{c21}$, and $R^{d21}$ is independently selected from H, $C_{1-6}$ alkyl, and $C_{1-6}$ haloalkyl; and each $R^{2B}$ is independently selected from halo and OH.

8. The compound of claim 1, or a pharmaceutically acceptable salt thereof, wherein $R^2$ is selected from cyclopropyl, oxazolyl, triazolyl, pyrazolyl, pyridyl, pyrimidinyl, dihydropyridin-(2H)-yl, and pyridinonyl, each of which is optionally substituted with 1 or 2 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, and $S(O)\ R^{b21}$, wherein said $C_{1-6}$ alkyl of $R^{2A}$ is optionally substituted with 1, 2, or 3 independently selected $R^{2B}$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl; and each $R^{2B}$ is independently selected from halo and OH.

9. The compound of claim 1, or a pharmaceutically acceptable salt thereof, wherein $R^2$ is selected from 1-(trifluoromethyl)cycloprop-1-yl, 1-ethyl-1H-pyrazol-5-yl, 1-propyl-1H-pyrazol-5-yl, 1-methyl-6-oxo-1,6-dihydropyridin-3-yl, pyrimidin-4-yl, 3,6-dihydropyridin-4-yl-1 (2H)-carboxamide, pyridin-4-yl, 4-(1-hydroxyethyl)-2-methyloxazol-5-yl, 2,2-difluoro-1-hydroxyethyl)-2-methyloxazol-5-yl, 1-ethyl-1H-1,2,3-triazol-5-yl, and 1-methyl-1H-1,2,3-triazol-5-yl.

10. The compound of claim 1, or a pharmaceutically acceptable salt thereof, wherein $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)\ OR^{a4}$, $NR^{c4}C(O)\ NR^{c4}R^{d4}$, $S(O)\ R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, phenyl, $C_{3-7}$ cycloalkyl, 5-6 membered heteroaryl, and 4-7 membered heterocycloalkyl, wherein said $C_{1-6}$ alkyl, phenyl, $C_{3-7}$ cycloalkyl, 5-6 membered heteroaryl, and 4-7 membered heterocycloalkyl of $R^{a4}$, $R^{b4}$, $R^{c4}$, and $R^{d4}$ are each optionally substituted by 1, 2, or 3 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{4A}$ are each optionally substituted by 1 or 2 independently selected $R^{4B}$ substituents;

each $R^{a41}$, $R^{b41}$, $R^{c41}$, and $R^{d41}$ is independently selected from H, $C_{1-6}$ alkyl, and $C_{1-6}$ haloalkyl, wherein said $C_{1-6}$ alkyl of $R^{a41}$, $R^{b41}$, $R^{c41}$, and $R^{d41}$ is optionally substituted by 1, 2, or 3 independently selected $R^{4B}$ substituents; and each $R^{4B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

11. The compound of claim 1, or a pharmaceutically acceptable salt thereof, wherein $R^4$ is selected from phenyl, 5-6 membered heteroaryl, 4-7 membered heterocycloalkyl, phenyl-$C_{1-3}$ alkyl-, (5-10 membered heteroaryl)-$C_{1-3}$ alkyl-, (4-7 membered heterocycloalkyl)-$C_{1-3}$ alkyl-, $C(O)R^{b4}$, $C(O)NR^{c4}R^{d4}$, and $NR^{c4}R^{d4}$, wherein the phenyl, 5-6 membered heteroaryl, 4-7 membered heterocycloalkyl, phenyl-$C_{1-3}$ alkyl-, (5-10 membered heteroaryl)-$C_{1-3}$ alkyl-, and (4-7 membered heterocycloalkyl)-$C_{1-3}$ alkyl- of $R^4$ are each optionally substituted with 1 or 2 independently selected $R^{4A}$ substituents;

each $R^{a4}$, $R^{b4}$, $R^{c4}$, and $R^{d4}$ is independently selected from H, $C_{1-6}$ alkyl, phenyl, and 4-7 membered heterocycloalkyl, wherein said $C_{1-6}$ alkyl, phenyl, and 4-7 membered heterocycloalkyl of $R^{a4}$, $R^{b4}$, $R^{c4}$, and $R^{d4}$ are optionally substituted with 1, 2, or 3 independently selected $R^{4A}$ substituents;

each $R^{4A}$ is independently selected from halo, 4-7 membered heterocycloalkyl, and OH, wherein said 4-7 membered heterocycloalkyl of $R^{4A}$ is optionally substituted with 1 or 2 independently selected $R^{4B}$ substituents; and each $R^{4B}$ is independently selected from halo, OH, and $C_{1-4}$ alkyl.

12. The compound of claim 1, or a pharmaceutically acceptable salt thereof, wherein $R^4$ is selected from C(O)NH$C_{1-6}$ alkyl, C(O)-azetidinyl, C(O)-pyrrolidinyl, C(O)-piperidinyl, C(O)N($C_{1-6}$ alkyl) 2, NHC(O)O$C_{1-6}$ alkyl, (azetidinyl)-$C_{1-6}$ alkyl, (pyridyl)-$C_{1-6}$ alkyl, (phenyl)-$C_{1-6}$ alkyl, (fluorophenyl)-$C_{1-6}$ alkyl, 3,6-dihydro-2H-pyranyl, NH-(phenyl), pyridyl, and (pyrrolo[3,2-b]pyridinyl)-$C_{1-6}$ alkyl, wherein each $C_{1-6}$ alkyl and azetidinyl group is optionally substituted by 1 or 2 OH groups; and each pyridyl is optionally substituted by a methylpiperazinyl group.

13. The compound of claim 1, or a pharmaceutically acceptable salt thereof, wherein $R^4$ is selected from $C(O)NHCH_2CH_3$, $C(O)N(CH_3)\ (CH_2CH_3)$, $C(O)N(CH_2CH_3)_2$, $NHC(O)OCH_2CH_3$, C(O)-azetidinyl, C(O)-hydroxyazetidinyl, C(O)-pyrrolidinyl, C(O)-piperidinyl, $CH_2$-azetidinyl, $CH_2$-pyridyl, $CH_2$-fluorophenyl, CH(OH)-fluorophenyl, NH-phenyl, 3,6-dihydro-2H-pyranyl, (methylpiperazinyl)pyridinyl, and (1H-pyrrolo[3,2-b]pyridin-3-yl)methyl.

14. The compound of claim 1, or a pharmaceutically acceptable salt thereof, wherein $R^2$ is selected from H, D, halo, $C_{1-6}$ alkyl, $C_{1-6}$ haloalkyl, and CN.

15. The compound of claim 1, or a pharmaceutically acceptable salt thereof, wherein $R^2$ is selected from H, difluoroethyl, bromo, and CN.

16. The compound of claim 14, or a pharmaceutically acceptable salt thereof, wherein $R^4$ is selected from phenyl-$C_{1-6}$ alkyl-, (5-6 membered heteroaryl)-$C_{1-6}$ alkyl-, and $C(O)NR^{c4}R^{d4}$, wherein the phenyl-$C_{1-6}$ alkyl- and (5-6 membered heteroaryl)-$C_{1-6}$ alkyl- of $R^4$ are each optionally substituted with 1 or 2 substituents independently selected from OH and halo; and each $R^{a4}$, $R^{c4}$, and $R^{d4}$ is independently selected from H and $C_{1-6}$ alkyl.

17. The compound of claim 14, or a pharmaceutically acceptable salt thereof, wherein $R^4$ is selected from $—C(O)NHCH_2CH_3$, $—CH_2$-pyridyl, $CH_2$-fluorophenyl, and CH(OH)-fluorophenyl.

18. The compound of claim 3, or a pharmaceutically acceptable salt thereof, wherein:

$R^3$ is H or CN;

$Cy^1$ is phenyl which is substituted by 1 or 2 independently selected $R^7$ substituents;

each $R^7$ is independently selected from halo and CN;

$R^2$ is selected from phenyl, $C_{3-7}$ cycloalkyl, 5-6 membered heteroaryl and 4-7 membered heterocycloalkyl, wherein the phenyl, $C_{3-7}$ cycloalkyl, 5-6 membered heteroaryl and 4-7 membered heterocycloalkyl of $R^2$ are each optionally substituted with 1, 2, or 3 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, OC(O)NR: 21$R^{d21}$, $NR^{e21}R^{d21}$, $NR^{c21}C(O)R^{b21}$, $NR^{c21}C(O)OR^{a21}$, $NR^{c21}C(O)NR^{c21}R^{d21}$, $S(O)\ R^{b21}$, and $S(O)_2R^{b21}$, wherein said phenyl, $C_{3-7}$ cycloalkyl, 5-6 membered heteroaryl and 4-7 membered heterocycloalkyl of $R^{2A}$ are optionally substituted with 1, 2, or 3 independently selected $R^{2B}$ substituents;

each $R^{a21}$, $R^{b21}$, $R^{c21}$, and $R^{d21}$ is independently selected from H, $C_{1-6}$ alkyl, and $C_{1-6}$ haloalkyl;

each $R^{2B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $S(O)R^{b4}$, and $S(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, phenyl, $C_{3-7}$ cycloalkyl, 5-6 membered heteroaryl, and 4-7 membered heterocycloalkyl, wherein said $C_{1-6}$ alkyl, phenyl, $C_{3-7}$ cycloalkyl, 5-6 membered heteroaryl, and 4-7 membered heterocycloalkyl of $R^{a4}$, $R^{b4}$, $R^{c4}$, and $R^{d4}$ are each optionally substituted by 1, 2, or 3 independently selected $R^{4A}$ substituents;

each $R^{4A}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $S(O)R^{b41}$, and $S(O)_2R^{b41}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{4A}$ are each optionally substituted by 1 or 2 independently selected $R^{4B}$ substituents;

each $R^{a41}$, $R^{b41}$, $R^{c41}$, and $R^{d41}$ is independently selected from H, $C_{1-6}$ alkyl, and $C_{1-6}$ haloalkyl, wherein said $C_{1-6}$ alkyl of $R^{a41}$, $R^{b41}$, $R^{c41}$, and $R^{d41}$ is optionally substituted by 1, 2, or 3 independently selected $R^{4B}$ substituents; and each $R^{4B}$ is independently selected from halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

19. The compound of claim 3, or a pharmaceutically acceptable salt thereof, wherein:

$R^3$ is H or CN;

$Cy^1$ is 3-cyanophenyl or 3-cyano-2-fluorophenyl;

$R^2$ is selected from $C_{3-6}$ cycloalkyl, 5-6 membered heteroaryl, and 4-6 membered heterocycloalkyl, wherein the $C_{3-6}$ cycloalkyl, 5-6 membered heteroaryl, and 4-6 membered heterocycloalkyl of $R^2$ are each optionally substituted with 1 or 2 independently selected $R^{2A}$ substituents;

each $R^{2A}$ is independently selected from halo, $C_{1-4}$ alkyl, $C_{1-4}$ haloalkyl, and $C(O)NR^{e21}R^{d21}$, wherein said $C_{1-4}$ alkyl of $R^{2A}$ is optionally substituted with 1, 2, or 3 independently selected $R^{2B}$ substituents;

each $R^{a21}$, $R^{b21}$, $R^{e21}$, and $R^{d21}$ is independently selected from H, $C_{1-6}$ alkyl, and $C_{1-6}$ haloalkyl;

each $R^{2B}$ is independently selected from halo and OH;

$R^4$ is selected from phenyl, 5-6 membered heteroaryl, 4-7 membered heterocycloalkyl, phenyl-$C_{1-3}$ alkyl-, (5-10 membered heteroaryl)-$C_{1-3}$ alkyl-, (4-7 membered heterocycloalkyl)-$C_{1-3}$ alkyl-, $C(O)R^{b4}$, $C(O)NR^{c4}R^{d4}$, and $NR^{c4}R^{d4}$, wherein the phenyl, 5-6 membered heteroaryl, 4-7 membered heterocycloalkyl, phenyl-$C_{1-3}$ alkyl-, (5-10 membered heteroaryl)-$C_{1-3}$ alkyl-, and (4-7 membered heterocycloalkyl)-$C_{1-3}$ alkyl- of $R^4$ are each optionally substituted with 1 or 2 independently selected $R^{4A}$ substituents;

each $R^{a4}$, $R^{b4}$, $R^{c4}$, and $R^{d4}$ is independently selected from H, $C_{1-6}$ alkyl, phenyl, and 4-7 membered heterocycloalkyl, wherein said $C_{1-6}$ alkyl, phenyl, and 4-7 membered heterocycloalkyl of $R^{a4}$, $R^{b4}$, $R^{c4}$, and $R^{d4}$ are optionally substituted with 1, 2, or 3 independently selected $R^{4A}$ substituents;

each $R^{4A}$ is independently selected from halo, 4-7 membered heterocycloalkyl, and OH, wherein said 4-7 membered heterocycloalkyl of $R^{4A}$ is optionally substituted with 1 or 2 independently selected $R^{4B}$ substituents; and each $R^{4B}$ is independently selected from halo, OH, and $C_{1-4}$ alkyl.

20. The compound of claim 3, or a pharmaceutically acceptable salt thereof, wherein:

$R^3$ is H or CN;

$Cy^1$ is phenyl which is substituted by 1 or 2 independently selected $R^7$ substituents;

each $R^7$ is independently selected from halo and CN;

$R^2$ is selected from H, halo, $C_{1-6}$ alkyl, $C_{1-6}$ haloalkyl, and CN;

$R^4$ is selected from phenyl-$C_{1-6}$ alkyl-, (5-6 membered heteroaryl)-$C_{1-6}$ alkyl-, and $C(O)NR^{c4}R^{d4}$, wherein the phenyl-$C_{1-6}$ alkyl- and (5-6 membered heteroaryl)-$C_{1-6}$ alkyl- of $R^4$ are each optionally substituted with 1 or 2 substituents independently selected from OH and halo; and each $R^{a4}$, $R^{c4}$, and $R^{d4}$ is independently selected from H and $C_{1-6}$ alkyl.

21. The compound of claim 1, which is a compound of Formula (IIb):

(IIb)

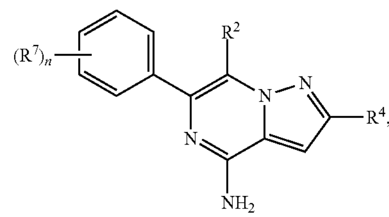

or a pharmaceutically acceptable salt thereof, wherein n is an integer from 0 to 4.

22. The compound of claim 1, which is a compound of Formula (IIc):

(IIc)

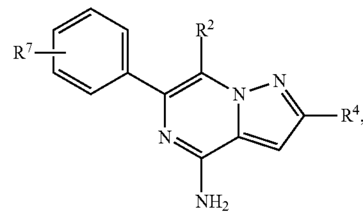

or a pharmaceutically acceptable salt thereof.

23. The compound of claim 1, which is a compound of Formula (IIIa):

(IIIa)

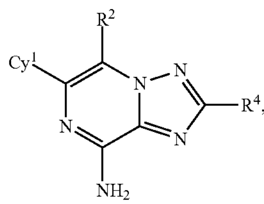

or a pharmaceutically acceptable salt thereof.

24. The compound of claim 1, or a pharmaceutically acceptable salt thereof, wherein $Cy^1$ is phenyl which is substituted by 1 or 2 independently selected $R^7$ substituents; and each $R^7$ is independently selected from halo and CN.

25. The compound of claim 1, or a pharmaceutically acceptable salt thereof, wherein $Cy^1$ is cyanophenyl.

26. The compound of claim 1, or a pharmaceutically acceptable salt thereof, wherein $Cy^1$ is 3-cyanophenyl or 3-cyano-2-fluorophenyl.

27. The compound of claim 1, or a pharmaceutically acceptable salt thereof, wherein $R^2$ is selected from $C_{6-10}$ aryl, $C_{3-10}$ cycloalkyl, 5-10 membered heteroaryl and 4-10 membered heterocycloalkyl, wherein the $C_{6-10}$ aryl, $C_{3-10}$ cycloalkyl, 5-10 membered heteroaryl and 4-10 membered heterocycloalkyl of $R^2$ are each optionally substituted with 1, 2, 3, or 4 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $S(O)R^{b21}$, and $S(O)_2R^{b21}$, wherein said $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{2A}$ are each optionally substituted by 1, 2, or 3 independently selected $R^{2B}$ substituents;

each $R^{a21}$, $R^{b21}$, $R^{c21}$, and $R^{d21}$ is independently selected from H, $C_{1-6}$ alkyl, and $C_{1-6}$ haloalkyl, wherein said $C_{1-6}$ alkyl of $R^{a21}$, $R^{b21}$, $R^{e21}$, and $R^{d21}$ is optionally substituted by 1, 2, or 3 independently selected $R^{2A}$ substituents; and each $R^{2B}$ is independently selected from D, halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino.

28. The compound of claim 1, or a pharmaceutically acceptable salt thereof, wherein $R^2$ is selected from 5-10 membered heteroaryl and 4-7 membered heterocycloalkyl, wherein the 5-10 membered heteroaryl and 4-7 membered heterocycloalkyl of $R^2$ are each optionally substituted with 1, 2, or 3 independently selected $R^{2A}$ substituents;

each $R^{2A}$ is independently selected from halo, $C_{1-6}$ alkyl, $C_{1-6}$ haloalkyl, and OH, wherein said $C_{1-6}$ alkyl of $R^{2A}$ is optionally substituted by 1, 2, or 3 independently selected $R^{2B}$ substituents; and each $R^{2B}$ is independently selected from D, halo, and OH.

29. The compound of claim 1, or a pharmaceutically acceptable salt thereof, wherein $R^2$ is selected from 6-oxo-1,6-dihydropyridin-3-yl, pyrimidin-4-yl, 1-methyl-6-oxo-1,6-dihydropyridin-3-yl, 1-methyl-6-oxo-1,6-dihydropyridazin-3-yl, 4-methyloxazol-5-yl, 4-ethyloxazol-5-yl, 3-methylpyridin-4-yl, 4-(2,2-difluoro-1-hydroxyethyl)-2-methyloxazol-5-yl, 2-methyl-4-(2,2,2-trifluoro-1-hydroxyethyl) oxazol-5-yl, 1-ethyl-1H-pyrazol-5-yl, 6-hydroxypyridin-3-yl, 2,6-dimethylpyridin-4-yl, 3-methyl-1H-pyrazol-4-yl, [1,2,4]triazolo[4,3-a]pyridin-6-yl, oxazol-5-yl, imidazo[1,2-a]pyridine-6-yl, 3-fluoropyridin-4-yl, and 1-(methyl-d3)-6-oxo-1,6-dihydropyridazin-3-yl.

30. The compound of claim 1, or a pharmaceutically acceptable salt thereof, wherein $R^2$ is H.

31. The compound of claim 1, or a pharmaceutically acceptable salt thereof, wherein $R^2$ is 6-oxo-1,6-dihydropyridin-3-yl or imidazo[1,2-a]pyridin-6-yl; and $R^4$ is H.

32. The compound of claim 1, or a pharmaceutically acceptable salt thereof, wherein $R^2$ is H; and $R^4$ is-NHC(O)$OC_{1-6}$ alkyl.

33. The compound of claim 1, or a pharmaceutically acceptable salt thereof, wherein:

$R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a4}$, $C(O)R^{b4}$, $C(O)NR^{c4}R^{d4}$, $C(O)OR^{a4}$, $NR^{c4}R^{d4}$, $S(O)_2NR^{c4}R^{d4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a41}$, $C(O)R^{b41}$, $C(O)NR^{c41}R^{d41}$, $C(O)OR^{a41}$, $NR^{c41}R^{d41}$, $S(O)_2NR^{c41}R^{d41}$, and $S(O)_2R^{b41}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, or 3 independently selected $R^{4B}$ substituents;

each $R^{a41}$, $R^{b41}$, $R^{c41}$ and $R^{d41}$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a41}$, $R^{b41}$, $R^{c41}$ and $R^{d41}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl-, CN, $OR^{a42}$, $C(O)R^{b42}$, $C(O)NR^{c42}R^{d42}$, $C(O)OR^{a42}$, $NR^{c42}R^{d42}$, $S(O)_2NR^{c42}R^{d42}$, and $S(O)_2R^{b42}$, wherein the $C_{1-6}$ alkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, $C_{1-6}$ haloalkyl, CN, $OR^{a43}$, $C(O)R^{b43}$, $C(O)NR^{c43}R^{d43}$, $C(O)OR^{a43}$, $NR^{c43}R^{d43}$, $S(O)_2NR^{c43}R^{d43}$, and $S(O)_2R^{b43}$, wherein the $C_{1-6}$ alkyl of $R^{4C}$ is optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents; and each $R^{4D}$ is independently selected from $C_{1-3}$ alkyl and OH.

34. The compound of claim 1, or a pharmaceutically acceptable salt thereof, wherein $R^4$ is selected from phenyl-$C_{1-3}$ alkyl-, (4-7 membered heterocycloalkyl)-$C_{1-3}$ alkyl-, (5-10 membered heteroaryl)-$C_{1-3}$ alkyl-, $OR^{a4}$, $C(O)R^{b4}$, and $S(O)_2R^{b4}$, wherein the phenyl-$C_{1-3}$ alkyl-, (4-7 membered heterocycloalkyl)-$C_{1-3}$ alkyl- and (5-10 membered heteroaryl)-$C_{1-3}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from phenyl, 4-7 membered heterocycloalkyl, and (5-6 membered heteroaryl)-$C_{1-3}$ alkyl-, wherein the phenyl, 4-7 membered heterocycloalkyl, and (5-6 membered heteroaryl)-$C_{1-3}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, 5-6 membered heteroaryl, (4-10 membered heterocycloalkyl)-$C_{1-3}$ alkyl-, $OR^{a41}$, $S(O)_2R^{b41}$, and $NR^{c41}R^{d41}$ wherein the $C_{1-6}$ alkyl, 5-6 membered heteroaryl, and (4-10 membered heterocycloalkyl)-$C_{1-3}$ alkyl- of $R^{4A}$ are each optionally substituted with 1, 2, or 3 independently selected $R^{4B}$ substituents;

each $R^{a41}$, $R^{b41}$, $R^{c41}$ and $R^{d41}$ is independently selected from H, $C_{1-6}$ alkyl, $C_{1-6}$ haloalkyl, and 5-6 membered heteroaryl, wherein the $C_{1-6}$ alkyl and 5-6 membered heteroaryl of $R^{a41}$, $R^{b41}$, $R^{c41}$ and $R^{d41}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, $C_{3-6}$ cycloalkyl, 4-7 membered heterocycloalkyl, (5-6 membered heteroaryl)-$C_{1-3}$ alkyl-, CN, $OR^{a42}$, $C(O)R^{b42}$, $C(O)OR^{a42}$, and $NR^{c42}R^{d42}$, wherein the $C_{1-6}$ alkyl, $C_{3-6}$ cycloalkyl, 4-7 membered heterocycloalkyl, and (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{3-6}$ cycloalkyl, 5-6 membered heteroaryl, and 5-7 membered heterocycloalkyl, wherein the $C_{1-6}$ alkyl, $C_{3-6}$ cycloalkyl, 5-6 membered heteroaryl, and 5-7 membered heterocycloalkyl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, CN, $C(O)NR^{c43}R^{d43}$, $C(O)OR^{a43}$, $NR^{c43}R^{d43}$, and $S(O)_2R^{b43}$, wherein the $C_{1-6}$ alkyl of $R^{4C}$ is optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents;

each $R^{4D}$ is independently selected from $C_{1-3}$ alkyl and OH.

35. The compound of claim 1, or a pharmaceutically acceptable salt thereof, wherein $R^4$ is selected from pyridin-2-ylmethyl, 1H-Pyrrolo[2,3-b]pyridin-1-yl, 7H-pyrrolo[2,3-b]pyridin-7-yl, 2-fluorophenoxy, hydroxy (pyridin-2-yl) methyl, 2-(1-methyl-1H-pyrazol-4-yl)benzyl, (imidazo[1,2-a]pyridin-8-yl)methyl, (pyrazolo[1,5-a]pyridin-7-yl)methyl, (2H-indazol-2-yl)methyl, (1H-indazol-1-yl)methyl, (2,6-difluorophenyl) (hydroxy)methyl, (2,5-difluorophenyl) (hydroxy)methyl, (2,3-difluorophenyl) (hydroxy)methyl, (2-fluorophenyl) (hydroxy)methyl, (2-chlorophenyl) (hydroxy)methyl, hydroxy (phenyl)methyl, phenylsulfonyl, azetidine-1-carbonyl, benzo[d]oxazol-4-ylmethyl, 2-fluoro-6-(1-methyl-1H-pyrazol-5-yl)benzyl, 2-fluoro-6-((6-methyl-5-oxo-2,6-diazaspiro[3.4]octan-2-yl)methyl)benzyl, 2-fluoro-6-((6-oxohexahydropyrrolo[1,2-a]pyrazin-2 (1H)-yl)methyl)benzyl, 2-fluoro-6-(((2-oxopyrrolidin-3-yl) amino)methyl)benzyl, 2-fluoro-6-((3-oxopiperazin-1-yl) methyl)benzyl, 2-fluoro-6-(((1-methyl-2-oxopyrrolidin-3-yl)amino)methyl)benzyl, 2-fluoro-6-(((2-methyl-2H-1,2,3-triazol-4-yl)amino)methyl)benzyl, 2-(((2-oxopyrrolidin-3-yl)amino)methyl)benzyl, amino (2,6-difluorophenyl) methyl, (2,6-difluorophenyl)(methylamino)methyl, (2,6-difluorophenyl) ((2-hydroxyethyl)amino)methyl, amino (2-fluorophenyl)methyl, amino (2,6-difluorophenyl)methyl, (3-(oxazol-5-yl) pyridin-2-yl)methyl, 2-fluoro-6-(1-methyl-1H-pyrazol-4-yl)benzyl, (1-((1-methyl-1H-imidazol-4-yl) sulfonyl) pyrrolidin-2-yl)methyl, 2-((1-acetylpiperidin-4-yl) methyl)-6-fluorobenzyl, (2-(difluoromethoxy)-6-fluorophenyl) (hydroxy)methyl, 2-fluoro-6-(1-((1-methyl-1H-pyrazol-4-yl)methyl)-1H-pyrazol-4-yl)benzyl, (2-((dimethylamino)methyl)-6-fluorophenyl) (hydroxy)methyl, 2-fluoro-6-(1-(pyridin-2-ylmethyl)-1H-pyrazol-4-yl)benzyl, (2-fluoro-6-(pyrrolidin-1-ylmethyl)phenyl) (hydroxy) methyl, 2-fluoro-6-(1-(2-(methylsulfonyl)ethyl)-1H-pyrazol-4-yl)benzyl, 2-fluoro-6-((6-oxohexahydropyrrolo[1,2-a] pyrazin-2 (1H)-yl)methyl)phenyl) (hydroxy)methyl, 2-fluoro-6-(1-((trans)-3-(methylamino)cyclobutyl)-1H-pyrazol-4-yl)benzyl, 2-(1-(2-cyanoethyl)-1H-pyrazol-4-yl)-6-fluorobenzyl, 2-fluoro-6-(1-(2-(3-hydroxyazetidin-1-yl)-2-oxoethyl)-1H-pyrazol-4-yl)benzyl, (3-methylpyridin-2-yl) methoxy, (3-((1-(pyridin-4-ylmethyl)-1H-pyrazol-4-yl) amino)pyridin-2-yl)methyl, (3-((1-(tetrahydro-2H-pyran-4-yl)-1H-pyrazol-4-yl)amino)pyridin-2-yl)methyl, (3-(1-methyl-1H-pyrazol-4-yl) pyridin-2-yl)methyl, 2-((3-hydroxypyrrolidin-1-yl)methyl)benzyl, and (6-methoxypyridin-2-yl)methyl.

36. The compound of claim 23, or a pharmaceutically acceptable salt thereof, wherein:

$Cy^1$ is phenyl which is substituted by 1 or 2 independently selected $R^7$ substituents;

each $R^7$ is independently selected from halo and CN;

$R^2$ is selected from H, $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $S(O)R^{b21}$, and $S(O)_2R^{b21}$, wherein said $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{2A}$ are each optionally substituted by 1, 2, or 3 independently selected $R^{2B}$ substituents;

each $R^{a21}$, $R^{b21}$, $R^{c21}$, and $R^{d21}$ is independently selected from H, $C_{1-6}$ alkyl, and $C_{1-6}$ haloalkyl, wherein said $C_{1-6}$ alkyl of $R^{a21}$, $R^{b21}$, $R^{c21}$, and $R^{d21}$ is optionally substituted by 1, 2, or 3 independently selected $R^{2A}$ substituents;

each $R^{2B}$ is independently selected from D, halo, OH, $C_{1-4}$ alkoxy, $C_{1-4}$ haloalkoxy, $C_{1-4}$ alkyl, $C_{1-4}$ haloalkyl, amino, $C_{1-3}$ alkylamino, and di($C_{1-3}$ alkyl)amino;

$R^4$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a4}$, $C(O)R^{b4}$, $C(O)NR^{c4}R^{d4}$, $C(O)OR^{a4}$, $NR^{c4}R^{d4}$, $S(O)_2NR^{c4}R^{d4}$, and $S(O)_2R^{b4}$, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a41}$, $C(O)R^{b41}$, $C(O)NR^{c41}R^{d41}$, $C(O)OR^{a41}$, $NR^{c41}R^{d41}$, $S(O)_2NR^{c41}R^{d41}$, and $S(O)_2R^{b41}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, or 3 independently selected $R^{4B}$ substituents;

each $R^{a41}$, $R^{b41}$, $R^{c41}$ and $R^{d41}$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a41}$, $R^{b41}$, $R^{c41}$ and $R^{d41}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl-, CN, $OR^{a42}$, $C(O)R^{b42}$, $C(O)NR^{c42}R^{d42}$, $C(O)OR^{a42}$, $NR^{c42}R^{d42}$, $S(O)_2NR^{c42}R^{d42}$, and $S(O)_2R^{b42}$, wherein the $C_{1-6}$ alkyl, phenyl, $C_{3-6}$ cycloalkyl, 4-7 membered heterocycloalkyl, 5-6 membered heteroaryl, phenyl-$C_{1-3}$ alkyl-, ($C_{3-6}$ cycloalkyl)-$C_{1-3}$ alkyl-, (4-7 membered heterocycloalkyl)-$C_{1-3}$ alkyl-, (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{1-6}$ haloalkyl, phenyl, $C_{3-6}$ cycloalkyl, 4-7 membered heterocycloalkyl, and 5-6 membered heteroaryl, wherein the $C_{1-6}$ alkyl, phenyl, $C_{3-6}$ cycloalkyl, 4-7 membered heterocycloalkyl, and 5-6 membered heteroaryl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, $C_{1-6}$ haloalkyl, CN, $OR^{a43}$, $C(O)R^{b43}$, $C(O)NR^{c43}R^{d43}$, $C(O)OR^{a43}$, $NR^{c43}R^{d43}$, $S(O)_2NR^{c43}R^{d43}$, and $S(O)_2R^{b43}$, wherein the $C_{1-6}$ alkyl of $R^{4C}$ is optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents; and each $R^{4D}$ is independently selected from $C_{1-3}$ alkyl and OH.

37. The compound of claim 23, or a pharmaceutically acceptable salt thereof, wherein:

$Cy^1$ is 3-cyanophenyl or 3-cyano-2-fluorophenyl;

$R^2$ is selected from H, 5-10 membered heteroaryl, and 4-7 membered heterocycloalkyl, wherein the 5-10 membered heteroaryl and 4-7 membered heterocycloalkyl of $R^2$ are each optionally substituted with 1, 2, or 3 independently selected $R^{2A}$ substituents;

each $R^{2A}$ is independently selected from halo, $C_{1-6}$ alkyl, $C_{1-6}$ haloalkyl, and OH, wherein said $C_{1-6}$ alkyl of $R^{2A}$ is optionally substituted by 1, 2, or 3 independently selected $R^{2B}$ substituents;

each $R^{2B}$ is independently selected from D, halo, and OH;

$R^4$ is selected from phenyl-$C_{1-3}$ alkyl-, (4-7 membered heterocycloalkyl)-$C_{1-3}$ alkyl-, (5-10 membered heteroaryl)-$C_{1-3}$ alkyl-, $OR^{a4}$, $C(O)R^{b4}$, and $S(O)_2R^{b4}$, wherein the phenyl-$C_{1-3}$ alkyl-, (4-7 membered heterocycloalkyl)-$C_{1-3}$ alkyl- and (5-10 membered heteroaryl)-$C_{1-3}$ alkyl- of $R^4$ are each optionally substituted with 1, 2, or 3 independently selected $R^{4A}$ substituents;

each $R^{a4}$, $R^{b4}$, $R^{c4}$, and $R^{d4}$ is independently selected from phenyl, 4-7 membered heterocycloalkyl, and (5-6 membered heteroaryl)-$C_{1-3}$ alkyl-, wherein the phenyl, 4-7 membered heterocycloalkyl, and (5-6 membered heteroaryl)-$C_{1-3}$ alkyl- of $R^{a4}$, $R^{b4}$, $R^{c4}$ and $R^{d4}$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, 5-6 membered heteroaryl, (4-10 membered heterocycloalkyl)-$C_{1-3}$ alkyl-, $OR^{a41}$, $S(O)_2R^{b41}$, and $NR^{c41}R^{d41}$, wherein the $C_{1-6}$ alkyl, 5-6 membered heteroaryl, and (4-10 membered heterocycloalkyl)-$C_{1-3}$ alkyl- of $R^{4A}$ are each optionally substituted with 1, 2, or 3 independently selected $R^{4B}$ substituents;

each $R^{a41}$, $R^{b41}$, $R^{c41}$ and $R^{d41}$ is independently selected from H, $C_{1-6}$ alkyl, $C_{1-6}$ haloalkyl, and 5-6 membered heteroaryl, wherein the $C_{1-6}$ alkyl and 5-6 membered heteroaryl of $R^{a41}$, $R^{b41}$, $R^{c41}$ and $R^{d41}$ are each optionally substituted with 1, 2, or 3 independently selected $R^{4B}$ substituents;

each $R^{4B}$ is independently selected from halo, $C_{1-6}$ alkyl, $C_{1-6}$ haloalkyl, $C_{3-6}$ cycloalkyl, 4-7 membered heterocycloalkyl, (5-6 membered heteroaryl)-$C_{1-3}$ alkyl-, CN, $OR^{a42}$, $C(O)R^{b42}$, $C(O)OR^{a42}$, and $NR^{c42}R^{d42}$, wherein the $C_{1-6}$ alkyl, $C_{3-6}$ cycloalkyl, 4-7 membered heterocycloalkyl, and (5-6 membered heteroaryl)-$C_{1-3}$ alkyl- of $R^{4B}$ are each optionally substituted with 1, 2, or 3 independently selected $R^{4C}$ substituents;

each $R^{a42}$, $R^{b42}$, $R^{c42}$ and $R^{d42}$ is independently selected from H, $C_{1-6}$ alkyl, $C_{3-6}$ cycloalkyl, 5-6 membered heteroaryl, and 5-7 membered heterocycloalkyl, wherein the $C_{1-6}$ alkyl, $C_{3-6}$ cycloalkyl, 5-6 membered heteroaryl, and 5-7 membered heterocycloalkyl of $R^{a42}$, $R^{b42}$, $R^{c42}$ and $R^{d42}$ are each optionally substituted with 1, 2, or 3 independently selected $R^{4C}$ substituents;

each $R^{4C}$ is independently selected from $C_{1-6}$ alkyl, CN, $C(O)NR^{c43}R^{d43}$, $C(O)OR^{a43}$, $NR^{c43}R^{d43}$, and $S(O)_2R^{b43}$, wherein the $C_{1-6}$ alkyl of $R^{4C}$ is optionally substituted with 1 or 2 independently selected $R^{4D}$ substituents;

each $R^{a43}$, $R^{b43}$, $R^{c43}$ and $R^{d43}$ is independently selected from H, $C_{1-6}$ alkyl, and $C_{1-6}$ haloalkyl, wherein the $C_{1-6}$ alkyl of $R^{a43}$, $R^{b43}$, $R^{c43}$ and $R^{d43}$ are each optionally substituted with 1 or 2 independently selected $R^{4D}$ substituents;

or, any $R^{c43}$ and $R^{d43}$, attached to the same N atom, together with the N atom to which they are attached, form a 4-, 5-, or 6-membered heterocycloalkyl group, wherein the 4-, 5-, or 6-membered heterocycloalkyl group is optionally substituted with 1, 2, 3, or 4 independently selected $R^{4D}$ substituents; and each $R^{4D}$ is independently selected from $C_{1-3}$ alkyl and OH.

38. The compound of claim 1, or a pharmaceutically acceptable salt thereof, wherein:

$R^2$ is selected from 5-6 membered heteroaryl and 4-6 membered heterocycloalkyl, wherein the 5-6 membered heteroaryl and 4-6 membered heterocycloalkyl are each optionally substituted with 1 or 2 $C_{1-3}$ alkyl groups;

$R^4$ is phenyl-$C_{1-3}$ alkyl- or pyridyl-$C_{1-3}$ alkyl-, wherein the phenyl-$C_{1-3}$ alkyl- and pyridyl-$C_{1-3}$ alkyl- are each optionally substituted with 1, 2, or 3 substituents independently selected from OH and halo; and $Cy^1$ is cyanophenyl.

39. The compound of claim 1, which is a compound of Formula (IIIb):

(IIIb)

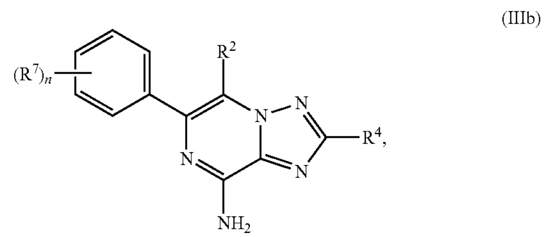

or a pharmaceutically acceptable salt thereof, wherein n is an integer from 0 to 4.

40. The compound of claim 1, which is a compound of Formula (IIIc):

(IIIc)

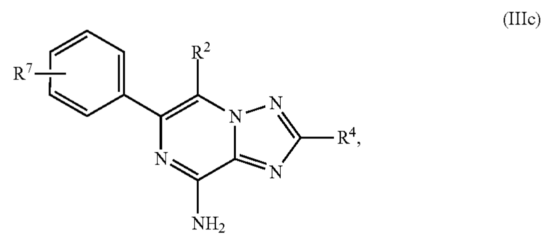

or a pharmaceutically acceptable salt thereof.

41. The compound of claim 1, selected from:

4-Amino-6-(3-cyanophenyl)-N-ethyl-7-(1-ethyl-1H-pyrazol-5-yl) pyrazolo[1,5-a]pyrazine-2-carboxamide;

4-Amino-6-(3-cyanophenyl)-N-ethyl-7-(1-propyl-1H-pyrazol-5-yl) pyrazolo[1,5-a]pyrazine-2-carboxamide;

4-Amino-6-(3-cyanophenyl)-N-ethyl-7-(1-methyl-6-oxo-1,6-dihydropyridin-3-yl) pyrazolo[1,5-a]pyrazine-2-carboxamide;

4-Amino-6-(3-cyanophenyl)-N-ethyl-7-(pyrimidin-4-yl) pyrazolo[1,5-a]pyrazine-2-carboxamide;

4-Amino-6-(3-cyanophenyl)-7-(1,1-difluoroethyl)-N-ethylpyrazolo[1,5-a]pyrazine-2-carboxamide;

4-Amino-6-(3-cyanophenyl)-N-ethyl-7-(1-(trifluoromethyl)cyclopropyl) pyrazolo[1,5-a]pyrazine-2-carboxamide;

3-(4-Amino-2-(azetidine-1-carbonyl)-7-(pyrimidin-4-yl) pyrazolo[1,5-a]pyrazin-6-yl)benzonitrile;

3-(4-Amino-7-(pyrimidin-4-yl)-2-(pyrrolidine-1-carbonyl) pyrazolo[1,5-a]pyrazin-6-yl)benzonitrile;

3-(4-Amino-2-(piperidine-1-carbonyl)-7-(pyrimidin-4-yl) pyrazolo[1,5-a]pyrazin-6-yl)benzonitrile;
4-Amino-6-(3-cyanophenyl)-N,N-diethyl-7-(pyrimidin-4-yl) pyrazolo[1,5-a]pyrazine-2-carboxamide;
4-Amino-6-(3-cyanophenyl)-N-ethyl-N-methyl-7-(pyrimidin-4-yl) pyrazolo[1,5-a]pyrazine-2-carboxamide;
3-(4-Amino-2-(3-hydroxyazetidine-1-carbonyl)-7-(pyrimidin-4-yl) pyrazolo[1,5-a]pyrazin-6-yl)benzonitrile;
3-(4-Amino-2-(azetidin-1-ylmethyl)-7-(pyrimidin-4-yl) pyrazolo[1,5-a]pyrazin-6-yl)benzonitrile;
Ethyl (8-amino-6-(3-cyanophenyl)-[1,2,4]triazolo[1,5-a]pyrazin-2-yl) carbamate;
3-(8-Amino-5-(6-oxo-1,6-dihydropyridin-3-yl)-[1,2,4]triazolo[1,5-a]pyrazin-6-yl)benzonitrile;
3-(4-Amino-2-(pyridin-2-ylmethyl) pyrazolo[1,5-a]pyrazin-6-yl)benzonitrile;
3-(4-Amino-2-(pyridin-2-ylmethyl)-7-(pyrimidin-4-yl) pyrazolo[1,5-a]pyrazin-6-yl)benzonitrile;
3-(4-Amino-7-(1-ethyl-1H-pyrazol-5-yl)-2-(pyridin-2-ylmethyl) pyrazolo[1,5-a]pyrazin-6-yl)benzonitrile;
4-(4-Amino-6-(3-cyanophenyl)-2-(2-fluorobenzyl) pyrazolo[1,5-a]pyrazin-7-yl)-5,6-dihydropyridine-1 (2H)-carboxamide;
4-Amino-6-(3-cyanophenyl)-2-(2-fluorobenzyl) pyrazolo[1,5-a]pyrazine-7-carbonitrile;
4-Amino-6-(3-cyanophenyl)-2-(2-fluorobenzyl) pyrazolo[1,5-a]pyrazine-3-carbonitrile;
3-(4-Amino-7-bromo-2-((2-fluorophenyl) (hydroxy) methyl) pyrazolo[1,5-a]pyrazin-6-yl)benzonitrile;
3-(4-Amino-2-((2-fluorophenyl) (hydroxy)methyl)-7-(pyrimidin-4-yl) pyrazolo[1,5-a]pyrazin-6-yl)benzonitrile;
3-(4-Amino-2-(3,6-dihydro-2H-pyran-4-yl)-7-(pyrimidin-4-yl) pyrazolo[1,5-a]pyrazin-6-yl)benzonitrile;
3-(4-Amino-2-(phenylamino)-7-(pyridin-4-yl) pyrazolo[1,5-a]pyrazin-6-yl)benzonitrile;
3-(4-Amino-2-(2-(4-methylpiperazin-1-yl) pyridin-4-yl)-7-(pyridin-4-yl) pyrazolo[1,5-a]pyrazin-6-yl)benzonitrile;
3-(8-Amino-2-(pyridin-2-ylmethyl)-5-(pyrimidin-4-yl)-[1,2,4]triazolo[1,5-a]pyrazin-6-yl)benzonitrile;
3-(8-Amino-5-(1-methyl-6-oxo-1,6-dihydropyridin-3-yl)-2-(pyridin-2-ylmethyl)-[1,2,4]triazolo[1,5-a]pyrazin-6-yl)benzonitrile;
3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile;
(S)-1-(2-((8-Amino-6-(3-cyanophenyl)-5-(pyrimidin-4-yl)-[1,2,4]triazolo[1,5-a]pyrazin-2-yl)methyl)-3-fluorobenzyl) pyrrolidine-3-carboxylic acid;
1-(2-((8-Amino-6-(3-cyanophenyl)-5-(pyrimidin-4-yl)-[1,2,4]triazolo[1,5-a]pyrazin-2-yl)methyl)-3-fluorobenzyl) azetidine-3-carboxylic acid;
3-(2-((1H-Pyrrolo[2,3-b]pyridin-1-yl)methyl)-8-amino-5-(pyrimidin-4-yl)-[1,2,4]triazolo[1,5-a]pyrazin-6-yl) benzonitrile;
3-(2-((7H-pyrrolo[2,3-b]pyridin-7-yl)methyl)-8-amino-5-(pyrimidin-4-yl)-[1,2,4]triazolo[1,5-a]pyrazin-6-yl) benzonitrile;
3-(4-Amino-7-(4-(1-hydroxyethyl)-2-methyloxazol-5-yl)-2-(pyridin-2-ylmethyl) pyrazolo[1,5-a]pyrazin-6-yl)benzonitrile;
3-(4-Amino-7-(4-(2,2-difluoro-1-hydroxyethyl)-2-methyloxazol-5-yl)-2-(pyridin-2-ylmethyl) pyrazolo[1,5-a]pyrazin-6-yl)benzonitrile;
3-(4-Amino-7-(1-ethyl-1H-1,2,3-triazol-5-yl)-2-(pyridin-2-ylmethyl) pyrazolo[1,5-a]pyrazin-6-yl)benzonitrile;
3-(4-Amino-7-(1-methyl-1H-1,2,3-triazol-5-yl)-2-(pyridin-2-ylmethyl) pyrazolo[1,5-a]pyrazin-6-yl)benzonitrile;
3-(4-Amino-2-((2-fluorophenyl) (hydroxy)methyl)-7-(pyrimidin-4-yl) pyrazolo[1,5-a]pyrazin-6-yl)benzonitrile;
3-(8-Amino-2-(2-fluorophenoxy)-5-(pyrimidin-4-yl)-[1,2,4]triazolo[1,5-a]pyrazin-6-yl)benzonitrile;
3-(8-Amino-2-(hydroxy (pyridin-2-yl)methyl)-5-(4-methyloxazol-5-yl)-[1,2,4]triazolo[1,5-a]pyrazin-6-yl) benzonitrile;
3-(8-Amino-2-(2-(1-methyl-1H-pyrazol-4-yl)benzyl)-5-(pyrimidin-4-yl)-[1,2,4]triazolo[1,5-a]pyrazin-6-yl) benzonitrile;
3-(8-Amino-5-(4-methyloxazol-5-yl)-2-(pyridin-2-ylmethyl)-[1,2,4]triazolo[1,5-a]pyrazin-6-yl)benzonitrile;
3-(8-Amino-5-(4-ethyloxazol-5-yl)-2-(pyridin-2-ylmethyl)-[1,2,4]triazolo[1,5-a]pyrazin-6-yl)benzonitrile;
3-(8-Amino-5-(3-methylpyridin-4-yl)-2-(pyridin-2-ylmethyl)-[1,2,4]triazolo[1,5-a]pyrazin-6-yl)benzonitrile;
3-(8-Amino-2-(imidazo[1,2-a]pyridin-8-ylmethyl)-5-(pyrimidin-4-yl)-[1,2,4]triazolo[1,5-a]pyrazin-6-yl)benzonitrile;
3-(8-Amino-2-(pyrazolo[1,5-a]pyridin-7-ylmethyl)-5-(pyrimidin-4-yl)-[1,2,4]triazolo[1,5-a]pyrazin-6-yl) benzonitrile;
3-(2-((2H-Indazol-2-yl)methyl)-8-amino-5-(pyrimidin-4-yl)-[1,2,4]triazolo[1,5-a]pyrazin-6-yl)benzonitrile;
3-(2-((1H-Indazol-1-yl)methyl)-8-amino-5-(pyrimidin-4-yl)-[1,2,4]triazolo[1,5-a]pyrazin-6-yl)benzonitrile;
3-(8-Amino-2-((2,6-difluorophenyl) (hydroxy)methyl)-5-(pyrimidin-4-yl)-[1,2,4]triazolo[1,5-a]pyrazin-6-yl) benzonitrile;
3-(8-Amino-2-((2,5-difluorophenyl) (hydroxy)methyl)-5-(pyrimidin-4-yl)-[1,2,4]triazolo[1,5-a]pyrazin-6-yl) benzonitrile;
3-(8-Amino-2-((2,3-difluorophenyl) (hydroxy)methyl)-5-(pyrimidin-4-yl)-[1,2,4]triazolo[1,5-a]pyrazin-6-yl) benzonitrile;
3-(8-Amino-2-((2-fluorophenyl) (hydroxy)methyl)-5-(pyrimidin-4-yl)-[1,2,4]triazolo[1,5-a]pyrazin-6-yl) benzonitrile;
3-(8-Amino-2-((2-chlorophenyl) (hydroxy)methyl)-5-(pyrimidin-4-yl)-[1,2,4]triazolo[1,5-a]pyrazin-6-yl) benzonitrile;
3-(8-Amino-2-(hydroxy (phenyl)methyl)-5-(pyrimidin-4-yl)-[1,2,4]triazolo[1,5-a]pyrazin-6-yl)benzonitrile;
3-(8-Amino-2-(phenylsulfonyl)-5-(pyrimidin-4-yl)-[1,2,4]triazolo[1,5-a]pyrazin-6-yl)benzonitrile;
3-(8-Amino-2-(azetidine-1-carbonyl)-5-(4-methyloxazol-5-yl)-[1,2,4]triazolo[1,5-a]pyrazin-6-yl)benzonitrile;
3-(8-amino-5-(6-hydroxypyridin-3-yl)-2-(pyridin-2-ylmethyl)-[1,2,4]triazolo[1,5-a]pyrazin-6-yl)benzonitrile;
3-(8-amino-2-(benzo[d]oxazol-4-ylmethyl)-5-(pyrimidin-4-yl)-[1,2,4]triazolo[1,5-a]pyrazin-6-yl)benzonitrile;
3-(8-amino-2-(2-fluoro-6-(1-methyl-1H-pyrazol-5-yl) benzyl)-5-(pyrimidin-4-yl)-[1,2,4]triazolo[1,5-a]pyrazin-6-yl)benzonitrile;
(R)-1-(2-((8-amino-6-(3-cyanophenyl)-5-(pyrimidin-4-yl)-[1,2,4]triazolo[1,5-a]pyrazin-2-yl)methyl)-3-fluorobenzyl)-3-methylpyrrolidine-3-carboxylic acid;
3-(8-amino-2-(2-fluoro-6-((6-methyl-5-oxo-2,6-diazaspiro[3.4]octan-2-yl)methyl)benzyl)-5-(pyrimidin-4-yl)-[1,2,4]triazolo[1,5-a]pyrazin-6-yl)benzonitrile;

3-(8-amino-2-(2-fluoro-6-((6-oxohexahydropyrrolo[1,2-a]pyrazin-2 (1H)-yl)methyl)benzyl)-5-(pyrimidin-4-yl)-[1,2,4]triazolo[1,5-a]pyrazin-6-yl)benzonitrile;

(S)-3-(8-amino-2-(2-fluoro-6-(((2-oxopyrrolidin-3-yl) amino)methyl)benzyl)-5-(pyrimidin-4-yl)-[1,2,4]triazolo[1,5-a]pyrazin-6-yl)benzonitrile;

2-((2-((8-amino-6-(3-cyanophenyl)-5-(pyrimidin-4-yl)-[1,2,4]triazolo[1,5-a]pyrazin-2-yl)methyl)-3-fluorobenzyl)amino) acetamide;

3-(8-amino-2-(2-fluoro-6-((3-oxopiperazin-1-yl)methyl) benzyl)-5-(pyrimidin-4-yl)-[1,2,4]triazolo[1,5-a] pyrazin-6-yl)benzonitrile;

(1S,3S)-3-((2-((8-amino-6-(3-cyanophenyl)-5-(pyrimidin-4-yl)-[1,2,4]triazolo[1,5-a]pyrazin-2-yl)methyl)-3-fluorobenzyl)amino)cyclobutane-1-carboxylic acid 3-(8-amino-2-(2-fluoro-6-(((1-methyl-2-oxopyrrolidin-3-yl)amino)methyl)benzyl)-5-(pyrimidin-4-yl)-[1,2,4]triazolo[1,5-a]pyrazin-6-yl)benzonitrile;

3-(8-amino-2-(2-fluoro-6-(((2-methyl-2H-1,2,3-triazol-4-yl)amino)methyl)benzyl)-5-(pyrimidin-4-yl)-[1,2,4]triazolo[1,5-a]pyrazin-6-yl)benzonitrile;

(S)-3-(8-amino-2-(2-(((2-oxopyrrolidin-3-yl)amino) methyl)benzyl)-5-(pyrimidin-4-yl)-[1,2,4]triazolo[1,5-a]pyrazin-6-yl)benzonitrile;

(R)-1-(2-((8-amino-6-(3-cyanophenyl)-5-(4-methyloxazol-5-yl)-[1,2,4]triazolo[1,5-a]pyrazin-2-yl)methyl)-3-fluorobenzyl)-3-methylpyrrolidine-3-carboxylic acid;

3-(8-amino-2-(amino (2,6-difluorophenyl)methyl)-5-(4-methyloxazol-5-yl)-[1,2,4]triazolo[1,5-a]pyrazin-6-yl) benzonitrile;

3-(8-amino-2-((2,6-difluorophenyl)(methylamino) methyl)-5-(4-methyloxazol-5-yl)-[1,2,4]triazolo[1,5-a] pyrazin-6-yl)benzonitrile;

3-(8-amino-2-((2,6-difluorophenyl) ((2-hydroxyethyl) amino)methyl)-5-(4-methyloxazol-5-yl)-[1,2,4]triazolo[1,5-a]pyrazin-6-yl)benzonitrile;

3-(8-amino-2-(amino (2-fluorophenyl)methyl)-5-(4-methyloxazol-5-yl)-[1,2,4]triazolo[1,5-a]pyrazin-6-yl) benzonitrile;

3-(8-amino-2-(amino (2,6-difluorophenyl)methyl)-5-(1-methyl-6-oxo-1,6-dihydropyridazin-3-yl)-[1,2,4]triazolo[1,5-a]pyrazin-6-yl)benzonitrile;

3-(8-amino-2-((3-(oxazol-5-yl) pyridin-2-yl)methyl)-5-(pyrimidin-4-yl)-[1,2,4]triazolo[1,5-a]pyrazin-6-yl) benzonitrile;

3-(8-amino-2-(2-fluoro-6-(1-methyl-1H-pyrazol-4-yl) benzyl)-[1,2,4]triazolo[1,5-a]pyrazin-6-yl)-2-fluorobenzonitrile;

(S)-3-(8-amino-2-(2-fluoro-6-(((1-methyl-2-oxopyrrolidin-3-yl)amino)methyl)benzyl)-[1,2,4]triazolo[1,5-a] pyrazin-6-yl)-2-fluorobenzonitrile;

3-(8-amino-2-(2-fluoro-6-((6-methyl-5-oxo-2,6-diazaspiro[3.4]octan-2-yl)methyl)benzyl)-[1,2,4]triazolo [1,5-a]pyrazin-6-yl)-2-fluorobenzonitrile;

3-(8-amino-5-(4-methyloxazol-5-yl)-2-(pyridin-2-ylmethyl)-[1,2,4]triazolo[1,5-a]pyrazin-6-yl)-2-fluorobenzonitrile;

3-(8-amino-5-(4-(2,2-difluoro-1-hydroxyethyl)-2-methyloxazol-5-yl)-2-(pyridin-2-ylmethyl)-[1,2,4]triazolo [1,5-a]pyrazin-6-yl)-2-fluorobenzonitrile;

3-(8-amino-5-(2-methyl-4-(2,2,2-trifluoro-1-hydroxyethyl) oxazol-5-yl)-2-(pyridin-2-ylmethyl)-[1,2,4]triazolo[1,5-a]pyrazin-6-yl)-2-fluorobenzonitrile;

3-(8-amino-5-(1-methyl-6-oxo-1,6-dihydropyridin-3-yl)-2-(pyridin-2-ylmethyl)-[1,2,4]triazolo[1,5-a]pyrazin-6-yl)-2-fluorobenzonitrile;

3-(8-amino-2-((1-((1-methyl-1H-imidazol-4-yl) sulfonyl) pyrrolidin-2-yl)methyl)-[1,2,4]triazolo[1,5-a]pyrazin-6-yl)-2-fluorobenzonitrile;

3-(2-(2-((1-acetylpiperidin-4-yl)methyl)-6-fluorobenzyl)-8-amino-[1,2,4]triazolo[1,5-a]pyrazin-6-yl)-2-fluorobenzonitrile;

3-(8-amino-2-((2,6-difluorophenyl) (hydroxy)methyl)-5-(1-ethyl-1H-pyrazol-5-yl)-[1,2,4]triazolo[1,5-a] pyrazin-6-yl)benzonitrile;

3-(8-amino-2-((2,6-difluorophenyl) (hydroxy)methyl)-5-(2,6-dimethylpyridin-4-yl)-[1,2,4]triazolo[1,5-a] pyrazin-6-yl)benzonitrile;

3-(2-((1H-pyrrolo[3,2-b]pyridin-3-yl)methyl)-4-amino-7-(pyrimidin-4-yl) pyrazolo[1,5-a]pyrazin-6-yl)benzonitrile;

3-(8-amino-2-((2-(difluoromethoxy)-6-fluorophenyl) (hydroxy)methyl)-5-(pyrimidin-4-yl)-[1,2,4]triazolo[1,5-a]pyrazin-6-yl)benzonitrile;

3-(8-amino-2-(2-fluoro-6-(1-((1-methyl-1H-pyrazol-4-yl)methyl)-1H-pyrazol-4-yl)benzyl)-[1,2,4]triazolo[1,5-a]pyrazin-6-yl)-2-fluorobenzonitrile;

3-(8-amino-2-((2-((dimethylamino)methyl)-6-fluorophenyl) (hydroxy)methyl)-5-(pyrimidin-4-yl)-[1,2,4]triazolo[1,5-a]pyrazin-6-yl)benzonitrile;

3-(8-amino-2-((2,6-difluorophenyl) (hydroxy)methyl)-5-(3-methyl-1H-pyrazol-4-yl)-[1,2,4]triazolo[1,5-a] pyrazin-6-yl)benzonitrile;

3-(5-([1,2,4]triazolo[4,3-a]pyridin-6-yl)-8-amino-2-((2,6-difluorophenyl) (hydroxy)methyl)-[1,2,4]triazolo[1,5-a]pyrazin-6-yl)benzonitrile;

3-(8-amino-2-((2,6-difluorophenyl) (hydroxy)methyl)-5-(oxazol-5-yl)-[1,2,4]triazolo[1,5-a]pyrazin-6-yl)benzonitrile;

3-(8-amino-2-(2-fluoro-6-(1-(pyridin-2-ylmethyl)-1H-pyrazol-4-yl)benzyl)-[1,2,4]triazolo[1,5-a]pyrazin-6-yl)-2-fluorobenzonitrile;

3-(8-amino-2-((2,6-difluorophenyl) (hydroxy)methyl)-5-(3-methylpyridin-4-yl)-[1,2,4]triazolo[1,5-a]pyrazin-6-yl)benzonitrile;

3-(8-amino-2-((2-fluoro-6-(pyrrolidin-1-ylmethyl)phenyl) (hydroxy)methyl)-5-(pyrimidin-4-yl)-[1,2,4]triazolo[1,5-a]pyrazin-6-yl)benzonitrile;

3-(8-amino-2-(2-fluoro-6-(1-(2-(methylsulfonyl)ethyl)-1H-pyrazol-4-yl)benzyl)-[1,2,4]triazolo[1,5-a]pyrazin-6-yl)-2-fluorobenzonitrile;

3-(8-amino-2-((2-fluoro-6-((6-oxohexahydropyrrolo[1,2-a]pyrazin-2 (1H)-yl)methyl)phenyl) (hydroxy)methyl)-[1,2,4]triazolo[1,5-a]pyrazin-6-yl)-2-fluorobenzonitrile;

2-(4-(2-((8-amino-6-(3-cyano-2-fluorophenyl)-[1,2,4]triazolo[1,5-a]pyrazin-2-yl)methyl)-3-fluorophenyl)-1H-pyrazol-1-yl)-N,N-dimethylacetamide;

2-(4-(2-((8-amino-6-(3-cyano-2-fluorophenyl)-[1,2,4]triazolo[1,5-a]pyrazin-2-yl)methyl)-3-fluorophenyl)-1H-pyrazol-1-yl) acetamide;

3-(8-amino-2-(2-fluoro-6-(1-((trans)-3-(methylamino)cyclobutyl)-1H-pyrazol-4-yl)benzyl)-[1,2,4]triazolo[1,5-a]pyrazin-6-yl)-2-fluorobenzonitrile;

3-(8-amino-2-(2-(1-(2-cyanoethyl)-1H-pyrazol-4-yl)-6-fluorobenzyl)-[1,2,4]triazolo[1,5-a]pyrazin-6-yl)-2-fluorobenzonitrile;

3-(8-amino-2-(2-fluoro-6-(1-(2-(3-hydroxyazetidin-1-yl)-2-oxoethyl)-1H-pyrazol-4-yl)benzyl)-[1,2,4]triazolo[1,5-a]pyrazin-6-yl)-2-fluorobenzonitrile;

3-(8-amino-2-((3-methylpyridin-2-yl) methoxy)-5-(pyrimidin-4-yl)-[1,2,4]triazolo[1,5-a]pyrazin-6-yl)benzonitrile;

3-(8-Amino-2-((3-((1-(pyridin-4-ylmethyl)-1H-pyrazol-4-yl)amino)pyridin-2-yl)methyl)-[1,2,4]triazolo[1,5-a]pyrazin-6-yl)-2-fluorobenzonitrile;

3-(8-amino-2-((3-((1-(tetrahydro-2H-pyran-4-yl)-1H-pyrazol-4-yl)amino)pyridin-2-yl)methyl)-[1,2,4]triazolo[1,5-a]pyrazin-6-yl)-2-fluorobenzonitrile;

3-(8-Amino-2-((3-(1-methyl-1H-pyrazol-4-yl) pyridin-2-yl)methyl)-5-(pyrimidin-4-yl)-[1,2,4]triazolo[1,5-a]pyrazin-6-yl)benzonitrile;

(S)-3-(8-Amino-2-(2-((3-hydroxypyrrolidin-1-yl)methyl)benzyl)-5-(pyrimidin-4-yl)-[1,2,4]triazolo[1,5-a]pyrazin-6-yl)benzonitrile;

3-(8-Amino-5-(imidazo[1,2-a]pyridin-6-yl)-[1,2,4]triazolo[1,5-a]pyrazin-6-yl)benzonitrile;

3-(8-amino-2-(azetidine-1-carbonyl)-5-(3-fluoropyridin-4-yl)-[1,2,4]triazolo[1,5-a]pyrazin-6-yl)benzonitrile;

3-(8-amino-2-((2,6-difluorophenyl) (hydroxy)methyl)-5-(2,6-dimethylpyridin-4-yl)-[1,2,4]triazolo[1,5-a]pyrazin-6-yl)-2-fluorobenzonitrile;

3-(8-amino-5-(1-(methyl-d3)-6-oxo-1,6-dihydropyridazin-3-yl)-2-(pyridin-2-ylmethyl)-[1,2,4]triazolo[1,5-a]pyrazin-6-yl)benzonitrile; and 3-(8-amino-2-((6-methoxypyridin-2-yl)methyl)-5-(1-methyl-6-oxo-1,6-dihydropyridazin-3-yl)-[1,2,4]triazolo[1,5-a]pyrazin-6-yl)benzonitrile, or a pharmaceutically acceptable salt thereof.

42. A pharmaceutical composition comprising a compound of claim 1, or a pharmaceutically acceptable salt thereof, and a pharmaceutically acceptable excipient or carrier.

* * * * *